(12) United States Patent
KC

(10) Patent No.: US 12,012,401 B2
(45) Date of Patent: Jun. 18, 2024

(54) PROCESS FOR PREPARING N-(5-(3-(7-(3-FLUOROPHENYL)-3H-IMIDAZO[4,5-C]PYRIDIN-2-YL)-1H-INDAZOL-5-YL)PYRIDIN-3-YL)-3-METHYLBUTANAMIDE

(71) Applicant: BioSplice Therapeutics, Inc., San Diego, CA (US)

(72) Inventor: Sunil Kumar KC, San Diego, CA (US)

(73) Assignee: BioSplice Therapeutics, Inc., San Diego, CA (US)

( * ) Notice: Subject to any disclaimer, the term of this patent is extended or adjusted under 35 U.S.C. 154(b) by 530 days.

(21) Appl. No.: 17/205,558

(22) Filed: Mar. 18, 2021

(65) Prior Publication Data

US 2022/0024914 A1 Jan. 27, 2022

Related U.S. Application Data

(63) Continuation of application No. 16/813,021, filed on Mar. 9, 2020, now Pat. No. 10,981,909, which is a
(Continued)

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC ... C07D 471/04; C07B 2200/13; A61P 19/02; A61P 25/28; A61P 35/00; A61P 43/00; A61K 31/4439
(Continued)

(56) References Cited

U.S. PATENT DOCUMENTS

| | | | |
|---|---|---|---|
| 4,164,559 A | 8/1979 | Miyata et al. | |
| 4,474,752 A | 10/1984 | Haslam et al. | |

(Continued)

FOREIGN PATENT DOCUMENTS

| | | |
|---|---|---|
| CN | 1394205 | 1/2003 |
| CN | 1671710 | 9/2005 |

(Continued)

OTHER PUBLICATIONS

"Application +A2:A31of Hamish Christopher Swan Wood, Norman Whittaker, Irene Stirling and Kyuji Ohta," 582 F.2d 638 (Fed. Cir. 1978), 2 pages.
(Continued)

*Primary Examiner* — Taylor V Oh
(74) *Attorney, Agent, or Firm* — Fish & Richardson P.C.

(57) ABSTRACT

Provided herein is a synthetic process for preparing a compound of Formula (1).

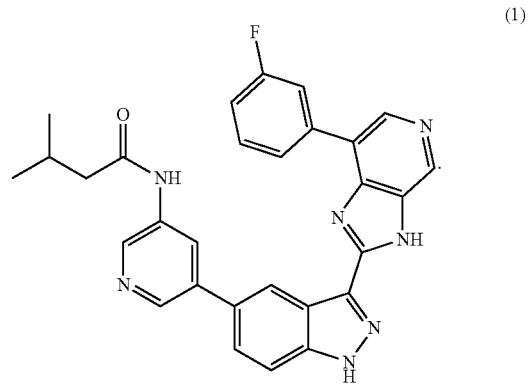

(1)

The disclosure also provides useful intermediates and salts, amorphous and polymorph forms of the compound of Formula (1). These compounds are useful for various disease including cancer, abnormal cellular proliferation, angiogenesis, Alzheimer's disease, and osteoarthritis as well as Wnt-related diseases.

18 Claims, 29 Drawing Sheets

Related U.S. Application Data continuation of application No. 16/115,222, filed on Aug. 28, 2018, now Pat. No. 10,633,380, which is a continuation of application No. 15/611,150, filed on Jun. 1, 2017, now Pat. No. 10,072,004.

(60) Provisional application No. 62/418,657, filed on Nov. 7, 2016, provisional application No. 62/344,170, filed on Jun. 1, 2016.

(58) Field of Classification Search
USPC .......................................................... 514/303
See application file for complete search history.

(56) References Cited

U.S. PATENT DOCUMENTS

| | | | |
|---|---|---|---|
| 4,603,139 A | 7/1986 | King | |
| 5,037,844 A | 8/1991 | Hamminga et al. | |
| 5,922,733 A | 7/1999 | Forbes et al. | |
| 6,120,484 A | 9/2000 | Silverstein | |
| 6,358,978 B1 | 3/2002 | Ritzeler et al. | |
| 6,377,849 B1 | 4/2002 | Lenarz et al. | |
| 6,440,102 B1 | 8/2002 | Arenberg et al. | |
| 6,555,539 B2 | 4/2003 | Reich et al. | |
| 6,648,873 B2 | 11/2003 | Arenberg et al. | |
| 6,831,175 B2 | 12/2004 | Li et al. | |
| 6,884,890 B2 | 4/2005 | Kania et al. | |
| 6,897,208 B2 | 5/2005 | Edwards et al. | |
| 6,911,211 B2 | 6/2005 | Eini et al. | |
| 6,919,461 B2 | 7/2005 | Reich et al. | |
| 7,008,953 B2 | 3/2006 | Kephart et al. | |
| 7,064,215 B2 | 6/2006 | Renhowe et al. | |
| 7,232,912 B2 | 6/2007 | Reich et al. | |
| 7,285,565 B2 | 10/2007 | Zhu et al. | |
| 7,390,815 B2 | 6/2008 | Davies et al. | |
| 7,429,609 B2 | 9/2008 | Ohi et al. | |
| 7,452,993 B2 | 11/2008 | Arnold et al. | |
| 7,468,376 B2 | 12/2008 | Rosales et al. | |
| 7,482,342 B2 | 1/2009 | D'Orchymont et al. | |
| 7,488,737 B2 | 2/2009 | Xie et al. | |
| 7,491,710 B2 | 2/2009 | Cherrier et al. | |
| 7,541,367 B2 | 6/2009 | Chiu et al. | |
| 7,626,021 B2 | 12/2009 | Arnold et al. | |
| 7,642,278 B2 | 1/2010 | Jansen et al. | |
| 7,666,867 B2 | 2/2010 | Makriyannis et al. | |
| 7,812,043 B2 | 10/2010 | Lau et al. | |
| 7,829,558 B2 | 11/2010 | Arnold et al. | |
| 7,842,711 B2 | 11/2010 | D'Orchymont et al. | |
| 7,902,217 B2 | 3/2011 | Xie et al. | |
| 7,943,616 B2 | 5/2011 | Cox et al. | |
| 8,008,481 B2 | 8/2011 | Ericsson et al. | |
| 8,088,772 B2 | 1/2012 | Garcia et al. | |
| 8,129,519 B2 | 3/2012 | Cholody et al. | |
| 8,158,647 B2 | 4/2012 | Blaney et al. | |
| 8,252,812 B2 | 8/2012 | Hood et al. | |
| 8,288,425 B2 | 10/2012 | Edwards et al. | |
| 8,304,408 B2 | 11/2012 | Wrasidlo et al. | |
| 8,450,340 B2 | 5/2013 | Hood et al. | |
| 8,604,052 B2 | 12/2013 | Hood et al. | |
| 8,618,128 B1 | 12/2013 | Hood et al. | |
| 8,637,508 B2 | 1/2014 | Badiger et al. | |
| 8,664,241 B2 | 3/2014 | Hood et al. | |
| 8,673,936 B2 | 3/2014 | Hood et al. | |
| 8,697,887 B2 | 4/2014 | Hood et al. | |
| 8,703,794 B2 | 4/2014 | Hood et al. | |
| 8,815,897 B2 | 8/2014 | Hood et al. | |
| 8,822,478 B2 | 9/2014 | Hood et al. | |
| 8,846,714 B2 | 9/2014 | Hood et al. | |
| 8,883,822 B2 | 11/2014 | Hood et al. | |
| 8,901,150 B2 | 12/2014 | Hood et al. | |
| 8,987,298 B2 | 3/2015 | Hood et al. | |
| 9,012,472 B2 | 4/2015 | Hood et al. | |
| 9,056,874 B2 | 6/2015 | Adams et al. | |
| 9,067,939 B2 | 6/2015 | Hood et al. | |
| 9,090,613 B2 | 7/2015 | Hood et al. | |
| 9,174,967 B2 | 11/2015 | Körber et al. | |
| 9,199,991 B2 | 12/2015 | Hood et al. | |
| 9,221,793 B2 | 12/2015 | Hood et al. | |
| 9,233,104 B2 | 1/2016 | Hood et al. | |
| 9,346,812 B2 | 5/2016 | Calabrese et al. | |
| 9,381,192 B2 | 7/2016 | Hood et al. | |
| 9,428,509 B2 | 8/2016 | Calabrese et al. | |
| 9,538,272 B2 | 1/2017 | Auclair et al. | |
| 9,540,398 B2 | 1/2017 | KC et al. | |
| 9,586,977 B2 | 3/2017 | Hood et al. | |
| 9,745,271 B2 | 8/2017 | Hood et al. | |
| 9,763,927 B2 | 9/2017 | Hood et al. | |
| 9,763,951 B2 | 9/2017 | Kumar KC et al. | |
| 9,802,916 B2 | 10/2017 | Hood et al. | |
| 9,815,854 B2 | 11/2017 | Kumar KC et al. | |
| 9,828,372 B2 | 11/2017 | Kumar KC et al. | |
| 9,844,536 B2 | 12/2017 | Kumar KC et al. | |
| 9,855,272 B2 | 1/2018 | Hood et al. | |
| 9,951,048 B1 | 4/2018 | Kumar KC et al. | |
| 10,072,004 B2 | 9/2018 | KC | |
| 10,131,677 B2 | 11/2018 | Sunil et al. | |
| 10,206,929 B2 | 2/2019 | Kumar KC et al. | |
| 10,280,166 B2 | 5/2019 | Kumar KC et al. | |
| 10,342,788 B2 | 7/2019 | Hood et al. | |
| 10,407,425 B2 | 9/2019 | Hood et al. | |
| 10,519,169 B2 | 12/2019 | Kumar KC et al. | |
| 10,526,347 B2 | 1/2020 | Kumar KC et al. | |
| 10,544,139 B2 | 1/2020 | Hood et al. | |
| 10,633,380 B2 | 4/2020 | KC et al. | |
| 10,654,832 B2 | 5/2020 | Kumar KC et al. | |
| 10,882,860 B2 | 1/2021 | Hood et al. | |
| 10,899,757 B2 | 1/2021 | Hood et al. | |
| 10,947,228 B2 | 3/2021 | Hood et al. | |
| 10,981,909 B2 | 4/2021 | KC | |
| 11,066,388 B2 | 7/2021 | Hood et al. | |
| 11,446,288 B2 | 9/2022 | Dellamary | |
| 11,560,378 B2 | 1/2023 | Hood et al. | |
| 11,667,632 B2 | 6/2023 | Hood et al. | |
| 11,684,615 B2 | 6/2023 | Deshmukh et al. | |
| 11,697,649 B2 | 7/2023 | Hood et al. | |
| 11,780,823 B2 | 10/2023 | Hood et al. | |
| 2002/0103229 A1 | 8/2002 | Bhagwat et al. | |
| 2002/0161022 A1 | 10/2002 | Reich et al. | |
| 2003/0199516 A1 | 10/2003 | Moser et al. | |
| 2004/0048868 A1 | 3/2004 | Edwards et al. | |
| 2004/0077681 A1 | 4/2004 | Rawlings et al. | |
| 2004/0176325 A1 | 9/2004 | Munson et al. | |
| 2004/0236101 A1 | 11/2004 | Makriyannis et al. | |
| 2005/0009894 A1 | 1/2005 | Babin et al. | |
| 2005/0026960 A1 | 2/2005 | Kephart et al. | |
| 2005/0070546 A1 | 3/2005 | Arrington et al. | |
| 2005/0090529 A1 | 4/2005 | McAlpine et al. | |
| 2005/0192262 A1 | 9/2005 | Hagstrom et al. | |
| 2005/0208582 A1 | 9/2005 | Ohi et al. | |
| 2005/0261339 A1 | 11/2005 | Ohi et al. | |
| 2006/0004000 A1 | 1/2006 | D'Orchymont et al. | |
| 2006/0014756 A1 | 1/2006 | Edwards et al. | |
| 2006/0079564 A1 | 4/2006 | Jansen et al. | |
| 2006/0094706 A1 | 5/2006 | Paruch et al. | |
| 2006/0111322 A1 | 5/2006 | Reich et al. | |
| 2006/0116519 A1 | 6/2006 | Ma et al. | |
| 2006/0135589 A1 | 6/2006 | Berdino et al. | |
| 2006/0142345 A1 | 6/2006 | Kephart et al. | |
| 2006/0167056 A1 | 7/2006 | Rynberg et al. | |
| 2006/0264897 A1 | 11/2006 | Lobl | |
| 2007/0027140 A1 | 2/2007 | Lau et al. | |
| 2007/0049598 A1 | 3/2007 | Billedeau et al. | |
| 2007/0060616 A1 | 3/2007 | Bennett et al. | |
| 2007/0078147 A1 | 4/2007 | Schumacher et al. | |
| 2007/0185187 A1 | 8/2007 | D'Orchymont et al. | |
| 2007/0219257 A1 | 9/2007 | Beachy et al. | |
| 2007/0282101 A1 | 12/2007 | Ericsson et al. | |
| 2008/0004270 A1 | 1/2008 | Gill et al. | |
| 2008/0132495 A1 | 6/2008 | Berdini et al. | |
| 2008/0255085 A1 | 10/2008 | Arvidsson et al. | |
| 2008/0262205 A1 | 10/2008 | Haar et al. | |
| 2008/0287452 A1 | 11/2008 | Bursavich et al. | |
| 2009/0005356 A1 | 1/2009 | Blaney et al. | |
| 2009/0005377 A1 | 1/2009 | Almansa Rosales et al. | |

(56) References Cited

U.S. PATENT DOCUMENTS

| | | |
|---|---|---|
| 2009/0048249 A1 | 2/2009 | Chiu et al. |
| 2009/0054397 A1 | 2/2009 | Ohi et al. |
| 2009/0099062 A1 | 4/2009 | Lee et al. |
| 2009/0203690 A1 | 8/2009 | Akritopoulou-Zanze et al. |
| 2009/0247504 A1 | 10/2009 | Churcher et al. |
| 2009/0264446 A9 | 10/2009 | Rosales et al. |
| 2009/0286983 A1 | 11/2009 | Almansa Rosales et al. |
| 2010/0280063 A1 | 11/2010 | Price et al. |
| 2010/0298377 A1 | 11/2010 | Aletru et al. |
| 2011/0009353 A1 | 1/2011 | Chen-Kiang et al. |
| 2011/0021467 A1 | 1/2011 | D'Orchymont et al. |
| 2011/0034441 A1 | 2/2011 | Hood et al. |
| 2011/0034491 A1 | 2/2011 | Hood et al. |
| 2011/0034497 A1 | 2/2011 | Hood et al. |
| 2011/0082144 A1 | 4/2011 | Lau et al. |
| 2011/0178075 A1 | 7/2011 | Xie et al. |
| 2011/0190290 A1 | 8/2011 | Hood et al. |
| 2012/0053345 A1 | 3/2012 | Ericson et al. |
| 2012/0059047 A1 | 3/2012 | Prins et al. |
| 2012/0129837 A1 | 5/2012 | Cholody et al. |
| 2012/0277229 A1 | 11/2012 | Bearss et al. |
| 2013/0039906 A1 | 2/2013 | Do et al. |
| 2013/0267495 A1 | 10/2013 | Hood et al. |
| 2013/0267548 A1 | 10/2013 | Follmann et al. |
| 2014/0194441 A1 | 7/2014 | Kumar KC et al. |
| 2014/0263319 A1 | 9/2014 | Fazi et al. |
| 2014/0364451 A1 | 12/2014 | John et al. |
| 2015/0087687 A1 | 3/2015 | Brown et al. |
| 2015/0111872 A1 | 4/2015 | Desroy et al. |
| 2015/0266825 A1 | 9/2015 | Hood et al. |
| 2016/0068529 A1 | 3/2016 | KC et al. |
| 2016/0068547 A1 | 3/2016 | KC et al. |
| 2016/0068548 A1 | 3/2016 | KC et al. |
| 2016/0068549 A1 | 3/2016 | KC et al. |
| 2016/0068550 A1 | 3/2016 | KC et al. |
| 2016/0068551 A1 | 3/2016 | KC et al. |
| 2016/0075701 A1 | 3/2016 | Kumar KC |
| 2016/0090380 A1 | 3/2016 | Kumar KC |
| 2016/0101092 A1 | 4/2016 | Hood et al. |
| 2016/0297812 A1 | 10/2016 | Hood et al. |
| 2017/0202846 A1 | 7/2017 | Hood et al. |
| 2017/0224697 A1 | 8/2017 | Kumar KC et al. |
| 2017/0333409 A1 | 11/2017 | Hood et al. |
| 2017/0349584 A1 | 12/2017 | Kumar KC et al. |
| 2018/0086754 A1 | 3/2018 | Kumar KC et al. |
| 2018/0133199 A1 | 5/2018 | Dellamary |
| 2018/0141963 A1 | 5/2018 | Kumar KC et al. |
| 2018/0148444 A1 | 5/2018 | Kumar KC et al. |
| 2018/0153873 A1 | 6/2018 | Hood et al. |
| 2018/0162840 A1 | 6/2018 | Kumar KC et al. |
| 2018/0177787 A1 | 6/2018 | Kumar KC et al. |
| 2018/0185343 A1 | 7/2018 | Deshmukh et al. |
| 2018/0201624 A1 | 7/2018 | Kumar KC et al. |
| 2018/0207141 A1 | 7/2018 | Kumar KC et al. |
| 2018/0214427 A1 | 8/2018 | KC et al. |
| 2018/0214428 A1 | 8/2018 | KC et al. |
| 2018/0214429 A1 | 8/2018 | KC et al. |
| 2018/0215753 A1 | 8/2018 | KC et al. |
| 2018/0221341 A1 | 8/2018 | KC et al. |
| 2018/0221350 A1 | 8/2018 | KC et al. |
| 2018/0221351 A1 | 8/2018 | KC et al. |
| 2018/0221352 A1 | 8/2018 | KC et al. |
| 2018/0221353 A1 | 8/2018 | KC et al. |
| 2018/0221354 A1 | 8/2018 | KC et al. |
| 2018/0222891 A1 | 8/2018 | KC et al. |
| 2018/0222923 A1 | 8/2018 | KC et al. |
| 2018/0228780 A1 | 8/2018 | KC et al. |
| 2018/0228781 A1 | 8/2018 | KC et al. |
| 2018/0228782 A1 | 8/2018 | KC et al. |
| 2018/0228783 A1 | 8/2018 | KC et al. |
| 2018/0228784 A1 | 8/2018 | KC et al. |
| 2018/0228785 A1 | 8/2018 | KC et al. |
| 2018/0230142 A1 | 8/2018 | KC et al. |
| 2018/0237416 A1 | 8/2018 | Hood et al. |
| 2018/0250269 A1 | 9/2018 | KC et al. |
| 2018/0256588 A1 | 9/2018 | Hood et al. |
| 2018/0318292 A1 | 11/2018 | Hood et al. |
| 2018/0325910 A1 | 11/2018 | Kumar KC et al. |
| 2018/0370989 A1 | 12/2018 | Kumar KC et al. |
| 2019/0055238 A1 | 2/2019 | Kumar KC et al. |
| 2019/0071440 A1 | 3/2019 | Hood et al. |
| 2019/0112304 A1 | 4/2019 | Hood et al. |
| 2019/0119276 A1 | 4/2019 | Kumar KC et al. |
| 2019/0119303 A1 | 4/2019 | Kumar KC et al. |
| 2019/0134013 A1 | 5/2019 | Hood et al. |
| 2019/0194187 A1 | 6/2019 | Kumar KC |
| 2019/0352279 A1 | 11/2019 | Kumar KC et al. |
| 2020/0155525 A1 | 5/2020 | Hood et al. |
| 2021/0002273 A1 | 1/2021 | KC |
| 2021/0121448 A1 | 4/2021 | Deshmukh et al. |
| 2021/0145807 A1 | 5/2021 | Dellamary |
| 2021/0292318 A1 | 9/2021 | Hood et al. |
| 2021/0292319 A1 | 9/2021 | Hood et al. |
| 2023/0000842 A1 | 1/2023 | Deshmukh et al. |
| 2023/0013144 A1 | 1/2023 | Hood et al. |
| 2023/0047396 A1 | 2/2023 | Hood et al. |
| 2023/0139639 A1 | 5/2023 | Dellamary |

FOREIGN PATENT DOCUMENTS

| | | |
|---|---|---|
| CN | 1829713 | 9/2006 |
| CN | 101440092 | 5/2009 |
| CN | 102105464 A | 6/2011 |
| CN | 103929963 | 7/2014 |
| EA | 200200768 A1 | 2/2003 |
| FR | 3011239 A1 | 4/2015 |
| KR | 20140074943 | 6/2014 |
| KR | 20140143796 | 12/2014 |
| KR | 20150004803 | 1/2015 |
| KZ | 20122 | 1/2010 |
| RU | 2331640 | 8/2008 |
| RU | 2350271 | 3/2009 |
| RU | 2416610 C2 | 4/2011 |
| RU | 2472508 C2 | 1/2013 |
| RU | 2018120728 A | 12/2019 |
| WO | WO 1987/05297 | 9/1987 |
| WO | WO 1996/02537 | 2/1996 |
| WO | WO 2001/02369 | 1/2001 |
| WO | WO 2001/053268 | 7/2001 |
| WO | WO 2003/004488 | 1/2003 |
| WO | WO 2003/035005 | 5/2003 |
| WO | WO 2003/035065 | 5/2003 |
| WO | WO 2003/035644 | 5/2003 |
| WO | WO 2003/051366 | 6/2003 |
| WO | WO 2003/070236 | 8/2003 |
| WO | WO 2003/070706 | 8/2003 |
| WO | WO 2003/097610 | 11/2003 |
| WO | WO 2003/101968 | 12/2003 |
| WO | WO 2003/101993 | 12/2003 |
| WO | WO 2004/014864 | 2/2004 |
| WO | WO 2004/031158 | 4/2004 |
| WO | WO 2004/076450 | 9/2004 |
| WO | WO 2005/002552 A2 | 1/2005 |
| WO | WO 2005/009997 | 2/2005 |
| WO | WO 2005/012256 A1 | 2/2005 |
| WO | WO 2005/012301 A1 | 2/2005 |
| WO | WO 2005/014554 | 2/2005 |
| WO | WO 2005/047266 | 5/2005 |
| WO | WO 2005/049019 | 6/2005 |
| WO | WO 2005/092890 | 10/2005 |
| WO | WO 2005/099703 | 10/2005 |
| WO | WO 2005/110410 | 11/2005 |
| WO | WO 2006/001894 | 1/2006 |
| WO | WO 2006/015124 | 2/2006 |
| WO | WO 2006/024945 | 3/2006 |
| WO | WO 2006/054143 | 5/2006 |
| WO | WO 2006/054151 | 5/2006 |
| WO | WO 2006/063302 | 6/2006 |
| WO | WO 2006/063841 | 6/2006 |
| WO | WO 2006/130673 | 12/2006 |
| WO | WO 2007/061360 | 5/2007 |
| WO | WO 2007/077435 A1 | 7/2007 |
| WO | WO 2007/107346 | 9/2007 |
| WO | WO 2007/117465 | 10/2007 |

(56) References Cited

FOREIGN PATENT DOCUMENTS

| WO | WO 2007/147874 A1 | 12/2007 |
|---|---|---|
| WO | WO 2008/007113 A2 | 1/2008 |
| WO | WO 2008/048502 A1 | 4/2008 |
| WO | WO 2008/061109 | 5/2008 |
| WO | WO 2008/071397 | 6/2008 |
| WO | WO 2008/071398 | 6/2008 |
| WO | WO 2008/071451 | 6/2008 |
| WO | WO 2008/124848 | 10/2008 |
| WO | WO 2008/137408 | 11/2008 |
| WO | WO 2008/140792 | 11/2008 |
| WO | WO 2008/147713 | 12/2008 |
| WO | WO 2008/150914 | 12/2008 |
| WO | WO 2008/154241 | 12/2008 |
| WO | WO 2008/156757 | 12/2008 |
| WO | WO 2009/011850 | 1/2009 |
| WO | WO 2009/016072 | 2/2009 |
| WO | WO 2009/029609 A1 | 3/2009 |
| WO | WO 2009/061345 | 5/2009 |
| WO | WO 2009/152868 | 12/2009 |
| WO | WO 2010/064875 | 6/2010 |
| WO | WO 2010/107765 | 9/2010 |
| WO | WO 2010/111060 | 9/2010 |
| WO | WO 2010/132725 | 11/2010 |
| WO | WO 2011/003065 A2 | 1/2011 |
| WO | WO 2011/011722 | 1/2011 |
| WO | WO 2011/019648 | 2/2011 |
| WO | WO 2011/019651 | 2/2011 |
| WO | WO 2011/050245 | 4/2011 |
| WO | WO 2011/079076 | 6/2011 |
| WO | WO 2011/084486 | 7/2011 |
| WO | WO 2011/123890 | 10/2011 |
| WO | WO 2012/068589 | 5/2012 |
| WO | WO 2012/104388 | 8/2012 |
| WO | WO 2012/129562 | 9/2012 |
| WO | WO 2013/024011 | 2/2013 |
| WO | WO 2013/030138 A1 | 3/2013 |
| WO | WO 2013/040215 A1 | 3/2013 |
| WO | WO 2013/113722 | 8/2013 |
| WO | WO 2013/166396 A2 | 11/2013 |
| WO | WO 2015/143380 | 9/2015 |
| WO | WO 2016/040185 A1 | 3/2016 |
| WO | WO 2016/040193 A1 | 3/2016 |
| WO | WO 2017/079759 A1 | 5/2017 |
| WO | WO 2017/079765 | 5/2017 |
| WO | WO 2020/006115 A1 | 1/2020 |

OTHER PUBLICATIONS

Adaimy et al., "Mutation in WNT10A Is Associated with an Autosomal Recessive Ectodermal Dysplasia: The Odonto-onychodermal Dysplasia," Am. J. Hum. Genet., (Oct. 2007), 81(4), 821-828.
Ai et al., "Optimal Method to Stimulate Cytokine Production and Its Use in Immunotoxicity Assessment," Int J Environ Res Public Health, Sep. 2013, 10(9):3834-3842.
Anastas and Moon, "WNT signalling pathways as therapeutic targets in cancer," Nat Rev Cancer, 13(1):11-26, Jan. 2013.
Andres, "Molecular genetics and animal models in autistic disorder," Brain Research Bulletin, (2002), 57(1), 109-119.
Barker and Clevers, "Mining the Wnt pathway for cancer therapeutics," Nat Rev Drug Discov., 5(12):997-1014, Dec. 2006.
Barroga et al., "Discovery of an Intra-Articular Injection Small Molecule Inhibitor of the Wnt Pathway (SM04690) As a Potential Disease Modifying Treatment for Knee Osteoarthritis," 2015 ACR/ARHP Annual Meeting, Abst. No. 2007, Sep. 29, 2015, retrieved on Sep. 27, 2018, URL <https://acrabstracts.org/abstract/discovery-of-an-intra-articular-injection-small-molecule-inhibitor-of-the-wnt-pathway-sm04690-as-a-potential-disease-modifying-treatment-for-knee-osteoarthritis/>, 3 pages.
Bass, "Why the difference between tendinitis and tendinosis matters," International Journal of Therapeutic Massage and Bodywork, vol. 5, No. 1, Mar. 2012.
Bendele, "Animal Models of Arthritis: Relevance to Human Disease," Toxicol Pathol 1999 27: 134-142.
Bernstein, "Polymorphism in Molecular Crystals," Analytical Techniques for Polymorphs, 2002, 115-118, 272.
Beyer et al., "Extended report: β-catenin is a central mediator of pro-fibrotic Wnt signaling in systemic sclerosis," Ann Rheum Dis, 71:761-767, online Feb. 2012.
Bharath et al., "Evaluation of Myofibroblasts by Expression of Alpha Smooth Muscle Actin: A Marker in Fibrosis, Dysplasia and Carcinoma," Journal of Clinical and Diagnostic Research, 2014, 8(4):ZC14-ZC17.
Biason-Lauber et al., "A WNT4 Mutation Associated with Müllerian-Duct Regression and Virilization in a 46,XX Woman," N. Engl. J. Med., (Aug. 2004), 351(8), 792-798.
Blaydon et al., "The gene encoding R-spondin 4 (RSPO4), a secreted protein implicated in Wnt signaling, is mutated in inherited anonychia," Nat. Genet., (Nov. 2006), 38(11), 1245-1247.
Blom et al., "Involvement of the Wnt signaling pathway in experimental and human osteoarthritis: prominent role of Wnt-induced signaling protein 1," Arthritis Rheum., 60(2):501-512, Feb. 2009.
Bollong et al, "Small molecule-mediated ininhibition of myofibroblast transdifferentiation for the treatment of fibrosis," PNAS, 2017, 114:18:4679-4684.
Boyden et al., "High Bone Density Due to a Mutation in LDL-Receptor-Related Protein 5," N. Engl. J. Med., (May 2002), 346(20):1513-1521.
Brack et al., "Increased Wnt signaling during aging alters muscle stem cell fate and increases fibrosis," Science, 317(5839):807-810, Aug. 2007.
Braga et al., "Making crystals from crystals: a green route to crystal engineering and polymorphism," J. Royal Soc. Chem. Commun., 2005, 3635-3645.
Brown et al., "Toxicity and toxicokinetics of the cyclin-dependent kinase inhibitor AG-024322 in cynomolgus monkeys following intravenous infusion," Cancer Chemother Pharmacol., 62(6):1091-1101, Epub May 2008.
Byrn et al., "Pharmaceutical solids: a strategic approach to regulatory considerations," Pharmaceutical Research, Jul. 1995, 12(7):945-954.
Caira, "Crystalline Polymorphism of Organic Compounds," Topics in Current Chemistry, Jan. 1998, 198:163-208.
Carpino et al., "Alpha-SMA expression in hepatic stellate cells and quantitative analysis of hepatic fibrosis in cirrhosis and in recurrent chronic hepatitis after liver transplantation," Digestive and Liver Disease, 2005, 37:349-356.
Chanput et al., "Transcription profiles of LPS-stimulated THP-1 monocytes and macrophages: a tool to study inflammation modulating effects of food-derived compounds," Food Funct, Dec. 2010, 1(3):254-61.
Chilosi et al., "The pathogenesis of COPD and IPF: Distinct horns of the same devil?" Respiratory Research, 13:3, 2012.
Chou et al., "Quantitative analysis of dose-effect relationships: the combined effects of multiple drugs or enzyme inhibitors," Advances in Enzyme Regulation (1984), 22, 27-55.
Chou, "Drug combination studies and their synergy quantification using the Chou-Talalay method," Cancer Res., 70(2):440-446, Jan. 2010.
Chou, "Graphic rule for drug metabolism systems," Current Drug Metabolism, (May 2010) 11(4): 369-378.
Christodoulides et al., "WNT10B mutations in human obesity," Diabetologia, (2006) 49(4):678-684.
Clevers and Nusse, "Wnt/β-catenin signaling and disease," Cell, (Jun. 2012), 149(6):1192-1205.
Clevers, "Wnt/β-catenin signaling in development and disease," Cell, Nov. 3, 2006, 127(3):469-480.
Clinicaltrials.gov [online]. ClinicalTrials.gov Identifier: NCT02095548, "Phase 1, Dose Escalation Study Evaluating the Safety, Tolerability, Pharmacokinetics and Pharmacodynamics of SM04690 in Moderate to Severe Knee Osteoarthritis (OA)," Mar. 26, 2014, [retrieved on Aug. 1, 2018]. Retrieved from the Internet: URL<https://clinicaltrials.gov/ct2/show/NCT02095548?term=NCT02095548&rank=1>, 7 pages.
Clinicaltrials.gov [online]. ClinicalTrials.gov Identifier: NCT02536833, "A Study Evaluating the Safety, Tolerability, and Efficacy of SM04690

(56) References Cited

OTHER PUBLICATIONS

Injected in the Target Knee Joint of Moderately to Severely Symptomatic Osteoarthritis Subjects," Sep. 1, 2015, [retrieved on 2018-08-01]. Retrieved from the Internet: URL<https://clinicaltrials.gov/ct2/show/NCT02536833?term=NCT02536833&rank=1>, X pages.
Corr, "Wnt-beta-catenin signaling in the pathogenesis of osteoarthritis," Nat Clin Pract Rheumatol., 4(10):550-556, Oct. 2008.
D'Alessio et al., "Benzodipyrazoles: a new class of potent CDK2 inhibitors," Bioorganic & Medicinal Chemistry Letters (2005), 15(5), 1315-1319.
Damia, "Contemporary pre-clinical development of anticancer agents—What are the optimal preclinical models?" European Journal of Cancer, 2009, 45, 2768-2781, p. 2778.
Dann et al., "Insights into Wnt binding and signaling from the structures of two Frizzled cysteine-rich domains," Nature, (Jul. 2001), 412, pp. 86-90.
Datta et al., "Novel therapeutic approaches for pulmonary fibrosis," Br J Pharmacol., 163(1):141-172, May 2011.
Davidovich et al., "Detection of Polymorphism by Powder X-Ray Diffraction: Interferences by Preferred Orientation," American Pharmaceutical Review, 2004, 7:(1):10, 12, 14, 16, and 100.
Davidson et al., "Emerging links between CDK cell cycle regulators and Wnt signaling," Trends Cell Biol., Aug. 2010, 20(8):453-460.
De Ferrari and Inestrosa, "Wnt signaling function in Alzheimer's disease," Brain Research Reviews, (2000), 33(1): 1-12.
De Ferrari and Moon, "The ups and downs of Wnt signaling in prevalent neurological disorders," Oncogene, (2006) 25(57): 7545-7553.
De Ferrari et al., "Common genetic variation within the Low-Density Lipoprotein Receptor-Related Protein 6 and late-onset Alzheimer's disease," Proc. Natl. Acad. Sci. USA, (May 2007), 104(22):9434-9439.
Dean, "Analytical Chemistry Handbook," 1995, 10.24-10.26.
Dermer, "Another Anniversary for the War on Cancer," Nature Biotechnology, 12:320 (1994).
Deshmkukh et al., "Abstract: A Small Molecule Inhibitor of the Wnt Pathway (SM04755) as a Potential Topical Treatment for Tendinopathy," Abstract from the Orthobiologic Institute (TOBI) Annual Symposium, Las Vegas, Nevada, Jun. 7, 2018, 1 page.
Deshmkukh et al., "Abstract: Discovery of a Small Molecule Inhibitor of the Wnt Pathway (SM04755) as a Potential Topical Treatment for Tendinopathy," Abstract from Osteoarthritis Research Society International (OARSI), Las Vegas, Nevada, Apr. 27, 2017, 2 pages.
Deshmkukh et al., "Abstract: Discovery of a Small Molecule Inhibitor of the Wnt Pathway (SM04755) as a Potential Topical Treatment for Tendinopathy," Abstract from the World Congress on Osteoporosis Osteoarthritis and Musculoskeletal Disease, Florence, Italy, Mar. 23, 2017, 2 pages.
Deshmkukh et al., "Abstract: Experimental Tendinopathy Treatment with SM04755, a Topical Small Molecule Inhibitor of the Wnt Pathway," Abstract from Osteoarthritis Research Society International (OARSI), Liverpool, England, Apr. 26, 2018, 3 pages.
Deshmkukh et al., "Abstract: Experimental Tendinopathy Treatment with SM04755, a Topical Small Molecule Wnt Pathway Inhibitor," Abstract from the Orthobiologic Institute (TOBI) Annual Symposium, Las Vegas, Nevada, Jun. 7, 2018, 2 pages.
Deshmkukh et al., "Poster: A Small Molecule Inhibitor of the Wnt Pathway (SM04755) as a Potential Topical Treatment for Tendinopathy," Poster from the Orthobiologic Institute (TOBI) Annual Symposium, Las Vegas, Nevada, Jun. 7, 2018, 1 page.
Deshmkukh et al., "Poster: Discovery of a Small Molecule Inhibitor of the Wnt Pathway (SM04755) as a Potential Topical Treatment for Tendinopathy," Poster from the World Congress on Osteoporosis Osteoarthritis and Musculoskeletal Disease, Florence, Italy, Mar. 23, 2017, 1 page.
Deshmkukh et al., "Poster: Experimental Tendinopathy Treatment with SM04755, a Topical Small Molecule Wnt Pathway Inhibitor," Poster from the Orthobiologic Institute (TOBI) Annual Symposium, Las Vegas, Nevada, Jun. 7, 2018, 2 pages.
Deshmkukh et al., "Presentation: Experimental Tendinopathy Treatment with SM04755, a Topical Small Molecule Inhibitor of the Wnt Pathway," Presentation from Osteoarthritis Research Society International (OARSI), Liverpool, England, Apr. 26, 2018, 17 pages.
Deshmukh et al., "Abstract #EULAR-6427: Discovery of a Small Molecule Inhibitor of the Wnt Pathway (SM04755) as a Potential Topical Treatment for Tendinopathy," Abstract from Annual European Congress of Rheumatology (EULAR), Madrid, Spain, Jun. 14, 2017, 2 pages.
Deshmukh et al., "Abstract #THU0522: Experimental Tendinopathy Treatment with SM04755, a Topical Small Molecule Inhibitor of the Wnt Pathway," Abstract from Annual European Congress of Rheumatology (EULAR), Amsterdam, Netherlands, Jun. 13-16, 2018, 2 pages.
Deshmukh et al., "Abstract: Discovery of a Small Molecule Inhibitor of the Wnt Pathway (SM04755) as a Potential Topical Treatment for Tendinopathy," Abstract from Orthopaedic Research Society Annual Meeting, New Orleans, Louisiana, Mar. 19, 2017, 1 page.
Deshmukh et al., "Abstract: Discovery of a Small Molecule Inhibitor of the Wnt Pathway (SM04755) as a Potential Topical Treatment for Tendinopathy," Abstract from Regenerative Medicine and Biology From Development to Regeneration, St. Louis, Missouri, May 4, 2017, 2 pages.
Deshmukh et al., "Abstract: Experimental tendinopathy treatment with SM04755, a topical small molecule inhibitor of the Wnt pathway," Abstract from Orthopaedic Research Society Annual Meeting, New Orleans, Louisiana, Mar. 10, 2018, 2 pages.
Deshmukh et al., "Poster # 1459: Experimental tendinopathy treatment with SM04755, a topical small molecule inhibitor of the Wnt pathway," Poster from Orthopaedic Research Society Annual Meeting, New Orleans, Louisiana, Mar. 19, 2018, 1 page.
Deshmukh et al., "Poster #443: Discovery of a Small Molecule Inhibitor of the Wnt Pathway (SM04755) as a Potential Topical Treatment for Tendinopathy," Poster from Osteoarthritis Research Society International (OARSI), Las Vegas, Nevada, Apr. 27, 2017, 1 page.
Deshmukh et al., "Poster #SAT067: Discovery of a Small Molecule Inhibitor of the Wnt Pathway (SM04755) as a Potential Topical Treatment for Tendinopathy," Poster from Annual European Congress of Rheumatology (EULAR), Madrid, Spain, Jun. 14, 2017, 1 page.
Deshmukh et al., "Poster #THU0522: Experimental Tendinopathy Treatment with SM04755, a Topical Small Molecule Inhibitor of the Wnt Pathway," Poster from Annual European Congress of Rheumatology (EULAR), Amsterdam, Netherlands, Jun. 13-16, 2018, 1 page.
Deshmukh et al., "Poster: Discovery of a Small Molecule Inhibitor of the Wnt Pathway (SM04755) as a Potential Topical Treatment for Tendinopathy," Poster from Regenerative Medicine and Biology From Development to Regeneration, St. Louis, Missouri, May 4, 2017, 2 pages.
Deshmukh et al., "Presentation: Discovery of a Small Molecule Inhibitor of the Wnt Pathway (SM04755) as a Potential Topical Treatment for Tendinopathy," Presentation from Orthopaedic Research Society Annual Meeting, New Orleans, Louisiana, Mar. 19, 2017, 19 pages.
Deshmukh et al., "A Small Molecule, SM04690, Has Inhibitory Effects on the Wnt Pathway and Inflammation in Vitro, with Potential Implications for the Treatment of Osteoarthritis," [abstract] Arthritis Rheumatol. 2016; 68 (suppl 10). https://acrabstracts.org/abstract/a-small-molecule-sm04690-has-inhibitory-effects-on-the-wnt-pathway-and-inflammation-in-vitro-with-potential-implications-for-the-treatment-of-osteoarthritis/. Accessed Dec. 28, 2020.
Deshmukh et al., "A small-molecule inhibitor of the Wnt pathway (SM04690) as a potential disease modifying agent for the treatment of osteoarthritis of the knee," Osteoarthritis and Cartilage, Jan. 2018, 26(1):18-27.
Deshmukh et al., "Abstract #1104: Discovery of a Small Molecule Inhibitor of the Wnt Pathway (SM04755) As a Potential Topical Treatment for Chronic Tendinopathy," Abstract from 2016 ACR/ARHP Annual Meeting, Nov. 14, 2016, 3 pages.
Deshmukh et al., "Experimental Tendinopathy Treatment with SM04755, a Topical, Small Molecule Inhibitor of the Wnt Path-

(56) References Cited

OTHER PUBLICATIONS way," Abstract of Oral Presentation at #1952 at the American College of Rheumatology (ACR) Conference 2018, Chicago, Illinois, Oct. 19-24, 2018, 2 pages.

Deshmukh et al., "Experimental Tendinopathy Treatment with SM04755, a Topical, Small Molecule Inhibitor of the Wnt Pathway," Slides Present at #1952 at the American College of Rheumatology (ACR) Conference 2018, Chicago, Illinois, Oct. 19-24, 2018, 22 pages.

Deshmukh et al., "Poster #1104: Discovery of a Small Molecule Inhibitor of the Wnt Pathway (SM04755) As a Potential Topical Treatment for Chronic Tendinopathy," Poster from 2016 ACR/ARHP Annual Meeting, Nov. 14, 2016, 3 pages.

Dessalew et al., "3D-QSAR CoMFA and CoMSIA study on benzodipyrazoles as cyclin dependent kinase 2 inhibitors," Medicinal Chemistry, (2008), 4(4), 313-321.

Dong et al., "QSAR study of Akt/protein kinase B (PKB) inhibitors using support vector machine," European Journal of Medicinal Chemistry, (Oct. 2009), pp. 44(10): 4090-4097.

Doumpas et al., "TCF/LEF dependent and independent transcriptional regulation of Wnt/b-catenin target genes" The EMBO Journal, Nov. 13, 2018 1-14.

Du Bois, "Strategies for treating idiopathic pulmonary fibrosis," Nature Reviews Drug Discovery, 9(2):129-140 (Feb. 2010).

Edamoto et al., "Alterations of RB1, p53 and Wnt pathways in hepatocellular carcinomas associated with hepatitis C, hepatitis B and alcoholic liver cirrhosis," Int J Cancer., 106(3):334-341, Sep. 1, 2003.

Egloff et al., "Gastrin-releasing peptide receptor expression in non-cancerous bronchial epithelia is associated with lung cancer: a case-control study," Respiratory Research, 13:9, Feb. 2012.

Enzo et al., "The Wnt/β-catenin pathway in human fibrotic-like diseases and its eligibility as a therapeutic target," Molecular and Cellular Therapies, 2015, 3(1), 13 pages.

Espada et al., "Wnt signalling and cancer stem cells," Clin. Transl. Oncol., (2009), 11(7), 411-27.

Ewan et al., "A useful approach to identify novel small-molecule inhibitors of Wnt-dependent transcription," Cancer Res. (2010), 70(14), 5963-5973.

Exhibit A: Otsuka Pharmaceutical Co., Ltd., v. Sandoz, Inc., Sun Pharmaceutical Industries, Ltd., Synthon BV, Synthon Holding BV, Synthon Laboratories, Inc., and Synton Pharmaceuticals, Inc., and Apotex Inc. and Apotex Corp., and Teva Pharmaceuticals USA, Inc., Barr Laboratories, Inc., and Barr Pharmaceuticals, Inc., Decision on Appeal, 2011-1126,-1127, May 7, 2012, 33 pages.

Extended European Search Report in Application No. 211705405, dated Oct. 19, 2021, 6 pages.

Florez et al., "TCF7L2 Polymorphisms and Progression to Diabetes in the Diabetes Prevention Program," N. Engl. J. Med., (Jul. 2006), 355(3):241-250.

Forestier et al., "Prevalence of generalized osteoarthritis in a population with knee osteoarthritis," Joint Bone Spine, May 2011, 78(3):275-278.

Freese et al., "Wnt signaling in development and disease," Neurobiology of Disease, (2010) 38(2):148-153.

Fujii et al., "An antagonist of dishevelled protein-protein interaction suppresses beta-catenin-dependent tumor cell growth," Cancer Res., 67(2):573-579, Jan. 2007.

Fukuzawa et al., "Beckwith-Wiedemann Syndrome-associated Hepatoblastoma: Wnt Signal Activation Occurs Later in Tumorigenesis in Patients with 11p15.5 Uniparental Disomy," Pediatric and Developmental Pathology (2003), 6(4): 299-306.

Giles et al., "Caught up in a Wnt storm: Wnt signaling in cancer," Biochim Biophys Acta., Jun. 2003, 1653(1):1-24.

Gitter et al., "Characteristics of human synovial fibroblast activation by IL-1 beta and TNF alpha," Immunology, Feb. 1989, 66(2):196-200.

Gudjonsson et al., "Mouse models of psoriasis," Journal of Investigative Dermatology, Jun. 1, 2007, 127(6):1292-1308.

Guillory (in Brittain ed.), "Polymorphism in Pharmaceutical Solids," NY: Marcel Dekker, Inc., 1999, 1-2, 125-181, 183-226.

Gunther et al., "Prevalence of generalised osteoarthritis in patients with advanced hip and knee osteoarthritis: the Ulm Osteoarthritis Study," Ann. Rheum. Dis., Dec. 1998, 57(12):717-723.

Guo et al., "Wnt/β-Catenin Signaling: a Promising New Target for Fibrosis Diseases," Physiol. Res., 2012, 61:337-346.

Handeli and Simon, "A small-molecule inhibitor of Tcf/beta-catenin signaling down-regulates PPARgamma and PPARdelta activities," Mol Cancer Ther., 7(3):521-529, Mar. 2008.

Hayami et al., "Characterization of articular cartilage and subchondral bone changes in the rat anterior cruciate ligament transection and meniscectomized models of osteoarthritis," Bone, Feb. 2006, 38(2):234-243.

Henderson Jr. et al., "Inhibition of Wnt/beta-catenin/CREB binding protein (CBP) signaling reverses pulmonary fibrosis," Proc Natl Acad Sci U S A., 107(32):14309-14314, Epub Jul. 2010.

Hood et al., "Discovery of a small molecule inhibitor of the Wnt pathway (SM04690) as a potential disease modifying treatment for knee osteoarthritis," Osteoarthritis and Cartilage, Apr. 1, 2016, 24:S14-15.

Hu et al., "Discovery of indazoles as inhibitors of Tpl2 kinase," Bioorganic & Medicinal Chemistry Letters, (Aug. 2011) 21(16): 4758-4761.

Huang et al., "Tankyrase inhibition stabilizes axin and antagonizes Wnt signaling," Nature, (Oct. 2009), 461(7264): 614-620.

Huang et al., "Synthesis of 3-(1H-benzimidazol-2-yl)-5-isoquinolin-4-ylpyrazolo[1,2-b]pyridine, a potent cyclin dependent kinase 1 (CDK1) inhibitor," Bioorganic & Medicinal Chemistry Letters, (2007) 17(5): 1243-1245.

Hübner et al., "Standardized quantification of pulmonary fibrosis in histological samples," Biotechniques, 44(4):507-511, 514-517, Apr. 2008.

Ikejima et al., "Interleukin-1 induces tumor necrosis factor (TNF) in human peripheral blood mononuclear cells in vitro and a circulating TNF-like activity in rabbits," J Infect Dis, Jul. 1990, 162(1):215-23.

Im et al., "Wnt inhibitors enhance chondrogenesis of human mesenchymal stem cells in a long-term pellet culture," Biotechnol Lett., 33(5):1061-1068, Epub Jan. 2011.

Inestrosa and Toledo, "The role of Wnt signaling in neuronal dysfunction in Alzheimer's Disease," Mol Neurodegener, 3:9, doi:10.1186/1750-1326-3-9, 13 pages, Jul. 2008.

International Preliminary Report on Patentability for International Application No. PCT/US2017/035411, dated Dec. 4, 2018, 12 pages.

International Search Report and Written Opinion for PCT/US2017/035411 dated Oct. 6, 2017, 18 pages.

Invitation to Pay Additional Fees for Application No. PCT/US2017/035411, dated Aug. 4, 2017, 12 pages.

Ivanisevic et al., "Use of X-ray Powder Diffraction In the Pharmaceutical Industry," Pharnn. Sci. Encycl., 2010, p. 1-42.

Jain & Mohammedi, "Polymorphism in Pharmacy," Indian Drugs, 1986, 23:(6):315-329.

Janssens et al., "The Wnt-dependent signaling pathways as target in oncology drug discovery," Invest New Drugs., 24(4):263-280, Jul. 2006.

Jenkins et al., "Germline mutations in WTX cause a sclerosing skeletal dysplasia but do not predispose to tumorigenesis," Nat. Genet. (Jan. 2009), 41(1), 95-100.

Jessen et al., "Peripheral white blood cell toxicity induced by broad spectrum cyclin-dependent kinase inhibitors," Journal of Applied Toxicology (Jan. 2007), 27(2), 133-142.

Johnson et al., "A stem cell-based approach to cartilage repair," Science, 336(6082):717-721, Epub Apr. 5, 2012.

Johnson et al., "Relationships between drug activity in NCI preclinical in vitro and in vivo models and early clinical trials," British Journal of Cancer, 2001, 84, 1424-1431.

Jordan, "Tamoxifen: A Most Unlikely Pioneering Medicine," Nature Reviews, Mar. 2003, 2:205-213.

Kanazawa et al., "Association of the Gene Encoding Wingless-Type Mammary Tumor Virus Integration-Site Family Member 5B (WNT5B) with Type 2 Diabetes," Am. J. Hum. Genet. (2004), 75(5), 832-843.

(56) References Cited

OTHER PUBLICATIONS

Karlberg et al., "Structural basis for the interaction between tankyrase-2 and a potent Wnt-signaling inhibitor," J. Med. Chem. (2010), 53(14), 5352-5.

Kibar et al., "Mutations in VANGL1 Associated with Neural-Tube Defects," N. Engl. J. Med., (Apr. 2007), 356(14):1432-1437.

Kim et al., "Blockade of the Wnt/β-Catenin Pathway Attenuates Bleomycin-Induced Pulmonary Fibrosis," Tohoku J. Exp. Med., 2011, 223:45-54.

King et al., "BUILD-3: a randomized, controlled trial of bosentan in idiopathic pulmonary fibrosis," Am J Respir Crit Care Med., 184(1):92-99, Epub Apr. 2011.

Kishimoto et al., "Wnt/beta-catenin signaling suppresses expressions of Ses, Mkx and Tnmd in tendon-derived cells," PLOS ONE, Jul. 27, 2017, 12(7), E0182051, pp. 1-17.

Kuwajima et al., "Necdin Promotes GABAergic Neuron Differentiation in Cooperation with Dlx Homeodomain Proteins," Journal of Neuroscience (May 2006), 26(20), 5383-5392.

Lala and Orucevic, "Role of nitric oxide in tumor progression: lessons from experimental tumors," Cancer and Metastasi Review, vol. 17, Mar. 1998, pp. 91-106.

Lammi et al., "Mutations in AXIN2 Cause Familial Tooth Agenesis and Predispose to Colorectal Cancer," Am. J. Hum. Genet. (2004), 74(5), 1043-1050.

Ledford, "US cancer institute overhauls cell lines," Nature, Feb. 25, 2016, vol. 530, p. 391.

Leyns et al., "Frzb-1 Is a Secreted Antagonist of Wnt Signaling Expressed in the Spemann Organizer," Cell (Mar. 1997), 88(6), 747-756.

Li et al., "Artesunate attenuates the growth of human colorectal carcinoma and inhibits hyperactive Wnt/beta-catenin pathway," Int J Cancer., 121(6):1360-1365, Sep. 2007.

Lin et al., "Synthesis and evaluation of pyrazolo[3,4-b]pyridine CDK1 inhibitors as anti-tumor agents," Bioorganic & Medicinal Chemistry Letters, (Aug. 2007), 17(15): 4297-4302.

Liu et al., "Fibrotic lung fibroblasts show blunted inhibition by cAMP due to deficient cAMP response element-binding protein phosphorylation," J Pharmacol Exp Ther., 315(2):678-687, Epub Aug. 3, 2005.

Lories et al., "To Wnt or not to Wnt: the bone and joint health dilemma," Nat Rev Rheumatol., 9(6):328-339, Epub Mar. 2013.

Low et al., "Phenotypic fingerprinting of small molecule cell cycle kinase inhibitors for drug discovery," Curr Chem Genomics, 3:13-21, Mar. 2009.

Lu et al., "Structure—activity relationship studies of small-molecule inhibitors of Wnt response," Bioorganic & Medicinal Chemistry Letters, (Jul. 2009), 19(14):3825-3827.

Lui et al., "Expression of Wnt pathway mediators in metaplasic tissue in animal model and clinical samples of tendinopathy," Rheumatology, Sep. 1, 2013, 52(9):1609-1618.

Lui, "Histopathological changes in tendinopathypotential roles of BMPs?" Rheumatology, May 2013, 52:2116-2126.

Luo et al., "Fragile X Mental Retardation Protein Regulates Proliferation and Differentiation of Adult Neural Stem/Progenitor Cells," PLoS Genetics, (Apr. 2010), 6(4):e1000898, 15 pages.

Luu et al., "Wnt/beta-catenin signaling pathway as a novel cancer drug target," Curr Cancer Drug Targets., 4(8):653-671, Dec. 2004.

Luyten et al., "Wnt signaling and osteoarthritis," Bone, Apr. 1, 2009, 44(4):522-527.

MacDonald et al., "Wnt/beta-catenin signaling: components, mechanisms, and diseases," Dev. Cell (Jul. 2009), 17(1), 9-26.

Mandel et al., "SERKAL Syndrome: An Autosomal-Recessive Disorder Caused by a Loss-of-Function Mutation in WNT4," Am. J. Hum. Genet., (Jan. 2008), 82(1), 39-47.

Mani et al., "LRP6 Mutation in a Family with Early Coronary Disease and Metabolic Risk Factors," Science, (Mar. 2007), 315(5816), 1278-1282.

McBride et al., "Design and structure-activity relationship of 3-benzimidazol-2-y1-1H-indazoles as inhibitors of receptor tyrosine kinases," Bioorganic & Medicinal Chemistry Letters (2006), 16(13), 3595-3599.

McMahon et al., "VEGF receptor signaling in tumor angiogenesis," The Oncologist, 2005, pp. 3-10.

Med.unc.edu [online], "Buffers," 2006, retrieved on Oct. 12, 2021, retrieved from URL<https://www.med.unc.edu/pharm/sondeklab/wp-content/uploads/sites/868/2018/10/buffers_calbiochem.pdf>, 38 pages.

MedlinePlus, [online] "Cancer," [retrieved on Jul. 6, 2007]. Retrieved from the internet, URL http://www.nlnn.nih.govinnedlineplus/cancer.html>.

Misra et al., "1H-Pyrazolo[3,4-b]pyridine inhibitors of cyclin-dependent kinases: highly potent 2,6-Difluorophenacyl analogues," Bioorganic & Medicinal Chemistry Letters, (2003), 13:2405-2408.

Miyaura et al., "Palladium-catalyzed cross-coupling reactions of organoboron compounds," Chemical reviews, Nov. 1, 1995, 95(7):2457-2483.

Monner et al., "Induction of lymphokine synthesis in peripheral blood mononuclear cells with phorbol ester and calcium ionophore allows precise measurement of individual variations in capacity to produce IL 2," Lymphokine Res. 1986; 5 Suppl:S67-73.

Mora et al., "Emerging therapies for idiopathic pulmonary fibrosis, a progressive age-related disease," Nat Rev Drug Discov. Oct. 30, 2017; 16(11): 810.

Morissette et al., "High-throughput crystallization: polymorphs, salts, co-crystals and solvates of pharmaceutical solids," Advanced Drug Delivery Reviews, Feb. 25, 2004, 56(3):275-300.

Morrisey, "Wnt signaling and pulmonary fibrosis," Am J Pathol., 162(5):1393-1397, May 2003.

Muddassar et al., "Elucidation of binding mode and three dimensional quantitative structure-activity relationship studies of a novel series of protein kinase B/Akt inhibitors," Journal of Molecular Modeling, (2009), 15(2): 183-192.

Ngkelo et al., "LPS induced inflammatory responses in human peripheral blood mononuclear cells is mediated through NOX4 and Gia dependent PI-3 kinase signaling," Journal of Inflammation, Dec. 2012, 9(1):1, 7 pages.

Niemann et al., "Homozygous WNT3 Mutation Causes Tetra-Amelia in a Large Consanguineous Family," Am. J. Hum. Genet. (2004), 74(3), 558-563.

Nishisho et al., "Mutations of chromosome 5q21 genes in FAP and colorectal cancer patients," Science, (Aug. 1991), 253(5020):665-669.

Nusse, "Wnt signaling in disease and in development," Cell Res., 15(1):28-32, Jan. 2005.

Oates et al., "Increased DNA Methylation at the AXIN1 Gene in a Monozygotic Twin from a Pair Discordant for a Caudal Duplication Anomaly," Am. J. Hum. Genet. (2006 ), 79(1), 155-162.

Ocana, "Preclinical development of molecular targeted agents for cancer," Nat. Rev. Clin. Oncol. 2011, 8, 200-209.

Oduor et al., "Trypanosoma brucei glycogen synthase kinase-3, a target for anti-trypanosomal drug development: a public-private partnership to identify novel leads," PLoS Negl Trop Dis., 5(4):e1017, Apr. 2011.

Okerlund and Cheyette, "Synaptic Wnt signaling-a contributor to major psychiatric disorders?" J Neurodev Disord., (2011) 3(2):162-174.

Park et al., "Optimized THP-1 differentiation is required for the detection of responses to weak stimuli," Inflamm Res, Jan. 2007, 56(1):45-50.

Patani and Lavoie, "Bioisosterism: A Rational Approach in Drug Design," Chem. Rev, Jul. 25, 1996, vol. 96, p. 3147-3176.

Pinedo and Slamon, "Translational Research: the role of VEGF in tumor angiogenesis," The Oncologist, 2005, pp. 1-2.

Polakis, "Wnt signaling and cancer," Genes Dev., 14: 1837-1851, 2000.

Pritzker et al., "Osteoarthritis cartilage histopathology: grading and staging," Osteoarthr. Cartil., Jan. 2006, 14(1): 13-29.

PUBCHEM. Substance Record for SID 164345938. Deposit Date: Nov. 4, 2013. [retrieved on Nov. 16, 2015]. Retrieved from the

(56) References Cited

OTHER PUBLICATIONS

Internet. <URL: https://pubchem.ncbi.nlm.nih.gov/substance/164345938#section=Top>, 5 pages.
Qin et al., "Complexity of the genotype-phenotype correlation in familial exudative vitreoretinopathy with mutations in the LRP5 and/or FZD4 genes," Hum. Mutat. (2005), 26(2), 104-112.
Reya and Clevers, "Wnt signalling in stem cells and cancer," Nature 434: 843-850, Apr. 2005.
Richards et al., "Peripheral blood proteins predict mortality in idiopathic pulmonary fibrosis," Am J Respir Crit Care Med., 185(1):67-76, Jan. 2012.
Rivera et al., "An X Chromosome Gene, WTX, Is Commonly Inactivated in Wilms Tumor," Science, (Feb. 2007), 315(5812):642-645, published online Jan. 4, 2007.
Robitaille et al., "Mutant frizzled-4 disrupts retinal angiogenesis in familial exudative vitreoretinopathy," Nat. Genet., (Sep. 2002), 32(2):326-330.
Rodríguez-Spong et al., "General principles of pharmaceutical solid polymorphism: a supramolecular perspective," Advanced Drug Delivery Reviews, Feb. 23, 2004, 56(3):241-274.
Ryu et al., "Natural derivatives of curcumin attenuate the Wnt/beta-catenin pathway through down-regulation of the transcriptional coactivator p300," Biochem Biophys Res Commun., 377(4):1304-1308, print Dec. 2008, Epub Nov. 2008.
Salinas, "Wnt signaling in the vertebrate central nervous system: from axon guidance to synaptic function," Cold Spring Harb Perspect Biol., (2012) 4(2). pii: a008003, 15 pages.
Sato, "Upregulation of the Wnt/beta-catenin pathway induced by transforming growth factor-beta in hypertrophic scars and keloids," Acta Derm Venereol., 86(4):300-307, 2006.
Seah et al., "Neuronal Death Resulting from Targeted Disruption of the Snf2 Protein ATRX Is Mediated by p53," Journal of Neuroscience (Nov. 2008), 28(47), 12570-12580.
Seddon, "Pseudopolymorph: A Polemic," Crystal Growth & Design, 2004, v.4(6) p. 1087.
Shi et al., "Uniaxial mechanical tension promoted osteogenic differentiation of rat tendon-derived stem cells (rTDSCs) via the Wnt5a-RhoA pathway," Journal of Cellular Biochemistry, Oct. 2012, 113(10):3133-3142.
Shih et al., "Pharmacophore modeling and virtual screening to identify potential RET kinase inhibitors," Bioorg Med Chem Lett., 21(15):4490-4497, Epub Jun. 2011.
Shruster et al., "Wnt signaling enhances neurogenesis and improves neurological function after focal ischemic injury," PLoS One, (Jul. 2012), 7(7):e40843, 11 pages.
Silva et al., "Advances in Prodrug Design," Mini-Revs. In Med. Chem. (2005), 5: 893-914.
Solowiej et al., "Characterizing the Effects of the Juxtamembrane Domain on Vascular Endothelial Growth Factor Receptor-2 Enzymatic Activity, Autophosphorylation, and Inhibition by Axitinib," Biochemistry, (2009), 48(29), 7019-7031.
Sperber et al., "Cytokine secretion induced by superantigens in peripheral blood mononuclear cells, lamina propria lymphocytes, and intraepithelial lymphocytes," Clin Diagn Lab Immunol, Jul. 1995, 2(4):473-477.
Staines et al., "Cartilage development and degeneration: a Wnt situation," Cell Biochem Funct., 30(8):633-642, Epub Jun. 2012.
Sutherland et al., "A robust high-content imaging approach for probing the mechanism of action and phenotypic outcomes of cell-cycle modulators," Molecular Cancer Therapeutics, (Feb. 2011), 10(2): 242-254.
Swaney et al., "A novel, orally active LPA(1) receptor antagonist inhibits lung fibrosis in the mouse bleomycin model," Br J Pharmacol., 160(7):1699-1713, Aug. 2010.
Takahashi-Yanaga et al., "Celecoxib-induced degradation of T-cell factors-1 and-4 in human colon cancer cells," Biochem Biophys Res Commun., 377(4):1185-1190, print Dec. 2008, Epub Nov. 2008.

Tamamura et al., "Developmental regulation of Wnt/beta-catenin signals is required for growth plate assembly, cartilage integrity, and endochondral ossification," J Biol Chem., 280(19):19185-95. Epub Mar. 2005.
Thompson et al., "WNT/beta-catenin signaling in liver health and disease," Hepatology, 45(5):1298-1305, May 2007.
Trujillo et al., "2-(6-Phenyl-1H-indazol-3-y1)-1H-benzo[d]imidazoles: design and synthesis of a potent and isoform selective PKC-zeta inhibitor," Bioorg Med Chem Lett., 19(3):908-911, Epub Dec. 6, 2008.
Ugur et al., "Homozygous WNT10b mutation and complex inheritance in Split-Hand/Foot Malformation," Hum. Mol. Genet. (2008), 17(17), 2644-2653.
United States Court of Appeals for the Federal Circuit, Eli Lilly and Company, Plaintiff-Appellant, v. Actavis Elizabeth LLC, Defendant-Appellee, and Sun Pharmaceutical Industries, Ltd., Defendant-Appellee, and Sandoz, Inc., Defendant-Appellee, and Mylan Pharmaceuticals Inc., Defendant-Appellee, and Apotex Inc., Defendant-Appellee, and Aurobindo Pharma Ltd., Defendant-Appellee, and Teva Pharmaceuticals USA, Inc., Defendant-Appellee, Appeal from the United States District Court for the District of New Jersey in Case No. 07-CV-3770, Judge Dennis M. Cavanaugh, decided on Jul. 29, 2011, 20 pages.
Vippagunta et al., "Crystalline solids," Advanced Drug Delivery Reviews, 2001, 48:3-26.
Vulpetti et al., "Structure-Based Approaches to Improve Selectivity: CDK2-GSK3β Binding Site Analysis," Journal of Chemical Information and Modeling (2005), 45(5), 1282-1290.
Wagner et al., "The therapeutic potential of the Wnt signaling pathway in bone disorders," Curr Mol Pharmacol., 4(1):14-25, Jan. 2011.
Walters and Kleeberger, "Mouse models of bleomycin-induced pulmonary fibrosis," Current Protocols in Pharmacology, (2008) Chapter 5: Unit 5.46, 1-17.
Wang et al., "Mutations in X-linked PORCN, a putative regulator of Wnt signaling, cause focal dermal hypoplasia," Nat. Genet. (Jul. 2007), 39(7), 836-838.
Wantanabe and Dai, "Winning WNT: race to Wnt signaling inhibitors," Proc Natl Acad Sci USA, 108(15):5929-5930, Epub Mar. 2011.
Watts et al., "RhoA signaling modulates cyclin D1 expression in human lung fibroblasts; implications for idiopathic pulmonary fibrosis," Respir Res., 7:88, Jun. 15, 2006.
Weng et al., "Control of Dkk-1 ameliorates chondrocyte apoptosis, cartilage destruction, and subchondral bone deterioration in osteoarthritic knees," Arthritis Rheum., 62(5):1393-1402, May 2010.
Witherington et al., "5-Aryl-pyrazolo[3,4-b]pyridazines: potent inhibitors of glycogen synthase kinase-3 (GSK-3)," Bioorganic & Medicinal Chemistry Letters, (May 2003), 13(9):1581-1584.
Woods et al., "Mutations in WNT7A Cause a Range of Limb Malformations, Including Fuhrmann Syndrome and Al-Awadi/Raas-Rothschild/Schinzel Phocomelia Syndrome," Am. J. Hum. Genet. (Aug. 2006), 79(2), 402-408.
Yan et al., "Discovery of small molecule inhibitors of the Wnt/b-catenin signaling pathway by targeting b-catenin/Tcf4 interactions," Experimental Biology and Medicine, vol. 242, Jun. 2017, 1185-1197.
Yardy and Brewster, "Wnt signalling and prostate cancer," Prostate Cancer Prostatic Dis, 8(2):119-126, 2005.
Yazici et al., "Abstract #: 312: Safety, Efficacy and Biomarker Outcomes of a Novel, Intra-Articular, Injectable, Wnt Inhibitor (SM04690) in the Treatment of Osteoarthritis of the Knee: Interim, Exploratory Analysis of Results from a Randomized, Double-Blind, Placebo-Controlled Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.
Yazici et al., "Abstract #: 313: Magnetic Resonance Imaging Outcomes Using an Intra-Articular Injection (SM04690) in the Treatment of Osteoarthritis of the Knee: Interim, Exploratory Analysis of Results from a Randomized, Double-Blind, Placebo-Controlled, Phase 1 Study," Poster, Presented at 2015 ACR/

(56) References Cited

OTHER PUBLICATIONS

American College of Rheumatology Annual Meeting, San Francisco CA, Nov. 6-11, 2015; Arthritis Rheumatol. 2015; 67 (suppl 10): 1 page.
Yu et al., "Physical characterization of polymorphic drugs: an integrated characterization strategy," PSTT, 1998, 1(3):118-127.
Zhan et al., "Wnt signaling in cancer," Oncogene (2017) 36, 1461-1473.
Zhang et al., "Small-molecule synergist of the Wnt/beta-catenin signaling pathway," Proc Natl Acad Sci USA, 104(18):7444-7448, Epub Apr. 2007 and correction 104(30):12581, Jul. 2007.
Zheng, "Small-molecule inhibitors of Wnt signaling pathway: towards novel anticancer therapeutics," Future Med. Chem. (2015) 7(18), 2485-2505.
Zhong et al., "Characterization of in vitro and in vivo metabolism of AG-024322, a novel cyclin-dependent kinase (CDK) inhibitor," Health (2009), 1(4): 249-262.
Pharmacology, 10th ed., Kharkevich (ed)., 2010, pp. 73-74 (English Translation).
Pharmacology, Zhulenko (ed)., 2008, pp. 34-35 (English Translation).
Ator et al., "Overview of Drug Discovery and Development," Current Protocols in Pharmacology, 2006, Unit 9.9, 26 pages.
Deep et al., "New Combination Therapies with Cell Cycle Agents," Curr. Opin. Investig. Drugs, Jun. 2008, 9(6):591-604.
Hengstschlager et al., "Cyclin-dependent kinases at the G1-S transition of the mammalian cell cycle," Mutation Research, 1999, 436:1-9.
Kojima et al., "Optimization of development form in drug development," Pharmacia, 2016, 52(5):387-391.
Lapenna et al., "Cell cycle kinases as therapeutic targets for cancer," Nature Review-Drug Discovery, Jul. 2009, 8:547-566.
Malumbres et al., "CDK inhibitors in cancer therapy: what is next?" Trends in Pharmacological Sciences, Dec. 2007, 29(1):16-21.
Nakagami, "Preformation and Drug Development," Pharmacia, Mar. 1, 2003, 39 (3):204-208.
Nigg, "Mitotic Kinases as Regulators of Cell Division and its Checkpoints," Nature Reviews-Molecular Cell Biology, Jan. 2001, 2:21-32.
Santamaria et al., "Cdk1 is sufficient to drive the mammalian cell cycle," Nature, Aug. 16, 2007, 448:811-815.
Sharma et al., "Inhibitors of Cyclin Dependent Kinases: Useful Targets for Cancer Treatment," Current Cancer Drug Targets, 2008, 8(1):53-75.
Stahly, "The Importance of Salt Selection and Polymorph Screening for the Drug Product," Journal of Pharmaceutical Science and Technology Japan, 2006, 66(6):435-439.
U.S. Appl. No. 10/295,833, filed Nov. 18, 2002, Li et al.
U.S. Appl. No. 10/317,914, filed Dec. 12, 2002, Li et al.
U.S. Appl. No. 15/498,990, filed Apr. 27, 2017, Kumar KC et al.
U.S. Appl. No. 15/499,013, filed Apr. 17, 2017, Kumar KC et al.
U.S. Appl. No. 15/749,910, filed Feb. 2, 2018, Kumar KC et al.
U.S. Appl. No. 15/749,922, filed Feb. 2, 2018, Kumar KC et al.
U.S. Appl. No. 15/749,923, filed Feb. 2, 2018, Kumar KC et al.
U.S. Appl. No. 15/749,929, filed Feb. 2, 2018, Kumar KC et al.
U.S. Appl. No. 15/773,951, filed May 4, 2018, Hood et al.
U.S. Appl. No. 62/577,818, filed Oct. 27, 2017, Kumar KC et al.
U.S. Appl. No. 62/578,370, filed Oct. 27, 2017, Kumar KC et al.
U.S. Appl. No. 62/578,691, filed Oct. 30, 2017, Kumar KC et al.
U.S. Appl. No. 62/579,883, filed Oct. 31, 2017, Kumar KC et al.
U.S. Appl. No. 62/634,656, filed Feb. 23, 2018, Kumar KC et al.
Anastassiadis et al., "Comprehensive assay of kinase catalytic activity reveals features of kinase inhibitor selectivity," Nature Biotechnol., Oct. 2011, 29(11):1039-1045.
Breastcancer.org [online], "Types of Breast Cancer", 2001, retrieved on Sep. 10, 2018, retrieved from URL<breastcancer.org>, 1 page.
Cancer Drug Design and Discovery, Neidle (ed)., 2008, pp. 427-431.
Cancercenter.com [online], "Types of Brain Cancer", 1996, retrieved on Mar. 12, 2013, retrieved from URL<http://www.cancercenter.com/brain-cancer/types-of-brain-cancer.cfrn>, 3 pages.
Cecil Textbook of Medicine, 20th ed., Bennet and Plum (ed.), 1996. Volunne 1, pp. 1004-1010.
Chockalingam et al., "Elevated aggrecanase activity in a rat model of joint injury is attenuated by an aggrecanase specific inhibitor," Osteoarthritis Cartilage, Mar. 2011, 19(3):315-323.
Clevelandclinic.org [online], "Bone fractures," 2008, retrieved on Jun. 2018, retrieved from URL<https://my.clevelandclinic.org/health/diseases/15241-bone-fractures/management-and-treatment?view=print>, 5 pages.
De Ferrari et al., "Wnt signaling function in Alzheimer's disease," Brain Research Reviews, Aug. 2000, 33(1):1-12.
Dermer, "Another Anniversary for the War on Cancer," Bio/Technology, Mar. 1994, 12:320.
Freshney et al., "Culture of Animal Cells: A Manual of Basic Technique and Specialized Applications," Alan R. Liss, Inc., 1983, 7 pages.
Friedman et al., "Therapy for fibrotic diseases: nearing the starting line," Science Translational Medicine, Jan. 2013, 5(167):167sr1, 17 pages.
Golub et al., "Molecular Classification of Cancer: Class Discovery and Class Prediction by Gene Expression Monitoring," Science, Oct. 15, 1999, 286(5439):531-537.
Guo et al., "Wnt/β-catenin signaling is sufficient and necessary for synovial joint formation," Genes & Development, Oct. 1, 2004, 18(19):2404-2417.
International Preliminary Report on Patentability in International Application No. PCT/US2017/057536, dated May 2, 2019, 9 pages.
International Preliminary Report on Patentability in International Appln. No. PCT/US2013/031055, dated Oct. 16, 2014, 9 pages.
International Search Report and Written Opinion in International Appln. No. PCT/US2013/031055, dated May 21, 2013, 14 pages.
Iwai et al., "Anti-tumor efficacy of a novel CLK inhibitor via targeting RNA splicing and MYC-dependent vulnerability," EMBO Molecular Medicine, Jun. 2018, 10(6):e8289, 15 pages.
Johnson et al., "A stem cell-based approach to cartilage repair," Science, Apr. 5, 2012, 336(6082):717-721, Supplementary Material Figs. S1-S16.
Lacy et al., "Generation and characterization of ABT-981, a dual variable domain immunoglobulin (DVD-Ig(TM)) molecule that specifically and potently neutralizes both IL-1α and IL-1β," Mabs, May 2015, 7(3):605-619.
Lymphoma Association, "Gastric MALT Lymphoma," Feb. 28, 2011, 10 pages.
Majithia et al., "Rheumatoid arthritis: diagnosis and management," The American Journal of Medicine, Nov. 1, 2007, 120(11):936-939.
Mayoclinic.org [online], "Osteoarthritis", 2017, retrieved on Sep. 2, 2018, retrieved from URL<https://www.mayoclinic.org/diseases-conditions/osteoarthritis/symptoms-causes/syc-20351925>, 8 pages.
Medicinenet.com [online], "Definition of Cancer," 1996, retrieved on Sep. 16, 2005, 1 page.
Moon et al., "WNT and β-catenin signalling: diseases and therapies," Nature Reviews Genetics, Sep. 2004, 5(9):691-701.
National Cancer Institute, "Adult Brain Tumors Treatment," National Institutes of Health, Jan. 24, 2013, 21 pages.
Nusse et al., "Three decades of Wnts: a Personal Perspective on How a Scientific Field Developed," The EMBO Journal, Jun. 13, 2012, 31(12):2670-2684.
Olsen et al., "Bone development," Annual Review of Cell and Developmental Biology, Nov. 2000, 16(1):191-220.
Parsons et al., "Benzo[d]imidazole Transient Receptor Potential Vanilloid 1 Antagonists for the Treatment of Pain: Discovery of trans-2-(2-{2-[2-(4-Trifluoromethyl-phenyl)-vinyl]-1H-benzimidazol-5-yl}-phenyl)-propan-2-ol (Mavatrep)," Journal of Medicinal Chemistry, May 2015, 58(9):3867-3874.
Piersanti et al., "Synthesis of benzo[1,2-d;3,4-d']diimidazole and 1H-pyrazolo[4,3-b]pyridine as putative A2A receptor antagonists," Organic & Biomolecular Chemistry, Aug. 2007, 5(16):2567-2571.
Riggs et al., "The discovery of a dual TTK protein kinase/CDC2-like kinase (CLK2) inhibitor for the treatment of triple negative

(56) References Cited

OTHER PUBLICATIONS breast cancer initiated from a phenotypic screen," Journal of Medicinal Chemistry, Nov. 9, 2017, 60(21):8989-9002.
Rother et al., "Efficacy and safety of epicutaneous ketoprofen in Transfersome (IDEA-033) versus oral celecoxib and placebo in osteoarthritis of the knee: multicentre randomised controlled trial," Annals of the Rheumatic Diseases, Sep. 2007, 66(9):1178-1183.
Tchetina et al., "Increased type II collagen degradation and very early focal cartilage degeneration is associated with upregulation of chondrocyte differentiation related genes in early human articular cartilage lesions," The Journal of Rheumatology, May 1, 2005, 32(5):876-886.
Thomas et al., "Identification of a novel 3, 5-disubstituted pyridine as a potent, selective, and orally active inhibitor of Akt1 kinase," Bioorganic & Medicinal Chemistry Letters, Jul. 15, 2006, 16(14):3740-3744.
Yamada et al., "Emergence of TNIK inhibitors in cancer therapeutics," Cancer Science, May 2017, 108(5):818-823.
Zhu et al. "Design and synthesis of pyridine-pyrazolopyridine-based inhibitors of protein kinase B/Akt," Bioorganic & Medicinal Chemistry, Mar. 2007, 15(6):2441-2452.
U.S. Appl. No. 12/852,681, filed Aug. 9, 2010, John Hood.
U.S. Appl. No. 12/968,505, filed Dec. 15, 2010, John Hood.
U.S. Appl. No. 13/855,874, filed Apr. 3, 2013, John Hood.
U.S. Appl. No. 13/938,692, filed Jul. 10, 2013, John Hood.
U.S. Appl. No. 14/331,427, filed Jul. 15, 2014, John Hood.
U.S. Appl. No. 14/465,056, filed Aug. 21, 2014, John Hood.
U.S. Appl. No. 14/718,354, filed May 21, 2015, John Hood.
U.S. Appl. No. 15/244,687, filed Aug. 23, 2016, John Hood.
U.S. Appl. No. 15/812,629, filed Nov. 14, 2017, John Hood.
U.S. Appl. No. 12/852,706, filed Aug. 9, 2010, John Hood.
U.S. Appl. No. 13/552,188, filed Jul. 18, 2012, John Hood.
U.S. Appl. No. 13/938,691, filed Jul. 10, 2013, John Hood.
U.S. Appl. No. 14/019,103, filed Sep. 5, 2013, John Hood.
U.S. Appl. No. 14/334,005, filed Jul. 17, 2014, John Hood.
U.S. Appl. No. 14/741,645, filed Jun. 17, 2015, John Hood.
U.S. Appl. No. 15/184,553, filed Jun. 16, 2016, John Hood.
U.S. Appl. No. 15/681,035, filed Aug. 18, 2017, John Hood.
U.S. Appl. No. 13/614,296, filed Sep. 13, 2012, John Hood.
U.S. Appl. No. 14/019,229, filed Sep. 5, 2013, John Hood.
U.S. Appl. No. 14/940,958, filed Nov. 13, 2015, John Hood.
U.S. Appl. No. 15/709,057, filed Sep. 19, 2017, John Hood.
U.S. Appl. No. 16/576,308, filed Sep. 19, 2019, John Hood.
U.S. Appl. No. 17/346,808, filed Jun. 14, 2021, John Hood.
U.S. Appl. No. 13/800,963, filed Mar. 13, 2013, John Hood.
U.S. Appl. No. 14/019,940, filed Sep. 6, 2013, John Hood.
U.S. Appl. No. 14/178,749, filed Feb. 12, 2014, John Hood.
U.S. Appl. No. 14/621,195, filed Feb. 12, 2015, John Hood.
U.S. Appl. No. 14/939,434, filed Nov. 12, 2015, John Hood.
U.S. Appl. No. 15/968,555, filed May 1, 2018, John Hood.
U.S. Appl. No. 16/518,337, filed Jul. 22, 2019, John Hood.
U.S. Appl. No. 17/168,747, filed Feb. 5, 2021, John Hood.
U.S. Appl. No. 18/315,047, filed May 10, 2023, John Hood.
U.S. Appl. No. 13/887,177, filed May 3, 2013, John Hood.
U.S. Appl. No. 14/019,147, filed Sep. 5, 2013, John Hood.
U.S. Appl. No. 14/454,279, filed Aug. 7, 2014, John Hood.
U.S. Appl. No. 14/621,222, filed Feb. 12, 2015, John Hood.
U.S. Appl. No. 14/962,681, filed Dec. 8, 2015, John Hood.
U.S. Appl. No. 15/420,398, filed Jan. 31, 2017, John Hood.
U.S. Appl. No. 16/032,905, filed Jul. 11, 2018, John Hood.
U.S. Appl. No. 16/452,700, filed May 29, 2019, John Hood.
U.S. Appl. No. 14/149,948, filed Jan. 8, 2014, Sunil Kumar KC.
U.S. Appl. No. 15/889,403, filed Feb. 6, 2018, Sunil Kumar KC.
U.S. Appl. No. 16/252,055, filed Jan. 18, 2019, Sunil Kumar KC.
U.S. Appl. No. 14/847,259, filed Sep. 8, 2015, Sunil Kumar KC.
U.S. Appl. No. 15/298,346, filed Oct. 20, 2016, Sunil Kumar KC.
U.S. Appl. No. 15/716,803, filed Sep. 27, 2017, Sunil Kumar KC.
U.S. Appl. No. 14/847,336, filed Sep. 8, 2015, Sunil Kumar KC.
U.S. Appl. No. 15/661,231, filed Jul. 27, 2017, Sunil Kumar KC.
U.S. Appl. No. 16/015,996, filed Jun. 22, 2018, Sunil Kumar KC.
U.S. Appl. No. 14/847,299, filed Sep. 8, 2015, Sunil Kumar KC.
U.S. Appl. No. 15/591,566, filed May 10, 2017, Sunil Kumar KC.
U.S. Appl. No. 16/224,160, filed Dec. 18, 2018, Sunil Kumar KC.
U.S. Appl. No. 14/847,287, filed Sep. 8, 2015, Sunil Kumar KC.
U.S. Appl. No. 15/363,086, filed Nov. 29, 2016, Sunil Kumar KC.
U.S. Appl. No. 15/808,602, filed Nov. 9, 2017, Sunil Kumar KC.
U.S. Appl. No. 14/847,344, filed Sep. 8, 2015, Sunil Kumar KC.
U.S. Appl. No. 15/257,398, filed Sep. 6, 2016, Sunil Kumar KC.
U.S. Appl. No. 15/673,834, filed Aug. 10, 2017, Sunil Kumar KC.
U.S. Appl. No. 14/847,394, filed Sep. 8, 2015, Sunil Kumar KC.
U.S. Appl. No. 15/357,494, filed Nov. 21, 2016, Sunil Kumar KC.
U.S. Appl. No. 15/716,894, filed Sep. 27, 2017, Sunil Kumar KC.
U.S. Appl. No. 14/847,371, filed Sep. 8, 2015, Sunil Kumar KC.
U.S. Appl. No. 15/267,939, filed Sep. 16, 2016, Sunil Kumar KC.
U.S. Appl. No. 15/843,818, filed Dec. 15, 2017, Sunil Kumar KC.
U.S. Appl. No. 14/847,379, filed Sep. 8, 2015, Sunil Kumar KC.
U.S. Appl. No. 15/668,992, filed Aug. 4, 2017, Sunil Kumar KC.
U.S. Appl. No. 16/162,155, filed Oct. 16, 2018, Kumar et al.
U.S. Appl. No. 15/773,951, filed May 4, 2018, John Hood.
U.S. Appl. No. 16/710,099, filed Dec. 11, 2019, John Hood.
U.S. Appl. No. 17/108,544, filed Dec. 1, 2020, John Hood.
U.S. Appl. No. 15/749,587, filed Feb. 1, 2018, Sunil Kumar KC.
U.S. Appl. No. 15/749,586, filed Feb. 1, 2018, Sunil Kumar KC.
U.S. Appl. No. 15/749,592, filed Feb. 1, 2018, Sunil Kumar KC.
U.S. Appl. No. 15/749,606, filed Feb. 1, 2018, Sunil Kumar KC.
U.S. Appl. No. 15/749,608, filed Feb. 1, 2018, Sunil Kumar KC.
U.S. Appl. No. 15/749,701, filed Feb. 1, 2018, Sunil Kumar KC.
U.S. Appl. No. 15/749,706, filed Feb. 1, 2018, Sunil Kumar KC.
U.S. Appl. No. 15/749,713, filed Feb. 1, 2018, Sunil Kumar KC.
U.S. Appl. No. 15/749,718, filed Feb. 1, 2018, Sunil Kumar KC.
U.S. Appl. No. 15/749,721, filed Feb. 1, 2018, Sunil Kumar KC.
U.S. Appl. No. 15/749,741, filed Feb. 1, 2018, Sunil Kumar KC.
U.S. Appl. No. 15/749,727, filed Feb. 1, 2018, Sunil Kumar KC.
U.S. Appl. No. 15/749,739, filed Feb. 1, 2018, Sunil Kumar KC.
U.S. Appl. No. 15/749,737, filed Feb. 1, 2018, Sunil Kumar KC.
U.S. Appl. No. 15/749,742, filed Feb. 1, 2018, Sunil Kumar KC.
U.S. Appl. No. 15/749,868, filed Feb. 2, 2018, Sunil Kumar KC.
U.S. Appl. No. 15/749,929, filed Feb. 2, 2018, Sunil Kumar KC.
U.S. Appl. No. 15/749,910, filed Feb. 2, 2018, Sunil Kumar KC.
U.S. Appl. No. 15/749,923, filed Feb. 2, 2018, Sunil Kumar KC.
U.S. Appl. No. 15/749,922, filed Feb. 2, 2018, Sunil Kumar KC.
U.S. Appl. No. 15/611,150, filed Jun. 1, 2017, Sunil Kumar KC.
U.S. Appl. No. 16/115,222, filed Aug. 28, 2018, Sunil Kumar KC.
U.S. Appl. No. 16/813,021, filed Mar. 9, 2020, Sunil Kumar KC.
U.S. Appl. No. 15/773,737, filed May 4, 2018, John Hood.
U.S. Appl. No. 17/112,282, filed Dec. 4, 2020, John Hood.
U.S. Appl. No. 15/806,321, filed Nov. 7, 2017, Luis A. Dellamary.
U.S. Appl. No. 16/939,713, filed Jul. 27, 2020, Luis A. Dellamary.
U.S. Appl. No. 17/873,818, filed Jul. 26, 2022, Luis A. Dellamary.
U.S. Appl. No. 18/487,565, filed Oct. 16, 2023, Luis A. Dellamary.
U.S. Appl. No. 15/790,544, filed Oct. 23, 2017, Vishal Deshmukh.
U.S. Appl. No. 16/915,316, filed Jun. 29, 2020, Vishal Deshmukh.
U.S. Appl. No. 17/423,761, filed Jul. 16, 2021, Vishal Deshmukh.

PROCESS FOR PREPARING N-(5-(3-(7-(3-FLUOROPHENYL)-3H-IMIDAZO[4,5-C]PYRIDIN-2-YL)-1H-INDAZOL-5-YL)PYRIDIN-3-YL)-3-METHYLBUTANAMIDE

RELATED APPLICATIONS

This application is a continuation application of U.S. application Ser. No. 16/813,021, filed on Mar. 9, 2020, which is a continuation application of U.S. application Ser. No. 16/115,222, now U.S. Pat. No. 10,633,380, filed Aug. 28, 2018, which is a continuation application of U.S. application Ser. No. 15/611,150, now U.S. Pat. No. 10,072,004, filed Jun. 1, 2017, and claims the benefit of U.S. Provisional Application Nos. 62/344,170, filed Jun. 1, 2016 and 62/418,657, filed Nov. 7, 2016, which are incorporated herein by reference in their entirety.

TECHNICAL FIELD

Provided herein is a process for preparing N-(5-(3-(7-(3-fluorophenyl)-3H-imidazo[4,5-c]pyridin-2-yl)-1H-indazol-5-yl)pyridin-3-yl)-3-methylbutanamide, including amorphous and polymorph forms thereof. Also provided herein are intermediates and pharmaceutically acceptable salts of N-(5-(3-(7-(3-fluorophenyl)-3H-imidazo[4,5-c]pyridin-2-yl)-1H-indazol-5-yl)pyridin-3-yl)-3-methylbutanamide. This compound is useful for the treatment of various diseases including cancer, abnormal cellular proliferation, angiogenesis, Alzheimer's disease, osteoarthritis and other Wnt-related diseases.

BACKGROUND

The compound of Formula 1:

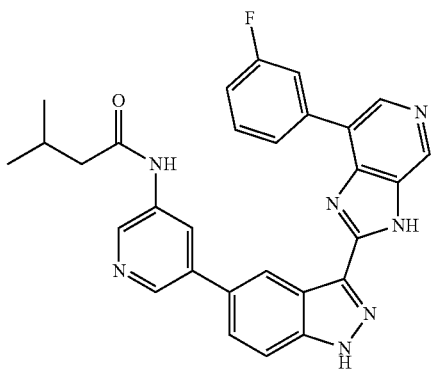

(1)

N-(5-(3-(7-(3-fluorophenyl)-3H-imidazo[4,5-c]pyridin-2-yl)-1H-indazol-5-yl)pyridin-3-yl)-3-methylbutanamide, is a Wnt inhibitor. The compound of Formula (1) can be prepared as disclosed in U.S. Pat. No. 8,252,812, incorporated by reference herein in its entirety. There exists a need for alternative synthetic procedures for the preparation of the compound of Formula (1). Such alternative synthetic procedures are disclosed herein.

SUMMARY

Provided herein is a process for preparing a compound of Formula (1)

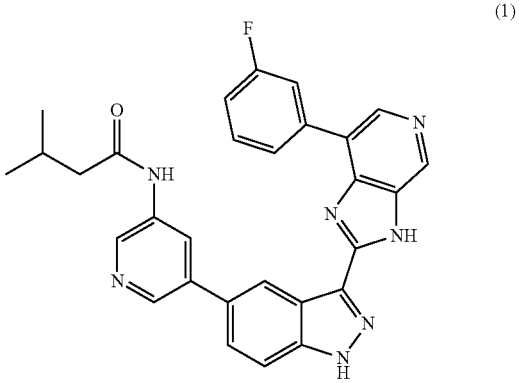 [SMILES: CC(C)CC(=O)Nc1cncc(-c2ccc3[nH]nc(-c4nc5c(-c6cccc(F)c6)cncc5[nH]4)c3c2)c1]

(1)

or a pharmaceutically acceptable salt thereof, the process comprising:
(a) reacting a compound of Formula (2)

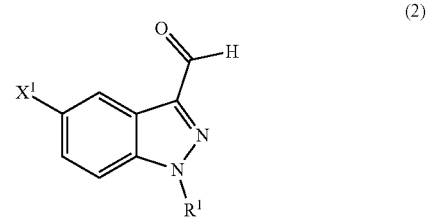

(2)

or a salt thereof, wherein:
$R^1$ is a nitrogen protecting group, and
$X^1$ is a first leaving group;
with a compound of Formula (4)

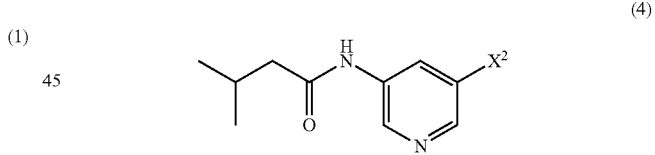

(4)

or a salt thereof, wherein $X^2$ is a second leaving group;
to prepare a compound of Formula (5)

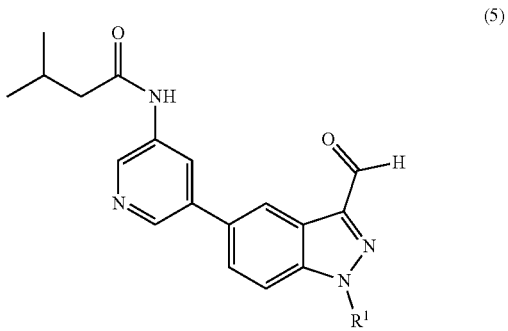

(5)

or a salt thereof;

(b) reacting the compound of Formula (5), or the salt thereof, with a compound of Formula (6)

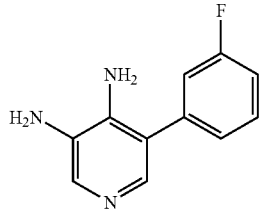
(6)

or a salt thereof, to prepare a compound of Formula (7)

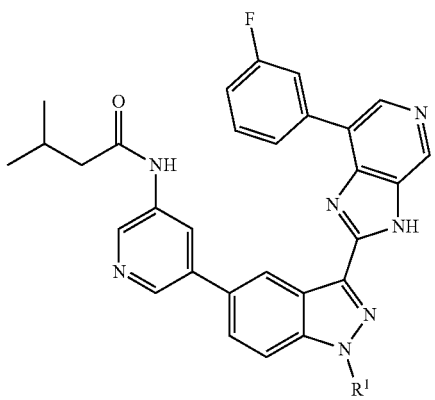
(7)

or a salt thereof; and (c) deprotecting the compound of Formula (7), or the salt thereof, to prepare the compound of Formula (1), or the pharmaceutically acceptable salt thereof.

Also provided herein is a process for preparing a compound of Formula (1):

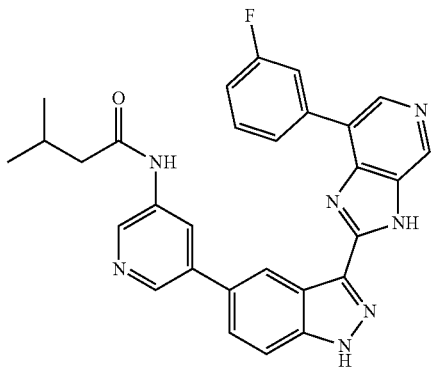
(1)

or a pharmaceutically acceptable salt thereof, the process comprising:

(a) reacting a compound of Formula (2)

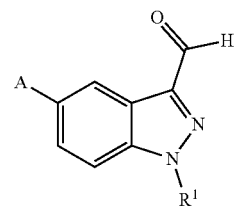
(2)

or salt thereof, wherein:
$R^1$ is a nitrogen protecting group, and
$X^1$ is selected from the group consisting of —Cl, —Br, —I, and —OTf;
with a boron reagent to prepare a compound of Formula (3)

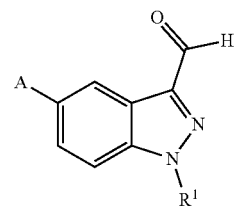
(3)

or salt thereof, wherein A is selected from the group consisting of a boronic acid, a boronic ester, a boronate, a borinate, a boranate, a boranamide, an N-coordinated boronate, and a trifluoroborate;

(b) reacting the compound of Formula (3), or the salt thereof, with a compound of Formula (4)

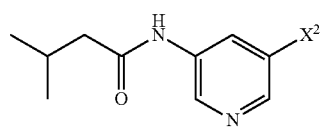
(4)

or a salt thereof, wherein $X^2$ is selected from the group consisting of —Cl, —Br, —I, and —OTf; to prepare a compound of Formula (5)

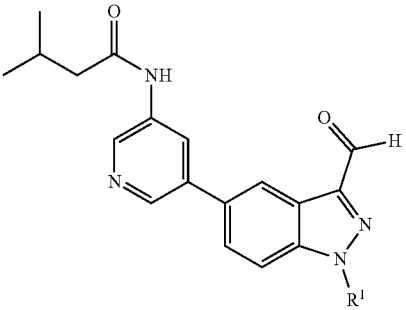
(5)

or a salt thereof;

(c) reacting the compound of Formula (5), or the salt thereof, with a compound of Formula (6)

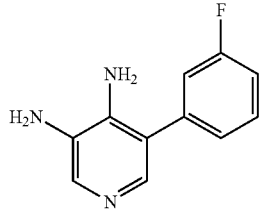

(6)

or a salt thereof, to prepare a compound of Formula (7)

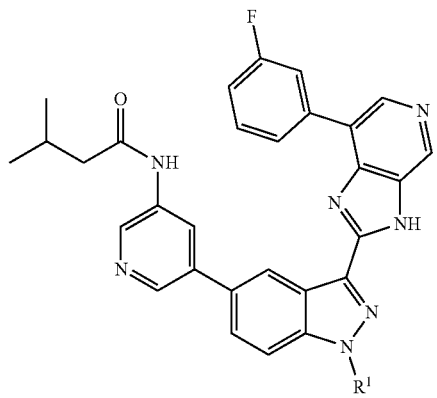

(7)

or a salt thereof; and
(d) deprotecting the compound of Formula (7), or the salt thereof, to prepare the compound of Formula (1), or the pharmaceutically acceptable salt thereof.

Further provided herein is a process for preparing a compound of Formula (1):

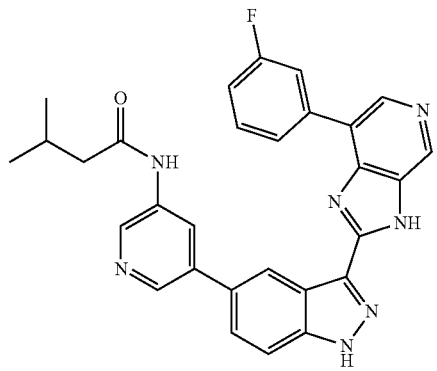

(1)

or a salt thereof, the process comprising:
(a) reacting a compound of Formula (8)

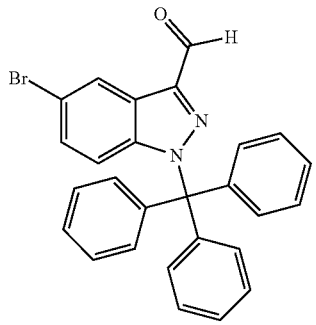

(8)

or a salt thereof, with bis(pinacolato)diboron to produce a compound of Formula (9)

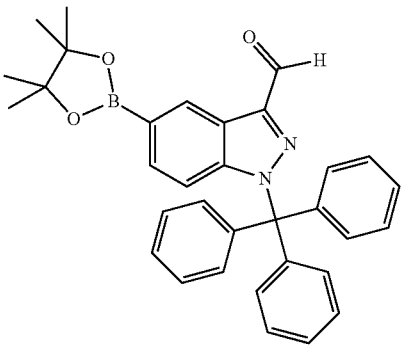

(9)

or a salt thereof;
(b) reacting the compound of Formula (9), or the salt thereof, with a compound of Formula (10)

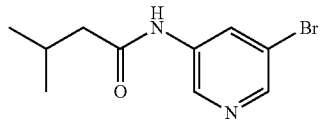

(10)

or a salt thereof, to prepare a compound of Formula (11)

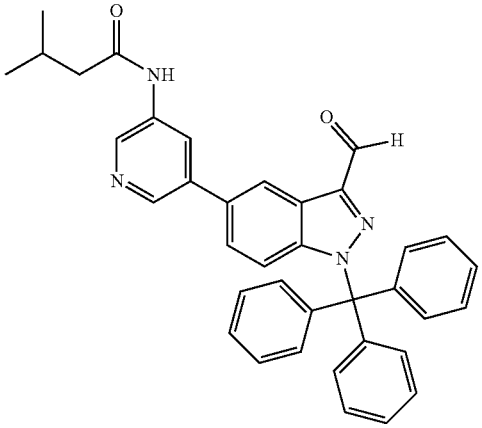

(11)

or a salt thereof;

(c) reacting the compound of Formula (11), or the salt thereof, with a compound of Formula (6)

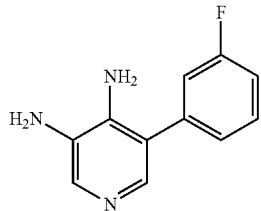
(6)

or a salt thereof, to prepare a compound of Formula (12)

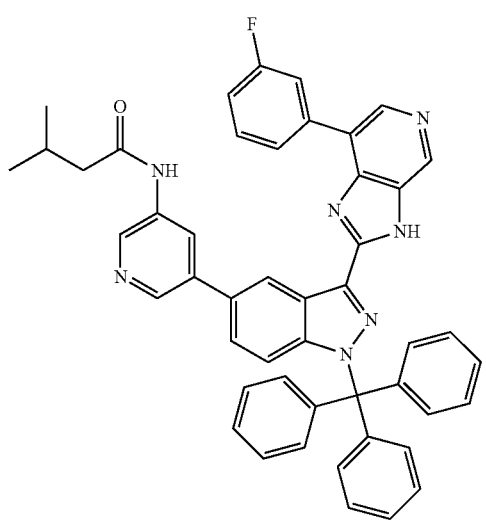
(12)

or a salt thereof; and (d) deprotecting the compound of Formula (12), or the salt thereof, to prepare the compound of Formula (1), or a salt thereof.

The disclosure also provides a process for preparing a compound of Formula (1)

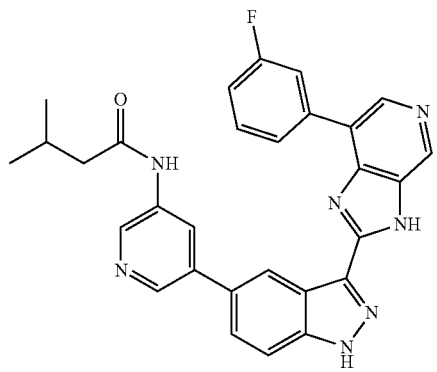
(1)

or a salt thereof, the process comprising:

(a) reacting a compound of Formula (8)

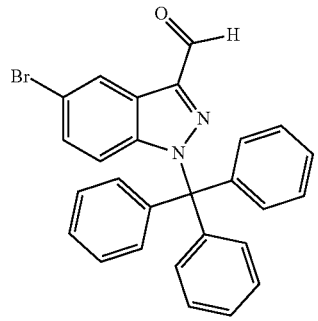
(8)

or a salt thereof, with bis(pinacolato)diboron and Pd(dppf)Cl$_2$ to produce a compound of Formula (9)

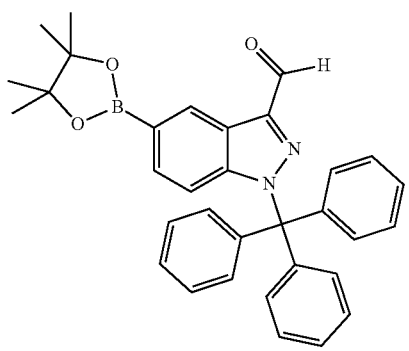
(9)

or a salt thereof;

(b) reacting the compound of Formula (9), or the salt thereof, with a compound of Formula (10)

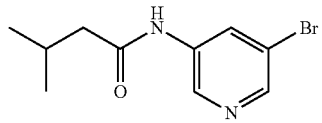
(10)

or a salt thereof, with Pd(PPh$_3$)$_4$ and K$_3$PO$_4$ to prepare a compound of Formula (11)

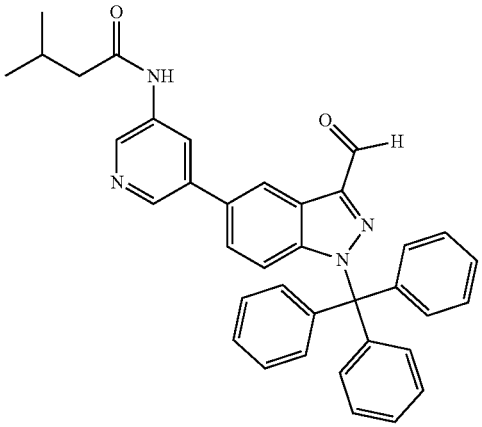
(11)

or a salt thereof;

(c) reacting the compound of Formula (11), or the salt thereof, with a compound of Formula (6)

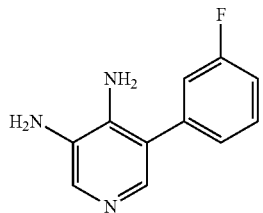

(6)

or a salt thereof, to prepare a compound of Formula (12)

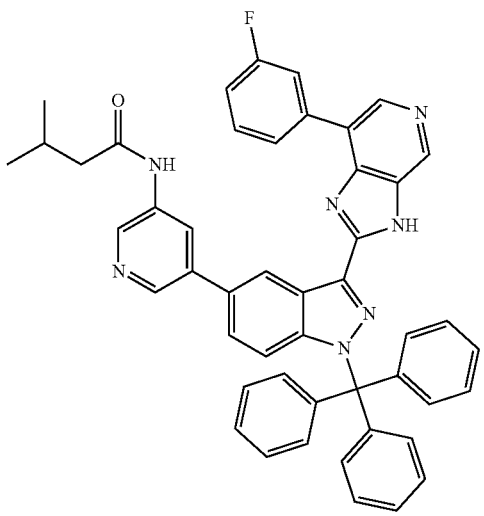

(12)

or a salt thereof; and (d) deprotecting the compound of Formula (12), or the salt thereof, to prepare the compound of Formula (1), or a salt thereof, wherein deprotecting the compound of Formula (12) to prepare the compound of Formula (1) comprises reacting the compound of Formula (12) with TFA. In some embodiments, the TFA is neat TFA. In some embodiments, the ratio of mass equivalents of TFA to the compound of Formula (12), or a salt thereof, is about 2:1 to about 16:1. In some embodiments, the ratio of mass equivalents of TFA to the compound of Formula (12), or a salt thereof, is about 7:1 to about 9:1. In some embodiments, the ratio of mass equivalents of TFA to the compound of Formula (12), or a salt thereof, is about 8:1.

In some embodiments of the process provided herein, deprotecting the compound of Formula (12), or a salt thereof, is performed at a temperature of about 15° C. to about 25° C. In some embodiments, deprotecting the compound of Formula (12), or a salt thereof, is performed at a temperature of about 20° C.

In some embodiments of the process provided herein, deprotecting the compound of Formula (12), or a salt thereof, is performed for a time of about 2 hours to about 7 hours. In some embodiments, deprotecting the compound of Formula (12), or a salt thereof, is performed for a time of about 3 hours to about 7 hours. In some embodiments, deprotecting the compound of Formula (12), or a salt thereof, is performed for a time of about 2 hours to about 4 hours. In some embodiments, deprotecting the compound of Formula (12), or a salt thereof, is performed for a time of about 5 hours. In some embodiments, deprotecting the compound of Formula (12), or a salt thereof, is performed for a time of about 3 hours.

In some embodiments of the process provided herein, deprotecting the compound of Formula (12), or a salt thereof, comprises forming a first mixture; and adding water to the first mixture at a temperature of about 0° C. to about 10° C. to form a second mixture. In some embodiments, water is added at a temperature of about 5° C. to form the second mixture. In some embodiments, the process comprises reslurrying the second mixture for a time of about 0.5 hours to about 1 hour. In some embodiments, the process comprises reslurrying the second mixture for a time of about 0.75 hours. In some embodiments, the process comprises reslurrying the second mixture at a temperature of about 0° C. to about 10° C. In some embodiments, the process comprises reslurrying the second mixture at a temperature of about 5° C.

In some embodiments, the process further comprises filtering the second mixture to provide a filtrate. In some embodiments, the process further comprises adding water to the filtrate at a temperature of about 0° C. to about 10° C. to form a third mixture. In some embodiments, water is added to the filtrate at a temperature of about 5° C. to form the third mixture. In some embodiments, the process comprises reslurrying the third mixture at a temperature of about 5° C. to about 15° C.

In some embodiments, the process comprises reslurrying the third mixture at a temperature of about 10° C. In some embodiments, the process comprises reslurrying the third mixture for a time of about 1 hour to about 2 hours. In some embodiments, the process comprises reslurrying the third mixture for a time of about 1.5 hours. In some embodiments, the process further comprises filtering the third mixture to provide a first residual solid.

In some embodiments of the process provided herein, the process further comprises adding ethanol to the first residual solid to form a fourth mixture. In some embodiments, the process comprises reslurrying the fourth mixture at a temperature of about 25° C. to about 35° C. In some embodiments, the process comprises reslurrying the fourth mixture at a temperature of about 30° C. In some embodiments, the process comprises reslurrying the fourth mixture for a time of about 2 hours to about 4 hours. In some embodiments, the process comprises reslurrying the fourth mixture for a time of about 3 hours. In some embodiments, the process comprises filtering the fourth mixture to provide a second residual solid.

In some embodiments of the process provided herein, the process comprises adding water to the second residual solid to form a fifth mixture. In some embodiments, the process comprises reslurrying the fifth mixture at a temperature of about 20° C. to about 30° C. In some embodiments, the process comprises reslurrying the fifth mixture at a temperature of about 25° C. In some embodiments, the process comprises reslurrying the fifth mixture for a time of about 0.5 hour to about 1.5 hours. In some embodiments, the process comprises reslurrying the fifth mixture for a time of about 1 hour.

In some embodiments of the process provided herein, the process comprises adding a base to the fifth mixture to form a sixth mixture. In some embodiments, the base is selected from the group consisting of: lithium carbonate, sodium carbonate, potassium carbonate, cesium carbonate, sodium hydrogen carbonate, potassium hydrogen carbonate, sodium sulfate, potassium sulfate, cesium sulfate, lithium phosphate, sodium phosphate, potassium phosphate, and cesium phosphate. In some embodiments, the base is sodium carbonate. In some embodiments, the process comprises reslurrying the sixth mixture at a temperature of about 20° C. to about 30° C. In some embodiments, the process comprises reslurrying the sixth mixture at a temperature of about 25° C. In some embodiments, the process comprises reslurrying the sixth mixture for a time of about 5 hours to about 7 hours. In some embodiments, the process comprises reslurrying the sixth mixture for a time of about 6 hours. In some embodiments, the process further comprises filtering the sixth mixture to provide a third residual solid.

In some embodiments of the process provided herein, the process further comprises adding water to the third residual solid to form a seventh mixture. In some embodiments, the process comprises reslurrying the seventh mixture at a temperature of about 20° C. to about 30° C. In some embodiments, the process comprises reslurrying the seventh mixture at a temperature of about 25° C. In some embodiments, the process comprises reslurrying the seventh mixture for a time of about 5 hours to about 8 hours. In some embodiments, the process comprises reslurrying the seventh mixture for a time of about 6.5 hours. In some embodiments, the process further comprises filtering the seventh mixture to provide a fourth residual solid.

In some embodiments of the process provided herein, the process further comprises (a) adding water to the fourth residual solid to provide an eighth mixture; (b) reslurrying the eighth mixture; and (c) filtering the eighth mixture to provide a fifth residual solid. In some embodiments, steps (a)-(c) are performed an additional one or more times.

In some embodiments of the process provided herein, the process further comprises adding isopropanol to the fifth residual solid to form a ninth mixture. In some embodiments, the process comprises reslurrying the ninth mixture at a temperature of about 20° C. to about 30° C. In some embodiments, the process comprises reslurrying the ninth mixture at a temperature of about 25° C. In some embodiments, the process comprises reslurrying the ninth mixture for a time of about 1 hour to about 3 hours. In some embodiments, the process comprises reslurrying the ninth mixture for a time of about 2 hours. In some embodiments, the process further comprises filtering the ninth mixture to provide a sixth residual solid.

Also provided herein is a process for preparing a compound of Formula (1)

or a salt thereof, the process comprising:
(a) reacting the compound of Formula (5)

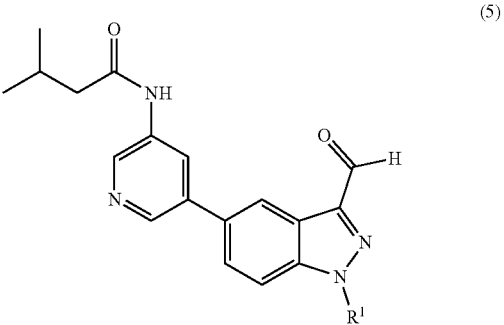

or a salt thereof, wherein $R^1$ is a nitrogen protecting group, with a compound of Formula (6)

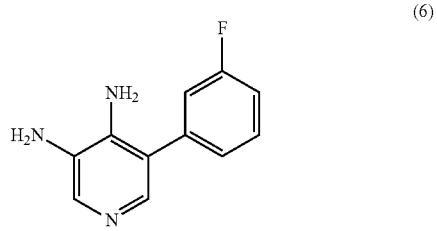 [SMILES: Nc1cncc(-c2cccc(F)c2)c1N]

or a salt thereof, to prepare a compound of Formula (7)

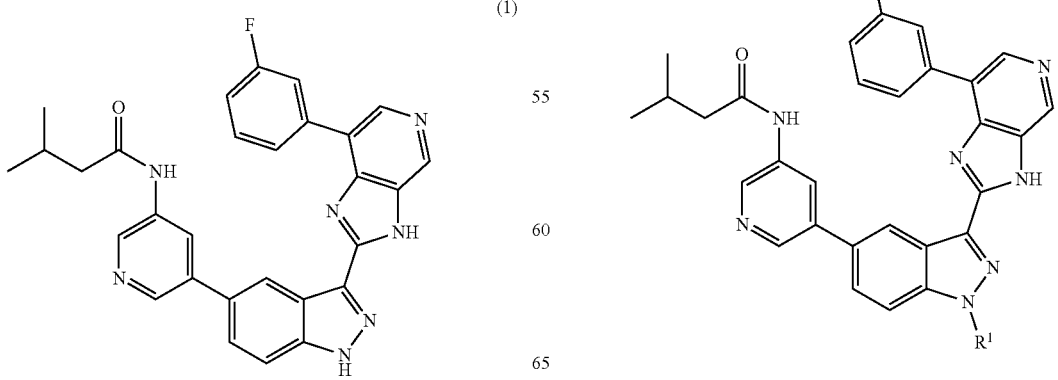

or a salt thereof.

Further provided herein is a process for preparing a compound of Formula (1)

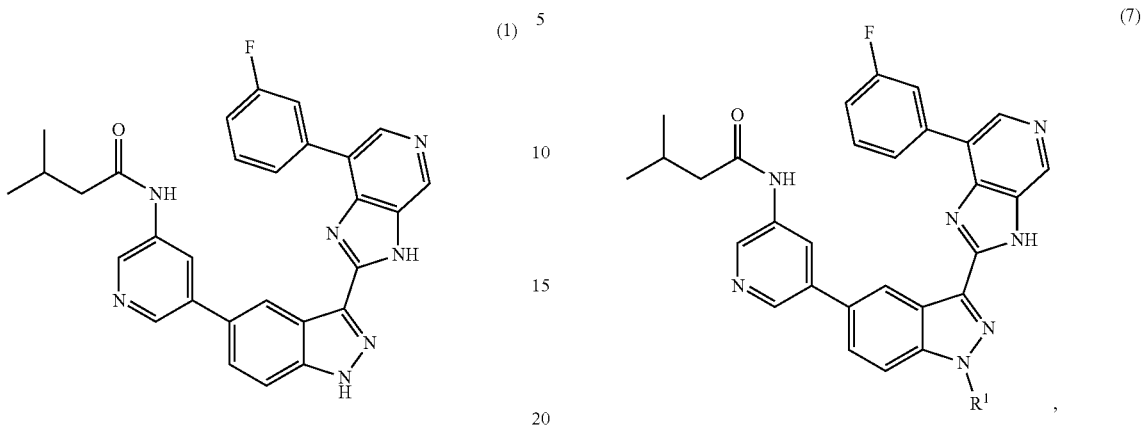

or a salt thereof, the process comprising:
reacting a compound of Formula (2)

or a salt thereof, wherein X¹ is selected from the group consisting of —Cl, —Br, —I, and —OTf, and R¹ is a nitrogen protecting group, with a boron reagent to prepare a compound of Formula (3)

or a salt thereof, wherein:
A is selected from the group consisting of a boronic acid, a boronic ester, a boronate, a borinate, a boranate, a boranamide, an N-coordinated boronate, and a trifluoroborate.

This disclosure also provides a process for preparing a compound of Formula (7)

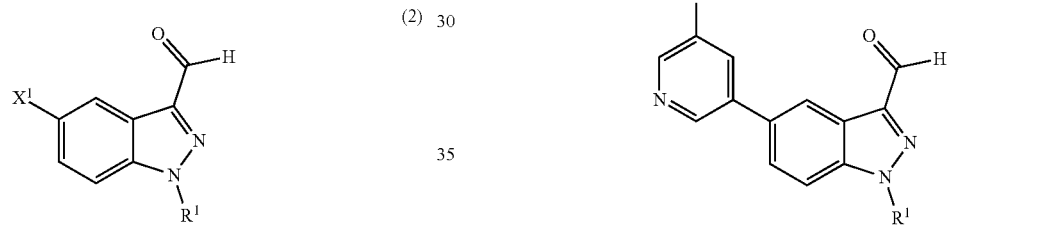

or a salt thereof, wherein R¹ is nitrogen protecting group, comprising reacting a compound of Formula (5)

or a salt thereof, with a compound of Formula (6)

or a salt thereof, to prepare a compound of Formula (7), or the salt thereof.

Also provided herein is a process for preparing a compound of Formula (3)

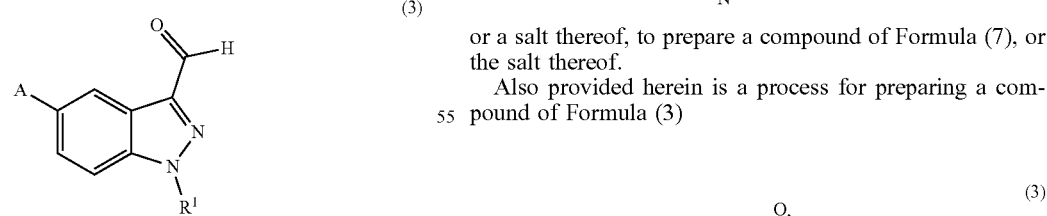

or a salt thereof, wherein:
R[1] is a nitrogen protecting group, and
A is selected from the group consisting of a boronic acid, a boronic ester, a boronate, a borinate, a boranate, a boranamide, an N-coordinated boronate, and a trifluoroborate;
comprising reacting a compound of Formula (2)

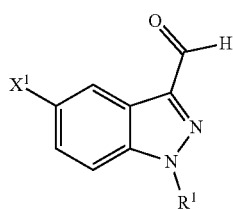

(2)

or a salt thereof, wherein X[1] is selected from the group consisting of —Cl, —Br, —I, and —OTf with a boron reagent to prepare a compound of Formula (3), or the salt thereof.

Further provided herein is a process for preparing a compound of Formula (1)

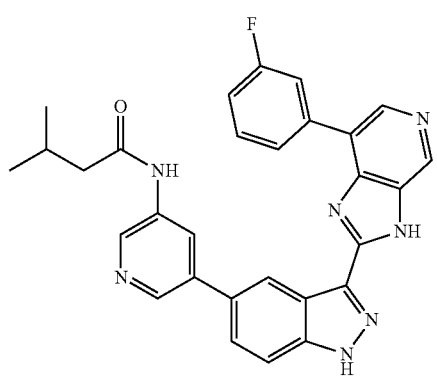

(1)

or a salt thereof, the process comprising deprotecting a compound of Formula (12)

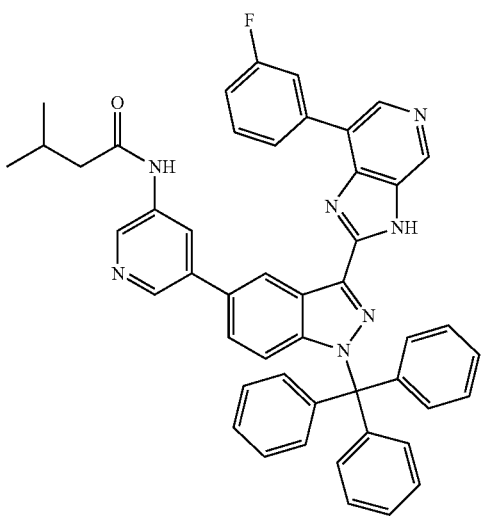

(12)

or a salt thereof, to prepare the compound of Formula (1) or a salt thereof.

This disclosure provides a process for preparing a pharmaceutical composition, including mixing (i) a compound of Formula (1)

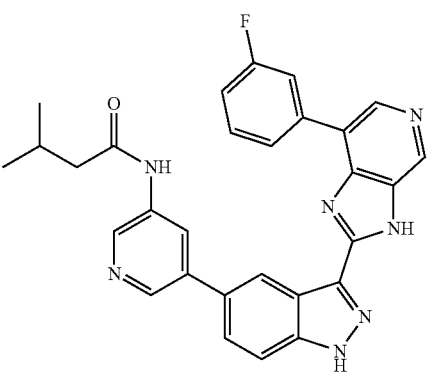

(1)

or salt thereof, prepared by any of the processes described herein, and (ii) a pharmaceutically acceptable carrier (excipient), to form the composition.

Also provided is a process for preparing a polymorph form of a compound of Formula (1)

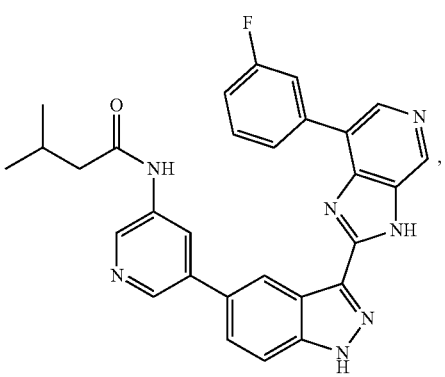 [SMILES: CC(C)CC(=O)Nc1cncc(-c2ccc3[nH]nc(-c4nc5c(-c6cccc(F)c6)cncc5[nH]4)c3c2)c1]

the process comprising: (a) preparing the compound of Formula (1) according to any one of the processes provided herein; and (b) converting the compound of Formula (1) to the polymorph form. In some embodiments, step (b) comprises reslurrying the compound of Formula (1) or a composition comprising the compound of Formula (1) in a solvent or mixture of solvents to generate the polymorph form. In some embodiments, reslurrying is performed at room temperature. In some embodiments, reslurrying is performed at a temperature of about 50° C. In some embodiments, reslurrying is performed at a temperature of about 30° C. to about 35° C. In some embodiments, reslurrying is performed for a time of about 10 hours to about 80 hours. In some embodiments, reslurrying is performed for a time of about 58 hours to about 80 hours.

In some embodiments, the process further comprises a filtering step to provide the polymorph form as a residual solid.

In some embodiments, the reslurrying comprises a solvent or mixture of solvents selected from methanol, water, or a mixture thereof.

In some embodiments, the polymorph form of the compound of Formula (1) is a non-stoichiometric hydrate of polymorph Form 1 having between 1% and about 20% by weight water.

Also provided is a process for preparing a polymorph form of a compound of Formula (1)

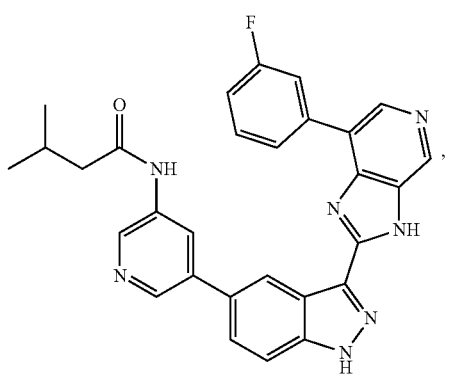

(1)

the process comprising converting the compound of Formula (1) to the polymorph form. In some embodiments, the process comprises reslurrying the compound of Formula (1) or a composition comprising the compound of Formula (1) in a solvent or mixture of solvents to generate the polymorph form. In some embodiments, the reslurrying is performed at room temperature. In some embodiments, the reslurrying is performed at a temperature of about 50° C. In some embodiments, the reslurrying is performed at a temperature of about 30° C. to about 35° C. In some embodiments, the reslurrying is performed for a time of about 10 hours to about 80 hours. In some embodiments, the reslurrying is performed for a time of about 58 hours to about 80 hours. In some embodiments, the process further comprises a filtering step to provide the polymorph form as a residual solid.

In some embodiments, the reslurrying comprises a solvent or mixture of solvents selected from methanol, water, or a mixture thereof.

In some embodiments, the polymorph form of the compound of Formula (1) is a non-stoichiometric hydrate of polymorph Form 1 having between 1% and about 20% by weight water.

DESCRIPTION OF DRAWINGS

FIG. 1A is an x-ray powder diffraction scan of fully dried Form 1. FIG. 1B is a differential scanning calorimetry scan of Form 1. FIG. 1C is a thermal gravimetric analysis scan of Form 1. FIG. 1D is a dynamic vapor sorption scan of Form 1.

FIG. 2A is an x-ray powder diffraction scan of fully dried Form 2. FIG. 2B is a differential scanning calorimetry scan of Form 2. FIG. 2C is a thermal gravimetric analysis scan of Form 2.

FIG. 2D is an x-ray powder diffraction scan of fully dried Form 2*. FIG. 2E is a differential scanning calorimetry scan of Form 2*. FIG. 2F is a thermal gravimetric analysis scan of Form 2*.

FIG. 2G is an x-ray powder diffraction scan of Form 2. FIG. 2H is a differential scanning calorimetry scan of Form 2.

FIG. 3A is an x-ray powder diffraction scan of fully dried Form 3. FIG. 3B is a differential scanning calorimetry scan of Form 3. FIG. 3C is a thermal gravimetric analysis scan of Form 3.

FIG. 4A is an x-ray powder diffraction scan of fully dried Form 4. FIG. 4B is a differential scanning calorimetry scan of Form 4. FIG. 4C is a thermal gravimetric analysis scan of Form 4.

FIG. 4D is an x-ray powder diffraction scan of fully dried Form 4*. FIG. 4E is a differential scanning calorimetry scan of Form 4*. FIG. 4F is a thermal gravimetric analysis scan of Form 4*.

FIG. 4G is an x-ray powder diffraction scan of Form 4. FIG. 4H is a differential scanning calorimetry scan of Form 4. FIG. 4I is a thermal gravimetric analysis scan of Form 4**.

FIG. 5A is an x-ray powder diffraction scan of fully dried Form 5. FIG. 5B is a differential scanning calorimetry scan of Form 5. FIG. 5C is a thermal gravimetric analysis scan of Form 5.

FIG. 5D is an x-ray powder diffraction scan of Form 5*.

FIG. 6A is an x-ray powder diffraction scan of Form 6. FIG. 6B is a differential scanning calorimetry scan of Form 6.

FIG. 7A is an x-ray powder diffraction scan of fully dried Form 7. FIG. 7B is a differential scanning calorimetry scan of Form 7. FIG. 7C is a thermal gravimetric analysis scan of Form 7.

FIG. 8A is an x-ray powder diffraction scan of fully dried Form 8. FIG. 8B is a differential scanning calorimetry scan of Form 8. FIG. 8C is a thermal gravimetric analysis scan of Form 8.

FIG. 9A is an x-ray powder diffraction scan of fully dried Form 9. FIG. 9B is a differential scanning calorimetry scan of Form 9. FIG. 9C is a thermal gravimetric analysis scan of Form 9. FIG. 9D is a dynamic vapor sorption scan of Form 9.

FIG. 10A is an x-ray powder diffraction scan of fully dried Form 10. FIG. 10B is a differential scanning calorimetry scan of Form 10. FIG. 10C is a thermal gravimetric analysis scan of Form 10. FIG. 10D is an x-ray powder diffraction scan of Form 10*. FIG. 10E is a differential scanning calorimetry scan of Form 10*.

FIG. 11A is an x-ray powder diffraction scan of fully dried Form 11. FIG. 11B is a differential scanning calorimetry scan of Form 11. FIG. 11C is a thermal gravimetric analysis scan of Form 11. FIG. 11D is an x-ray powder diffraction scan of fully dried Form 11*. FIG. 11E is a differential scanning calorimetry scan of Form 11*. FIG. 11F is a thermal gravimetric analysis scan of Form 11*.

FIG. 12A is an x-ray powder diffraction scan of Form 12. FIG. 12B is a differential scanning calorimetry scan of Form 12. FIG. 12C is a thermal gravimetric analysis scan of Form 12.

FIG. 13A is an x-ray powder diffraction scan of Form 13. FIG. 13B is a differential scanning calorimetry scan of Form 13. FIG. 13C is a thermal gravimetric analysis scan of Form 13. FIG. 13D is a dynamic vapor sorption scan of Form 13.

DETAILED DESCRIPTION

1. Definitions

Figure 1A:
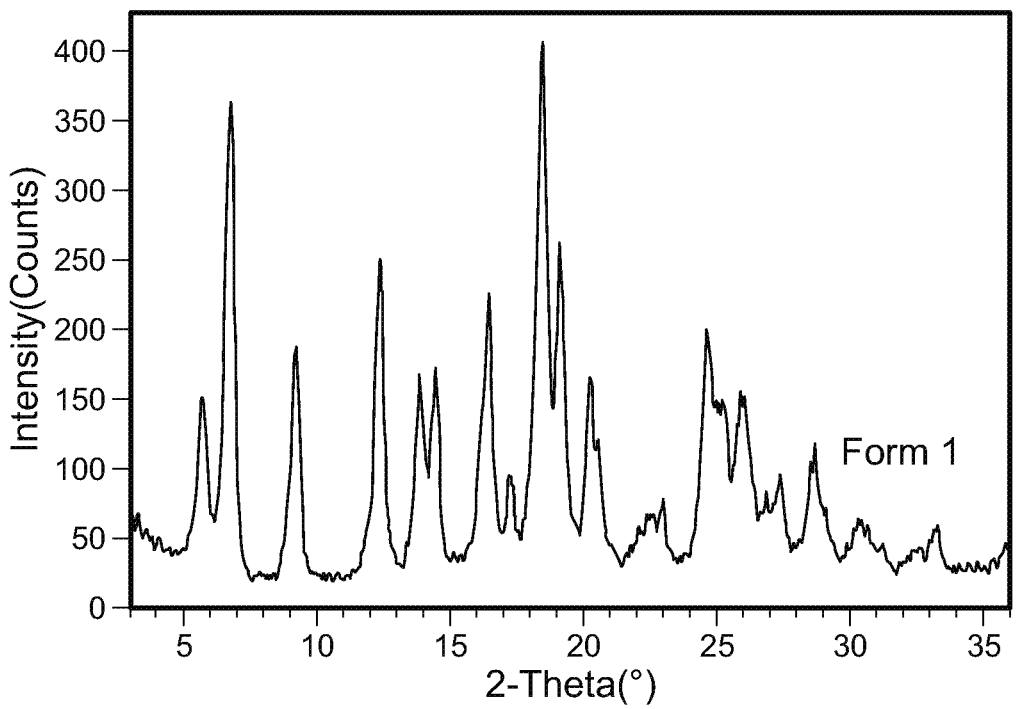
FIGS. 1A-1D are scans of polymorph Form 1 of the compound of Formula (I).

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

Unless defined otherwise, all technical and scientific terms used herein have the same meaning as is commonly understood by one of ordinary skill in the art to which this disclosure belongs. In the event that there is a plurality of definitions for terms cited herein, those in this section prevail unless otherwise stated. All patents, applications, published applications, and other publications cited herein are incorporated by reference in their entirety.

For the terms "for example" and "such as," and grammatical equivalences thereof, the phrase "and without limitation" is understood to follow unless explicitly stated otherwise. As used herein, the term "about" is meant to account for variations due to experimental error. As used herein, the singular forms "a," "an," and "the" include plural referents unless the context clearly dictates otherwise.

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to: chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethanesulfonate, ethanesulfonate, benzenesulfonate, p-toluenesulfonate, p-trifluoromethylbenzenesulfonate, hydroxide, aluminates, and borates. Exemplary cations include, but are not limited to: monovalent alkali metal cations, such as lithium, sodium, potassium, and cesium, and divalent alkaline earth metals, such as beryllium, magnesium, calcium, strontium, and barium. Also included are transition metal cations, such as gold, silver, copper and zinc, as well as non-metal cations, such as ammonium salts.

Compounds provided herein can also include all isotopes of atoms occurring in the intermediates or final compounds. Isotopes include those atoms having the same atomic number but different mass numbers. For example, isotopes of hydrogen include hydrogen, deuterium, and tritium.

The term "compound," as used herein, is meant to include all stereoisomers, geometric isomers, tautomers, and isotopes of the structures depicted. Compounds herein identified by name or structure as one particular tautomeric form are intended to include other tautomeric forms unless otherwise specified.

The term "polymorph," as used herein, refers to crystals of the same molecule having different physical properties as a result of the order of the molecules in the crystal lattice. Polymorphs of a single compound have one or more different chemical, physical, mechanical, electrical, thermodynamic, and/or biological properties from each other. Differences in physical properties exhibited by polymorphs can affect pharmaceutical parameters such as storage stability, compressibility, density (important in composition and product manufacturing), dissolution rates (an important factor in determining bio-availability), solubility, melting point, chemical stability, physical stability, powder flowability, water sorption, compaction, and particle morphology. Differences in stability can result from changes in chemical reactivity (e.g. differential oxidation, such that a dosage form discolors more rapidly when comprised of one polymorph than when comprised of another polymorph) or mechanical changes (e.g., crystal changes on storage as a kinetically favored polymorph converts to a thermodynamically more stable polymorph) or both (e.g., one polymorph is more hygroscopic than the other). As a result of solubility/dissolution differences, some transitions affect potency and/or toxicity. In addition, the physical properties of the crystal may be important in processing; for example, one polymorph might be more likely to form solvates or might be difficult to filter and wash free of impurities (i.e., particle shape and size distribution might be different between one polymorph relative to the other). "Polymorph" does not include amorphous forms of the compound. As used herein, "amorphous" refers to a noncrystalline form of a compound which may be a solid state form of the compound or a solubilized form of the compound. For example, "amorphous" refers to a compound without a regularly repeating arrangement of molecules or external face planes.

The term "anhydrous," as used herein, refers to a crystal form of the compound of Formula (I) that has 1% or less by weight water. For example, 0.5% or less, 0.25% or less, or 0.1% or less by weight water.

The term "solvate" as used herein refers to a crystalline form of a compound of Formula (I), such as a polymorph form of the compound, where the crystal lattice comprises one or more solvents of crystallization.

The term "non-stoichiometric hydrate" refers to a crystalline form of a compound of Formula I that comprises water, but wherein variations in the water content do not cause significant changes to the crystal structure. In some embodiments, a non-stoichiometric hydrate can refer to a crystalline form of a compound of Formula I that has channels or networks throughout the crystal structure into which water molecules can diffuse. During drying of non-stoichiometric hydrates, a considerable proportion of water can be removed without significantly disturbing the crystal network, and the crystals can subsequently rehydrate to give the initial non-stoichiometric hydrated crystalline form. Unlike stoichiometric hydrates, the dehydration and rehydration of non-stoichiometric hydrates is not accompanied by a phase transition, and thus all hydration states of a non-stoichiometric hydrate represent the same crystal form. In some embodiments, a non-stoichiometric hydrate can have up to about 20% by weight water, such as, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or greater than 1% water by weight. In some embodiments, a non-stoichiometric hydrate can have between 1% and about 20% by weight water, such as between 1% and about 5%, 1% and about 10%, 1% and about 15%, about 2% and about 5%, about 2% and about 10%, about 2% and about 15%, about 2% and about 20%, about 5% and about 10%, about 5% and about 15%, about 5% and about 20%, about 10% and about 15%, about 10% and about 20%, or about 15% and about 20% by weight water.

In some embodiments the % water by weight in a crystal form, such as a non-stoichiometric hydrate, is determined by the Karl Fischer titration method. In some embodiments, the crystal form is dried prior to Karl Fischer titration.

"Purity," when used in reference to a composition including a polymorph of the compound of Formula (1), refers to the percentage of one specific polymorph form relative to another polymorph form or an amorphous form of the compound of Formula (1) in the referenced composition. For example, a composition comprising polymorph Form 1 having a purity of 90% would comprise 90 weight parts Form 1 and 10 weight parts of other polymorph and/or amorphous forms of the compound of Formula (1).

As used herein, a compound or composition is "substantially free of" one or more other components if the compound or composition contains no significant amount of such other components. Such components can include starting materials, residual solvents, or any other impurities that can result from the preparation of and/or isolation of the compounds and compositions provided herein. In some embodiments, a polymorph form provided herein is substantially free of other polymorph forms. In some embodiments, a particular polymorph of the compound of Formula (1) is "substantially free" of other polymorphs if the particular polymorph constitutes at least about 95% by weight of the compound of Formula (1) present. In some embodiments, a particular polymorph of the compound of Formula (1) is "substantially free" of other polymorphs if the particular polymorph constitutes at least about 97%, about 98%, about 99%, or about 99.5% by weight of the compound of Formula (1) present. In certain embodiments, a particular polymorph of the compound of Formula (1) is "substantially free" of water if the amount of water constitutes no more than about 2%, about 1%, or about 0.5% by weight of the polymorph.

As used herein, a compound is "substantially present" as a given polymorph if at least about 50% by weight of the compound is in the form of that polymorph. In some embodiments, at least about 60% by weight of the compound is in the form of that polymorph. In some embodiments, at least about 70% by weight of the compound is in the form of that polymorph. In some embodiments, at least about 80% by weight of the compound is in the form of that polymorph. In some embodiments, at least about 90% by weight of the compound is in the form of that polymorph. In some embodiments, at least about 95% by weight of the compound is in the form of that polymorph. In some embodiments, at least about 96% by weight of the compound is in the form of that polymorph. In some embodiments, at least about 97% by weight of the compound is in the form of that polymorph. In some embodiments, at least about 98% by weight of the compound is in the form of that polymorph. In some embodiments, at least about 99% by weight of the compound is in the form of that polymorph. In some embodiments, at least about 99.5% by weight of the compound is in the form of that polymorph.

In some embodiments, the compounds provided herein, including salts and amorphous and polymorph forms thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt or amorphous or polymorph form thereof. Methods for isolating compounds and their salts are routine in the art.

As used herein, the term "inert atmosphere" refers to a substantially oxygen free environment and primarily consists of non-reactive gases. Exemplary inert atmospheres include a nitrogen atmosphere or an argon atmosphere.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "ambient temperature" and "room temperature" or "RT", as used herein, are understood in the art, and refer generally to a temperature, e.g. a reaction temperature, that is about the temperature of the room in which the reaction is carried out, for example, a temperature from about 20° C. to about 30° C., typically around 25° C.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; in some embodiments, a non-aqueous media like ether, ethyl acetate, alcohol (e.g., methanol, ethanol, isopropanol, or butanol), or acetonitrile (ACN) can be used. Lists of suitable salts can be found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety. Conventional methods for preparing salt forms are described, for example, in Handbook of Pharmaceutical Salts: Properties, Selection, and Use, Wiley-VCH, 2002.

2. Processes for Preparing a Compound of Formula (1) and Intermediates Thereof Provided herein is a process for preparing a compound of Formula (1)

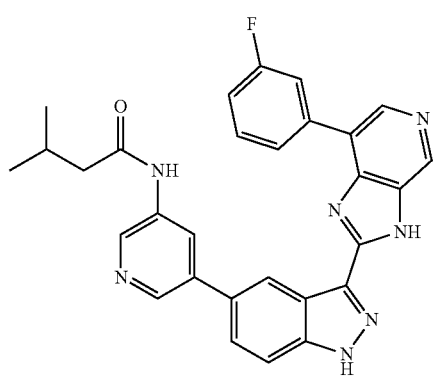

(1)

including salts and amorphous and polymorph forms thereof. The process includes:

(a) reacting a compound of Formula (2)

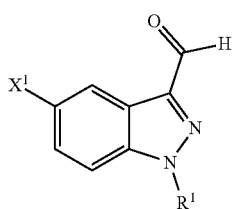

(2)

or a salt thereof, wherein $R^1$ is a nitrogen protecting group, and $X^1$ is a first leaving group, with a compound of Formula (4)

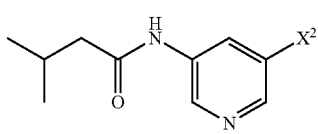

(4)

or a salt thereof, wherein $X^2$ is a second leaving group; to prepare a compound of Formula (5)

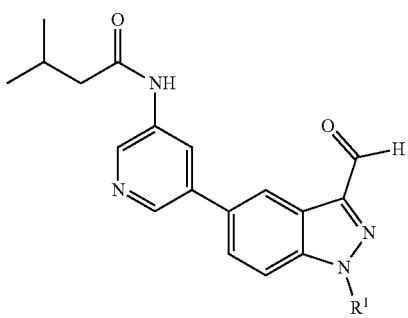

(5)

or a salt thereof;

(b) reacting the compound of Formula (5), or the salt thereof, with a compound of Formula (6)

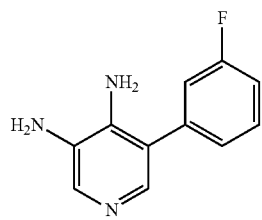

(6)

or a salt thereof, to prepare a compound of Formula (7)

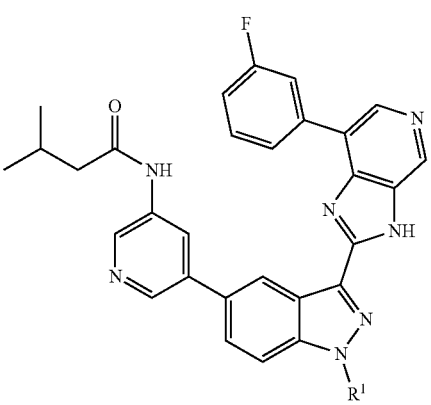

(7)

or a salt thereof; and (c) deprotecting the compound of Formula (7), or the salt thereof, to prepare the compound of Formula (1). In some embodiments, the process further comprises forming a salt of the compound of Formula (1). In some embodiments, the process further comprises preparing a polymorph form of the compound of Formula (1). In some embodiments, the polymorph form of the compound of Formula (1) is Form 1. In some embodiment, the polymorph form of the compound of Formula (1) is a non-stoichiometric hydrate of polymorph Form 1 having between 1% and about 20% by weight water.

As used herein, the term "leaving group" refers to an atom or group of atoms that departs with a pair of electrons in heterolytic bond cleavage. A leaving group can be a stable anion of a strong acid, such as a halide (e.g., fluoride, chloride, bromide, iodide) or a sulfonate ester (e.g., methanesulfonate, trifluoromethanesulfonate, 4-methylbenzenesulfonate). A leaving group can also be a group, such as a chloride, a bromide, an iodide, or a trifluoromethanesulfonate group, that is capable of undergoing oxidative addition to palladium during a palladium-catalyzed reaction, such as a palladium-catalyzed Suzuki-Miyaura cross-coupling reaction.

As used herein, the term "nitrogen protecting group" refers to any group that is capable of reversibly protecting a nitrogen functionality (e.g., an amine). Suitable nitrogen protecting groups can be found in the relevant chapters of standard reference works such as *Protective Groups in Organic Chemistry*, J. F. W. McOmie, Plenum Press, London and New York, 1973; *Greene's Protective Groups in*

*Organic Synthesis*, P. G. M. Wuts, fourth edition, Wiley, New York, 2006; and *Protecting Groups*, P. J. Kocienski, third edition, Thieme, New York, 2005.

Non-limiting examples of nitrogen protecting groups include acetyl, benzyl, cumyl, benzhydryl, trityl (Trt), benzyloxycarbonyl (Cbz), 9-fluorenylmethyloxycarbonyl (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tert-butyl-dimethylsilyl, triethylsilyl (TES), triisopropylsilyl, trimethylsilylethoxymethyl (SEM), t-butoxycarbonyl (BOC), t-butyl, 1-methyl-1,1-dimethylbenzyl, (phenyl)methyl benzene, pyridinyl, and pivaloyl.

As an example, the compound of Formula (1), or a salt or amorphous or polymorph form thereof, can be prepared as shown in Scheme 1, wherein $X^1$, $X^2$, and $R^1$ are as defined above.

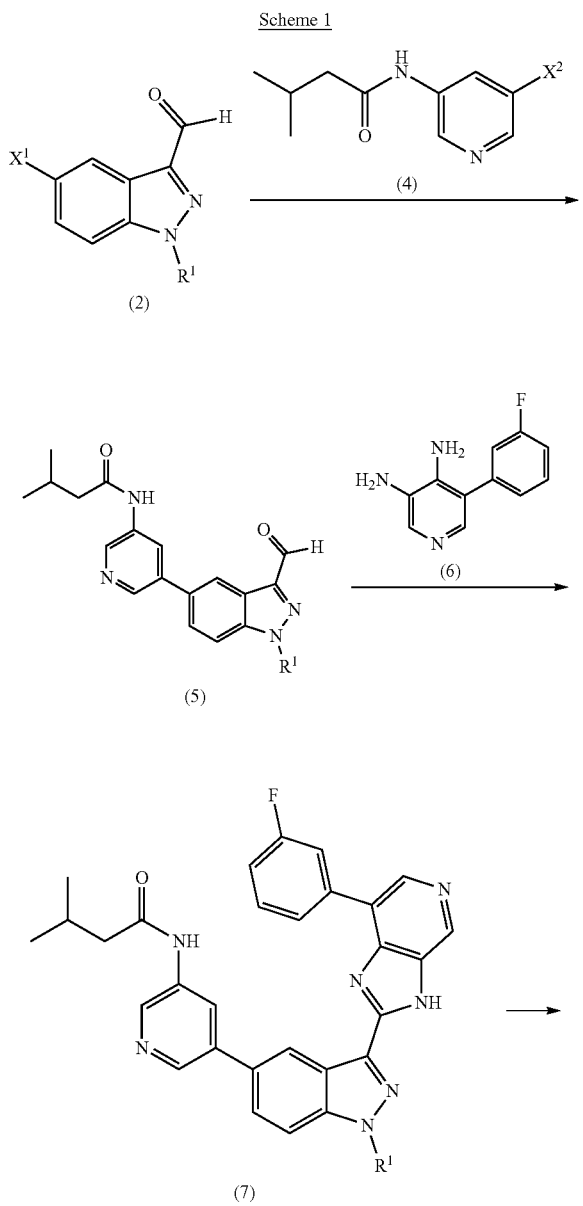

Scheme 1

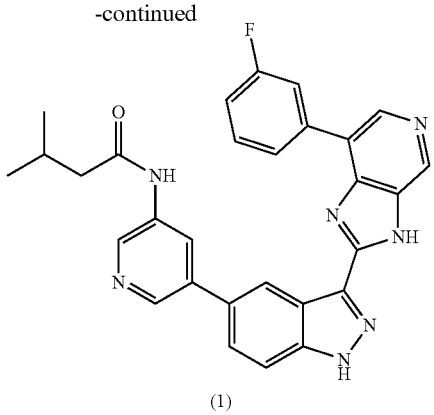

(1)

In some embodiments, reacting a compound of Formula (2), or a salt thereof, with a compound of Formula (4), or a salt thereof, to prepare a compound of Formula (5), or a salt thereof, is performed in the presence of a palladium catalyst, a nickel catalyst, a tin catalyst, a copper catalyst, or combinations thereof. In some embodiments, reacting a compound of Formula (2), or a salt thereof, with a compound of Formula (4), or a salt thereof, to prepare a compound of Formula (5), or a salt thereof, is performed in the presence of a palladium catalyst.

As used herein, the term "palladium catalyst" refers to a catalyst that contains palladium, such as Pd(0) and Pd(II), and any necessary ligands required for the catalyst to react. The term "palladium catalyst" can also refer to a palladium catalyst on a solid support.

As used herein, the term "nickel catalyst" refers to a catalyst that contains nickel, such as Ni(0) and Ni(II), and any necessary ligands required for the catalyst to react. The term "nickel catalyst" can also refer to a nickel catalyst on a solid support.

As used herein, the term "copper catalyst" refers to a catalyst that contains copper, such as Cu(0) and Cu(II), and any necessary ligands required for the catalyst to react. The term "copper catalyst" can also refer to a copper catalyst on a solid support.

In some embodiments, a compound of Formula (2), or a salt thereof, can be converted into a more reactive intermediate prior to reacting with a compound of Formula (4), or a salt thereof. In some embodiments, a compound of Formula (2), or a salt thereof, can be converted into a more reactive intermediate via borylation prior to reacting with a compound of Formula (4), or a salt thereof.

Reacting a compound of Formula (5), or a salt thereof, with a compound of Formula (6), or a salt thereof, to prepare a compound of Formula (7), or a salt thereof, can be performed in the presence of $Na_2SO_3$, elemental sulfur, or a combination thereof. In some embodiments, reacting a compound of Formula (5), or a salt thereof, with a compound of Formula (6), or a salt thereof, to prepare a compound of Formula (7), or a salt thereof, is performed in the presence of $Na_2SO_3$. The $Na_2SO_3$ can be ground $Na_2SO_3$. For example, the ground $Na_2SO_3$ can have a particle size of about 100 microns to about 300 microns or about 150 microns to about 250 microns. In some embodiments, the ground $Na_2SO_3$ has a particle size of about 150 microns to about 250 microns. In some embodiments, reacting the compound of Formula (5), or a salt thereof, with the compound of Formula (6), or a salt thereof, to prepare the compound of Formula (7), or a salt thereof, is performed in the presence of $SO_2$.

Reacting a compound of Formula (5), or a salt thereof, with a compound of Formula (6), or a salt thereof, to prepare the compound of Formula (7), or a salt thereof, can be performed in the presence of an organic solvent. In some embodiments, the organic solvent is N-methyl-2-pyrrolidone, dimethylacetamide, n-butanol, or a combination thereof. In some embodiments, reacting the compound of Formula (5), or a salt thereof, with the compound of Formula (6), or a salt thereof, to prepare the compound of Formula (7), or a salt thereof, is performed in the presence of N-methyl-2-pyrrolidone.

In some embodiments, reacting a compound of Formula (5), or a salt thereof, with a compound of Formula (6), or a salt thereof, to prepare a compound of Formula (7), or a salt thereof, is performed under an inert atmosphere. For example, the inert atmosphere can be a nitrogen (N2) atmosphere or an argon atmosphere. In some embodiments, reacting the compound of Formula (5), or a salt thereof, with the compound of Formula (6), or a salt thereof, to prepare the compound of Formula (7), or a salt thereof, is performed under a N2 atmosphere.

In some embodiments, reacting a compound of Formula (5), or a salt thereof, with a compound of Formula (6), or a salt thereof, to prepare a compound of Formula (7), or a salt thereof, is performed at a temperature of about 75° C. to about 150° C., about 100° C. to about 120° C., or about 110° C. to about 115° C. In some embodiments, reacting the compound of Formula (5), or a salt thereof, with the compound of Formula (6), or a salt thereof, to prepare the compound of Formula (7), or a salt thereof, is performed at a temperature of about 100° C., 105° C., 110° C., 115° C., or about 120° C.

In some embodiments, reacting a compound of Formula (5), or a salt thereof, with a compound of Formula (6), or a salt thereof, to prepare a compound of Formula (7), or a salt thereof, is performed for a time of about 5 hours to about 10 hours or about 7 hours to about 9 hours. In some embodiments, reacting the compound of Formula (5), or a salt thereof, with the compound of Formula (6), or a salt thereof, to prepare the compound of Formula (7), or a salt thereof, is performed for a time of about 5 hours, 6 hours, 7 hours, 8 hours, 9 hours, or about 10 hours.

Reacting a compound of Formula (5), or a salt thereof, with a compound of Formula (6), or a salt thereof, to prepare a compound of Formula (7), or a salt thereof, can be performed at a temperature of about 75° C. to about 150° C. or about 100° C. to about 120° C. for a time of about 5 hours to about 10 hours. In some embodiments, reacting the compound of Formula (5), or a salt thereof, with the compound of Formula (6), or a salt thereof, to prepare the compound of Formula (7), or a salt thereof, is performed at a temperature of about 110° C. to about 115° C. for a time of about 7 hours to about 9 hours.

In some embodiments, the process further includes preparing a salt of the compound of Formula (7) prior to deprotecting the compound of Formula (7) to prepare the compound of Formula (1), or a salt or amorphous or polymorph form thereof. In some embodiments, the process further includes preparing an oxalate salt, a citrate salt, or an acetate salt of the compound of Formula (7) prior to deprotecting the compound of Formula (7), or the salt thereof, to prepare the compound of Formula (1), or a salt or amorphous or polymorph form thereof. In some embodiments, the process further includes preparing an oxalate salt of the compound of Formula (7) prior to deprotecting the compound of Formula (7), or the salt thereof, to prepare the compound of Formula (1), or salt or amorphous or polymorph form thereof.

Preparing a salt of a compound can include preparing the salt of the compound from the free base form of the compound; for example by reacting the compound with an acid or preparing it from another salt, by anion exchange.

In some embodiments, the process further includes preparing a free base form of the compound of Formula (7) prior to deprotecting the compound of Formula (7) to prepare the compound of Formula (1), or salt or amorphous or polymorph form thereof.

In some embodiments, the process further includes precipitating the compound of Formula (7), or a salt thereof, in an organic solvent prior to deprotecting the compound of Formula (7), or the salt thereof, to prepare the compound of Formula (1), or a salt or amorphous or polymorph form thereof. In some embodiments, the process further includes precipitating the compound of Formula (7), or a salt thereof, in a non-polar organic solvent prior to deprotecting the compound of Formula (7), or the salt thereof, to prepare the compound of Formula (1), or a salt or amorphous or polymorph form thereof. In some embodiments, the organic solvent is an aromatic hydrocarbon, such as benzene, toluene, and xylene, or an aliphatic organic solvent, such as hexane, heptane and octane. In some embodiments, the process further includes precipitating the compound of Formula (7), or a salt thereof, in n-heptane prior to deprotecting the compound of Formula (7), or the salt thereof, to prepare the compound of Formula (1), or a salt or amorphous or polymorph form thereof.

In some embodiments, prior to deprotecting the compound of Formula (7), or a salt thereof, to prepare the compound of Formula (1), or a salt or amorphous or polymorph form thereof, the process further includes one or more of: (a) preparing a salt of the compound of Formula (7); (b) preparing a free base form of the compound of Formula (7) from the salt of the compound of Formula (7); and (c) precipitating the free base form of the compound of Formula (7) in a non-polar organic solvent.

In some embodiments, prior to deprotecting a compound of Formula (7), or a salt thereof, to prepare a compound of Formula (1), or a salt or amorphous or polymorph form thereof, the process further includes one or more of: (a) preparing an oxalate salt, a citrate salt, or an acetate salt of a compound of Formula (7); (b) preparing a free base form of a compound of Formula (7) from the salt of a compound of Formula (7); and (c) precipitating the free base form of a compound of Formula (7) in an aliphatic organic solvent such as hexane, heptane and octane.

In some embodiments, prior to deprotecting the compound of Formula (7), or a salt thereof, to prepare the compound of Formula (1), or a salt or amorphous or polymorph form thereof, the process further includes one or more of: (a) preparing an oxalate salt of the compound of Formula (7); (b) preparing a free base form of the compound of Formula (7) from the oxalate salt of the compound of Formula (7); and (c) precipitating the free base form compound of Formula (7) in n-heptane, prior to deprotecting the compound of Formula (7) to prepare the compound of Formula (1), or a salt or amorphous or polymorph form thereof.

In some embodiments, the compound of Formula (7), or a salt thereof, is isolated prior to preparing the compound of Formula (1), or a salt or amorphous or polymorph form thereof. In some embodiments, the compound of Formula (7), or a salt thereof, is isolated with a purity of greater than about 90%, 92%, 94%, 96%, 98%, or greater than about 99%. In some embodiments, the compound of Formula (7), or a salt thereof, is isolated with a purity of greater than about 99%. In some embodiments, the purity is determined by chromatography. In some embodiments, the purity is determined by high-performance liquid chromatography (HPLC) analysis.

Also provided herein is a process for preparing a compound of Formula (1):

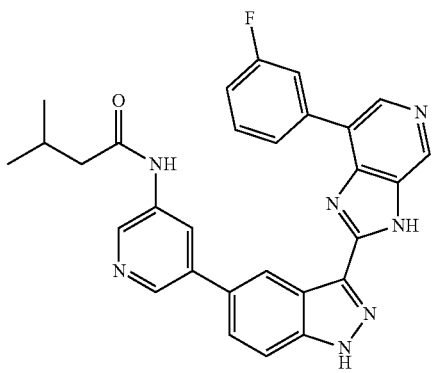

(1)

including salts and amorphous and polymorph forms thereof. The process includes:

(a) reacting a compound of Formula (2)

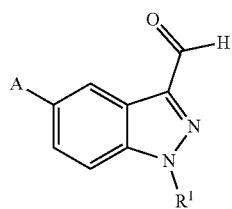

(2)

or salt thereof, wherein $R^1$ is a nitrogen protecting group, and $X^1$ is a halide or a sulfonate (e.g., —Cl, —Br, —I, or —OTf), with a boron reagent to prepare a compound of Formula (3)

(3)

or salt thereof, wherein A is selected from the group consisting of a boronic acid, a boronic ester, a boronate, a borinate, a boranate, a boranamide, an N-coordinated boronate, and a trifluoroborate;

(b) reacting the compound of Formula (3), or the salt thereof, with a compound of Formula (4)

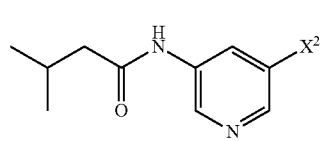

(4)

or salt thereof, wherein $X^2$ is a halide or a sulfonate (e.g., —Cl, —Br, —I, or —OTf);

to prepare a compound of Formula (5)

(5)

or a salt thereof;

(c) reacting the compound of Formula (5), or the salt thereof, with a compound of Formula (6)

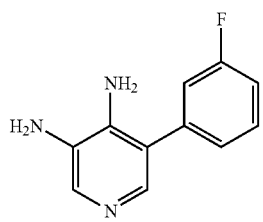

(6)

or a salt thereof, to prepare a compound of Formula (7)

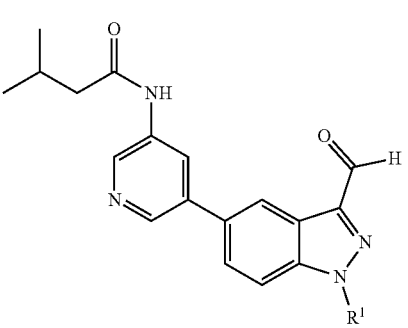

(7)

or a salt thereof; and (d) deprotecting the compound of Formula (7), or the salt thereof, to prepare the compound of Formula (1). In some embodiments, the process further comprises forming a salt of the compound of Formula (1). In some embodiments, the process further comprises forming a polymorph form of the compound of Formula (1) thereof. In some embodiments, the polymorph form of the compound of Formula (1) is Form 1. In some embodiments, the polymorph form of the compound of Formula (1) is a non-stoichiometric hydrate of polymorph Form 1 having between 1% and about 20% by weight water.

In some embodiments, a compound of Formula (1), or a salt or amorphous or polymorph form thereof, can be prepared as shown in Scheme 2, wherein $X^1$, $X^2$, A, and $R^1$ are as defined above.

Scheme 2

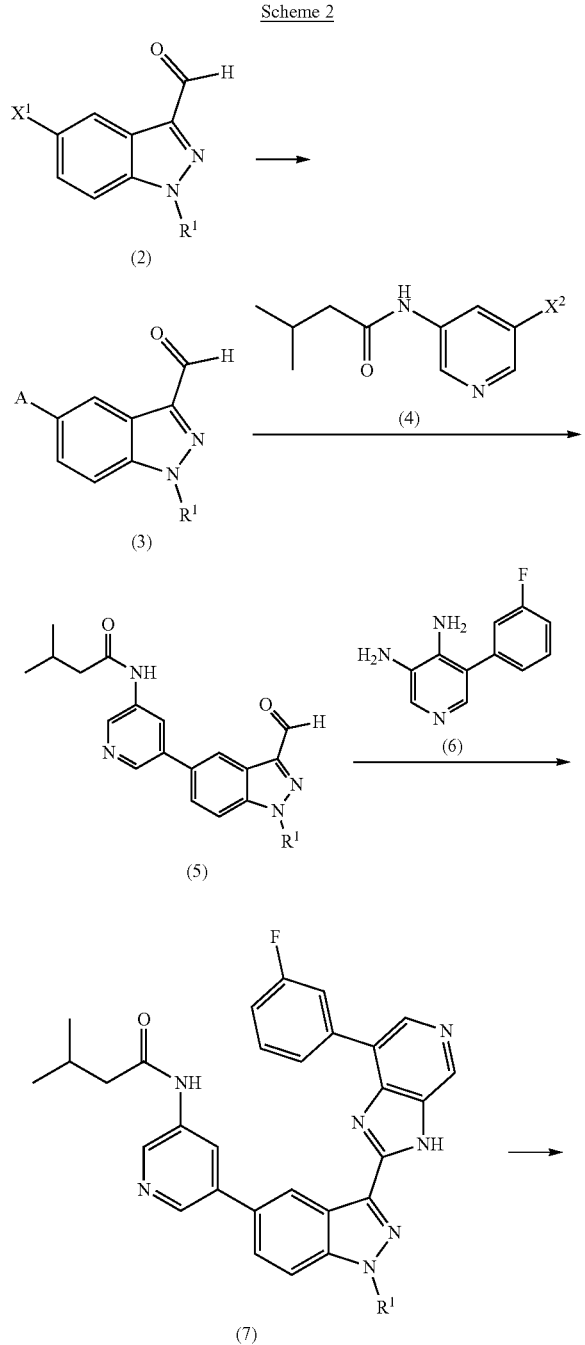

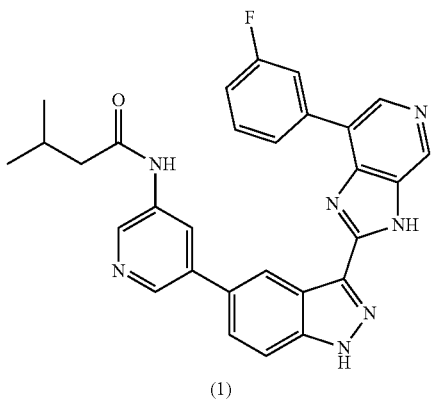

(1)

In some embodiments, the nitrogen protecting group is an acetyl, benzyl, cumyl, benzhydryl, trityl, benzyloxycarbonyl (Cbz), 9-fluorenylmethyloxycarbonyl (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tert-butyl-dimethylsilyl, triethylsilyl (TES), triisopropylsilyl, trimethylsilylethoxymethyl (SEM), t-butoxycarbonyl (BOC), t-butyl, 1-methyl-1, 1-dimethylbenzyl, (phenyl)methyl benzene, pyridinyl, and pivaloyl. In some embodiments, the nitrogen protecting group is a trityl (triphenylmethyl) group.

In some embodiments, $X^1$ is selected from the group consisting of —Cl, —Br, —I, and —OTf. In some embodiments, $X^1$ is —OTf.

In some embodiments, $X^2$ is selected from the group consisting of —Cl, —Br, —I, and —OTf. In some embodiments, $X^2$ is —OTf.

In some embodiments, the nitrogen protecting group is not a tetrahydropyran-2-yl.

In some embodiments, A is selected from the group consisting of:

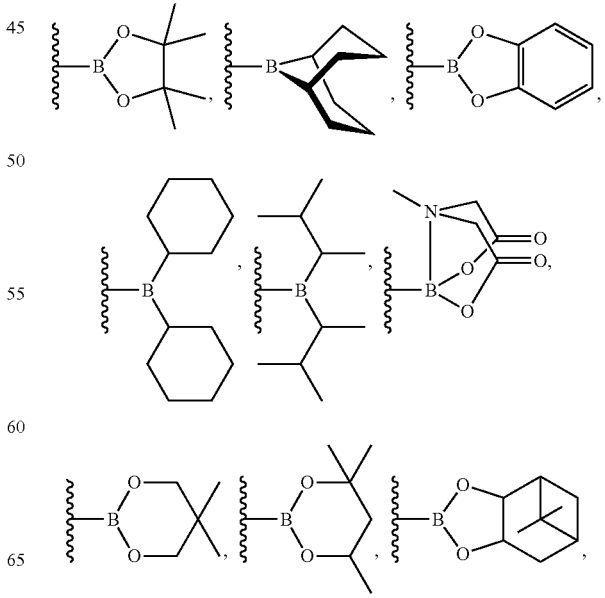

-continued

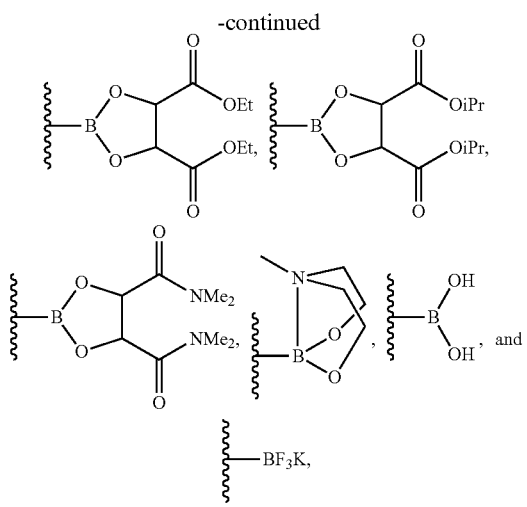

where the wavy line indicates the point of attachment of A.

In some embodiments, A is

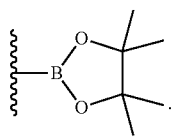 [SMILES: *B1OC(C)(C)C(C)(C)O1]

In some embodiments, $X^1$ is —Br. In some embodiments, $X^1$ is —I. In some embodiments, $X^1$ is not —I.

In some embodiments, $X^2$ is —Br. In some embodiments, $X^2$ is —I. In some embodiments, $X^2$ is not —I.

Reacting a compound of Formula (2), or a salt thereof, with the boron reagent to prepare a compound of Formula (3), or a salt thereof, can be performed in the presence of a palladium catalyst. The palladium catalyst can be a Pd(0) catalyst. In some embodiments, the palladium catalyst is selected from the group consisting of palladium(II)acetate, Pd(dppf)Cl$_2$, Pd(dba)$_2$, tetrakis(triphenylphosphine)palladium(0), (MeCN)$_2$PdCl$_2$, and tris(dibenzylideneacetone)dipalladium(0). In some embodiments, the palladium catalyst is Pd(dppf)Cl$_2$.

In some embodiments, the ratio of molar equivalents of the palladium catalyst to the compound of Formula (2) is about 0.01:1 to about 0.1:1 or about 0.02:1 to about 0.5:1. The ratio of molar equivalents of the palladium catalyst to the compound of Formula (2) can be about 0.01:1, 0.02:1, 0.03:1, 0.04:1, 0.05:1, or about 0.1:1. In some embodiments, the ratio of molar equivalents of the palladium catalyst to the compound of Formula (2) is 0.03:1.

In some embodiments, reacting a compound of Formula (2), or a salt thereof, with the boron reagent to prepare a compound of Formula (3), or a salt thereof, is performed in the presence of a polar aprotic solvent. In some embodiments, reacting a compound of Formula (2), or a salt thereof, with the boron reagent to prepare a compound of Formula (3) is performed in the presence of N,N-dimethylformamide (DMF), 1,4-dioxane, N,N-dimethylacetamide, or combinations thereof.

Reacting a compound of Formula (2), or a salt thereof, with the boron reagent to prepare a compound of Formula (3), or a salt thereof, can be performed at a temperature of about 80° C. to about 110° C., about 85° C. to about 100° C., or about 90° C. to about 95° C. For example, reacting the compound of Formula (2), or a salt thereof, with the boron reagent to prepare the compound of Formula (3), or a salt thereof, can be performed at a temperature of about 80° C., 85° C., 90° C., 95° C., 100° C., 105° C., or about 110° C. In some embodiments, reacting the compound of Formula (2), or a salt thereof, with the boron reagent to prepare the compound of Formula (3), or a salt thereof, is performed at a temperature of about 92° C.

Reacting a compound of Formula (2), or a salt thereof, with the boron reagent to prepare a compound of Formula (3) can be performed for a time of about 10 hours to about 25 hours or about 16 hours to about 20 hours. For example, reacting the compound of Formula (2), or a salt thereof, with the boron reagent to prepare the compound of Formula (3), or a salt thereof, can be performed for a time of about 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or about 25 hours. In some embodiments, the period of time is between about 15 hours and about 25 hours.

In some embodiments, reacting a compound of Formula (2), or a salt thereof, with the boron reagent to prepare a compound of Formula (3), or a salt thereof, is performed at a temperature of about 80° C. to about 110° C. for a time of about 15 hours to about 25 hours. In some embodiments, reacting the compound of Formula (2), or a salt thereof, with the boron reagent to prepare the compound of Formula (3), or a salt thereof, is performed at a temperature of about 85° C. to about 95° C. for a time of about 16 hours to about 20 hours.

Reacting a compound of Formula (3), or a salt thereof, with a compound of Formula (4), or a salt thereof, to prepare a compound of Formula (5), or a salt thereof, can be performed in the presence of a palladium catalyst. In some embodiments, a Suzuki-Miyaura cross-coupling reaction is used to prepare the compound of Formula (5), or a salt thereof, from the compound of Formula (3), or a salt thereof, and Formula (4), or a salt thereof. In some embodiments, the palladium catalyst is selected from the group consisting of PdCl$_2$(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]2, Pd(DIPHOS)$_2$, Cl$_2$Pd (Bipy), [PdCl (Ph$_2$PCH$_2$PPh$_2$)]$_2$, Cl$_2$Pd[P(o-tolyl)$_3$]$_2$, Pd$_2$ (dba)$_3$/P(o-tolyl)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Pd[P(t-Bu)$_3$]$_2$, PdCl$_2$(dppe), PdCl$_2$(dppp), PdCl$_2$[PCy$_3$]$_2$, and Cl$_2$Pd[P(4-COOH-Ph) (Ph)$_2$]$_2$. In some embodiments, the palladium catalyst is Pd(PPh$_3$)$_4$.

The ratio of molar equivalents of the palladium catalyst to the compound of Formula (3), or a salt thereof, can be about 0.01:1 to about 0.1:1 or about 0.02:1 to about 0.5:1. The ratio of molar equivalents of the palladium catalyst to the compound of Formula (3) or a salt thereof, can be about 0.01:1, 0.02:1, 0.03:1, 0.04:1, 0.05:1, or about 0.1:1. In some embodiments, the ratio of molar equivalents of the palladium catalyst to the compound of Formula (3) is 0.03:1. Reacting a compound of Formula (3), or a salt thereof, with a compound of Formula (4), or a salt thereof, can be performed in the presence of a base. In some embodiments, the base is selected from the group consisting of Na$_2$CO$_3$, Ba(OH)$_2$, K$_3$PO$_4$, Cs$_2$CO$_3$, K$_2$CO$_3$, TlOH, KF, CsF, KOtBu, NEt$_3$, Bu$_4$F, and NaOH. In some embodiments, the base is K$_3$PO$_4$. The ratio of base to the compound of Formula (4) can be about 0.5:1, 1:1, 1.5:1, 2:1, 3.0:1, 4:1 or about 5:1. In some embodiments, the ratio of base to the compound of Formula (4), or a salt thereof, is about 3.0:1.

Reacting a compound of Formula (3), or a salt thereof, with a compound of Formula (4), or a salt thereof, to prepare a compound of Formula (5), or a salt thereof, can be performed in the presence of an organic solvent. In some embodiments, the organic solvent is selected from the group consisting of toluene, dimethylsulfoxide (DMSO), dimethylformamide (DMF), acetone, acetonitrile, 1,4-dioxane, dimethylacetamide (DMA), tetrahydrofuran (THF), and dimethoxyethane, or a combination thereof. In some embodiments, reacting the compound of Formula (3), or a salt thereof, with the compound of Formula (4), or a salt thereof, to prepare the compound of Formula (5), or a salt thereof, is performed in the presence of 1,4-dioxane. In some embodiments, reacting the compound of Formula (3), or a salt thereof, with the compound of Formula (4), or a salt thereof, to prepare the compound of Formula (5), or a salt thereof, is performed in the presence 1,4-dioxane, DMA, THF, dimethoxyethane, or a combination thereof and water. In some embodiments, reacting the compound of Formula (3), or a salt thereof, with the compound of Formula (4), or a salt thereof, to prepare the compound of Formula (5), or a salt thereof, is performed in the presence of 1,4-dioxane and water.

In some embodiments, reacting a compound of Formula (3), or a salt thereof, with a compound of Formula (4), or a salt thereof, to prepare a compound of Formula (5), or a salt thereof, is performed under an inert atmosphere. For example, the inert atmosphere can be a nitrogen (N2) atmosphere or an argon atmosphere. In some embodiments, reacting the compound of Formula (3), or a salt thereof, with the compound of Formula (4), or a salt thereof, to prepare the compound of Formula (5), or a salt thereof, is performed under an N2 atmosphere.

In some embodiments, reacting the compound of Formula (3), or a salt thereof, with the compound of Formula (4), or a salt thereof, to prepare the compound of Formula (5), or a salt thereof, is performed at a temperature of about 70° C. to about 110° C., 80° C. to about 100° C., or about 85° C. to about 95° C. In some embodiments, reacting the compound of Formula (3), or a salt thereof, with the compound of Formula (4), or a salt thereof, to prepare the compound of Formula (5), or a salt thereof, is performed at a temperature of about 70° C., 80° C., 85° C., 90° C., 95° C., 100° C., or about 110° C. In some embodiments, reacting the compound of Formula (3), or a salt thereof, with the compound of Formula (4), or a salt thereof, to prepare the compound of Formula (5), or a salt thereof, is performed at a temperature of about 90° C.

In some embodiments, reacting a compound of Formula (3), or a salt thereof, with a compound of Formula (4), or a salt thereof, to prepare a compound of Formula (5), or a salt thereof, is performed for a time of about 1 hour to about 5 hours or about 2 to about 3 hours. For example, reacting the compound of Formula (3), or a salt thereof, with the compound of Formula (4), or a salt thereof, to prepare the compound of Formula (5), or a salt thereof, can be performed for a time of about 1 hour, 2 hours, 3 hours, 4 hours, or about 5 hours.

Reacting a compound of Formula (3) or a salt thereof, with a compound of Formula (4), or a salt thereof, to prepare a compound of Formula (5), or a salt thereof, can be performed at a temperature of about 80° C. to about 100° C. for a time of about 1 hour to about 5 hours. In some embodiments, reacting the compound of Formula (3), or a salt thereof, with the compound of Formula (4), or a salt thereof, to prepare the compound of Formula (5), or a salt thereof, is performed at a temperature of about 85° C. to about 95° C. for a time of about 2 hours to about 3 hours.

In some embodiments, the process further includes precipitating a compound of Formula (5), or a salt thereof, prior to reacting a compound of Formula (5), or a salt thereof, with a compound of Formula (6), or a salt thereof, to prepare a compound of Formula (7), or a salt thereof. In some embodiments, the process further includes precipitating a compound of Formula (5) in water prior to reacting a compound of Formula (5) with a compound of Formula (6), or a salt thereof, to prepare a compound of Formula (7), or a salt thereof.

In some embodiments, the process further includes preparing a salt of a compound of Formula (5) prior to reacting a compound of Formula (5), or the salt thereof, with a compound of Formula (6), or a salt thereof, to prepare a compound of Formula (7), or a salt thereof. For example, the process can further include preparing an oxalate salt, citrate salt, or acetate salt of the compound of Formula (5) prior to reacting the compound of Formula (5), or the salt thereof, with the compound of Formula (6), or a salt thereof, to prepare the compound of Formula (7), or a salt thereof. In some embodiments, the process further includes preparing an oxalate salt of the compound of Formula (5) prior to reacting the compound of Formula (5), or the salt thereof, with the compound of Formula (6), or a salt thereof, to prepare the compound of Formula (7), or a salt thereof.

In some embodiments, the process can further include preparing a free base form of a compound of Formula (5) prior to reacting a compound of Formula (5) with a compound of Formula (6), or a salt thereof, to prepare a compound of Formula (7), or a salt thereof. In some embodiments, the process further includes precipitating a compound of Formula (5), or a salt thereof, in an organic solvent prior to reacting a compound of Formula (5), or a salt thereof, with a compound of Formula (6), or a salt thereof, to prepare a compound of Formula (7), or a salt thereof. In some embodiments, the process further includes precipitating the compound of Formula (5), or a salt thereof, in a non-polar organic solvent prior to reacting the compound of Formula (5), or a salt thereof, with the compound of Formula (6), or a salt thereof, to prepare the compound of Formula (7), or a salt thereof. In some embodiments, the non-polar organic solvent is an aromatic hydrocarbon, such as benzene, toluene and xylene, or an aliphatic organic solvent, such as hexane, heptane and octane. In some embodiments, the process further includes precipitating the compound of Formula (5), or a salt thereof, in n-heptane prior to reacting the compound of Formula (5), or a salt thereof, with the compound of Formula (6), or a salt thereof, to prepare the compound of Formula (7), or a salt thereof.

In some embodiments, prior to reacting a compound of Formula (5), or a salt thereof, with a compound of Formula (6), or a salt thereof, to prepare a compound of Formula (7), or a salt thereof, the process further includes one or more of: (a) precipitating the compound of Formula (5); (b) preparing a salt of the compound of Formula (5) from the precipitated compound of Formula (5); (c) preparing a free base form of the compound of Formula (5) from the salt of the compound of Formula (5); and (d) precipitating the free base form of the compound of Formula (5).

In some embodiments, prior to reacting a compound of Formula (5), or a salt thereof, with a compound of Formula (6), or a salt thereof, to prepare a compound of Formula (7), or a salt thereof, the process further includes one or more of: (a) precipitating the compound of Formula (5) in water; (b) preparing an oxalate salt, a citrate salt, or an acetate salt of the compound of Formula (5) from the precipitated compound of Formula (5); (c) preparing a free base form of the compound of Formula (5) from the salt of the compound of Formula (5); and (d) precipitating the free base form of the compound of Formula (5) in a non-polar organic solvent. In some embodiments, the non-polar organic solvent is an aliphatic organic solvent. In some embodiments, the aliphatic organic solvent is selected from the group consisting of hexane, heptane and octane.

In some embodiments, prior to reacting a compound of Formula (5), or a salt thereof, with the compound of Formula (6), or a salt thereof, to prepare a compound of Formula (7), or a salt thereof, the process further includes one or more of: (a) precipitating the compound of Formula (5) in water; (b) preparing an oxalate salt of the compound of Formula (5) from the precipitated compound of Formula (5); (c) preparing a free base form of the compound of Formula (5) from the salt of the compound of Formula (5); and (d) precipitating the free base form of the compound of Formula (5) in n-heptane.

In some embodiments, a compound of Formula (5), or a salt thereof, is isolated prior to preparing a compound of Formula (7), or a salt thereof. In some embodiments, a compound of Formula (5), or a salt thereof, is isolated with a purity of greater than about 90%, 92%, 94%, 96%, 98%, or greater than about 99%. In some embodiments, the compound of Formula (5), or a salt thereof, can be isolated with a purity of greater than about 98%. In some embodiments, the purity is determined by chromatography. In some embodiments, the purity is determined by high-performance liquid chromatography (HPLC) analysis.

Reacting a compound of Formula (5), or a salt thereof, with a compound of Formula (6), or a salt thereof, to prepare a compound of Formula (7), or a salt thereof, can be performed in the presence of $Na_2SO_3$, elemental sulfur, or a combination thereof. In some embodiments, reacting a compound of Formula (5), or a salt thereof, with a compound of Formula (6), or a salt thereof, to prepare a compound of Formula (7), or a salt thereof, is performed in the presence of $Na_2SO_3$. The $Na_2SO_3$ can be ground $Na_2SO_3$. For example, the ground $Na_2SO_3$ can have a particle size of about 100 microns to about 300 microns. In some embodiments, the ground $Na_2SO_3$ has a particle size of about 150 microns to about 250 microns. In some embodiments, reacting the compound of Formula (5), or a salt thereof, with the compound of Formula (6), or a salt thereof, to prepare the compound of Formula (7), or a salt thereof, is performed in the presence of $SO_2$.

Reacting a compound of Formula (5), or a salt thereof, with a compound of Formula (6), or a salt thereof, to prepare a compound of Formula (7), or a salt thereof, can be performed in the presence of an organic solvent. In some embodiments, the organic solvent is selected from the group consisting of N-methyl-2-pyrrolidone, dimethylacetamide, n-butanol, or a combination thereof. In some embodiments, reacting the compound of Formula (5), or a salt thereof, with the compound of Formula (6), or a salt thereof, to prepare the compound of Formula (7), or a salt thereof, is performed in the presence of N-methyl-2-pyrrolidone.

In some embodiments, reacting a compound of Formula (5), or a salt thereof, with a compound of Formula (6), or a salt thereof, to prepare a compound of Formula (7), or a salt thereof, is performed under an inert atmosphere. For example, the inert atmosphere can be a nitrogen (N2) atmosphere or an argon atmosphere. In some embodiments, reacting the compound of Formula (5), or a salt thereof, with the compound of Formula (6), or a salt thereof, to prepare the compound of Formula (7), or a salt thereof, is performed under an N2 atmosphere.

In some embodiments, reacting a compound of Formula (5), or a salt thereof, with a compound of Formula (6), or a salt thereof, to prepare a compound of Formula (7), or a salt thereof, is performed at a temperature of about 75° C. to about 150° C., about 100° C. to about 120° C., or about 110° C. to about 115° C. For example, reacting the compound of Formula (5), or a salt thereof, with the compound of Formula (6), or a salt thereof, to prepare the compound of Formula (7), or a salt thereof, can be performed at a temperature of about 100° C., 105° C., 110° C., 115° C., or about 120° C.

In some embodiments, reacting a compound of Formula (5), or a salt thereof, with a compound of Formula (6), or a salt thereof, to prepare a compound of Formula (7), or a salt thereof, is performed for a time of about 5 hours to about 10 hours or about 7 hours to about 9 hours. For example, reacting the compound of Formula (5), or a salt thereof, with the compound of Formula (6), or a salt thereof, to prepare the compound of Formula (7), or a salt thereof, can be performed for a time of about 5 hours, 6 hours, 7 hours, 8 hours, 9 hours, or about 10 hours.

Reacting the compound of Formula (5), or a salt thereof, with a compound of Formula (6), or a salt thereof, to prepare a compound of Formula (7), or a salt thereof, can be performed at a temperature of about 75° C. to about 150° C., such as about 100° C. to about 120° C., for a time of about 5 hours to about 10 hours. In some embodiments, reacting the compound of Formula (5), or a salt thereof, with the compound of Formula (6), or a salt thereof, to prepare the compound of Formula (7), or a salt thereof, is performed at a temperature of about 110° C. to about 115° C. for a time of about 7 hours to about 9 hours.

In some embodiments, the process further includes preparing a salt of a compound of Formula (7) prior to deprotecting a compound of Formula (7), or the salt thereof, to prepare the compound of Formula (1), or a salt thereof. For example, the process can further include preparing an oxalate salt, a citrate salt, or an acetate salt of the compound of Formula (7) prior to deprotecting the compound of Formula (7), or the salt thereof, to prepare the compound of Formula (1), or a salt thereof. In some embodiments, the process further includes preparing an oxalate salt of the compound of Formula (7) prior to deprotecting the compound of Formula (7), or the salt thereof, to prepare the compound of Formula (1), or a salt or amorphous or polymorph form thereof.

In some embodiments, the process further includes preparing a free base form of a compound of Formula (7) prior to deprotecting a compound of Formula (7), or a salt thereof, to prepare the compound of Formula (1), or a salt or amorphous or polymorph form thereof.

In some embodiments, the process further includes precipitating a compound of Formula (7), or a salt thereof, prior to deprotecting a compound of Formula (7), or a salt thereof, to prepare the compound of Formula (1), or a salt thereof. In some embodiments, the process further includes precipitating a compound of Formula (7), or a salt thereof, in an organic solvent prior to deprotecting a compound of Formula (7), or a salt thereof, to prepare the compound of Formula (1), or a salt or amorphous or polymorph form thereof. For example, the process can further include precipitating the compound of Formula (7), or a salt thereof, in a non-polar organic solvent prior to deprotecting the compound of Formula (7), or a salt thereof, to prepare the compound of Formula (1), or a salt or amorphous or polymorph form thereof. In some embodiments, the non-polar organic solvent is an aromatic hydrocarbon, such as benzene, toluene and xylene, or an aliphatic organic solvent, such as hexane, heptane and octane. In some embodiments, the process further includes precipitating the compound of Formula (7), or a salt thereof, in n-heptane prior to deprotecting the compound of Formula (7), or a salt thereof, to prepare the compound of Formula (1), or a salt or amorphous or polymorph form thereof.

In some embodiments, prior to deprotecting the compound of Formula (7), or a salt thereof, to prepare the compound of Formula (1), or a salt or amorphous or polymorph form thereof, the process further includes one or more of: (a) preparing a salt of the compound of Formula (7); (b) preparing a free base form of the compound of Formula (7) from the salt of the compound of Formula (7); and (c) precipitating the free base form compound of Formula (7) in a non-polar organic solvent.

In some embodiments, prior to deprotecting the compound of Formula (7), or a salt thereof, to prepare the compound of Formula (1), or a salt or amorphous or polymorph form thereof, the process further includes one or more of: (a) preparing an oxalate salt, a citrate salt, or an acetate salt of the compound of Formula (7); (b) preparing a free base form of the compound of Formula (7) from the salt of the compound of Formula (7); and (c) precipitating the free base form of the compound of Formula (7) in an aliphatic organic solvent, such as hexane, heptane and octane.

In some embodiments, prior to deprotecting the compound of Formula (7), or a salt thereof, to prepare the compound of Formula (1), or a salt or amorphous or polymorph form thereof, the process further includes one or more of: (a) preparing an oxalate salt of the compound of Formula (7); (b) preparing a free base form of the compound of Formula (7) from the oxalate salt of the compound of Formula (7); and (c) precipitating the free base form compound of Formula (7) in n-heptane.

In some embodiments, the compound of Formula (7), or a salt thereof, is isolated prior to preparing the compound of Formula (1), or a salt or amorphous or polymorph form thereof. In some embodiments, the compound of Formula (7), or a salt thereof, is isolated with a purity of greater than about 90%, 92%, 94%, 96%, 98%, or greater than about 99%. In some embodiments, the compound of Formula (7), or a salt thereof, is isolated with a purity of greater than about 99%. In some embodiments, the purity is determined by chromatography. In some embodiments, the purity is determined by high-performance liquid chromatography (HPLC) analysis.

Also provided herein is a process for preparing a compound of Formula (1):

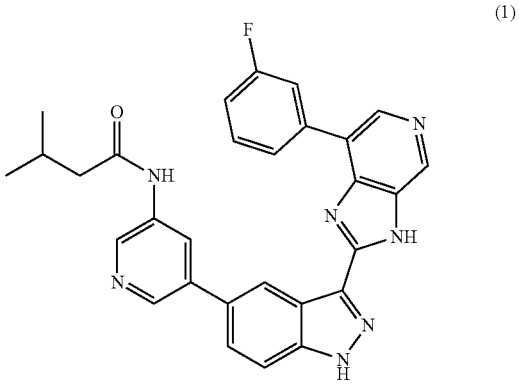 [SMILES: CC(C)CC(=O)Nc1cncc(-c2ccc3[nH]nc(-c4nc5c(-c6cccc(F)c6)cncc5[nH]4)c3c2)c1]

(1)

including salts and amorphous and polymorph forms thereof. The process includes:

(a) reacting a compound of Formula (8)

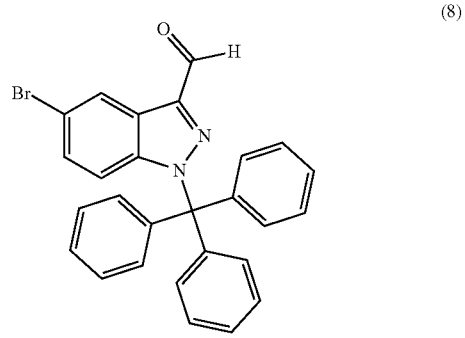 [SMILES: O=Cc1nn(C(c2ccccc2)(c2ccccc2)c2ccccc2)c2ccc(Br)cc12]

(8)

or a salt thereof, with bis(pinacolato)diboron to produce a compound of Formula (9)

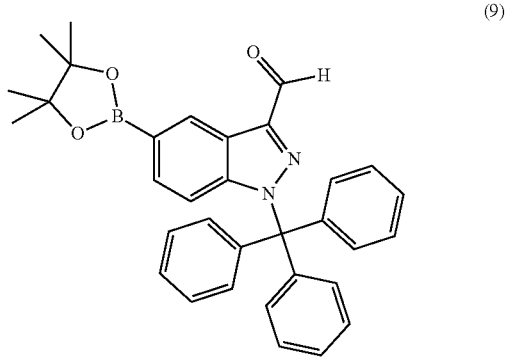 [SMILES: CC1(C)OB(c2ccc3c(c2)c(C=O)nn3C(c2ccccc2)(c2ccccc2)c2ccccc2)OC1(C)C]

(9)

or a salt thereof;

(b) reacting the compound of Formula (9), or the salt thereof, with a compound of Formula (10)

(10)
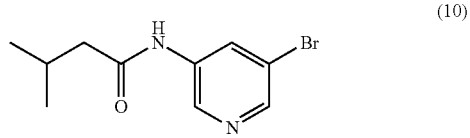

or a salt thereof, to prepare a compound of Formula (11)

(11)
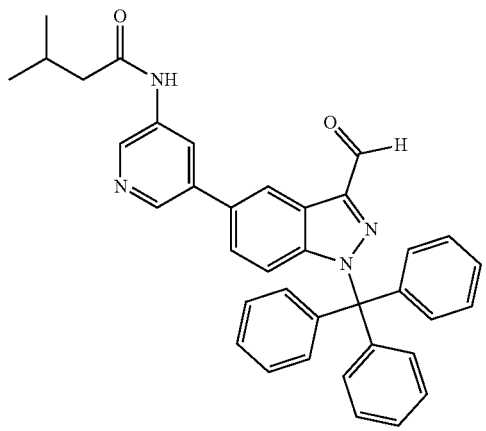

or a salt thereof;

(c) reacting the compound of Formula (11), or the salt thereof, with a compound of Formula (6)

(6)
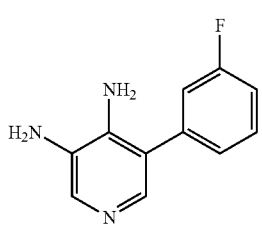

or a salt thereof, to prepare a compound of Formula (12)

(12)
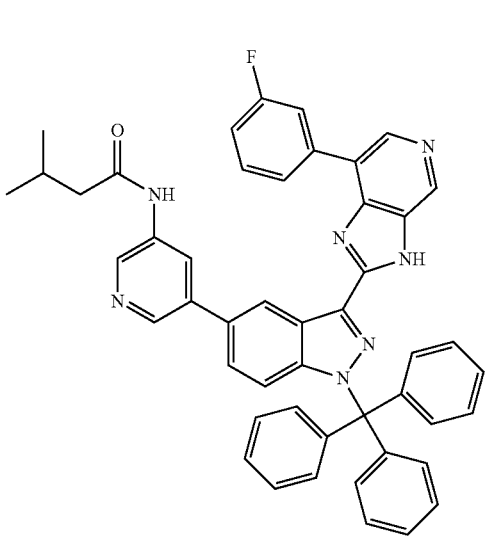

or a salt thereof; and (d) deprotecting the compound of Formula (12), or the salt thereof, to prepare the compound of Formula (1), or a salt or amorphous or polymorph form thereof.

In some embodiments, a compound of Formula (1), or a salt or amorphous or polymorph form thereof, is prepared as shown in Scheme 3.

Scheme 3

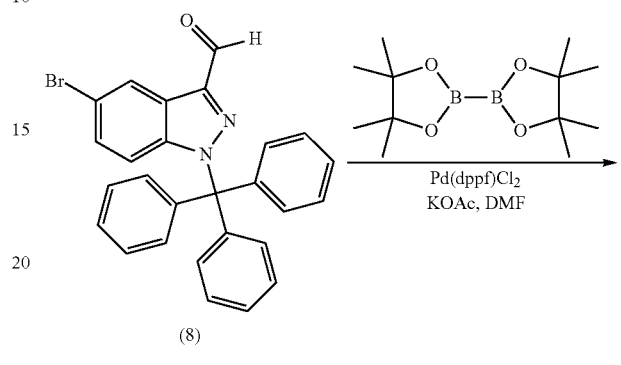

(8)

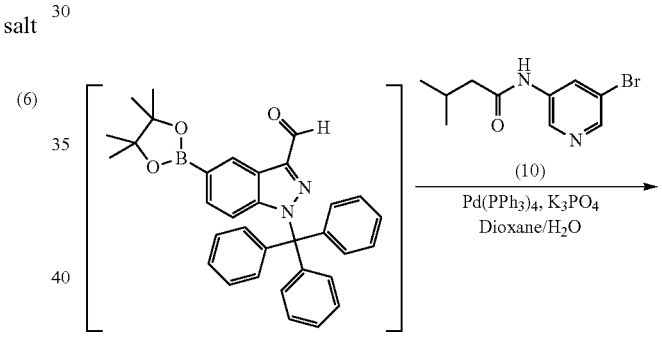

(9)

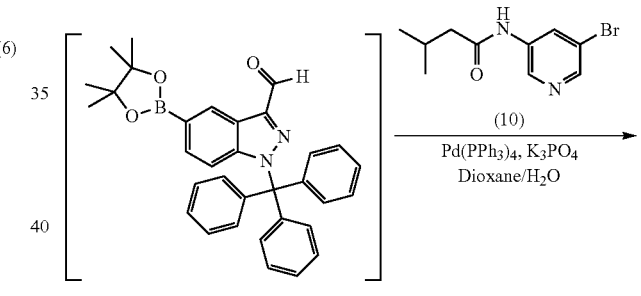

(11)

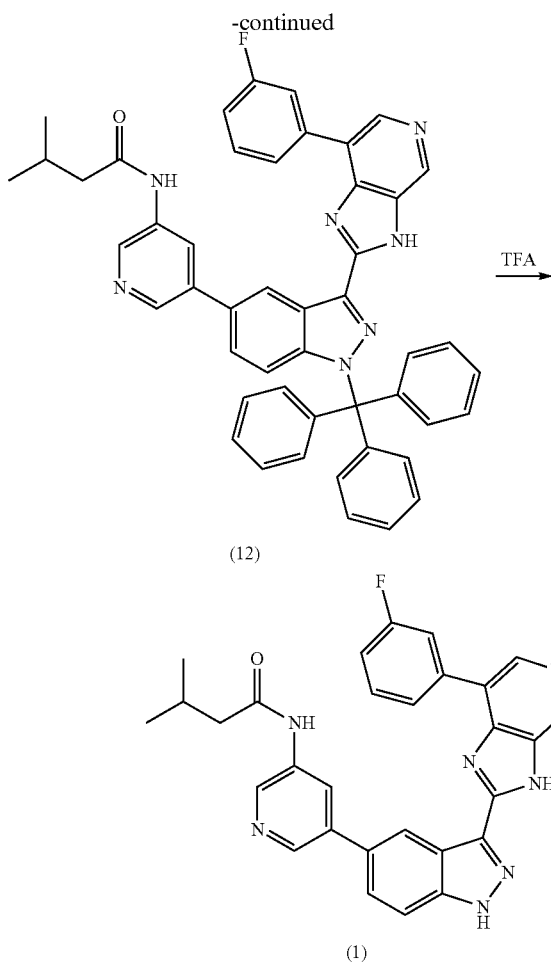

(12)

(1)

In some embodiments, reacting the compound of Formula (8), or a salt thereof, with the boron reagent to prepare the compound of Formula (9), or a salt thereof, is performed in the presence of a palladium catalyst. The palladium catalyst can be selected from the group consisting of palladium(II) acetate, Pd(dppf)Cl$_2$, Pd(dba)$_2$, tetrakis(triphenylphosphine)palladium(0), (MeCN)$_2$PdCl$_2$, and tris(dibenzylideneacetone)dipalladium(0). In some embodiments, the palladium catalyst is Pd(dppf)Cl$_2$.

The ratio of molar equivalents of the palladium catalyst to the compound of Formula (8), or a salt thereof, can be about 0.01:1 to about 0.1:1 or about 0.02:1 to about 0.5:1. The ratio of molar equivalents of the palladium catalyst to the compound of Formula (8), or a salt thereof, can be about 0.01:1, 0.02:1, 0.03:1, 0.04:1, 0.05:1, or about 0.1:1. In some embodiments, the ratio of molar equivalents of the palladium catalyst to the compound of Formula (8), or a salt thereof, is 0.03:1.

Reacting the compound of Formula (8), or a salt thereof, with the boron reagent to prepare the compound of Formula (9), or a salt thereof, can be performed at a temperature of about 80° C. to about 110° C., about 85° C. to about 100° C., or about 90° C. to about 95° C. For example, reacting the compound of Formula (8), or a salt thereof, with the boron reagent to prepare the compound of Formula (9), or a salt thereof, can be performed at a temperature of about 80° C., 85° C., 90° C., 95° C., 100° C., 105° C., or about 110° C. In some embodiments, reacting the compound of Formula (8), or a salt thereof, with the boron reagent to prepare the compound of Formula (9), or a salt thereof, is performed at a temperature of about 92° C.

Reacting the compound of Formula (8), or a salt thereof, with the boron reagent to prepare the compound of Formula (9), or a salt thereof, can be performed for a time of about 15 hours to about 25 hours or about 16 hours to about 20 hours. For example, reacting the compound of Formula (8), or a salt thereof, with the boron reagent to prepare the compound of Formula (9), or a salt thereof, can be performed for a time of about 15 hours, 16 hours, 17 hours, 18 hours, 19 hours, 20 hours, 21 hours, 22 hours, 23 hours, 24 hours, or about 25 hours.

In some embodiments, reacting the compound of Formula (8), or a salt thereof, with the boron reagent to prepare the compound of Formula (9), or a salt thereof, is performed at a temperature of about 80° C. to about 110° C. for a time of about 15 hours to about 25 hours. In some embodiments, reacting the compound of Formula (8), or a salt thereof, with the boron reagent to prepare the compound of Formula (9), or a salt thereof, is performed at a temperature of about 85° C. to about 95° C. for a time of about 16 hours to about 20 hours.

Reacting the compound of Formula (9), or a salt thereof, with the compound of Formula (10), or a salt thereof, to prepare the compound of Formula (11), or a salt thereof, can be performed in the presence of a palladium catalyst. In some embodiments, a Suzuki-Miyaura cross-coupling reaction is used to prepare the compound of Formula (11), or a salt thereof, from the compounds of Formula (9), or a salt thereof, and Formula (10), or a salt thereof. In some embodiments, the palladium catalyst is selected from the group consisting of PdCl$_2$(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]2, Pd(DIPHOS)$_2$, Cl$_2$Pd(Bipy), [PdCl (Ph$_2$PCH$_2$PPh$_2$)]$_2$, Cl$_2$Pd[P(o-tolyl)$_3$]$_2$, Pd$_2$(dba)$_3$/P(o-tolyl)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Pd[P(t-Bu)$_3$]$_2$, PdCl$_2$(dppe), PdCl$_2$(dppp), PdCl$_2$[PCy$_3$]$_2$, and Cl$_2$Pd[P(4-COOH-Ph)(Ph)$_2$]$_2$. In some embodiments, the palladium catalyst is Pd(PPh$_3$)$_4$.

The ratio of molar equivalents of the palladium catalyst to the compound of Formula (9), or a salt thereof, can be about 0.01:1 to about 0.1:1 or about 0.02:1 to about 0.5:1. The ratio of molar equivalents of the palladium catalyst to the compound of Formula (9), or a salt thereof, can be about 0.01:1, 0.02:1, 0.03:1, 0.04:1, 0.05:1, or about 0.1:1. In some embodiments, the ratio of molar equivalents of the palladium catalyst to the compound of Formula (9), or a salt thereof, is 0.03:1.

In some embodiments, reacting the compound of Formula (9), or a salt thereof, with the compound of Formula (10), or a salt thereof, to prepare the compound of Formula (11), or a salt thereof, is performed in the presence of a base. The base can be selected from the group consisting of Na$_2$CO$_3$, Ba(OH)$_2$, K$_3$PO$_4$, Cs$_2$CO$_3$, K$_2$CO$_3$, TlOH, KF, CsF, Bu$_4$F, and NaOH. In some embodiments, the base is K$_3$PO$_4$.

Reacting the compound of Formula (9), or a salt thereof, with the compound of Formula (10), or a salt thereof, to prepare the compound of Formula (11), or a salt thereof, can be performed in the presence of an organic solvent. For example, the organic solvent can be toluene, dimethylsulfoxide (DMSO), dimethylformamide (DMF), acetone, acetonitrile, 1,4-dioxane, dimethylacetamide (DMA), tetrahydrofuran (THF), dimethoxyethane, or a combination thereof. In some embodiments, reacting the compound of Formula (9), or a salt thereof, with the compound of Formula (10), or a salt thereof, to prepare the compound of Formula (11), or a salt thereof, is performed in the presence of 1,4-dioxane. In some embodiments, reacting the compound of Formula (9), or a salt thereof, with the compound of Formula (10), or a salt thereof, to prepare the compound of Formula (11), or a salt thereof, is performed in the presence 1,4-dioxane, DMA, THF, dimethoxyethane, or a combination thereof and water. In some embodiments, reacting the compound of Formula (9), or a salt thereof, with the compound of Formula (10), or a salt thereof, to prepare the compound of Formula (11), or a salt thereof, is performed in the presence of 1,4-dioxane and water.

In some embodiments, reacting the compound of Formula (9), or a salt thereof, with the compound of Formula (10), or a salt thereof, to prepare the compound of Formula (11), or a salt thereof, is performed under an inert atmosphere. For example, the inert atmosphere can be a nitrogen (N2) atmosphere or an argon atmosphere. In some embodiments, reacting the compound of Formula (9), or a salt thereof, with the compound of Formula (10), or a salt thereof, to prepare the compound of Formula (11), or a salt thereof, is performed under a N2 atmosphere.

In some embodiments, reacting the compound of Formula (9), or a salt thereof, with the compound of Formula (10), or a salt thereof, to prepare the compound of Formula (11), or a salt thereof, is performed at a temperature of about 70° C. to about 110° C., 80° C. to about 100° C., or about 85° C. to about 95° C. For example, reacting the compound of Formula (9), or a salt thereof, with the compound of Formula (10), or a salt thereof, to prepare the compound of Formula (11), or a salt thereof, can be performed at a temperature of about 70° C., 80° C., 85° C., 90° C., 95° C., 100° C., or about 110° C. In some embodiments, reacting the compound of Formula (9), or a salt thereof, with the compound of Formula (10), or a salt thereof, to prepare the compound of Formula (11), or a salt thereof, is performed at a temperature of about 90° C.

Reacting the compound of Formula (9), or a salt thereof, with the compound of Formula (10), or a salt thereof, to prepare the compound of Formula (11), or a salt thereof, can be performed at a temperature of about 80° C. to about 100° C. for a time of about 1 hour to about 5 hours. In some embodiments, reacting the compound of Formula (9), or a salt thereof, with the compound of Formula (10), or a salt thereof, to prepare the compound of Formula (11), or a salt thereof, is performed at a temperature of about 85° C. to about 95° C. for a time of about 2 hours to about 3 hours.

In some embodiments, reacting the compound of Formula (9), or a salt thereof, with the compound of Formula (10), or a salt thereof, to prepare the compound of Formula (11), or a salt thereof, is performed in the presence of a palladium catalyst and a base; under an inert atmosphere; and performed at a temperature of about 85° C. to about 95° C. for a time of about 2 hours to about 3 hours.

In some embodiments, the process further includes precipitating the compound of Formula (11) in water prior to reacting the compound of Formula (11), or a salt thereof, with the compound of Formula (6), or a salt thereof, to prepare the compound of Formula (12), or a salt thereof.

In some embodiments, the process further includes preparing a salt of the compound of Formula (11) prior to reacting the compound of Formula (11), or the salt thereof, with the compound of Formula (6), or a salt thereof, to prepare the compound of Formula (12), or a salt thereof. For example, the process can further include preparing an oxalate salt, citrate salt, or acetate salt of the compound of Formula (11) prior to reacting the compound of Formula (11), or the salt thereof, with the compound of Formula (6), or a salt thereof, to prepare the compound of Formula (12), or a salt thereof. In some embodiments, the process further includes preparing an oxalate salt of the compound of Formula (11), or a salt thereof, prior to reacting the compound of Formula (11), or a salt thereof, with the compound of Formula (6), or a salt thereof, to prepare the compound of Formula (12), or a salt thereof.

In some embodiments, the process further includes preparing a free base form of the compound of Formula (11) prior to reacting the compound of Formula (11) with the compound of Formula (6), or a salt thereof, to prepare the compound of Formula (12), or a salt thereof.

In some embodiments, the process further includes precipitating the compound of Formula (11), or a salt thereof, in an organic solvent prior to reacting the compound of Formula (11), or a salt thereof, with the compound of Formula (6), or a salt thereof, to prepare the compound of Formula (12), or a salt thereof. For example, the process can further include precipitating the compound of Formula (11), or a salt thereof, in a non-polar organic solvent prior to reacting the compound of Formula (11), or a salt thereof, with the compound of Formula (6), or a salt thereof, to prepare the compound of Formula (12), or a salt thereof. In some embodiments, the non-polar organic solvent is an aromatic hydrocarbon, such as benzene, toluene and xylene, or an aliphatic organic solvent, such as hexane, heptane and octane. In some embodiments, the process further includes precipitating the compound of Formula (11), or a salt thereof, in n-heptane prior to reacting the compound of Formula (11), or a salt thereof, with the compound of Formula (6), or a salt thereof, to prepare the compound of Formula (12), or a salt thereof.

In some embodiments, prior to reacting the compound of Formula (11), or a salt thereof, with the compound of Formula (6), or a salt thereof, to prepare the compound of Formula (12), or a salt thereof, the process further includes one or more of: (a) precipitating the compound of Formula (11) in water; (b) preparing a salt of the compound of Formula (11) from the precipitated compound of Formula (11); (c) preparing a free base form of the compound of Formula (11) from the salt of the compound of Formula (11); and (d) precipitating the free base form of the compound of Formula (11) in a non-polar organic solvent prior to reacting the compound of Formula (11) with the compound of Formula (6), or a salt thereof, to prepare the compound of Formula (12), or a salt thereof.

In some embodiments, prior to reacting the compound of Formula (11), or a salt thereof, with the compound of Formula (6), or a salt thereof, to prepare the compound of Formula (12), or a salt thereof, the process further includes one or more of (a) precipitating the compound of Formula (11) in water; (b) preparing an oxalate salt of the compound of Formula (11) from the precipitated compound of Formula (11); (c) preparing a free base form of the compound of Formula (11) from the salt of the compound of Formula (11); and (d) precipitating the free base form of the compound of Formula (11) in n-heptane.

In some embodiments, the compound of Formula (11), or a salt thereof, is isolated prior to preparing the compound of Formula (11), or a salt thereof. In some embodiments, the compound of Formula (11), or a salt thereof, is isolated with a purity of greater than about 90%, 92%, 94%, 96%, 98%, or greater than about 99%. In some embodiments, the compound of Formula (11), or a salt thereof, is isolated with a purity of greater than about 98%. In some embodiments, the purity is determined by chromatography. In some embodiments, the purity is determined by high-performance liquid chromatography (HPLC) analysis.

Reacting the compound of Formula (11), or a salt thereof, with the compound of Formula (6), or a salt thereof, to prepare the compound of Formula (12), or a salt thereof, can be performed in the presence of $Na_2SO_3$, elemental sulfur, or a combination thereof. In some embodiments, reacting the compound of Formula (11), or a salt thereof, with the compound of Formula (6), or a salt thereof, to prepare the compound of Formula (12), or a salt thereof, is performed in the presence of $Na_2SO_3$. The $Na_2SO_3$ can be ground $Na_2SO_3$. For example, the ground $Na_2SO_3$ can have a particle size of about 100 microns to about 300 microns or about 150 microns to about 250 microns. In some embodiments, the ground $Na_2SO_3$ has a particle size of about 150 microns to about 250 microns. In some embodiments, reacting the compound of Formula (11), or a salt thereof, with the compound of Formula (6), or a salt thereof, to prepare the compound of Formula (12), or a salt thereof, is performed in the presence of $SO_2$.

Reacting the compound of Formula (11), or a salt thereof, with the compound of Formula (6), or a salt thereof, to prepare the compound of Formula (12), or a salt thereof, can be performed in the presence of an organic solvent. In some embodiments, the organic solvent is N-methyl-2-pyrrolidone, dimethylacetamide, n-butanol, or a combination thereof. In some embodiments, reacting the compound of Formula (11), or a salt thereof, with the compound of Formula (6), or a salt thereof, to prepare the compound of Formula (12), or a salt thereof, is performed in the presence of N-methyl-2-pyrrolidone.

In some embodiments, reacting the compound of Formula (11), or a salt thereof, with the compound of Formula (6), or a salt thereof, to prepare the compound of Formula (12), or a salt thereof, is performed under an inert atmosphere. For example, the inert atmosphere can be a nitrogen (N2) atmosphere or an argon atmosphere. In some embodiments, reacting the compound of Formula (11), or a salt thereof, with the compound of Formula (6), or a salt thereof, to prepare the compound of Formula (12), or a salt thereof, is performed under an N2 atmosphere.

In some embodiments, reacting the compound of Formula (11), or a salt thereof, with the compound of Formula (6), or a salt thereof, to prepare the compound of Formula (12), or a salt thereof, is performed at a temperature of about 100° C. to about 120° C. or about 110° C. to about 115° C. For example, reacting the compound of Formula (11), or a salt thereof, with the compound of Formula (6), or a salt thereof, to prepare the compound of Formula (12), or a salt thereof, can be performed at a temperature of about 100° C., 105° C., 110° C., 115° C., or about 120° C.

In some embodiments, reacting the compound of Formula (11), or a salt thereof, with the compound of Formula (6), or a salt thereof, to prepare the compound of Formula (12), or a salt thereof, is performed for a time of about 5 hours to about 10 hours or about 7 hours to about 9 hours. For example, reacting the compound of Formula (11), or a salt thereof, with the compound of Formula (6), or a salt thereof, to prepare the compound of Formula (12), or a salt thereof, can be performed for a time of about 5 hours, 6 hours, 7 hours, 8 hours, 9 hours, or about 10 hours.

Reacting the compound of Formula (11), or a salt thereof, with the compound of Formula (6), or a salt thereof, to prepare the compound of Formula (12), or a salt thereof, can be performed at a temperature of about 75° C. to about 150° C., such as 100° C. to about 120° C., for a time of about 5 hours to about 10 hours. In some embodiments, reacting the compound of Formula (11), or a salt thereof, with the compound of Formula (6), or a salt thereof, to prepare the compound of Formula (12), or a salt thereof, is performed at a temperature of about 110° C. to about 115° C. for a time of about 7 hours to about 9 hours.

In some embodiments, the process further includes preparing a salt of the compound of Formula (12) prior to deprotecting the compound of Formula (12), or the salt thereof, to prepare the compound of Formula (1), or a salt thereof. For example, the process can further include preparing an oxalate salt, a citrate salt, or an acetate salt of the compound of Formula (12) prior to deprotecting the compound of Formula (12), or the salt thereof, to prepare the compound of Formula (1), or a salt or amorphous or polymorph form thereof. In some embodiments, the process further includes preparing an oxalate salt of the compound of Formula (12) prior to deprotecting the compound of Formula (12), or the salt thereof, to prepare the compound of Formula (1), or a salt or amorphous or polymorph form thereof.

In some embodiments, the process further includes preparing a free base form of the compound of Formula (12) prior to deprotecting the compound of Formula (12) to prepare the compound of Formula (1), or a salt or amorphous or polymorph form thereof.

In some embodiments, the process further includes precipitating the compound of Formula (12), or a salt thereof, in an organic solvent prior to deprotecting the compound of Formula (12), or a salt thereof, to prepare the compound of Formula (1), or a salt or amorphous or polymorph form thereof. For example, the process can further include precipitating the compound of Formula (12), or a salt thereof, in an organic solvent prior to deprotecting the compound of Formula (12), or a salt thereof, to prepare the compound of Formula (1), or a salt or amorphous or polymorph form thereof. In some embodiments, the process further includes precipitating the compound of Formula (12), or a salt thereof, in n-heptane prior to deprotecting the compound of Formula (12), or a salt thereof, to prepare the compound of Formula (1), or a salt or amorphous or polymorph form thereof.

In some embodiments, prior to deprotecting the compound of Formula (12), or a salt thereof, to prepare the compound of Formula (1), or a salt or amorphous or polymorph form thereof, the process further includes one or more of: (a) preparing a salt of the compound of Formula (12); (b) preparing a free base form of the compound of Formula (12) from the salt of the compound of Formula (12); and (c) precipitating the free base form compound of Formula (12) in a non-polar organic solvent.

In some embodiments, prior to deprotecting the compound of Formula (12), or a salt thereof, to prepare the compound of Formula (1), or a salt or amorphous or polymorph form thereof, the process further includes one or more of: (a) preparing an oxalate salt of the compound of Formula (12); (b) preparing a free base form of the compound of Formula (12) from the oxalate salt of the compound of Formula (12); and (c) precipitating the free base form compound of Formula (12) in n-heptane.

In some embodiments, the compound of Formula (12), or a salt thereof, is isolated prior to preparing the compound of Formula (1), or a salt or amorphous or polymorph form thereof. In some embodiments, the compound of Formula (12) or a salt thereof, is isolated with a purity of greater than about 90%, 92%, 94%, 96%, 98%, or greater than about 99%. In some embodiments, the compound of Formula (12), or a salt thereof, is isolated with a purity of greater than about 99%. In some embodiments, the purity is determined by chromatography. In some embodiments, the purity is determined by high-performance liquid chromatography (HPLC) analysis.

In some embodiments, the process further includes preparing the compound of Formula (8), or a salt thereof, by a process including protecting the compound (14)

(14)

or a salt thereof, with a trityl group. The process can further include preparing compound (14) from compound (13)

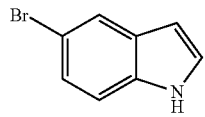
(13)

or a salt thereof, by reacting compound (13) with sodium nitrite to prepare the compound of Formula (14)

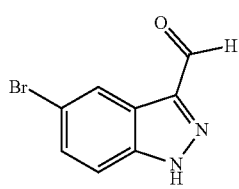
(14)

or a salt thereof.

In some embodiments, the process further includes preparing the compound of Formula (8), or a salt thereof, by a process including: (i) reacting a compound of Formula (13)

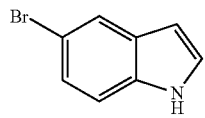
(13)

or a salt thereof, with a nitrite to prepare the compound of Formula (14)

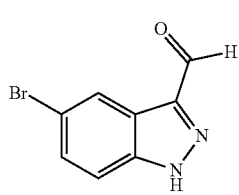
(14)

or a salt thereof; and (ii) protecting the compound of Formula (14), or the salt thereof, with a trityl group to prepare the compound of Formula (8), or the salt thereof. In some embodiments, the nitrite is selected from the group consisting of sodium nitrite, silver nitrite, calcium nitrite, and potassium nitrite.

For example, a compound of Formula (8), or a salt thereof, can be prepared as shown in Scheme 4.

Scheme 4

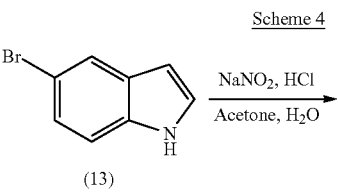
(13)

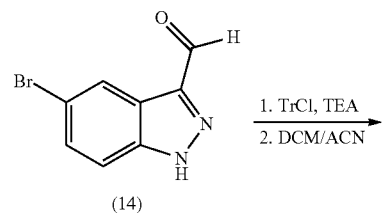
(14)

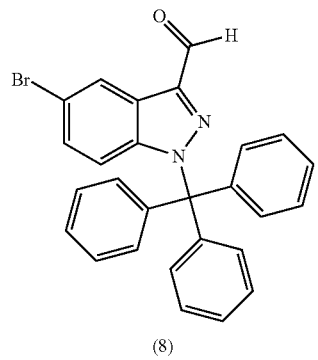
(8)

In some embodiments, the process further includes preparing the compound of Formula (10) by a process including: (i) reacting a compound of Formula (15)

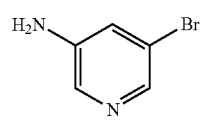
(15)

or a salt thereof, with a compound of Formula (20)

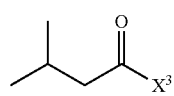
(20)

or a salt thereof, wherein $X^3$ is a leaving group, to prepare a compound of Formula (10), or the salt thereof.

For example, a compound of Formula (10) can be prepared as shown in Scheme 5.

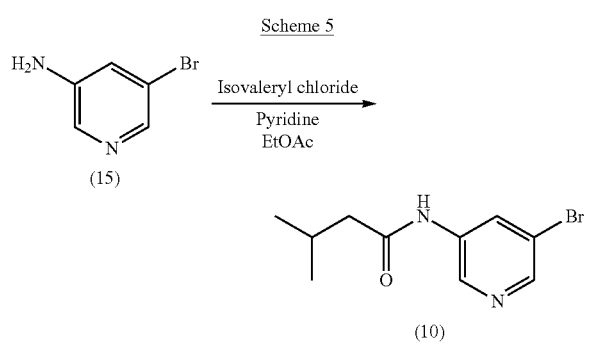

In some embodiments, X³ can be a halide. In some embodiments, X³ is —Cl. For example, the compound of Formula (20) can be isovaleryl chloride (i.e., where X³ is —Cl).

The ratio of molar equivalents of the compound of Formula (10), or a salt thereof, to the compound of Formula (20), or a salt thereof, can be at least 1:1, 1:1.1, 1:1.2, 1:1.3, 1:1.5, or at least 1:2. The ratio of molar equivalents of the compound of Formula (10), or a salt thereof, to the compound of Formula (20), or a salt thereof, can be about 1:1, 1:1.1, 1:1.2, 1:1.3, 1:1.5, or about 1:2. In some embodiments, the ratio of molar equivalents of the compound of Formula (10), or a salt thereof, to the compound of Formula (20), or a salt thereof, is about 1:1.3.

In some embodiments, the compound of Formula (6), or a salt thereof, is prepared by a process including: (i) reacting a compound of Formula (16)

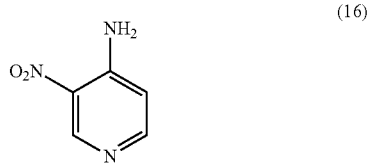

or a salt thereof, with Br₂ to prepare a compound of Formula (17)

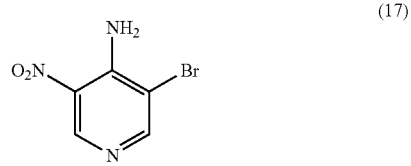

or a salt thereof; (ii) reacting the compound of Formula (17), or the salt thereof, with a compound of Formula (18)

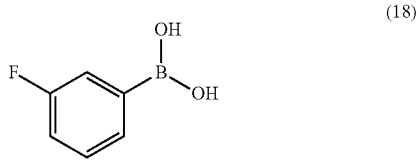

or a salt thereof, to prepare a compound of Formula (19)

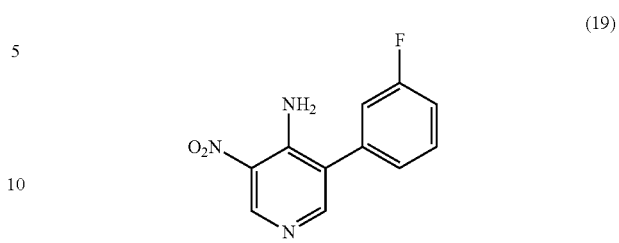

or a salt thereof; and (iii) selectively reducing the nitro group of the compound of Formula (19), or the salt thereof, to prepare a compound of Formula (6), or the salt thereof.

For example, a compound of Formula (6), or a salt thereof, can be prepared as shown in Scheme 6.

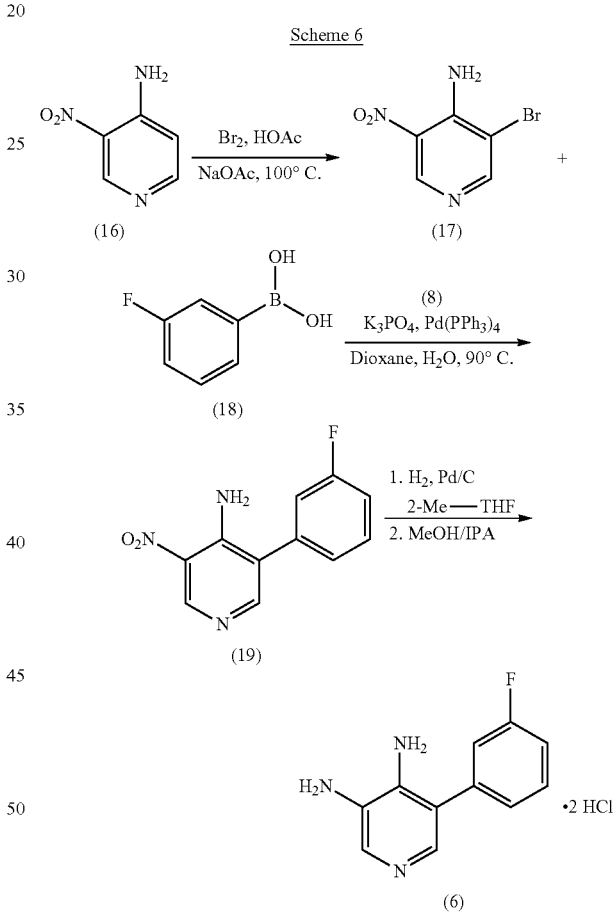

Reacting the compound of Formula (17), or a salt thereof, with the compound of Formula (18), or a salt thereof, to prepare the compound of Formula (19), or a salt thereof, can be performed in the presence of a palladium catalyst. In some embodiments, reacting the compound of Formula (17), or a salt thereof, with the compound of Formula (18), or a salt thereof, to prepare the compound of Formula (19), or a salt thereof, is carried out under an N2 atmosphere. In some embodiments, reacting the compound of Formula (17), or a salt thereof, with the compound of Formula (18), or a salt thereof, to prepare the compound of Formula (19), or a salt thereof, further comprises a palladium catalyst and is carried out under an N2 atmosphere.

In some embodiments, deprotecting the compound of Formula (12), or a salt thereof, to prepare the compound of Formula (1), or a salt thereof, is performed in the presence of an acid. In some embodiments, the acid is TFA. The TFA can be neat TFA. In some embodiments, deprotecting the compound of Formula (12), or a salt thereof, to prepare the compound of Formula (1), or a salt thereof, is accomplished by hydrogenolysis.

Also provided herein is a process for preparing a compound of Formula (1)

(1)

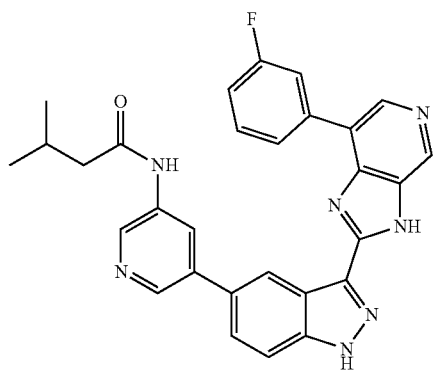

including salts and amorphous and polymorph forms thereof. The process includes: (a) reacting a compound of Formula (8)

(8)

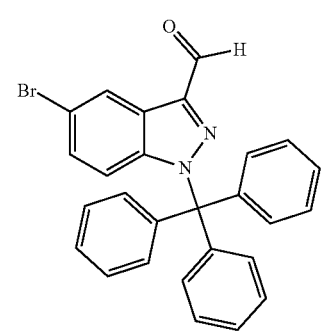

or a salt thereof, with bis(pinacolato)diboron and Pd(dppf)Cl$_2$ to produce a compound of Formula (9)

(9)

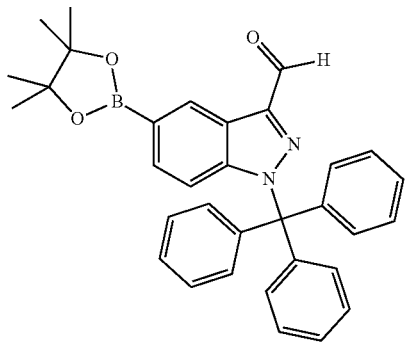

or a salt thereof; (b) reacting the compound of Formula (9), or the salt thereof, with a compound of Formula (10)

(10)

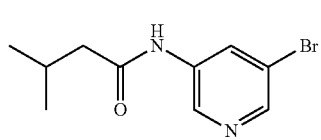

or a salt thereof, with Pd(PPh$_3$)$_4$ and K$_3$PO$_4$ to prepare a compound of Formula (11)

(11)

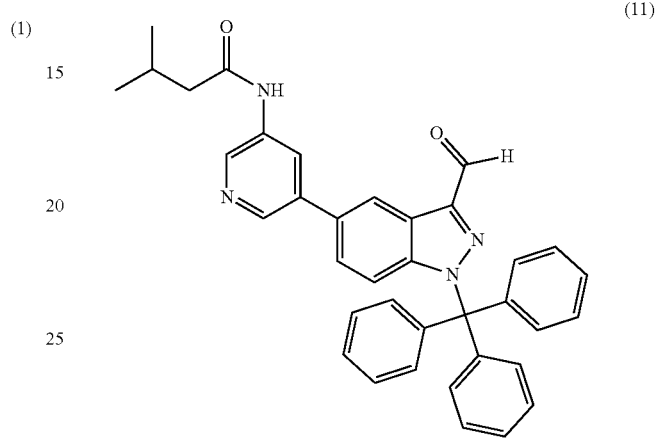

or a salt thereof; (c) reacting the compound of Formula (11), or the salt thereof, with a compound of Formula (6)

(6)

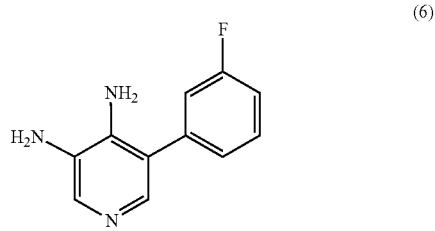 [SMILES: Nc1cncc(-c2cccc(F)c2)c1N]

or a salt thereof, to prepare a compound of Formula (12)

(12)

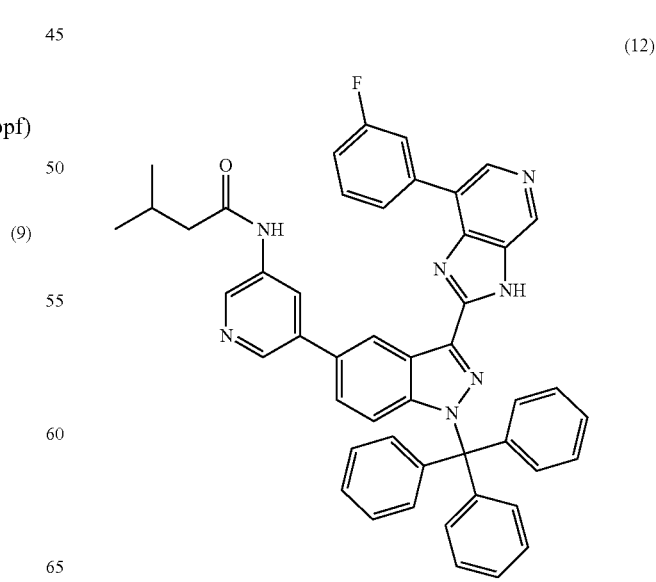

or a salt thereof; and (d) deprotecting the compound of Formula (12), or the salt thereof, to prepare the compound of Formula (1), wherein deprotecting the compound of Formula (12) to prepare the compound of Formula (1) comprises reacting the compound of Formula (12) with TFA. In some embodiments, the process further comprises forming a salt of the compound of Formula (1). In some embodiments, the process further comprises forming a polymorph form of the compound of Formula (1). In some embodiments, the polymorph form of the compound of Formula (1) is Form 1. In some embodiments, the polymorph form of the compound of Formula (1) is a non-stoichiometric hydrate of polymorph Form 1 having between 1% and about 20% by weight water.

In some embodiments, the ratio of molar equivalents of Pd(dppf)Cl$_2$ to the compound of Formula (8), or a salt thereof, is about 0.01:1 to about 0.1:1 or about 0.02:1 to about 0.5:1. For example, the ratio of molar equivalents of Pd(dppf)Cl$_2$ to the compound of Formula (8), or a salt thereof, can be about 0.01:1 to about 0.1:1. The ratio of Pd(dppf)Cl$_2$ to the compound of Formula (8), or a salt thereof, can be about 0.01:1, 0.02:1, 0.03:1, 0.04:1, 0.05:1, or about 0.1:1. In some embodiments, the ratio of molar equivalents of Pd(dppf)Cl$_2$ to the compound of Formula (8), or a salt thereof, is about 0.03:1.

In some embodiments, the ratio of molar equivalents of Pd(PPh$_3$)$_4$ to the compound of Formula (9), or a salt thereof, is about 0.01:1 to about 0.1:1 or about 0.02:1 to about 0.5:1. For example, the ratio of molar equivalents of Pd(PPh$_3$)$_4$ to the compound of Formula (9), or a salt thereof, can be about 0.01:1 to about 0.1:1. The ratio of Pd(PPh$_3$)$_4$ to the compound of Formula (9), or a salt thereof, can be about 0.01:1, 0.02:1, 0.03:1, 0.04:1, 0.05:1, or about 0.1:1. In some embodiments, the ratio of molar equivalents of Pd(PPh$_3$)$_4$ to the compound of Formula (9), or a salt thereof, is about 0.03:1.

Further provided herein is a process for preparing a compound of Formula (1)

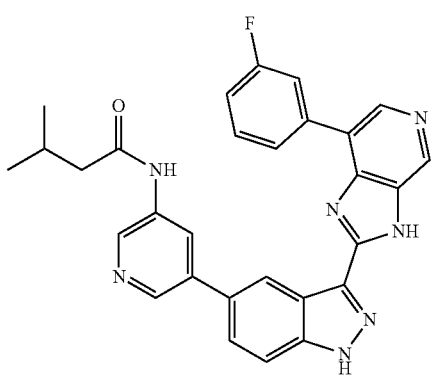

(1)

including salts and amorphous and polymorph forms thereof. The process includes reacting the compound of Formula (5)

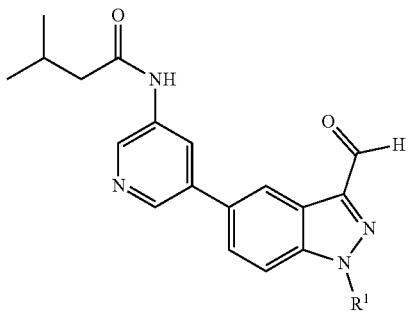

(5)

or a salt thereof, with a compound of Formula (6)

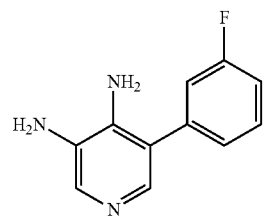

(6)

or a salt thereof, wherein R$^1$ is a nitrogen protecting group, to prepare a compound of Formula (7)

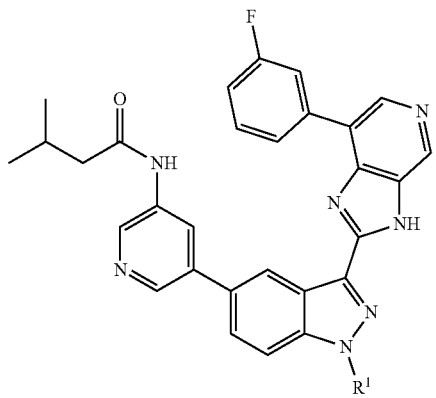

(7)

or a salt thereof.

In some embodiments, the nitrogen protecting group is an acetyl, benzyl, cumyl, benzhydryl, trityl, benzyloxycarbonyl (Cbz), 9-fluorenylmethyloxycarbonyl (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tert-butyl-dimethylsilyl, triethylsilyl (TES), triisopropylsilyl, trimethylsilylethoxymethyl (SEM), t-butoxycarbonyl (BOC), t-butyl, 1-methyl-1, 1-dimethylbenzyl, (phenyl)methyl benzene, pyridinyl, and pivaloyl. In some embodiments, the nitrogen protecting group is a trityl group.

In some embodiments, the nitrogen protecting group is not a tetrahydropyran-2-yl.

In some embodiments, the process further includes deprotecting the compound of Formula (7) or a salt thereof to prepare the compound of Formula (1)

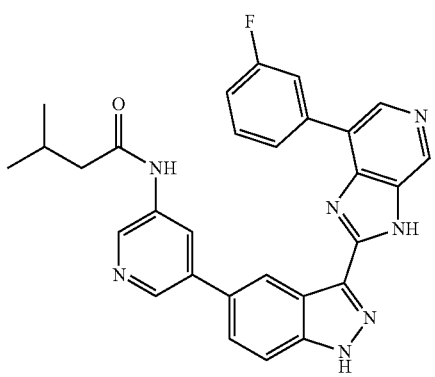

(1)

including salts and amorphous and polymorph forms thereof.

In some embodiments, the nitrogen protecting group is a trityl group and deprotecting the compound of Formula (7), or a salt thereof, to prepare the compound of Formula (1), or a salt thereof, includes reacting the compound of Formula (7), or a salt thereof, with TFA.

Also provided herein is a process for preparing a compound of Formula (1)

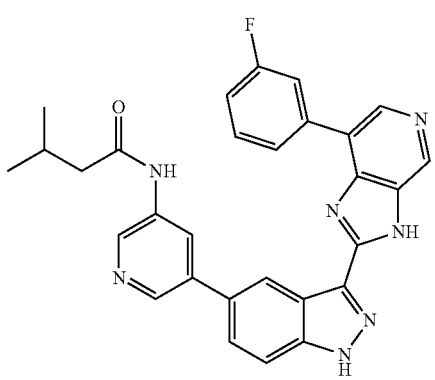

(1)

including salts and amorphous and polymorph forms thereof. The process includes reacting a compound of Formula (2)

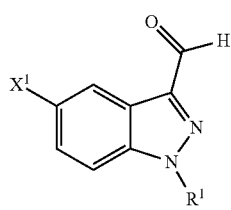

(2)

or a salt thereof, wherein $X^1$ is selected from the group consisting of —Cl, —Br, —I, and —OTf, and $R^1$ is an nitrogen protecting group, with a boron reagent to prepare a compound of Formula (3)

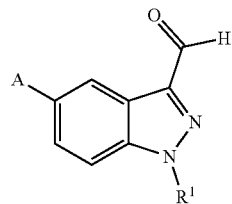

(3)

or a salt thereof, wherein A is selected from the group consisting of a boronic acid, a boronic ester, a boronate, a borinate, a boranate, a boranamide, an N-coordinated boronate, and a trifluoroborate.

In some embodiments, the nitrogen protecting group is selected from the group consisting of acetyl, benzyl, cumyl, benzhydryl, trityl, benzyloxycarbonyl (Cbz), 9-fluorenylmethyloxycarbonyl (Fmoc), benzyloxymethyl (BOM), pivaloyl-oxy-methyl (POM), trichloroethoxycarbonyl (Troc), 1-adamantyl oxycarbonyl (Adoc), allyl, allyloxycarbonyl, trimethyl silyl, tert-butyl-dimethyl silyl, tri ethyl silyl (TES), triisopropyl silyl, trimethylsilylethoxymethyl (SEM), t-butoxycarbonyl (BOC), t-butyl, 1-methyl-1,1-dimethylbenzyl, (phenyl)methyl benzene, pyridinyl, and pivaloyl. In some embodiments, the nitrogen protecting group is a trityl.

In some embodiments, the nitrogen protecting group is not a tetrahydropyran-2-yl.

In some embodiments, A is selected from the group consisting of:

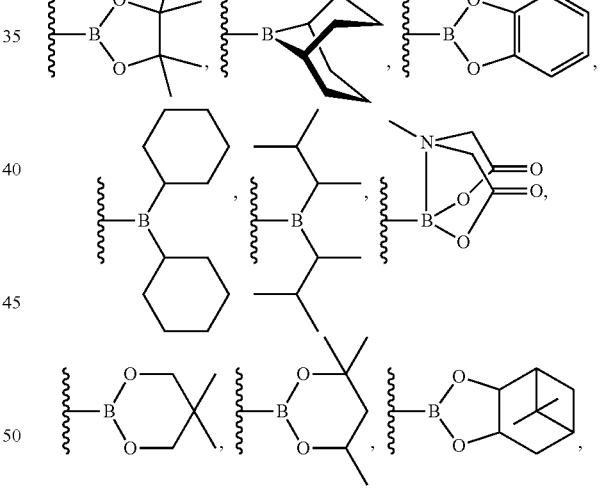

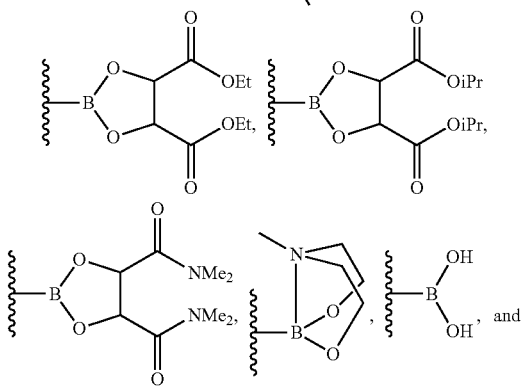

-continued

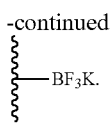

In some embodiments, A is:

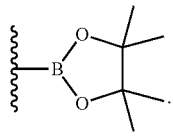 [SMILES: *B1OC(C)(C)C(C)(C)O1]

In some embodiments, $X^1$ is —Br. In some embodiments, $X^1$ is —I.

Reacting a compound of Formula (2), or a salt thereof, with the boron reagent to prepare a compound of Formula (3), or a salt thereof, can be performed in the presence of a palladium catalyst. The palladium catalyst can be selected from the group consisting of palladium(II)acetate, Pd(dppf)Cl$_2$, Pd(dba)$_2$, tetrakis(triphenylphosphine)palladium(0), (MeCN)$_2$PdCl$_2$, and tris(dibenzylideneacetone)dipalladium (0). In some embodiments, the palladium catalyst is Pd(dppf)Cl$_2$.

In some embodiments, the ratio of molar equivalents of the palladium catalyst to a compound of Formula (2), or a salt thereof, is about 0.01:1 to about 0.1:1 or about 0.02:1 to about 0.5:1. The ratio of molar equivalents of the palladium catalyst to the compound of Formula (2), or a salt thereof, can be about 0.01:1, 0.02:1, 0.03:1, 0.04:1, 0.05:1, or about 0.1:1. In some embodiments, the ratio of molar equivalents of the palladium catalyst to the compound of Formula (2), or a salt thereof, is 0.03:1.

In some embodiments, the process further includes isolating the compound of Formula (3), or a salt thereof.

In some embodiments, the process further includes reacting the compound of Formula (3), or the salt thereof, with a compound of Formula (4)

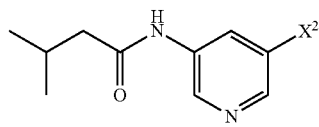

(4)

or a salt thereof, wherein $X^2$ is a leaving group; to prepare a compound of Formula (5)

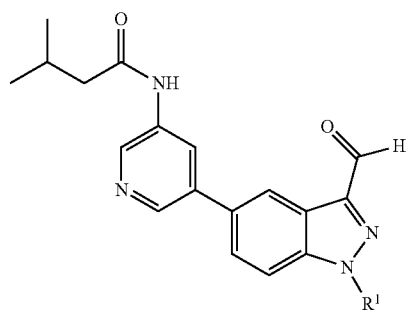

(5)

or a salt thereof.

In some embodiments, $X^2$ is selected from the group consisting of —Cl, —Br, —I, and —OTf. In some embodiments, $X^2$ is —Br.

In some embodiments, reacting a compound of Formula (3), or a salt thereof, with a compound of Formula (4), or a salt thereof, to prepare a compound of Formula (5), or a salt thereof, is performed in the presence of a palladium catalyst. The palladium catalyst can be selected from the group consisting of PdCl$_2$(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl (Ph$_2$PCH$_2$PPh$_2$)]$_2$, Cl$_2$Pd[P(o-tolyl)$_3$]$_2$, Pd$_2$(dba)$_3$/P(o-tolyl)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Pd[P(t-Bu)$_3$]$_2$, PdCl$_2$(dppe), PdCl$_2$(dppp), PdCl$_2$[PCy$_3$]$_2$, and Cl$_2$Pd[P(4-COOH-Ph)(Ph)$_2$]$_2$. In some embodiments, the palladium catalyst is Pd(PPh$_3$)$_4$.

The ratio of molar equivalents of the palladium catalyst to the compound of Formula (3), or a salt thereof, can be about 0.01:1 to about 0.1:1 or about 0.02:1 to about 0.5:1. The ratio of molar equivalents of the palladium catalyst to the compound of Formula (3), or a salt thereof, can be about 0.01:1, 0.02:1, 0.03:1, 0.04:1, 0.05:1, or about 0.1:1. In some embodiments, the ratio of molar equivalents of the palladium catalyst to the compound of Formula (3), or a salt thereof, is 0.03:1.

In some embodiments, reacting a compound of Formula (3), or a salt thereof, with a compound of Formula (4), or a salt thereof, is performed in the presence of a base. The base can be selected from the group consisting of Na$_2$CO$_3$, Ba(OH)$_2$, K$_3$PO$_4$, Cs$_2$CO$_3$, K$_2$CO$_3$, TlOH, KF, CsF, KOtBu, NEt$_3$, Bu$_4$F, and NaOH. In some embodiments, the base is K$_3$PO$_4$. The ratio of base to the compound of Formula (4), or a salt thereof, can be about 0.5:1, 1:1, 1.5:1, 2:1, 3.0:1, 4:1 or about 5:1. In some embodiments, the ratio of base to the compound of Formula (4), or a salt thereof, is about 3.0:1. In some embodiments, the ratio K$_3$PO$_4$ to the compound of Formula (4), or a salt thereof, is about 3.0:1.

Also provided herein is a process for preparing a compound of Formula (7)

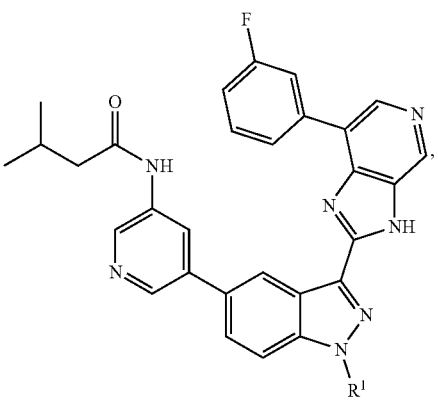

(7)

or a salt thereof, wherein R[1] is a nitrogen protecting group. The process includes reacting a compound of Formula (5)

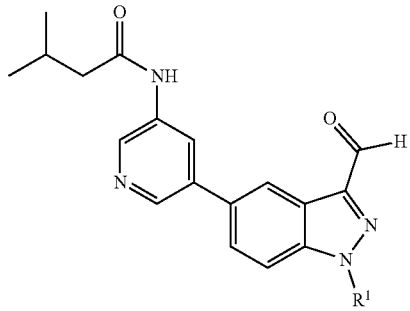

or a salt thereof, with a compound of Formula (6)

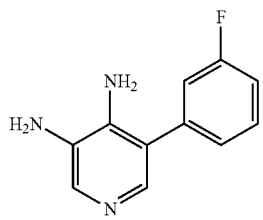

or a salt thereof, to prepare a compound of Formula (7). In some embodiments, the process further comprises forming a salt of the compound of Formula (7). In some embodiments, the process comprises performing the reaction between a compound of Formula (5) and a compound of Formula (6) in the presence of an acid. In some embodiments, the acid is hydrochloric acid (HCl). In some embodiments, up to 1 molar equivalent of an acid (with respect to a compound of Formula (6)) is added.

In some embodiments, the nitrogen protecting group is selected from the group consisting of acetyl, benzyl, cumyl, benzhydryl, trityl, benzyloxycarbonyl (Cbz), 9-fluorenylmethyloxycarbonyl (Fmoc), benzyloxymethyl (BOM), pivaloyl-oxy-methyl (POM), trichloroethoxycarbonyl (Troc), 1-adamantyl oxycarbonyl (Adoc), allyl, allyloxycarbonyl, trimethyl silyl, tert-butyl-dimethyl silyl, tri ethyl silyl (TES), triisopropyl silyl, trimethylsilylethoxymethyl (SEM), t-butoxycarbonyl (BOC), t-butyl, 1-methyl-1,1-dimethylbenzyl, (phenyl)methyl benzene, pyridinyl, and pivaloyl. In some embodiments, the nitrogen protecting group is a trityl.

In some embodiments, the nitrogen protecting group is not a tetrahydropyran-2-yl.

In some embodiments, reacting a compound of Formula (5), or a salt thereof, with a compound of Formula (6), or a salt thereof, to prepare a compound of Formula (7), or a salt thereof, is performed in the presence of Na$_2$SO$_3$, elemental sulfur, or a combination thereof. In some embodiments, reacting the compound of Formula (5), or a salt thereof, with the compound of Formula (6), or a salt thereof, to prepare the compound of Formula (7), or a salt thereof, is performed in the presence of Na$_2$SO$_3$. In some embodiments, the Na$_2$SO$_3$ is ground Na$_2$SO$_3$. For example, the ground Na$_2$SO$_3$ can have a particle size of about 100 microns to about 300 microns or about 150 microns to about 250 microns. In some embodiments, the ground Na$_2$SO$_3$ has a particle size of about 150 microns to about 250 microns. In some embodiments, reacting the compound of Formula (5), or a salt thereof, with the compound of Formula (6), or a salt thereof, to prepare the compound of Formula (7), or a salt thereof, is performed in the presence of SO$_2$.

In some embodiments, reacting a compound of Formula (5), or a salt thereof, with a compound of Formula (6), or a salt thereof, to prepare a compound of Formula (7), or a salt thereof, is performed in the presence of an organic solvent. In some embodiments, the organic solvent is N-methyl-2-pyrrolidone, dimethylacetamide, n-butanol, or a combination thereof. In some embodiments, reacting the compound of Formula (5), or a salt thereof, with the compound of Formula (6), or a salt thereof, to prepare the compound of Formula (7), or a salt thereof, is performed in the presence of N-methyl-2-pyrrolidone.

In some embodiments, reacting a compound of Formula (5), or a salt thereof, with a compound of Formula (6), or a salt thereof, to prepare a compound of Formula (7), or a salt thereof, is performed under an inert atmosphere. For example, the inert atmosphere can be a nitrogen (N2) atmosphere or an argon atmosphere. In some embodiments, reacting the compound of Formula (5), or a salt thereof, with the compound of Formula (6), or a salt thereof, to prepare the compound of Formula (7), or a salt thereof, is performed under a N2 atmosphere.

In some embodiments, reacting a compound of Formula (5), or a salt thereof, with a compound of Formula (6), or a salt thereof, to prepare a compound of Formula (7), or a salt thereof, is performed at a temperature of about 75° C. to about 150° C., about 100° C. to about 120° C., or about 110° C. to about 115° C. For example, reacting the compound of Formula (5), or a salt thereof, with the compound of Formula (6), or a salt thereof, to prepare the compound of Formula (7), can be performed at a temperature of about 100° C., 105° C., 110° C., 115° C., or about 120° C.

In some embodiments, reacting a compound of Formula (5), or a salt thereof, with a compound of Formula (6), or a salt thereof, to prepare a compound of Formula (7), or a salt thereof, is performed for a time of about 5 hours to about 10 hours or about 7 hours to about 9 hours. For example, reacting the compound of Formula (5), or a salt thereof, with the compound of Formula (6), or a salt thereof, to prepare the compound of Formula (7), or a salt thereof, can be performed for a time of about 5 hours, 6 hours, 7 hours, 8 hours, 9 hours, or about 10 hours.

Reacting a compound of Formula (5) or a salt thereof, with a compound of Formula (6) or a salt thereof, to prepare a compound of Formula (7) or a salt thereof, can be performed at a temperature of about 75° C. to about 150° C., about 100° C. to about 120° C. for a time of about 5 hours to about 10 hours. For example, reacting the compound of Formula (5) or a salt thereof, with the compound of Formula (6) or a salt thereof, to prepare the compound of Formula (7) or a salt thereof, can be performed at a temperature of about 110° C. to about 115° C. for a time of about 7 hours to about 9 hours.

Also provided herein is a process for preparing a compound of Formula (3)

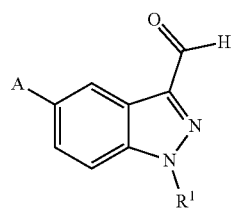

or a salt thereof, wherein R¹ is a nitrogen protecting group and A is selected from the group consisting of a boronic acid, a boronic ester, a boronate, a borinate, a boranate, a boranamide, an N-coordinated boronate, and a trifluoroborate. The process includes reacting a compound of Formula (2)

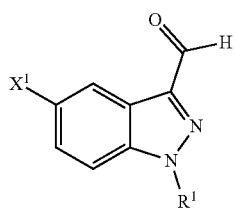

(2)

or a salt thereof, with a boron reagent to prepare a compound of Formula (3), or the salt thereof. In some embodiments, X¹ is selected from the group consisting of —Cl, —Br, —I, and —OTf.

In some embodiments, the nitrogen protecting group is selected from the group consisting of acetyl, benzyl, cumyl, benzhydryl, trityl, benzyloxycarbonyl (Cbz), 9-fluorenylmethyloxycarbonyl (Fmoc), benzyloxymethyl (BOM), pivaloyl-oxy-methyl (POM), trichloroethoxycarbonyl (Troc), 1-adamantyl oxycarbonyl (Adoc), allyl, allyloxycarbonyl, trimethylsilyl, tert-butyl-dimethyl silyl, tri ethyl silyl (TES), triisopropyl silyl, trimethylsilylethoxymethyl (SEM), t-butoxycarbonyl (BOC), t-butyl, 1-methyl-1,1-dimethylbenzyl, (phenyl)methyl benzene, pyridinyl, and pivaloyl.

In some embodiments, the nitrogen protecting group is a trityl group.

In some embodiments, the nitrogen protecting group is not a tetrahydropyran-2-yl.

In some embodiments, A is selected from the group consisting of:

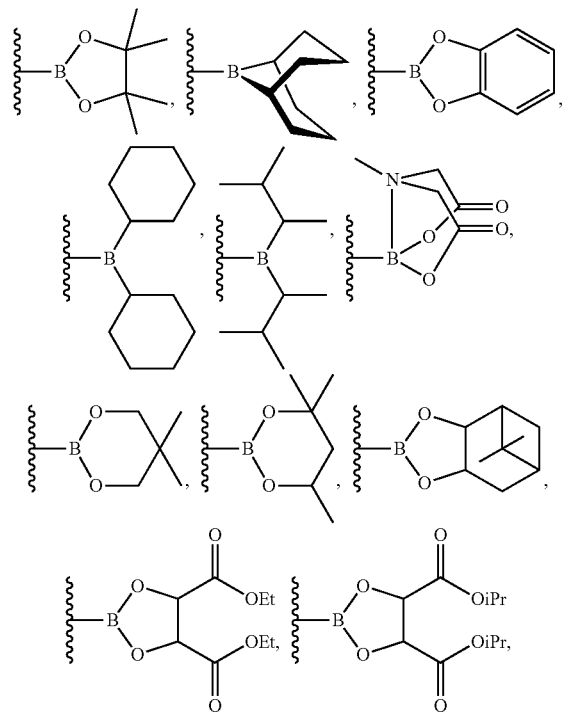

-continued

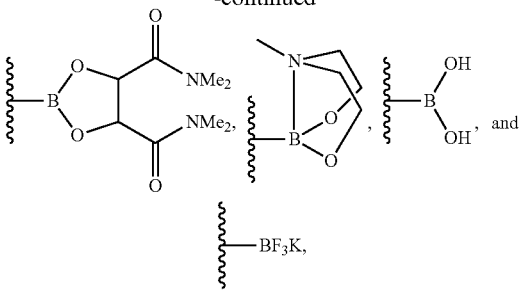

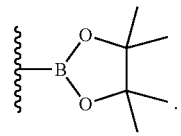 [SMILES: *B1OC(C)(C)C(C)(C)O1]

wherein the wavy line indicates the point of attachment of A.

In some embodiments, A is

In some embodiments, X¹ is —Br. In some embodiments, X¹ is —I. In some embodiments, X¹ is not —I.

In some embodiments, X² is —Br. In some embodiments, X² is —I. In some embodiments, X² is not —I.

In some embodiments, reacting a compound of Formula (2), or a salt thereof, with the boron reagent to prepare a compound of Formula (3), or a salt thereof, can be performed in the presence of a palladium catalyst. In some embodiments, the palladium catalyst is a Pd(0) catalyst. In some embodiments, the palladium catalyst is selected from the group consisting of palladium(II)acetate, Pd(dppf)Cl₂, Pd(dba)₂, tetrakis(triphenylphosphine)palladium(0), (MeCN)₂PdCl₂, and tris(dibenzylideneacetone)dipalladium (0). In some embodiments, the palladium catalyst is Pd(dppf)Cl₂.

In some embodiments, the ratio of molar equivalents of the palladium catalyst to the compound of Formula (2), or a salt thereof, is about 0.01:1 to about 0.1:1 or about 0.02:1 to about 0.5:1. The ratio of molar equivalents of the palladium catalyst to the compound of Formula (2), or a salt thereof, can be about 0.01:1, 0.02:1, 0.03:1, 0.04:1, 0.05:1, or about 0.1:1. In some embodiments, the ratio of molar equivalents of the palladium catalyst to the compound of Formula (2), or a salt thereof, is 0.03:1.

In some embodiments, reacting a compound of Formula (2), or a salt thereof, with the boron reagent to prepare a compound of Formula (3), or a salt thereof, is performed at a temperature of about 80° C. to about 110° C., about 85° C. to about 100° C., or about 90° C. to about 95° C. In some embodiments, reacting the compound of Formula (2), or a salt thereof, with the boron reagent to prepare the compound of Formula (3) is performed at a temperature of about 80° C., 85° C., 90° C., 95° C., 100° C., 105° C., or about 110° C. Reacting the compound of Formula (2), or a salt thereof, with the boron reagent to prepare the compound of Formula (3), or a salt thereof, can be performed at a temperature of about 92° C.

Reacting a compound of Formula (2), or a salt thereof, with the boron reagent to prepare a compound of Formula (3), or a salt thereof, can be performed for a time of about 15 hours to about 25 hours or about 16 hours to about 20 hours. For example, reacting the compound of Formula (2), or a salt thereof, with the boron reagent to prepare the compound of Formula (3) can be performed for a time of about 15 hours, 16 hours, 17 hours, 18 hours, 19 hours, 20 hours, 21 hours, 22 hours, 23 hours, 24 hours, or about 25 hours.

In some embodiments, reacting a compound of Formula (2), or a salt thereof, with the boron reagent to prepare a compound of Formula (3), or a salt thereof, can be performed at a temperature of about 80° C. to about 110° C. for a time of about 15 hours to about 25 hours. In some embodiments, reacting a compound of Formula (2), or a salt thereof, with the boron reagent to prepare a compound of Formula (3), or a salt thereof, is performed at a temperature of about 85° C. to about 95° C. for a time of about 16 hours to about 20 hours.

In some embodiments, the process further includes isolating the compound of Formula (3), or a salt thereof. In some embodiments, the compound of Formula (3), or a salt thereof, is isolated by filtration.

Also provided herein is a process for preparing a compound of Formula (4)

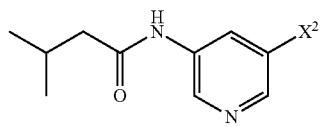

(4)

or a salt thereof, wherein $X^2$ is selected from the group consisting of —Cl, —Br, —I, and —OTf. The process includes reacting a compound of Formula (21)

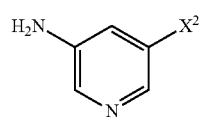

(21)

or a salt thereof, wherein $X^2$ is as defined above, with a compound of Formula (22)

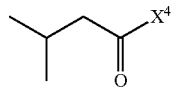

(22)

wherein $X^4$ is a leaving group, to prepare the compound of Formula (4), or a salt thereof. In some embodiments, the leaving group is a halide or an activated ester.

Also provided herein is a process for preparing a compound of Formula (5)

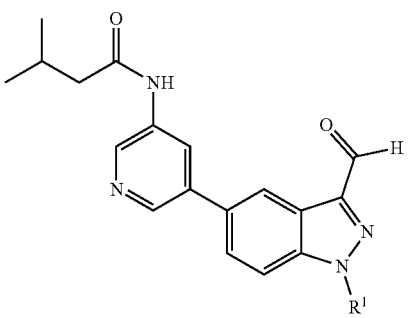

(5)

or a salt thereof, wherein $R^1$ is a nitrogen protecting group. The process includes reacting the compound of Formula (3)

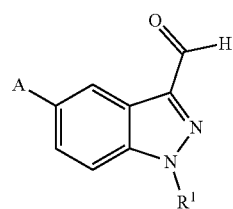

(3)

or the salt thereof, wherein A is selected from the group consisting of a boronic acid, a boronic ester, a boronate, a borinate, a boranate, a boranamide, an N-coordinated boronate, and a trifluoroborate, with a compound of Formula (4)

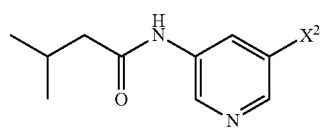

(4)

or salt thereof, wherein $X^2$ is selected from the group consisting of —Cl, —Br, —I, and —OTf;
to prepare the compound of Formula (5).

Also provide herein is a process for preparing a compound of Formula (1)

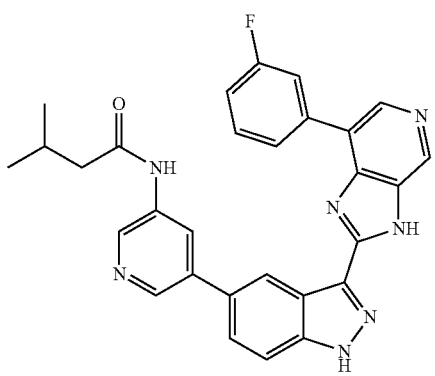

(1)

or a salt or amorphous or polymorph form thereof. The process includes deprotecting a compound of Formula (12)

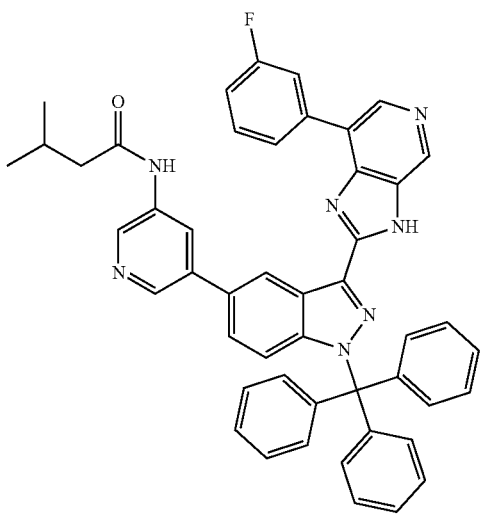

(12)

or a salt thereof, to prepare the compound of Formula (1). In some embodiments, the process further comprises forming a salt of the compound of Formula (1). In some embodiments, the process further comprises forming a polymorph form of the compound of Formula (1). In some embodiments, the polymorph is Form 1. In some embodiments, the polymorph is a non-stoichiometric hydrate of polymorph Form 1 having between 1% and about 20% by weight water.

Also provided herein is a process for preparing a polymorph form of a compound of Formula (1)

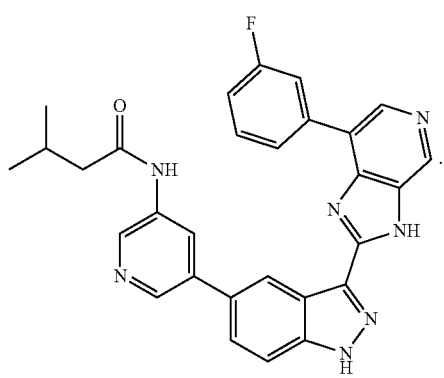

(1)

The process includes deprotecting a compound of Formula (12)

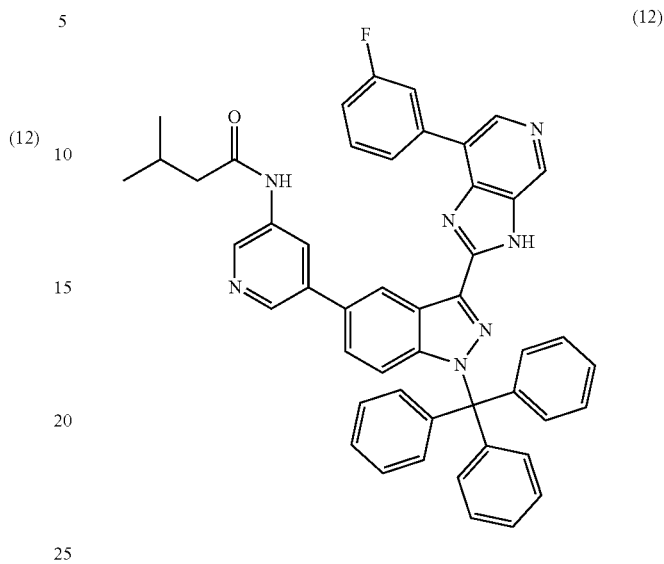

(12)

or a salt thereof, to prepare the compound of Formula (1), and preparing a polymorph form of the compound of Formula (1). In some embodiments, the polymorph form of the compound of Formula (1) is Form 1. In some embodiments, the polymorph form of the compound of Formula (1) is a non-stoichiometric hydrate of polymorph Form 1 having between 1% and about 20% by weight water.

In some embodiments, deprotecting the compound of Formula (12) to prepare the compound of Formula (1) comprises reacting the compound of Formula (12) with TFA to obtain a compound of Formula (1). In some embodiments, the process further comprises preparing a polymorph form of the compound of Formula (1). In some embodiments, the process comprises converting the compound of Formula (1) to a polymorph form. In some embodiments, the process comprises reslurrying a compound of Formula (I) or a composition comprising the compound of Formula (1) in a solvent or mixture of solvents to generate a polymorph form of the compound of Formula (1) as a residual solid. In some embodiments, the composition comprises a non-stoichiometric hydrate of polymorph Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

The compounds and intermediates provided herein, including salts thereof, can be prepared using known organic synthesis techniques and can be synthesized according to any of numerous possible synthetic routes.

The reactions for preparing the compounds provided herein can be carried out in suitable solvents which can be readily selected by one of skill in the art of organic synthesis. Suitable solvents can be substantially non-reactive with the starting materials (reactants), the intermediates, or products, at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The chemistry of protecting groups can be found, for example, in *Protecting Group Chemistry*, 1$^{st}$ Ed., Oxford University Press, 2000; *March's Advanced Organic Chemistry: Reactions, Mechanisms, and Structure*, 6$^{th}$ Ed., Wiley-Interscience Publication, 2006; and Peturssion, S. et al., "Protecting Groups in Carbohydrate Chemistry," *J. Chem. Educ.*, 74(11), 1297 (1997) (each of which is incorporated herein by reference in its entirety).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), which is incorporated herein by reference in its entirety) and normal phase silica chromatography.

In some embodiments, provided herein is a compound, or a pharmaceutically acceptable salt thereof, of Formula 20:

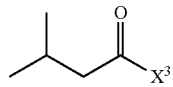

(20)

where:

X$^3$ is selected from the group consisting of —Cl, —Br, —I, —OH, and

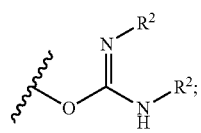

wherein each R$^2$ is independently selected from alkyl or cycloalkyl.

In some embodiments of Formula 20, X$^3$ is Cl.

In some embodiments, a compound, or a pharmaceutically acceptable salt thereof, of Formula 20 has the structure of Formula 22:

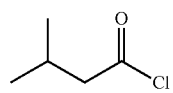

(22)

In some embodiments, provided herein is a compound, or a pharmaceutically acceptable salt thereof, of Formula 21:

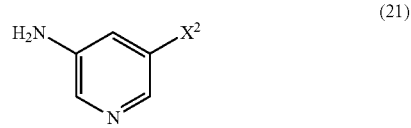

(21)

where:

X$^2$ is selected from the group consisting of —Cl, —Br, —I, and —OTf.

In some embodiments of Formula 21, X$^2$ is Br.

In some embodiments, a compound, or a pharmaceutically acceptable salt thereof, of Formula 21 has the structure of Formula 15:

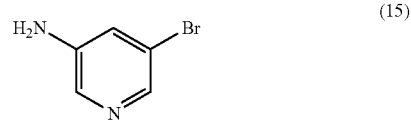

(15)

In some embodiments, provided herein is a compound, or a pharmaceutically acceptable salt thereof, of Formula 4:

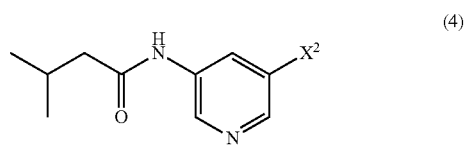

(4)

where:

X$^2$ is selected from the group consisting of —Cl, —Br, —I, and —OTf.

In some embodiments of Formula 4, X$^2$ is Br.

In some embodiments, a compound, or a pharmaceutically acceptable salt thereof, of Formula 4 has the structure of Formula 10:

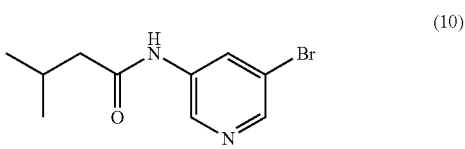

(10)

In some embodiments, provided herein is a compound, or a pharmaceutically acceptable salt thereof, of Formula 23:

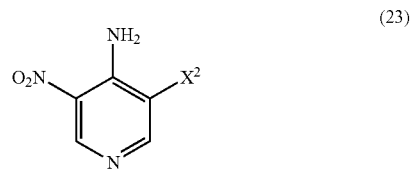

(23)

where:

X² is selected from the group consisting of —Cl, —Br, —I, and —OTf.

In some embodiments of Formula 23, X² is Br.

In some embodiments, a compound, or a pharmaceutically acceptable salt thereof, of Formula 23 has the structure of Formula 17:

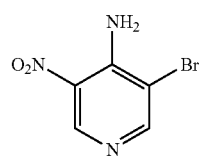

(17)

In some embodiments, provided herein is a compound, or a pharmaceutically acceptable salt thereof, of Formula 24:

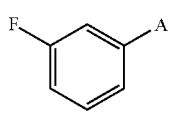

(24)

where:

A is selected from the group consisting of a boronic acid, a boronic ester, a boronate, a borinate, a boranate, a boranamide, an N-coordinated boronate, and a trifluoroborate.

In some embodiments of Formula 24, A is selected from the group consisting of:

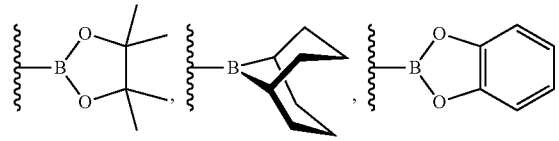

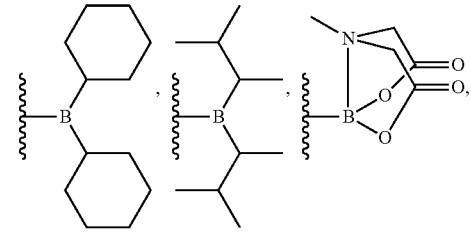

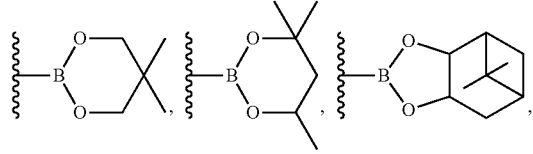

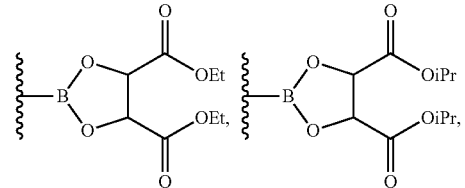

-continued

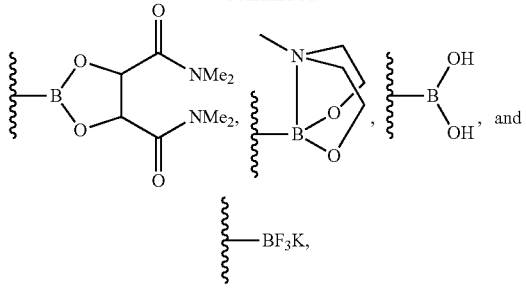

wherein the wavy line indicates the point of attachment of A.

In some embodiments of Formula 24, A is

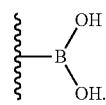

In some embodiments of Formula 24, A is

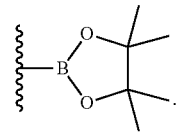 [SMILES: *B1OC(C)(C)C(C)(C)O1]

In some embodiments, a compound, or a pharmaceutically acceptable salt thereof, of Formula 24 has the structure of Formula 18:

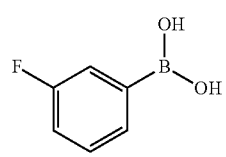

(18)

In some embodiments, provided herein is a compound, or a pharmaceutically acceptable salt thereof, of Formula 2:

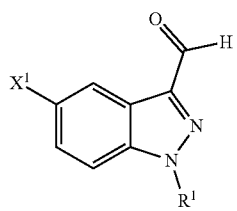

(2)

where:
X¹ is selected from the group consisting of —Cl, —Br, —I, and —OTf; and
R¹ is selected from the group consisting of an acetyl, benzyl, cumyl, benzhydryl, trityl, benzyloxycarbonyl (Cbz), 9-fluorenylmethyl oxycarbonyl (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tertbutyl-dimethylsilyl, triethylsilyl (TES), triisopropylsilyl, trimethylsilylethoxymethyl (SEM), t-butoxycarbonyl (BOC), t-butyl, 1-methyl-1,1-dimethylbenzyl, (phenyl)methyl benzene, pyridinyl, and pivaloyl.

In some embodiments of Formula 2, $X^1$ is Br.

In some embodiments of Formula 2, $R^1$ is a trityl group.

In some embodiments, a compound, or a pharmaceutically acceptable salt thereof, of Formula 2 has the structure of Formula 8:

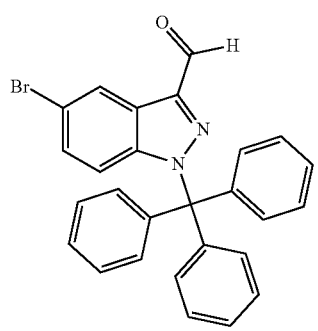

(8)

In some embodiments, provided herein is a compound, or a pharmaceutically acceptable salt thereof, of Formula 3:

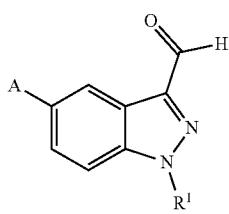

(3)

where:
A is selected from the group consisting of a boronic acid, a boronic ester, a boronate, a borinate, a boranate, a boranamide, an N-coordinated boronate, and a trifluoroborate; and
$R^1$ is selected from the group consisting of an acetyl, benzyl, cumyl, benzhydryl, trityl, benzyloxycarbonyl (Cbz), 9-fluorenylmethyl oxycarbonyl (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tert-butyl-dimethylsilyl, triethylsilyl (TES), triisopropylsilyl, trimethylsilylethoxymethyl (SEM), t-butoxycarbonyl (BOC), t-butyl, 1-methyl-1,1-dimethylbenzyl, (phenyl)methyl benzene, pyridinyl, and pivaloyl.

In some embodiments of Formula 3, A is selected from the group consisting of:

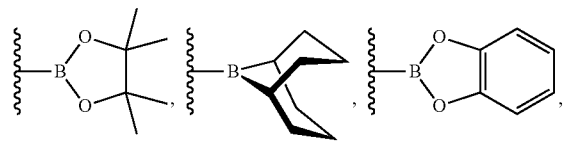

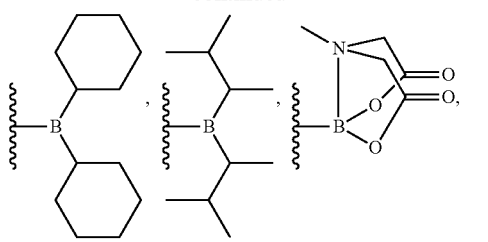

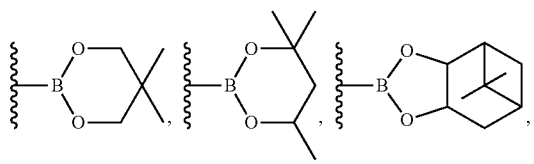

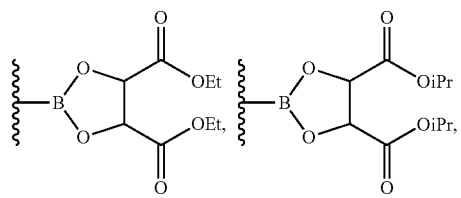

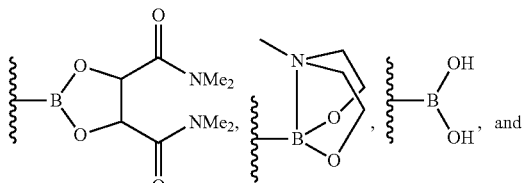

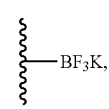

wherein the wavy line indicates the point of attachment of A.

In some embodiments of Formula 3, A is

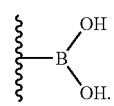

In some embodiments of Formula 3, A is

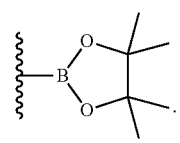 [SMILES: *B1OC(C)(C)C(C)(C)O1]

In some embodiments of Formula 3, $R^1$ is a trityl group.

In some embodiments, a compound, or a pharmaceutically acceptable salt thereof, of Formula 3 has the structure of Formula 9:

(9)

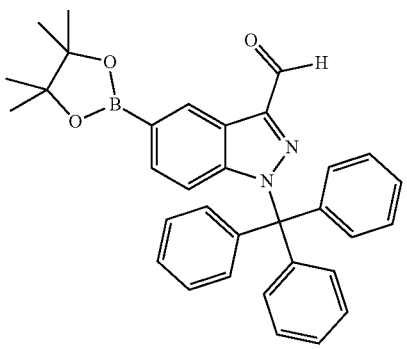

In some embodiments, provided herein is a compound, or a pharmaceutically acceptable salt thereof, of Formula 5:

(5)

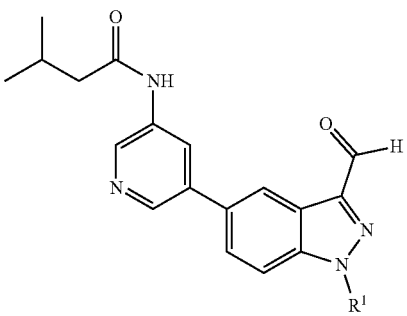

where:
R$^1$ is selected from the group consisting of an acetyl, benzyl, cumyl, benzhydryl, trityl, benzyloxycarbonyl (Cbz), 9-fluorenylmethyloxycarbonyl (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tert-butyl-dimethylsilyl, triethylsilyl (TES), triisopropylsilyl, trimethylsilylethoxymethyl (SEM), t-butoxycarbonyl (BOC), t-butyl, 1-methyl-1,1-dimethylbenzyl, (phenyl)methyl benzene, pyridinyl, and pivaloyl.

In some embodiments of Formula 5, R$^1$ is a trityl group.

In some embodiments, a compound, or a pharmaceutically acceptable salt thereof, of Formula 5 has the structure of Formula 11:

(11)

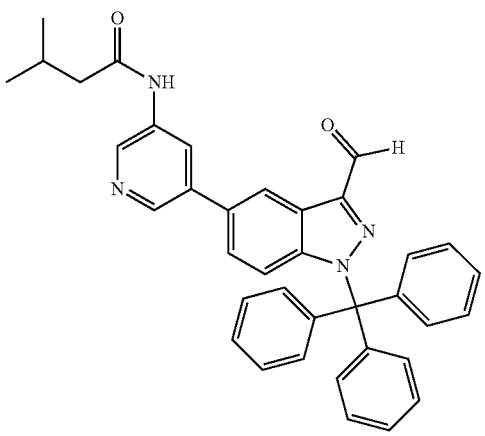

In some embodiments, provided herein is a compound, or a pharmaceutically acceptable salt thereof, of Formula 7:

(7)

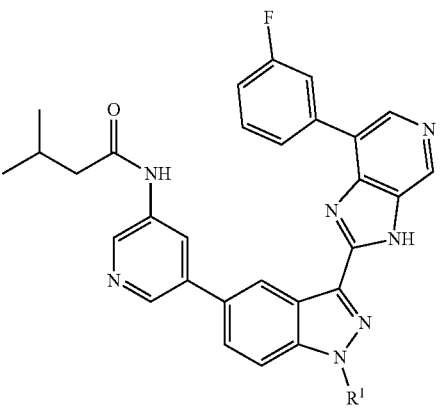

wherein:
R$^1$ is selected from the group consisting of an acetyl, benzyl, cumyl, benzhydryl, trityl, benzyloxycarbonyl (Cbz), 9-fluorenylmethyl oxycarbonyl (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tert-butyl-dimethylsilyl, triethylsilyl (TES), triisopropylsilyl, trimethylsilylethoxymethyl (SEM), t-butoxycarbonyl (BOC), t-butyl, 1-methyl-1,1-dimethylbenzyl, (phenyl)methyl benzene, pyridinyl, and pivaloyl.

In some embodiments of Formula 7, R$^1$ is a trityl group.

In some embodiments, a compound, or a pharmaceutically acceptable salt thereof, of Formula 7 has the structure of Formula 12:

(12)

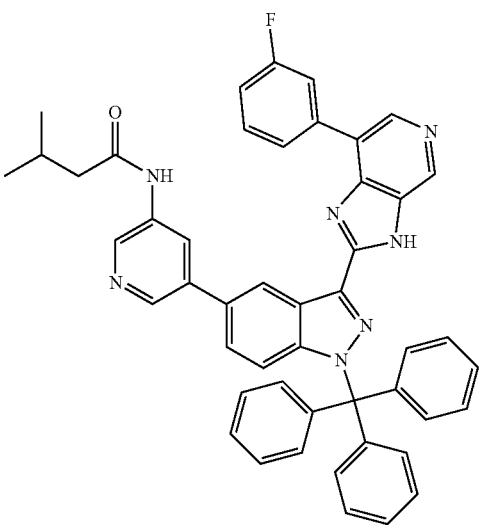

3. Process for Preparing Polymorph Forms of the Compound of Formula (1)

Provided is a process for preparing polymorph forms of the compound of Formula (1):

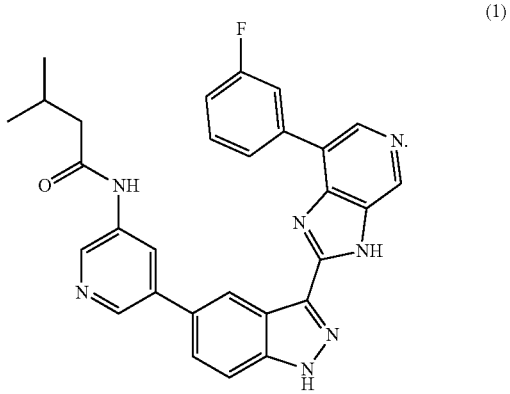 [SMILES: CC(C)CC(=O)Nc1cncc(-c2ccc3[nH]nc(-c4nc5c(-c6cccc(F)c6)cncc5[nH]4)c3c2)c1]

(1)

The polymorph forms of the compound of Formula (1) include, e.g., solvates, hydrates, non-stoichiometric hydrates, and non-solvated forms of the compound of Formula (1), including, for example, polymorph Forms 1, 2, 3, 4, 5, 6, 7, 8, 9, 10, 11, 12, and 13.

One such polymorph is a polymorph known as Form 1. Form 1 is an anhydrous polymorph of the compound of Formula (I). In one embodiment, Form 1 has an X-ray powder diffraction (XRPD or XRD) pattern, obtained with CuKα1-radiation, with at least peaks at °2θ values of 6.8±0.2, 12.4±0.2, and 18.5±0.2. In some embodiments, Form 1 has an XRPD pattern with at least peaks at °2θ values of 6.8±0.2, 12.4±0.2, 16.5±0.2, 18.5±0.2, and 19.2±0.2. In some embodiments, Form 1 has an XRPD pattern with at least peaks at °2θ values of 6.8±0.2, 9.3±0.2, 12.4±0.2, 13.9±0.2, 16.5±0.2, 18.5±0.2, 19.2±0.2, and 24.6±0.2. For example, in some embodiments, Form 1 has an XRPD pattern with at least peaks at °2θ values of 6.8±0.2, 9.3±0.2, 12.4±0.2, 13.9±0.2, 14.5±0.2, 16.5±0.2, 18.5±0.2, 19.2±0.2, 20.3±0.2, and 24.6±0.2.

In some embodiments, a composition comprising polymorph Form 1 is substantially pure. For example, the composition has a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than about 15% by weight of other forms of the compound of Formula (1). For example, the composition can contain less than 14%, 13%, 12%, 11%, 10%, 9%, 8%, 7%, 6%, 5%, 4%, 3%, 2%, 1% or less by weight of other anhydrous forms of the compound of Formula (1). In some embodiments, the composition contains less than about 15% by weight of the polymorph Form 9. For example, the composition can contain less than 14%, 13%, 12%, 11%, 10%, 9%, 8%, 7%, 6%, 5%, 4%, 3%, 2%, 1% or less by weight of the polymorph of Form 9. In some embodiments, the composition contains less than about 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 2, Form 3, Form 4, Form 5, Form 6, Form 7, Form 8, Form 9, Form 10, Form 11, a non-stoichiometric hydrate of Form 1 having between 1% and about 20% by weight water, or a combination of two or more thereof. In some embodiments, the composition contains less than 1% by weight water.

In some embodiments, polymorph Form 1 exhibits an endotherm between about 50-100° C. as measured by differential scanning calorimetry (DSC) related to sorbed water. In some embodiments, polymorph Form 1 exhibits a recrystallization event that is observed between about 270-290° C., e.g., around 280° C. In some embodiments, the endotherm and exotherm are observed when using a scan rate of 10° C. per minute.

In some embodiments, polymorph Form 1 recrystallizes into polymorph Form 9 with a melting point of around 363° C. In some embodiments, polymorph Form 1 undergoes a total mass loss of about 0.33% before around 100° C., e.g., from about 39° C. to about 100° C., as measured by thermal gravimetric analysis (TGA).

Provided herein is a process of preparing polymorph Form 1. In some embodiments, the process comprises drying a composition comprising the compound of Formula (1), including amorphous and polymorph forms thereof, to generate polymorph Form 1. In some embodiments, the composition comprises a non-stoichiometric hydrate of polymorph Form 1 having between 1% and about 20% by weight water. In some embodiments, the process comprises reslurrying a composition comprising the compound of Formula (1), including amorphous and polymorph forms thereof, in a solvent or mixture of solvents to generate polymorph Form 1 as a residual solid. In some embodiments, the reslurrying takes place at room temperature (RT). In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising the compound of Formula (1), including amorphous and polymorph forms thereof, in a solvent or mixture of solvents to generate polymorph Form 1 as a residual solid. In some embodiments, the compound of Formula (1) is a non-stoichiometric hydrate of polymorph Form 1 having between 1% and about 20% by weight water. In some embodiments, the solvent is methanol. In some embodiments, the solvent is toluene. In some embodiments, the solvent is heptane. In some embodiments, the solvent is dichloromethane (DCM). In some embodiments, the solvent is water. In some embodiments, the solvent is in a mixture with water, for example the solvent can be a mixture of water and acetonitrile, methanol, ethyl acetate (EA), methyl tert-butyl ether (MtBE), isopropyl alcohol (IPAc), methyl acetate (MA), methyl isobutyl ketone (MIBK), DCM, n-butyl acetate, heptane, toluene, or n-butanol. In some embodiments, the water is present in an amount of about 5% by weight. In some embodiments, the reslurrying takes place at room temperature. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the polymorph form of the compound of Formula (1) is a non-stoichiometric hydrate of polymorph Form 1 having between 1% and about 20% by weight water. In some embodiments, for example, above 30% relative humidity (RH), Form 1 readily sorbs water and shows a distinctive shift in Form 1 peaks from 6.8±0.2 to 6.2±0.2 and 12.6±0.2 to 11±0.2. In some embodiments, a non-stoichiometric hydrate of Form 1 comprises up to about 20% by weight water. For example, up to about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or greater than 1% water by weight. In some embodiments, a non-stoichiometric hydrate of Form 1 has between 1 to about 20% water by weight, e.g., between 1% and about 10%, about 5% and about 15%, about 10% and about 20%, 1% and about 5%, about 5% and about 10%, about 10% and about 15%, about 15% and about 20%, or about 17% and about 20% water by weight.

In some embodiments, a composition comprising a non-stoichiometric hydrate of polymorph Form 1 having between 1% and about 20% by weight water is substantially pure. For example, the composition can have a purity of at least about 90%. In some embodiments, the composition has a purity of at least about 95%. In some embodiments, the composition has a purity of at least about 98%. For example, the composition can have a purity of at least about 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1) (e.g., anhydrous forms of the compound of Formula (1)). In some embodiments, the composition contains less than 20% by weight of polymorph Form 9 having X-ray powder diffraction pattern comprising peaks at °2θ values of 4.9±0.2, 18.6±0.2, and 21.1±0.2. For example, the composition contains less than 15% by weight of Form 9, such as less than 14%, 13%, 12%, 11%, 10%, 9%, 8%, 7%, 6%, 5%, 4%, 3%, 2%, 1% or less by weight of other forms of the compound of Form 9. In some embodiments, the composition contains less than 15% of one or more other forms of the compound of Formula (1), such as less than 14%, 13%, 12%, 11%, 10%, 9%, 8%, 7%, 6%, 5%, 4%, 3%, 2%, 1% or less of one or more other forms of the compound of Formula (1). For example, the composition can contain less than about 15% of Form 1, Form 2, Form 3, Form 4, Form 5, Form 6, Form 7, Form 8, Form 9, Form 10, Form 11, or a combination of two or more thereof.

One example of a non-stoichiometric hydrate of polymorph Form 1 is referred to as Form 12.

In one embodiment, provided herein is a polymorph Form 12 having an XRPD pattern, obtained with CuKα1-radiation, with at least peaks at °2θ positions 6.4±0.2, 11.0±0.2, and 18.4±0.2. In some embodiments, Form 12 has an XRPD pattern with at least peaks at °2θ positions 6.4±0.2, 9.2±0.2, 11.0±0.2, 18.4±0.2, and 19.7±0.2. In some embodiments, Form 12 has an XRPD pattern with at least peaks at °2θ positions 6.4±0.2, 9.2±0.2, 11.0±0.2, 15.6±0.2, 18.4±0.2, 19.7±0.2, 24.4±0.2, and 25.2±0.2. For example, in some embodiments, Form 12 has an XRPD pattern with at least peaks at °2θ positions 6.4±0.2, 9.2±0.2, 11.0±0.2, 15.6±0.2, 16.1±0.2, 18.4±0.2, 19.7±0.2, 20.8±0.2, 24.4±0.2, and 25.2±0.2.

In some embodiments, provided herein is polymorph Form 12 that exhibits an endotherm between about 50-100° C. as measured by DSC. In some embodiments, polymorph Form 12 exhibits an exotherm at around 283° C. In some embodiments, the endotherms and exotherms are observed when using a scan rate of 10° C. per minute.

In some embodiments, provided herein is polymorph Form 12 that has a melting point of around 364° C. In some embodiments, polymorph Form 12 undergoes a weight loss of about 1.4% before around 100° C., e.g., from about 30° C. to about 100° C., as measured by TGA.

Another example of a non-stoichiometric hydrate of polymorph Form 1 is referred to as Form 13.

In one embodiment, polymorph Form 13 has an XRPD pattern, obtained with CuKα1-radiation, with at least peaks at °2θ values of 6.4±0.2, 11.0±0.2, and 18.4±0.2. In some embodiments, Form 13 has an XRPD pattern with at least peaks at °2θ values of 6.4±0.2, 9.2±0.2, 11.0±0.2, 18.4±0.2, and 19.7±0.2. In some embodiments, Form 13 has an XRPD pattern with at least peaks at °2θ values of 6.4±0.2, 9.2±0.2, 11.0±0.2, 15.6±0.2, 18.4±0.2, 19.7±0.2, 24.4±0.2, and 25.2±0.2. For example, in some embodiments, Form 13 has an XRPD pattern with at least peaks at °2θ values of 6.4±0.2, 9.2±0.2, 11.0±0.2, 15.6±0.2, 16.1±0.2, 18.4±0.2, 19.7±0.2, 20.8±0.2, 24.4±0.2, and 25.2±0.2.

In some embodiments, polymorph Form 13 exhibits an endotherm between about 50-100° C. as measured by DSC. In some embodiments, polymorph Form 13 exhibits an exotherm at between about 265-285° C., e.g., around 278° C. For example, in some embodiments, the endotherms and exotherms are observed when using a scan rate of 10° C. per minute.

In some embodiments, polymorph Form 13 has a melting point of around 363° C. In some embodiments, polymorph Form 13 undergoes a weight loss of about 1.9% before around 100° C. as measured by TGA.

Provided herein are methods of preparing a non-stoichiometric hydrate of polymorph Form 1. In some embodiments, the method comprises reslurrying a composition comprising the compound of Formula (I), including amorphous and polymorph forms thereof, in a solvent or mixture of solvents to generate a non-stoichiometric hydrate of polymorph Form 1 as a residual solid. In some embodiments, the composition comprising the compound of Formula (I) is a mixture of a non-stoichiometric hydrate of polymorph Form 1 and Form 1. In some embodiments, the reslurrying takes place at RT. In some embodiments, the reslurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a mixture of a non-stoichiometric hydrate of polymorph Form 1 and Form 1 in a solvent or mixture of solvents to generate a non-stoichiometric hydrate of polymorph Form 1 as a residual solid. In some embodiments, the solvent is in a mixture with water, for example the solvent can be a mixture of water and acetonitrile, methanol, MtBE, MA, MIBK, DCM, IPAc, n-butyl acetate, heptane, toluene, or n-butanol. In some embodiments, the water is present in an amount of about 5% by weight. In some embodiments, the reslurrying takes place at RT. In some embodiments, the reslurrying takes place at around 50° C.

In some embodiments, the polymorph form of the compound of Formula (1) is a polymorph known as Form 2. Form 2 is an anhydrous polymorph of the compound of Formula (1). In one embodiment, polymorph Form 2 has an XRPD pattern, obtained with CuKα1-radiation, with at least peaks at °2θ values of 7.0±0.2, 21.5±0.2, and 22.0±0.2. In some embodiments, Form 2 has an XRPD pattern with at least peaks at °2θ values of 7.0±0.2, 18.9±0.2, 21.5±0.2, 22.0±0.2, and 24.2±0.2. In some embodiments, Form 2 has an XRPD pattern with at least peaks at °2θ values of 7.0±0.2, 14.1±0.2, 18.9±0.2, 19.2±0.2, 21.5±0.2, 22.0±0.2, 24.2±0.2, and 26.4±0.2. For example, in some embodiments, Form 2 has an XRPD pattern with at least peaks at °2θ values of 7.0±0.2, 10.4±0.2, 14.1±0.2, 17.6±0.2, 18.9±0.2, 19.2±0.2, 21.5±0.2, 22.0±0.2, 24.2±0.2, and 26.4±0.2.

In some embodiments, a composition comprising polymorph Form 2 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 3, Form 4, Form 5, Form 6, Form 7, Form 8, Form 9, Form 10, Form 11, a non-stoichiometric hydrate of Form 1, or a combination of two or more thereof.

In some embodiments, polymorph Form 2 exhibits an endotherm between about 50-100° C. as measured by DSC. In some embodiments, polymorph Form 2 exhibits an endotherm between about 220-230° C. In some embodiments, polymorph Form 2 exhibits an exotherm between about 233-238° C. In some embodiments, polymorph Form 2 exhibits an exotherm between about 290-295° C. In some embodiments, the endotherms and exotherms are observed when using a scan rate of 10° C. per minute.

In some embodiments, polymorph Form 2 has a melting point of around 363° C. In some embodiments, polymorph Form 2 undergoes a weight loss of about 2.7% before around 116° C., e.g., from about 36° C. to about 116° C., as measured by TGA.

Provided herein is a process of preparing polymorph Form 2. In some embodiments, the process comprises reslurrying a composition comprising the compound of Formula (1), including amorphous and polymorph forms thereof, in a solvent or mixture of solvents to generate Form 2 as a residual solid. In some embodiments, the composition comprises a non-stoichiometric hydrate of polymorph Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of polymorph Form 1 having between 1% and about 20% by weight water in a solvent or mixture of solvents to generate polymorph Form 2 as a residual solid. In some embodiments, the solvent is acetonitrile. In some embodiments, the solvent is ethanol. In some embodiments, the solvent is in a mixture with water, for example the solvent can be a mixture of water and ethanol or water and n-propanol. In some embodiments, the water is present in an amount of about 5% by weight. In some embodiments, the reslurrying takes place at RT. In some embodiments, the reslurrying takes place at around 50° C.

In some embodiments, the polymorph form of the compound of Formula (1) is a polymorph known as Form 3. Form 3 is an anhydrous polymorph of the compound of Formula (1). In one embodiment, polymorph Form 3 has an XRPD pattern, obtained with CuKα1-radiation, with at least peaks at °2θ values of 7.2±0.2, 22.2±0.2, and 24.4±0.2. In some embodiments, Form 3 has an XRPD pattern with at least peaks at °2θ values of 6.3±0.2, 7.2±0.2, 21.6±0.2, 22.2±0.2, and 24.4±0.2. In some embodiments, Form 3 has an XRPD pattern with at least peaks at °2θ values of 6.3±0.2, 7.2±0.2, 11.0±0.2, 18.4±0.2, 19.0±0.2, 21.6±0.2, 22.2±0.2, and 24.4±0.2. For example, in some embodiments, Form 3 has an XRPD pattern with at least peaks at °2θ values of 6.3±0.2, 7.2±0.2, 11.0±0.2, 14.2±0.2, 17.8±0.2, 18.4±0.2, 19.0±0.2, 21.6±0.2, 22.2±0.2, and 24.4±0.2.

In some embodiments, a composition comprising polymorph Form 3 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 2, Form 4, Form 5, Form 6, Form 7, Form 8, Form 9, Form 10, Form 11, a non-stoichiometric hydrate of Form 1, or a combination of two or more thereof.

In some embodiments, polymorph Form 3 exhibits an exotherm between about 190-220° C., as measured by DSC. In some embodiments, polymorph Form 3 exhibits an exotherm at between about 225-235° C., e.g., around 230° C., as measured by DSC. In some embodiments, polymorph Form 3 exhibits an exotherm at between about 292-300° C., e.g., around 297° C., as measured by DSC. For example, in some embodiments, the endotherms and exotherms are observed when using a scan rate of 10° C. per minute.

In some embodiments, polymorph Form 3 has a melting point of around 365° C. In some embodiments, polymorph Form 3 undergoes a weight loss of about 1.6% before around 81° C. and a weight loss of about 1.7% between about 81-169° C. as measured by TGA.

Provided herein is a process of preparing polymorph Form 3. In some embodiments, the process comprises reslurrying a composition comprising the compound of Formula (1), including amorphous and polymorph forms thereof, in a solvent or mixture of solvents to generate Form 3 as a residual solid. In some embodiments, the composition comprises a non-stoichiometric hydrate of Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of Form 1 having between 1% and about 20% by weight water in a solvent or mixture of solvents to generate polymorph Form 3 as a residual solid. In some embodiments, the solvent is IPAc. In some embodiments, the solvent is n-butyl acetate. In some embodiments, the reslurrying takes place at RT. In some embodiments, the reslurrying takes place at around 50° C.

In some embodiments, the polymorph form of the compound of Formula (1) is a polymorph known as Form 4. Form 4 is an anhydrous polymorph of the compound of Formula (1). In one embodiment, polymorph Form 4 has an XRPD pattern, obtained with CuKα1-radiation, with at least peaks at °2θ values of 7.0±0.2, 21.8±0.2, and 25.1±0.2. In some embodiments, Form 4 has an XRPD pattern with at least peaks at °2θ values of 7.0±0.2, 19.5±0.2, 21.8±0.2, 23.2±0.2, and 25.1±0.2. In some embodiments, Form 4 has an XRPD pattern with at least peaks at °2θ values of 7.0±0.2, 17.6±0.2, 18.3±0.2, 19.5±0.2, 21.8±0.2, 23.2±0.2, 25.1±0.2, and 25.8±0.2. For example, in some embodiments, Form 4 has an XRPD pattern with at least peaks at °2θ values of 7.0±0.2, 9.6±0.2, 17.6±0.2, 18.3±0.2, 19.5±0.2, 21.8±0.2, 23.2±0.2, 25.1±0.2, 25.8±0.2, and 29.3±0.2.

In some embodiments, a composition comprising polymorph Form 4 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 2, Form 3, Form 5, Form 6, Form 7, Form 8, Form 9, Form 10, Form 11, a non-stoichiometric hydrate of Form 1, or a combination of two or more thereof.

In some embodiments, polymorph Form 4 exhibits an endotherm between about 50-100° C. as measured by DSC. In some embodiments, polymorph Form 4 exhibits an endotherm at between about 180-215° C. In some embodiments, polymorph Form 4 exhibits an endotherm between about 220-230° C. In some embodiments, polymorph Form 4 exhibits an exotherm at between about 230-240° C., e.g., around 235° C. In some embodiments, polymorph Form 4 exhibits an exotherm at between about 300-310° C. For example, in some embodiments, the endotherms and exotherms are observed when using a scan rate of 10° C. per minute.

In some embodiments, polymorph Form 4 has a melting point of between about 366-369° C., e.g., around 367° C. In some embodiments, polymorph Form 4 undergoes a weight loss of about 8.3% before around 200° C., e.g., from about 42° C. to about 200° C., as measured by TGA.

Provided herein is a process of preparing polymorph Form 4. In some embodiments, the process comprises reslurrying a composition comprising the compound of Formula (1), including amorphous and polymorph forms thereof, in a solvent or mixture of solvents to generate Form 4 as a residual solid. In some embodiments, the composition comprises a non-stoichiometric hydrate of Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of Form 1 having between 1% and about 20% by weight water in a solvent or mixture of solvents to generate polymorph Form 4 as a residual solid. In some embodiments, the solvent is EA. In some embodiments, the solvent is MA. In some embodiments, the solvent is MtBE. In some embodiments, the solvent is n-propanol. In some embodiments, the solvent is acetone. In some embodiments, the solvent is in a mixture with water, for example the solvent can be a mixture of water and MA, EA, or acetone. In some embodiments, the water is present in an amount of about 5% by weight. In some embodiments, the reslurrying takes place at RT. In some embodiments, the reslurrying takes place at around 50° C.

In some embodiments, the polymorph form of the compound of Formula (1) is a polymorph known as Form 5. Form 5 is an anhydrous polymorph of the compound of Formula (1). In one embodiment, polymorph Form 5 has an XRPD pattern, obtained with CuKα1-radiation, with at least peaks at °2θ values of 7.3±0.2, 22.3±0.2, and 24.5±0.2. In some embodiments, Form 5 has an XRPD pattern with at least peaks at °2θ values of 6.3±0.2, 7.3±0.2, 21.7±0.2, 22.3±0.2, and 24.5±0.2. In some embodiments, Form 5 has an XRPD pattern with at least peaks at °2θ values of 6.3±0.2, 7.3±0.2, 11.0±0.2, 19.1±0.2, 19.5±0.2, 21.7±0.2, 22.3±0.2, and 24.5±0.2. For example, in some embodiments, Form 5 has an XRPD pattern with at least peaks at °2θ values of 6.3±0.2, 7.3±0.2, 11.0±0.2, 14.3±0.2, 19.1±0.2, 19.5±0.2, 21.7±0.2, 22.3±0.2, 24.5±0.2, and 26.5±0.2.

In some embodiments, a composition comprising polymorph Form 5 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 2, Form 3, Form 4, Form 6, Form 7, Form 8, Form 9, Form 10, Form 11, a non-stoichiometric hydrate of Form 1, or a combination of two or more thereof.

In some embodiments, polymorph Form 5 exhibits an endotherm between about 50-100° C. as measured by DSC. In some embodiments, polymorph Form 5 exhibits an endotherm at between about 210-235° C., e.g., around 222° C. In some embodiments, polymorph Form 5 exhibits an exotherm at between about 227-240° C., e.g., around 235° C. In some embodiments, polymorph Form 5 exhibits an exotherm at between about 280-300° C., e.g., around 293° C. For example, in some embodiments, the endotherms and exotherms are observed when using a scan rate of 10° C. per minute.

In some embodiments, polymorph Form 5 has a melting point of around 363° C. In some embodiments, polymorph Form 5 undergoes a weight loss of about 3.1% before around 100° C. and about 1.7% between about 100-250° C. as measured by TGA.

Provided herein is a process of preparing polymorph Form 5. In some embodiments, the process comprises reslurrying a composition comprising the compound of Formula (1), including amorphous and polymorph forms thereof, in a solvent or mixture of solvents to generate Form 5 as a residual solid. In some embodiments, the composition comprises a non-stoichiometric hydrate of Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of Form 1 having between 1% and about 20% by weight water in a solvent or mixture of solvents to generate polymorph Form 5 as a residual solid. In some embodiments, the solvent is MtBE. In some embodiments, the reslurrying takes place at RT. In some embodiments, the reslurrying takes place at around 50° C.

In some embodiments, the polymorph form of the compound of Formula (1) is a polymorph known as Form 6. Form 6 is an anhydrous polymorph of the compound of Formula (1).

In some embodiments, a composition comprising polymorph Form 6 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 2, Form 3, Form 4, Form 5, Form 7, Form 8, Form 9, Form 10, Form 11, a non-stoichiometric hydrate of Form 1, or a combination of two or more thereof.

In some embodiments, polymorph Form 6 exhibits an exotherm between about 245-260° C. as measured by DSC. For example, in some embodiments, the endotherms and exotherms are observed when using a scan rate of 10° C. per minute. In some embodiments, polymorph Form 6 has a melting point of around 364° C.

Provided herein is a process of preparing polymorph Form 6. In some embodiments, the process comprises reslurrying a composition comprising the compound of Formula (1), including amorphous and polymorph forms thereof, in a solvent or mixture of solvents to generate Form 6 as a residual solid. In some embodiments, the composition comprises a non-stoichiometric hydrate of Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of Form 1 having between 1% and about 20% by weight water in a solvent or mixture of solvents to generate polymorph Form 6 as a residual solid. In some embodiments, the solvent is IPAc. In some embodiments, the solvent is in a mixture with water, for example the solvent can be a mixture of water and IPAc. In some embodiments, the water is present in an amount of about 5% by weight. In some embodiments, the reslurrying takes place at RT. In some embodiments, the reslurrying takes place at around 50° C.

In some embodiments, the polymorph of the compound of Formula (1) is a polymorph known as Form 7. Form 7 is an anhydrous polymorph of the compound of Formula (1). In one embodiment, polymorph Form 7 has an XRPD pattern, obtained with CuKα1-radiation, with at least peaks at °2θ values of 7.1±0.2, 21.6±0.2, and 23.2±0.2. In some embodiments, Form 7 has an XRPD pattern with at least peaks at °2θ values of 4.9±0.2, 7.1±0.2, 18.5±0.2, 21.6±0.2, and 23.2±0.2. In some embodiments, Form 7 has an XRPD pattern with at least peaks at °2θ values of 4.9±0.2, 7.1±0.2, 10.9±0.2, 18.5±0.2, 19.4±0.2, 21.6±0.2, 23.2±0.2, and 30.3±0.2. For example, in some embodiments, Form 7 has an XRPD pattern with at least peaks at °2θ values of 4.9±0.2, 7.1±0.2, 8.8±0.2, 10.9±0.2, 18.5±0.2, 19.4±0.2, 21.6±0.2, 22.1±0.2, 23.2±0.2, and 30.3±0.2.

In some embodiments, a composition comprising polymorph Form 7 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 2, Form 3, Form 4, Form 5, Form 6, Form 8, Form 9, Form 10, Form 11, a non-stoichiometric hydrate of Form 1, or a combination of two or more thereof.

In some embodiments, polymorph Form 7 exhibits an exotherm between about 227-235° C., e.g., around 232° C., as measured by DSC. In some embodiments, polymorph Form 7 exhibits an exotherm between about 299-305° C., e.g., around 303° C. For example, in some embodiments, the endotherms and exotherms are observed when using a scan rate of 10° C. per minute.

In some embodiments, polymorph Form 7 has a melting point of around 365° C. In some embodiments, polymorph Form 7 undergoes a weight loss of about 12% before around 200° C., e.g., from about 36° C. to about 200° C., as measured by TGA.

Provided herein is a process of preparing polymorph Form 7. In some embodiments, the process comprises reslurrying a composition comprising the compound of Formula (1), including amorphous and polymorph forms thereof, in a solvent or mixture of solvents to generate Form 7 as a residual solid. In some embodiments, the composition comprises a non-stoichiometric hydrate of Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of Form 1 having between 1% and about 20% by weight water in a solvent or mixture of solvents to generate polymorph Form 7 as a residual solid. In some embodiments, the solvent is methyl ethyl ketone (MEK). In some embodiments, the solvent is in a mixture with water, for example the solvent can be a mixture of water and MEK. In some embodiments, the water is present in an amount of about 5% by weight. In some embodiments, the reslurrying takes place at RT. In some embodiments, the reslurrying takes place at around 50° C.

In some embodiments, the polymorph form of the compound of Formula (1) is a polymorph known as Form 8. Form 8 is an anhydrous polymorph of the compound of Formula (1). In one embodiment, polymorph Form 8 has an XRPD pattern, obtained with CuKα1-radiation, with at least peaks at °2θ values of 6.9±0.2, 17.7±0.2, and 21.5±0.2. In some embodiments, Form 8 has an XRPD pattern with at least peaks at °2θ values of 6.9±0.2, 11.5±0.2, 17.7±0.2, 21.5±0.2, and 27.6±0.2. In some embodiments, Form 8 has an XRPD pattern with at least peaks at °2θ values of 6.9±0.2, 11.5±0.2, 15.3±0.2, 16.9±0.2, 17.7±0.2, 21.5±0.2, 27.6±0.2, and 28.9±0.2. For example, in some embodiments, Form 8 has an XRPD pattern with at least peaks at °2θ values of 6.9±0.2, 11.5±0.2, 12.7±0.2, 14.2±0.2, 15.3±0.2, 16.9±0.2, 17.7±0.2, 21.5±0.2, 27.6±0.2, and 28.9±0.2.

In some embodiments, a composition comprising polymorph Form 8 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 2, Form 3, Form 4, Form 5, Form 6, Form 7, Form 9, Form 10, Form 11, a non-stoichiometric hydrate of Form 1, or a combination of two or more thereof.

In some embodiments, polymorph Form 8 exhibits an endotherm between about 41-60° C. as measured by DSC. In some embodiments, polymorph Form 8 exhibits an exotherm at between about 221-235° C., e.g., around 231° C. In some embodiments, polymorph Form 8 exhibits an endotherm between about 279-290° C., e.g., around 285° C. For example, in some embodiments, the endotherms and exotherms are observed when using a scan rate of 10° C. per minute.

In some embodiments, polymorph Form 8 has a melting point of around 364° C. In some embodiments, polymorph Form 8 undergoes a weight loss of about 4.2% before around 190° C. and about 3.9% between about 190-261° C. as measured by TGA.

Provided herein is a process of preparing polymorph Form 8. In some embodiments, the process comprises reslurrying a composition comprising the compound of Formula (1), including amorphous and polymorph forms thereof, in a solvent or mixture of solvents to generate Form 8 as a residual solid. In some embodiments, the composition comprises a non-stoichiometric hydrate of Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of Form 1 having between 1% and about 20% by weight water in a solvent or mixture of solvents to generate polymorph Form 8 as a residual solid. In some embodiments, the solvent is MIBK. In some embodiments, the reslurrying takes place at RT. In some embodiments, the reslurrying takes place at around 50° C.

In some embodiments, the polymorph form of the compound of Formula (1) is a polymorph known as Form 9. Form 9 is an anhydrous polymorph of the compound of Formula (1). In one embodiment, polymorph Form 9 has an XRPD pattern, obtained with CuKα1-radiation, with at least peaks at °2θ values of 4.9±0.2, 18.6±0.2, and 21.1±0.2. In some embodiments, Form 9 has an XRPD pattern with at least peaks at °2θ values of 4.9±0.2, 18.6±0.2, 21.1±0.2, 24.1±0.2, and 25.2±0.2. In some embodiments, Form 9 has an XRPD pattern with at least peaks at °2θ values of 4.9±0.2, 15.3±0.2, 16.5±0.2, 18.6±0.2, 21.1±0.2, 22.4±0.2, 24.1±0.2, and 25.2±0.2. For example, in some embodiments, Form 9 has an XRPD pattern with at least peaks at °2θ values of 4.9±0.2, 10.1±0.2, 15.3±0.2, 16.5±0.2, 18.6±0.2, 21.1±0.2, 22.4±0.2, 24.1±0.2, 25.2±0.2, and 28.6±0.2.

In some embodiments, a composition comprising polymorph Form 9 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 2, Form 3, Form 4, Form 5, Form 6, Form 7, Form 8, Form 10, Form 11, a non-stoichiometric hydrate of Form 1, or a combination of two or more thereof.

In some embodiments, polymorph Form 9 exhibits a single melting endotherm at around 364° C. as measured by DSC. For example, in some embodiments, the endotherm is observed when using a scan rate of 10° C. per minute. In some embodiments, other polymorph forms provided herein, such as, e.g., Form 1 and Form 2, can convert to Form 9 when heated to just before melting (i.e., around 364° C.).

In some embodiments, polymorph Form 9 has a melting point of around 364° C. In some embodiments, polymorph Form 9 undergoes a weight loss of about 0.28% before around 100° C., e.g., from about 30.5° C. to about 100° C., as measured by TGA.

Provided herein is a process of preparing polymorph Form 9. In some embodiments, the process comprises reslurrying a composition comprising the compound of Formula (1), including amorphous and polymorph forms thereof, in a solvent or mixture of solvents to generate Form 9 as a residual solid. In some embodiments, the composition comprises a non-stoichiometric hydrate of Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of Form 1 having between 1% and about 20% by weight water in a solvent or mixture of solvents to generate polymorph Form 9 as a residual solid. In some embodiments, the solvent is n-butanol. In some embodiments, the solvent is IPAc. In some embodiments, the solvent is n-butyl acetate. In some embodiments, the solvent is in a mixture with water, for example the solvent can be a mixture of water and ethanol or water and n-propanol. In some embodiments, the water is present in an amount of about 5% by weight. In some embodiments, the reslurrying takes place at RT. In some embodiments, the reslurrying takes place at around 50° C.

In some embodiments, the polymorph form of the compound of Formula (1) is a polymorph known as Form 10. Polymorph Form 10 is associated with DMSO. For example, DMSO is on the surface of the polymorph. In one embodiment, polymorph Form 10 has an XRPD pattern, obtained with CuKα1-radiation, with at least peaks at °2θ values of 20.7±0.2, 21.7±0.2, and 24.2±0.2. In some embodiments, Form 10 has an XRPD pattern with at least peaks at °2θ values of 18.2±0.2, 19.0±0.2, 20.7±0.2, 21.7±0.2, and 24.2±0.2. In some embodiments, Form 10 has an XRPD pattern with at least peaks at °2θ values of 17.8±0.2, 18.2±0.2, 19.0±0.2, 20.7±0.2, 21.7±0.2, 23.4±0.2, 24.2±0.2, and 27.9±0.2. For example, in some embodiments, Form 10 has an XRPD pattern with at least peaks at °2θ values of 6.7±0.2, 17.8±0.2, 18.2±0.2, 19.0±0.2, 19.9±0.2, 20.7±0.2, 21.7±0.2, 23.4±0.2, 24.2±0.2, and 27.9±0.2.

In some embodiments, a composition comprising polymorph Form 10 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 2, Form 3, Form 4, Form 5, Form 6, Form 7, Form 8, Form 9, Form 11, a non-stoichiometric hydrate of Form 1, or a combination of two or more thereof.

In some embodiments, polymorph Form 10 exhibits an endotherm between about 212-237° C. as measured by DSC. In some embodiments, polymorph Form 10 exhibits an endotherm at between about 234-245° C., e.g., around 237° C. In some embodiments, polymorph Form 10 exhibits an exotherm between about 300-325° C., e.g., around 308° C. For example, in some embodiments, the endotherms and exotherms are observed when using a scan rate of 10° C. per minute.

In some embodiments, polymorph Form 10 has a melting point of between about 364-372° C., such as, e.g., around 369° C. In some embodiments, polymorph Form 10 undergoes a weight loss of about 0.6% before around 100° C., a weight loss of about 3.8% between about 100-170° C., and a weight loss of about 7.1% between about 170-260° C. as measured by TGA.

Provided herein is a process of preparing polymorph Form 10. In some embodiments, the process comprises reslurrying a composition comprising the compound of Formula (1), including amorphous and polymorph forms thereof, in a solvent or mixture of solvents to generate Form 10 as a residual solid. In some embodiments, the composition comprises a non-stoichiometric hydrate of Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of Form 1 having between 1% and about 20% by weight water in a solvent or mixture of solvents to generate polymorph Form 10 as a residual solid. In some embodiments, the solvent is DMSO. In some embodiments, the solvent is in a mixture with water, for example the solvent can be a mixture of water and DMSO. In some embodiments, the water is present in an amount of about 5% by weight. In some embodiments, the reslurrying takes place at RT. In some embodiments, the reslurrying takes place at around 50° C.

In some embodiments, the polymorph form of the compound of Formula (1) is a polymorph known as Form 11. Form 11 is an anhydrous polymorph of the compound of Formula (1). In one embodiment, polymorph Form 11 has an XRPD pattern, obtained with CuKα1-radiation, with at least peaks at °2θ values of 6.4±0.2, 18.5±0.2, and 22.4±0.2. In some embodiments, Form 11 has an XRPD pattern with at least peaks at °2θ values of 6.4±0.2, 17.8±0.2, 18.5±0.2, 19.9±0.2, and 22.4±0.2. In some embodiments, Form 11 has an XRPD pattern with at least peaks at °2θ values of 6.4±0.2, 8.4±0.2, 17.8±0.2, 18.5±0.2, 19.9±0.2, 22.4±0.2, 24.5±0.2, and 26.8±0.2. For example, in some embodiments, Form 11 has an XRPD pattern with at least peaks at °2θ values of 6.4±0.2, 8.4±0.2, 17.8±0.2, 18.5±0.2, 19.9±0.2, 20.3±0.2, 22.4±0.2, 22.9±0.2, 24.5±0.2, and 26.8±0.2.

In some embodiments, a composition comprising polymorph Form 11 is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (1). For example, in some embodiments, the composition is substantially free of other anhydrous forms of the compound of Formula (1). In some embodiments, the composition contains less than 15% by weight of other forms of the compound of Formula (1), such as less than 14%, 13%, 12%, 11%, 10%, 9%, 8%, 7%, 6%, 5%, 4%, 3%, 2%, 1% or less by weight of other forms of the compound of Formula (1). In some embodiments, the composition contains less than 15% by weight of one or more other forms of the compound of Formula (1), such as less than 14%, 13%, 12%, 11%, 10%, 9%, 8%, 7%, 6%, 5%, 4%, 3%, 2%, 1% or less by weight of one or more other forms of the compound of Formula (1). For example, the composition can contain less than about 15% of Form 1, Form 2, Form 3, Form 4, Form 5, Form 6, Form 7, Form 8, Form 9, Form 10, a non-stoichiometric hydrate of Form 1, or a combination of two or more thereof.

In some embodiments, polymorph Form 11 exhibits an endotherm between about 215-230° C. as measured by DSC. In some embodiments, polymorph Form 11 exhibits an exotherm at between about 230-240° C., e.g., around 235° C. In some embodiments, polymorph Form 11 exhibits an exotherm between about 300-315° C., e.g., around 310° C. For example, in some embodiments, the endotherms and exotherms are observed when using a scan rate of 10° C. per minute.

In some embodiments, polymorph Form 11 has a melting point of around 368° C. In some embodiments, polymorph Form 11 undergoes a weight loss of about 0.8% before around 100° C. and a weight loss of about 7.0% between about 100-249° C., as measured by TGA.

Provided herein is a process of preparing polymorph Form 11. In some embodiments, the process comprises reslurrying a composition comprising the compound of Formula (1), including amorphous and polymorph forms thereof, in a solvent or mixture of solvents to generate Form 11 as a residual solid. In some embodiments, the composition comprises a non-stoichiometric hydrate of Form 1 having between 1% and about 20% by weight water. In some embodiments, the reslurrying takes place at RT. In some embodiments, the reslurrying takes place at around 50° C. In some embodiments, the process further comprises drying the residual solid, for example, under vacuum. In some embodiments, the drying is at a temperature of between about 60° C. and 90° C., such as, e.g., around 75° C.

In some embodiments, the process comprises reslurrying a composition comprising a non-stoichiometric hydrate of Form 1 having between 1% and about 20% by weight water in a solvent or mixture of solvents to generate polymorph Form 11 as a residual solid. In some embodiments, the solvent is dimethylformamide (DMF). In some embodiments, the solvent is in a mixture with water, for example the solvent can be a mixture of water and DMF. In some embodiments, the water is present in an amount of about 5% by weight. In some embodiments, the reslurrying takes place at RT. In some embodiments, the reslurrying takes place at around 50° C.

4. Processes for Preparing Compositions Including the Compound of Formula (1)

Also provided herein is a process for preparing a pharmaceutical composition, including mixing (i) a compound of Formula (1), or salt or amorphous or polymorph form thereof, prepared according to any of the processes described herein, and (ii) a pharmaceutically acceptable carrier (excipient), to form the composition.

In making the compositions provided herein, the compound of Formula (1), or salt or amorphous or polymorph form thereof, can be mixed with an excipient, diluted by an excipient, or enclosed within such a carrier in the form of, for example, a capsule, sachet, paper, or other container. When the excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is formulated as a tablet or capsule.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers, such as a phosphate buffered saline solution, water, emulsions such as oil/water emulsion, and various types of wetting agents. Compositions comprising such carriers can be formulated by well-known conventional methods (see, for example, *Remington's Pharmaceutical Sciences*, 18th edition, A. Gennaro, ed., Mack Publishing Co., Easton, Pa., 1990; and Remington, *The Science and Practice of Pharmacy*, 20th Ed., Mack Publishing, 2000).

The compositions comprising the compound of Formula (1), or a pharmaceutically acceptable salt or amorphous or polymorph form thereof, can be formulated in a unit dosage form. In some embodiments, each dosage contains from about 1 mg to about 1,000 mg (1 g). The term "unit dosage form" refers to physically discrete units suitable as unitary dosages for human subjects and other patients, each unit containing a predetermined quantity of active material calculated to produce the desired therapeutic effect, in association with a suitable pharmaceutical excipient. In some embodiments, the active material is the compound of Formula (1), or a salt or amorphous or polymorph form thereof.

In some embodiments, the compositions provided herein contain from about 5 mg to about 50 mg of the compound of Formula (1), or a pharmaceutically acceptable salt or amorphous or polymorph form thereof. For example, the compositions provided herein can contain about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the compound of Formula (1), or a pharmaceutically acceptable salt or amorphous or polymorph form thereof.

In some embodiments, the compositions provided herein contain from about 50 mg to about 500 mg of the compound of Formula (1), or a pharmaceutically acceptable salt or amorphous or polymorph form thereof. For example, the compositions provided herein can contain about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the compound of Formula (1), or a pharmaceutically acceptable salt or amorphous or polymorph form thereof.

In some embodiments, the compositions provided herein contain from about 500 mg to about 1,000 mg of Formula (1), or a pharmaceutically acceptable salt or amorphous or polymorph form thereof. For example, the compositions provided herein can contain about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of Formula (1), or a pharmaceutically acceptable salt or amorphous or polymorph form thereof.

EXAMPLES

Example 1: Synthesis of N-(5-(3-(7-(3-fluorophenyl)-3H-imidazo[4,5-c]pyridin-2-yl)-1H-indazol-5-yl)pyridin-3-yl)-3-methylbutanamide (1)

The compound of Formula (1) was synthesized as detailed in Scheme 7 and described below.

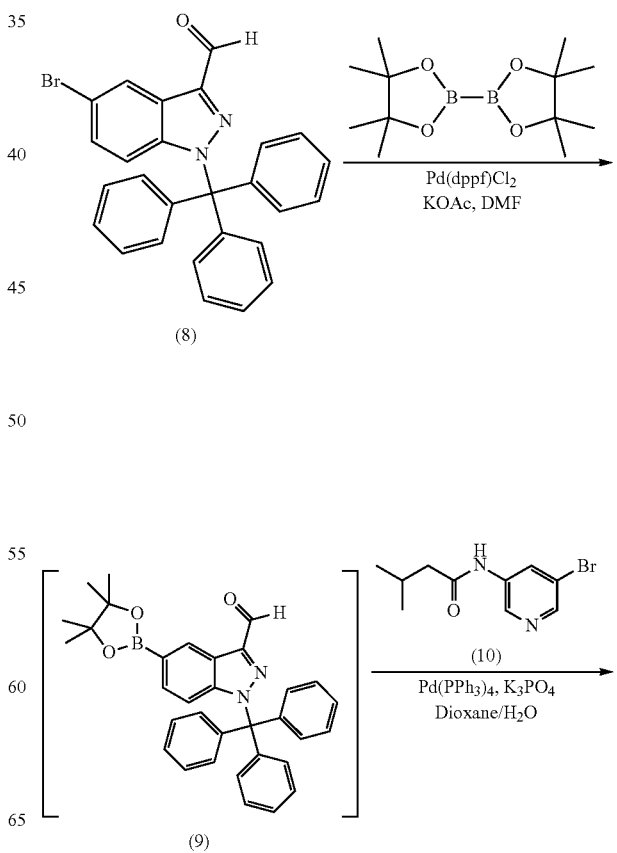

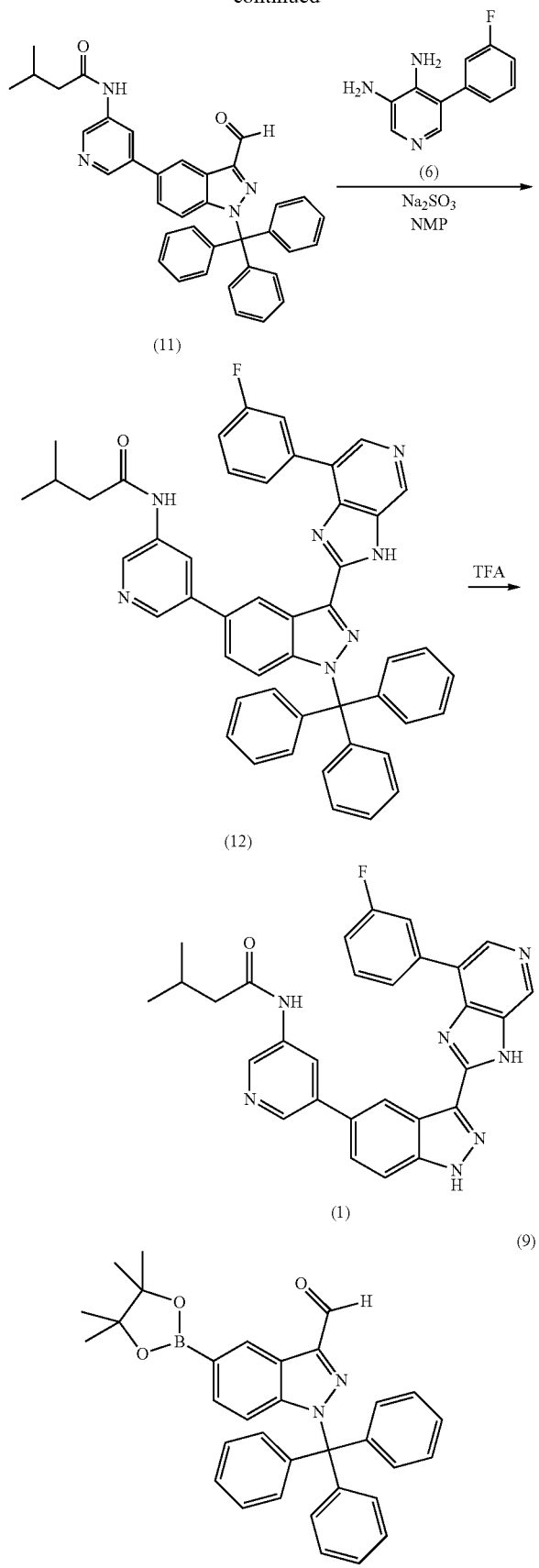

Synthesis of 5-(4,4,5,5-tetramethyl-1,3,2-dioxaborolan-2-yl)-1-trityl-1H-indazole-3-carbaldehyde (9)

To a multi-neck, 10 L, cylindrical jacketed reactor was added (8) (300.0 g, 1.0 equiv., 87.5% potency assumed), bis(pinacolato)diboron (171.2 g, 1.2 equiv.), and KOAc (110.2 g, 2.0 equiv.). DMF (1575 mL, 6 volumes) was added to the flask and the flask was evacuated and refilled with N2 three times. Next, Pd(dppf)Cl$_2$ (12.3 g, 0.03 equiv.) was added to the flask and the vessel was evacuated and refilled with N2 three times. The flask was heated to 90-95° C. using a temperature control unit (TCU) overnight (e.g., over 20 hours). The mixture was cooled to ambient temperature and H$_2$O (2100 mL) was added drop-wise to the vessel over 104 minutes while maintaining an internal temperature between 15-25° C. The precipitated solids were stirred for an additional 30 min and then the reaction mixture was filtered through filter paper on a Buchner funnel. Subsequently, the cake was rinsed with water (1575 mL, 6 vol). The cake was conditioned until it ceased dripping. The wet cake weighed 840 g. The cake was kept under hi-vac at ambient temperature overnight. The weight was reduced to 685 g.

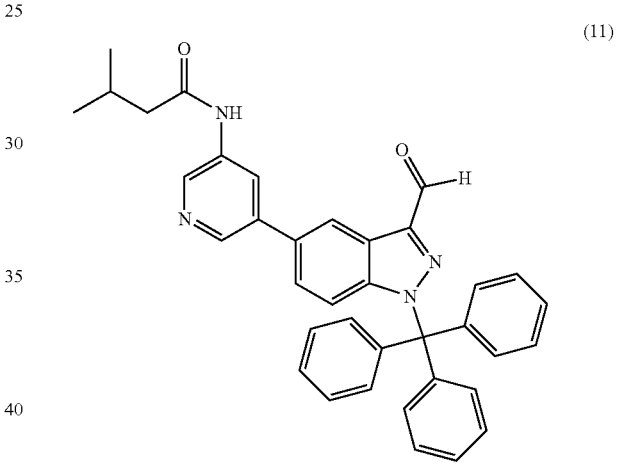

Synthesis of N-(5-(3-formyl-1-trityl-1H-indazol-5-yl)pyridin-3-yl)-3-methylbutanamide (11)

The crude boronate ester (9) was charged to a 5-L, 3-neck, round bottomed flask and (10) (N-(5-bromopyridin-3-yl)-3-methylbutanamide) (159.9 g, 1.0 equiv., 90.3% potency assumed), K$_3$PO$_4$ monohydrate (388.2 g, 3.00 equiv.), 1,4-dioxane (1269 mL, 5 v), and H$_2$O (390 mL, 1.5 v) were charged to the vessel. Agitation was started and the internal temperature increased from 17° C. to 26.7° C. The flask underwent a vacuum/N2 cycle 3 times. Next, Pd(PPh$_3$)$_4$ (19.7 g, 0.03 equiv.) was added to the flask. A vacuum/N2 cycle was completed 3 times. The flask was heated by a heating mantle to 85-95° C. in 70 min. After 180 minutes, the mixture was cooled to ambient temperature and no remaining 5-(4,4,5,5-tetramethyl-1,3,2-dioxaborolan-2-yl)-1-trityl-1H-indazole-3-carb aldehyde (9) was detected by HPLC.

The reaction mixture was cooled to room temperature and added drop-wise, via addition funnel, to a multi-neck, jacketed cylindrical reactor containing H$_2$O (4.8 L) over 126 minutes. The residual was rinsed with dioxane (200 mL) into the 10-L reactor. It was then stirred at 15-25° C. for 90 minutes and then filtered through filter paper over a Buchner funnel. The filtration took about 20 minutes, and the cake was rinsed with water (1.6 L). This took 25 minutes, and the cake was conditioned for 45 minutes. The cake was transferred to a drying dish and kept under hi-vac at room temperature overnight. The solids were charged back into the 10-L reactor after losing approximately 150 g weight. 2-methyl THF (1.69 L) was added to the flask. A dark brown solution was obtained after stirring for approximately 30 minutes at 40-50° C. A 9% oxalic acid solution (1348 g) was added drop-wise to the reactor in 39 minutes while keeping the temperature at 40-50° C. A slurry was formed, and it was aged for 4 h at 40-50° C. and then stirred at 0-10° C. for 16 h. The batch was filtered (17 minutes), and the reactor and the brown solids were rinsed with 615 mL of cold 2-methyl THF, which removed a significant amount of color from the solids. The pH of the filtrate was 1. The solids were charged back to the 10-L reactor, followed by the addition of 2-methyl-THF (1.69 L). A solution of 10% $K_2CO_3$ (1 L, 1067 g) was added to the slurry to adjust the pH to 9 at 10-20° C. in 24 minutes. The aqueous layer (lower, colorless) was removed and the organic layer was cooled to 5-10° C. Aqueous oxalic acid (1360 g) was added to the solution in 60 minutes. Solids precipitated from solution and, after aging overnight at 5-10° C., the solids (light brown) were collected by filtration (94 minutes) and washed with cold 2-methyl-THF (615 mL, 68 minutes), which removed a significant amount of color from the solids. The solids were charged back to the 10-L reactor and suspended in 2-methyl-THF (1.84 L). The pH of the mixture was adjusted to 9 with 10% $K_2CO_3$ (1.5 L) to form a biphasic homogeneous solution. The aqueous layer was removed and the organic layer was washed with 25% NaCl (400 mL) and $H_2O$ (1575 mL) twice. The pH of the aqueous phase was approximately 7 as determined by pH paper. The organic layer was transferred to heptanes (3860 mL) dropwise while stirring at a rate to keep the temperature below 25° C. The addition took 3.5 hours and a nice flowing slurry was obtained. The slurry was concentrated to approximately 5 vol on a rotovap under vacuum and then filtered through a Buchner funnel (2 minutes). The cake was washed with heptanes (2.32 L) and dried under hi-vac at 40-50° C. overnight to afford 225 g of N-(5-(3-formyl-1-trityl-1H-indazol-5-yl)pyridin-3-yl)-3-methylbutanamide (compound (11)) as an off-white powder in 71% yield. The crude compound (11), the first isolated compound (11) oxalate salt, the second isolated compound (11) oxalate salt, and the final product of compound (11) were analyzed. The purities were: 90.89%, 97.54%, 97.94%, and 98.27%, respectively.

(12)

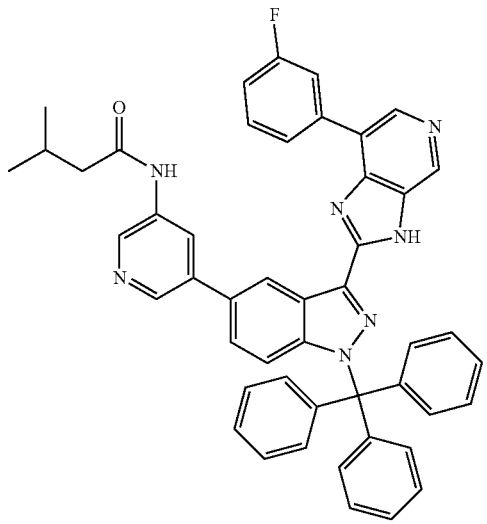

Synthesis of N-(5-(3-(7-(3-fluorophenyl)-3H-imidazo[4,5-c]pyridin-2-yl)-1-trityl-1H-indazol-5-yl)pyridin-3-yl)-3-methylbutanamide (12)

To a 2 L, multi-neck, round bottomed flask was charged compound (11) (70 g, 1.0 equiv., 98% purity), compound (6) (5-(3-fluorophenyl)pyridine-3,4-diamine) (34.37 g, 1.00 equiv., 97.6% potency), grinded $Na_2SO_3$ (30.6 g, 2.0 equiv.) and NMP (1065 mL). A 0.1 mL portion of the reaction was taken for Karl Fischer (KF) titration analysis, which showed 3129 ppm of $H_2O$ content. The reaction mixture was heated to 110-115° C. by a heating mantle. The reaction went to completion after 24 hours with 14.1% of compound (1), 78.3% of compound (12), and 0.42% of compound (11). The reaction mixture was quenched into a mixture of water (2135 mL), $NaHCO_3$ (103 g), and 1030 mL EtOAc in a 10-L reactor over 27 minutes. The flask was rinsed with NMP (67 mL) into the quench mixture. The mixture was filtered through a Celite pad and the filtration took 16 minutes. The reactor and the cake were rinsed with EtOAc (200 mL). The filtrate was transferred back to the 10-L reactor and the phases were separated. The aqueous layer was extracted with EtOAc (760 mL). The combined organic layer was washed with a mixture of water (525 mL) and 25% NaCl solution (125 mL). A 9% oxalic acid solution (308 g) was added dropwise to the organic layer in 45 minutes to obtain a pH of 1. The slurry was filtered through filter paper over 21 minutes. The reactor and cake were rinsed with EtOAc (380 mL) and this took another 10 minutes. An aliquot of the wet cake was analyzed for purity and the result showed a 87.89% by area under curve (AUC) purity for compound (12). The wet cake was charged back to a 5-L 4-neck RBF followed by the addition of MeOH (693 mL) and DCM (1654 mL). The mixture was heated up to reflux (35° C.) and Celite (47 g) was added. A Buchner funnel was set up with a Celite pad on the bottom and a pad of activated carbon (60 g, Darco™ G-60) on the top. The mixture was stirred at reflux for 70 minutes and then filtered hot through the Buchner funnel. The filtration took 13 minutes. The reactor and the cake were rinsed with a mixed solvent of MeOH/DCM (173 mL/414 mL). It took 10 minutes to complete. The dark brown solution was concentrated on a rotovap to approximately 4 vol and acetone (870 mL) was added. The mixture was concentrated to approximately 4 vol and once again acetone (2×870 mL) was added. The mixture was concentrated to approximately 3 vol and diluted with acetone (260 mL). $^1$H NMR analysis of the solvent showed 2.8% by weight of MeOH to acetone and the solvent swap was deemed complete. The slurry was filtered and the cake was rinsed with acetone (430 mL). An aliquot of the wet cake was analyzed and it had a purity of 99.10% AUC. The wet cake was charged back to a 5-L multi-neck RBF followed by the addition of 2-methyl-THF (878 mL). A 10% $K_2CO_3$ solution (440 mL) was added to the mixture over 20 minutes to obtain a pH of approximately 10. The mixture was transferred to a 2-L separatory funnel and the phases were separated. The organic layer was washed with 4.8% a $Na_2SO_4$ solution (2×526 mL) and then diluted with tert-butyl methyl ether (MTBE; 927 mL). The organic solution was added to heptanes over 1 hour and 51 minutes; keeping the temperature at 15-25° C. The resulting slurry was concentrated to approximately 3 vol on a rotovap to afford a very thick slurry. It was filtered through filter paper (total 15 minutes) and the cake was dried under hi-vac at 40-50° C. for 15 h. Compound (12) was obtained (61.1 g) in 66% yield. HPLC analysis showed 99.16% purity.

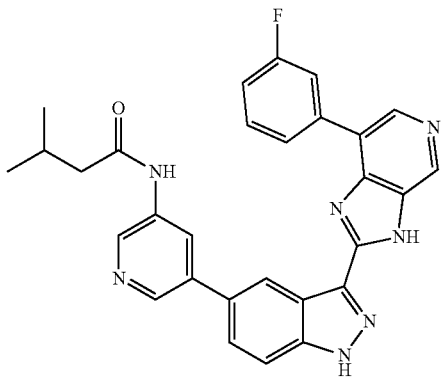

(1)

Synthesis of N-(5-(3-(7-(3-fluorophenyl)-3H-imidazo[4,5-c]pyridin-2-yl)-1H-indazol-5-yl)pyridin-3-yl)-3-methylbutanamide (1)

To a 1-L 3-neck round bottomed flask was charged TFA (250 mL). Compound (12) (55 g) was added portion-wise over 12 minutes to the flask while using an ice/water bath to control the temperature below 20° C. After 2 h, a sample was analyzed by HPLC and showed that no compound (12) was detectable. TFA (37 mL) was added to the brown solution to make up the rinse volume. $H_2O$ (275 mL) was added dropwise over 1 hour and 37 minutes to the TFA mixture at a rate to keep the temperature below 10° C. Solids precipitated during the addition. A free-flowing slurry was obtained at the beginning and turned into an extremely thick slurry at the end of the addition. The slurry was stirred at 0-10° C. for 84 minutes. The batch was filtered. The cake was rinsed with a 1.2:1 TFA/$H_2O$ solution (110 mL). The wet cake was conditioned at room temperature overnight. The wet cake was slurried in 90% EtOH/water (672 mL) for 3 hours and 40 minutes. The material was isolated by filtration through a tight weave filter cloth. The cake was rinsed with 90% EtOH/water (134 mL) and it took another 1 hour and 12 minutes. The wet cake was charged back to a 1-L RBF, followed by the addition of water (385 mL). A 5% $Na_2CO_3$ solution (19.25 g $Na_2CO_3$ was dissolved in 366 mL of water) was added to the slurry over 29 minutes. The slurry was stirred at approximately 20° C. for 5 h and then filtered through a tight weave filter cloth. The cake was rinsed with water (110 mL, it took 64 minutes) and then kept at room temperature overnight. The wet cake was reslurried in water (550 mL) at approximately 25° C. twice (5 hours and 2 hours, respectively). The filtrations took 47 min and 54 min, respectively. The wet cake was reslurried in 90% IPA/water (669 mL) at approximately 25° C. for 67 min and then filtered through a tight weave filter cloth. The filtration took 2 hours and 9 minutes. The cake was rinsed with 90% IPA/water (200 mL) and conditioned at RT overnight. The solid was reslurried in 90% MeOH/water (400 mL) at 30-35° C. for 46 hours and then filtered through a tight weave filter cloth. The cake was rinsed with 90% MeOH/water (134 mL). After drying, 18.48 g of compound (1) was obtained in 50% yield. HPLC analysis showed 99.33% purity.

Example 2: Synthesis of N-(5-(3-(7-(3-fluorophenyl)-3H-imidazo[4,5-c]pyridin-2-yl)-1H-indazol-5-yl)pyridin-3-yl)-3-methylbutanamide (1)

The synthesis of compound (1) (Scheme 8) started from the borylation of compound (8) with bis(pinacolato)diboron to form compound (9), followed by the in situ Suzuki-Miyaura cross-coupling with compound (10) to form compound (11). The cyclization of compound (11) with compound (6) gave compound (12). The synthesis was finalized with the deprotection of the trityl group of compound (12) to afford compound (1).

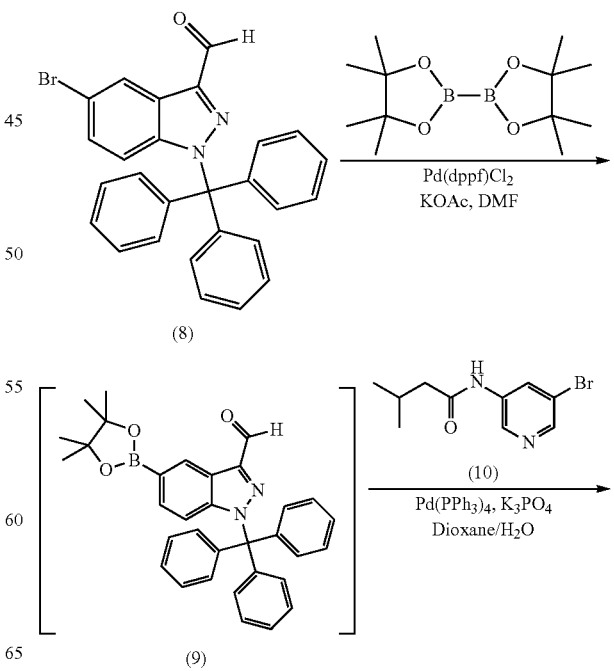

Scheme 8.

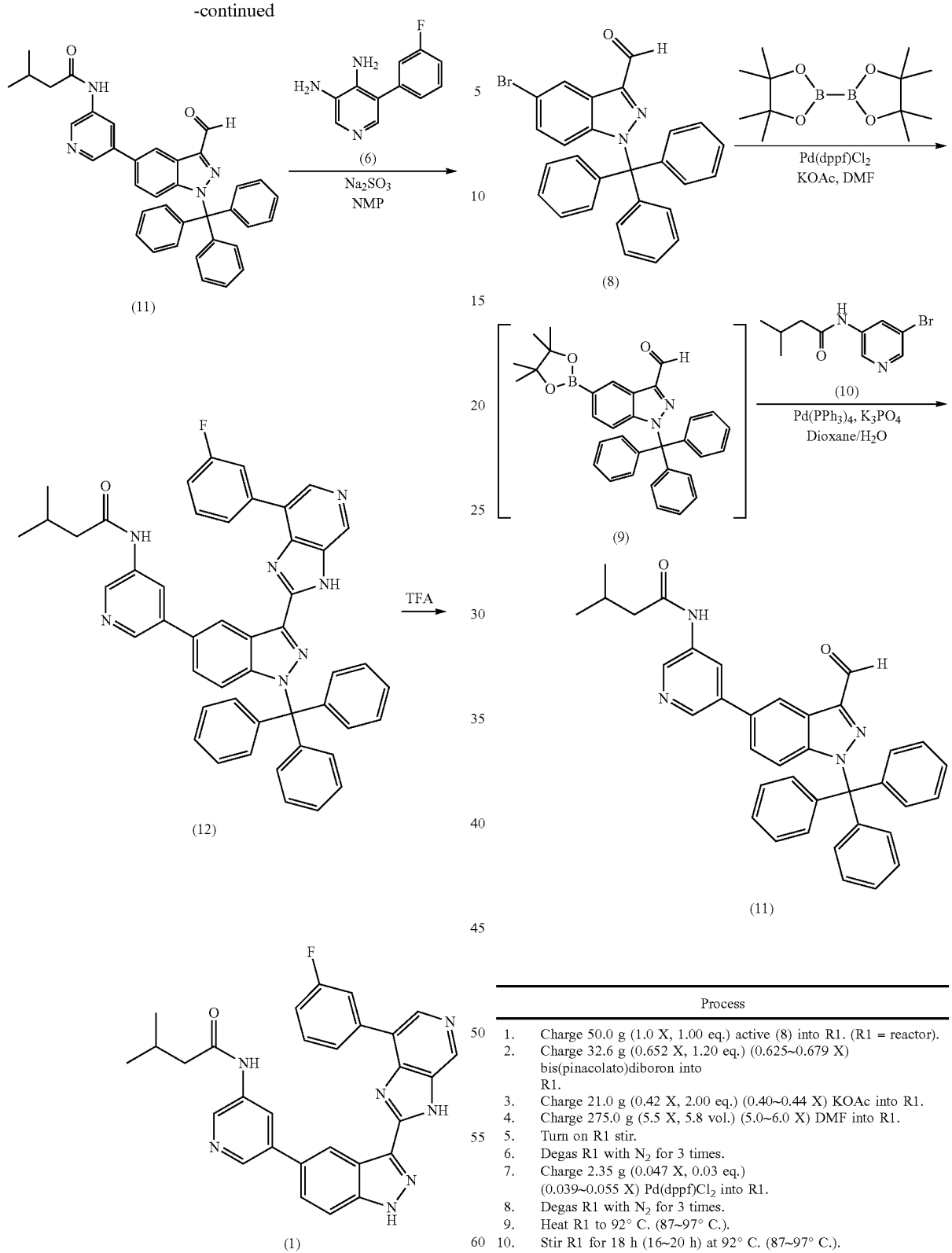

Borylation and Suzuki-Miyaura Cross-Coupling Reaction. Compound (11) was prepared and purified by first borylating compound (8) and subsequently performing a Suzuki-Miyaura cross-coupling reaction as described in the process below.

| | Process |
|---|---|
| 1. | Charge 50.0 g (1.0 X, 1.00 eq.) active (8) into R1. (R1 = reactor). |
| 2. | Charge 32.6 g (0.652 X, 1.20 eq.) (0.625~0.679 X) bis(pinacolato)diboron into R1. |
| 3. | Charge 21.0 g (0.42 X, 2.00 eq.) (0.40~0.44 X) KOAc into R1. |
| 4. | Charge 275.0 g (5.5 X, 5.8 vol.) (5.0~6.0 X) DMF into R1. |
| 5. | Turn on R1 stir. |
| 6. | Degas R1 with $N_2$ for 3 times. |
| 7. | Charge 2.35 g (0.047 X, 0.03 eq.) (0.039~0.055 X) Pd(dppf)Cl$_2$ into R1. |
| 8. | Degas R1 with $N_2$ for 3 times. |
| 9. | Heat R1 to 92° C. (87~97° C.). |
| 10. | Stir R1 for 18 h (16~20 h) at 92° C. (87~97° C.). |
| 11. | Cool the material in R1 to 20° C. (15~25° C.). |
| 12. | Add 375.0 g (7.5 X, 7.5 vol.) (7.0~8.0 X) process water at 20° C. (15~25° C.) into R1 dropwise via headtank NLT1.5 h. |
| 13. | Stir the material in R1 for 45 min (30~60 min) at 20° C. (15~25° C.). |
| 14. | Filter the material. Transfer the mother liquid into T1. |

| | Process |
|---|---|
| 15. | Rinse R1 with 300.0 g (6.0 X, 6.0 vol.) (5.5~6.5 X) process water and then transfer to funnel to slurry the cake. Transfer the mother liquid into T1. |
| 16. | Test the purity by HPLC: report. |
| 17. | Charge (9) into R1. |
| 18. | Charge 27.5 g (0.550 X, 1.00 eq.) (0.539~0.561X) active (10) into R1. |
| 19. | Charge 85.5 g (1.71 X, 3.0 eq.) (1.60~1.82 X) $K_3PO_4 \cdot 3H_2O$ into R1. |
| 20. | Charge 275.0 g (5.5 X, 5.3 vol.) (5.0~6.0 X) 1,4-dioxane into R1. |
| 21. | Charge 40.0 g (0.8 X, 0.8 vol.) (0.7~0.9 X) $H_2O$ into R1. |
| 22. | Turn on R1 stir. |
| 23. | Degas R1 with N2 three times. |
| 24. | Charge 3.71 g (0.0741 X, 0.03 eq.) (0.0692~0.0790 X) $Pd(PPh_3)_4$ into R1 under $N_2$ protect. |
| 25. | Degas R1 with $N_2$ three times. |
| 26. | Heat R1 to 90° C. (85~95° C.). |
| 27. | Stir R1 at 90° C. (85~95° C.) for 2.5 h (2.0~3.0 h). |
| 28. | Cool R1 to 20° C. (15~25° C.). |
| 29. | Transfer the material in R1 into drum. |
| 30. | Charge 775.0 g (15.5 X, 15.5 vol.) (15.0~16.0 X) process water into R1. |
| 31. | Add the material in step 29 drum into R1 slowly by dropwise while keeping R1 at 20° C. (15~25° C.) about 3.0 h (2.0~4.0 h). |
| 32. | Stir R1 for 45 min (30~60 min) at 20° C. (15~25° C.). |
| 33. | Filter the material in R1. Transfer the mother liquid into T2 (T2 = tank). |
| 34. | Rinse R1 with 300.0 g (6.0 X, 6.0 vol.) (5.5~6.5 X) process water and then transfer to funnel to slurry the solid. Transfer the mother liquid into T2. Test the wet cake of purity by HPLC: report. Test the residual F1 in T2: report. |
| 35. | Charge the solid in funnel into R1. |
| 36. | Charge 275.0 g (5.5 X, 6.4 vol.) (5.0~6.0 X) 2-Me-THF into R1. |
| 37. | Stir R1 for 45 min (30~60 min) at 20° C. (15~25° C.). |
| 38. | Heat R1 to 45° C. (40~50° C.). |
| 39. | Add 275.0 g (5.5 X, 2.85 eq.) (5.0~6.0 X) 10% aqueous oxalic acid slowly by dropwise into R1 at 45° C. (40~50° C.). |
| 40. | Stir R1 at 45° C. (40~50° C.) for 5 h (4~6 h). |
| 41. | Cool R1 to 7° C. (5~10° C.). |
| 42. | Stir R1 at 7° C. (5~10° C.) for 18 h (16~20 h). |
| 43. | Filter the material in R1, and transfer the mother liquid into T2. |
| 44. | Rinse R1 with 125.0 g (2.5 X, 2.9 vol.) (2.0~3.0 X) 2-Me-THF and then transfer to funnel to slurry the solid. Transfer the mother liquid into T3. |
| 45. | Charge the cake into R1. |
| 46. | Charge 275.0 g (5.5 X, 6.4 vol.) (5.0~6.0 X) 2-Me-THF into R1. |
| 47. | Stir R1 for 45 min (30~60 min) at 20° C. (15~25° C.). |
| 48. | Charge 300.0 g (6.0 X, 2.0 eq.) (5.0~7.0 X) 10% $K_2CO_3$ aqueous into R1. |
| 49. | Stir R1 for 45 min (30~60 min) at 20° C. (15~25° C.). |
| 50. | Transfer the bottom layer into T4. |
| 51. | Cool R1 to 7° C. (5~10° C.). |
| 52. | Add 275.0 g (5.5 X, 2.85 eq.) (5.0~6.0 X) 10% aqueous oxalic acid slowly by dropwise into R1 at 7° C. (5~10° C.). |
| 53. | Stir R1 at 7° C. (5~10° C.) for 5 h (4~6 h). |
| 54. | Filter the material in R1, and transfer the mother liquid into T2. |
| 55. | Rinse R1 with 125.0 g (2.5 X, 2.9 vol.) (2.0~3.0 X) 2-Me-THF and then transfer to funnel to slurry the solid. Transfer the mother liquid into T3. |
| 56. | Charge the cake into R1. |
| 57. | Charge 350.0 g (7.0 X, 8.1 vol.) (6.5~7.5 X) 2-Me-THF into R1. |
| 58. | Stir for 45 min (30~60 min) at 20° C. (15~25° C.). |
| 59. | Charge 300.0 g (6.0 X, 2.0 eq.) (5.0~7.0 X) 10% $K_2CO_3$ aqueous into R1. |
| 60. | Stir R1 for 45 min (30~60 min) at 20° C. (15~25° C.). |
| 61. | Transfer the bottom layer into T4. |
| 62. | Charge 350.0 g (7.0 X) (6.0~8.0 X) 5% NaCl aqueous into R1. |
| 63. | Stir R1 for 25 min (15~35 min) at 20° C. (15~25° C.). |
| 64. | Transfer the bottom layer into T3. |
| 65. | Charge 350.0 g (7.0 X) (6.0~8.0 X) 5% NaCl aqueous into R1. |
| 66. | Stir R1 for 25 min (15~35 min) at 20° C. (15~25° C.). |
| 67. | Transfer the bottom layer into T4. |
| 68. | Charge 350.0 g (7.0 X) (6.0~8.0 X) 5% NaCl aqueous into R1. |
| 69. | Stir R1 for 25 min (15~35 min) at 20° C. (15~25° C.). |
| 70. | Transfer the bottom layer into T4. |
| 71. | Transfer the material in R1 into drum. |
| 72. | Charge 475.0 g (9.5 X, 14.0 vol.) (9.0~10.0 X) n-heptane into R1. |
| 73. | Add the material in drum of step 71 into R1 slowly at 20° C. (15~25° C.). |
| 74. | Stir R1 for 45 min (30~60 min) at 20° C. (15~25° C.). |
| 75. | Concentrated R1 to 275.0 mL (5.5 vol.) (5.0~6.0 vol.) Under vacuum below 40° C.. |
| 76. | Adjust R1 to 20° C. (15~25° C.). |
| 77. | Filter the material in R1. The filtrate is transferred to T5. |
| 78. | Rinse R1 with 300.0 g (6.0 X, 8.8 vol.) (5.5~6.5 X) n-heptane and then transfer to filter. Transfer the mother liquid into T5. |
| 79. | Dry the product (11) at 45° C. (40~50° C.) for 18 h (16~20 h). |

Imidazopyridine formation. The compound of Formula (11) can be converted to the compound of Formula (12) and purified as described in the process below.

| Process |
| --- |
| 1) Charge 50.0 g (1.0 X, 1.00 eq.) active (11) into R1. (R1 = reactor).
| 2) Charge 24.5 g (0.49 X, 1.00 eq.) (0.48~0.50 X) active (6) bis hydrochloride salt into R1.
| 3) Charge 12.5 g (0.25 X, 1.10 eq.) (0.24~0.26 X) Na$_2$SO$_3$ into R1.
| 4) Charge 775.0 g (15.5 X, 15.5 vol.) (15.0~16.0 X) NMP in R1.
| 5) Stir R1 for 20 min (10~30 min).
| 6) Degas with N$_2$ twice.
| 7) Heat R1 to 112° C. (110~115° C.).
| 8) Stir R1 at 112° C. (110~115° C.) for 8 h (7~9 h).
| 9) Cool R1 to 25° C. (20~30° C.).
| 10) Transfer the material in R1 into drum.
| 11) Charge 1600.0 g (32 X) (31~33 X) 5% NaHCO$_3$ aqueous into R1 at 25° C. (20~30° C.).
| 12) Charge 675.0 g (13.5 X, 15.0 vol.) (13.0~14.0 X) EA (ethyl acetate) into R1.
| 13) Add the material in step 11 drum into R1 slowly while keeping R1 at 25° C. (20~30° C.).
| 14) Stir R1 for 45 min (30~60 min) at 25° C. (20~30° C.).
| 15) Stay R1 for 25 min (15~35 min) at 25° C. (20~30° C.).
| 16) Split the material in R1. Transfer the bottom layer into T1.
| 17) Filter the material in R1 through diatomite pad, transfer the filtrate into T2.
| 18) Rinse diatomite pad with 100.0 g (2.0 X, 2.2 vol.) (1.5~2.5 X) EA, transfer the filtrate into T2.
| 19) Transfer the filtrate in T1 into R1.
| 20) Charge 475.0 g (9.5 X, 10.6 vol.) (9.0~10.0 X) EA into R1 at 25° C. (20~30° C.).
| 21) Stir R1 for 25 min (15~35 min) at 25° C. (20~30° C.).
| 22) Stay R1 for 25 min (15~35 min) at 25° C. (20~30° C.).
| 23) Split the material in R1, transfer the aqueous layer into T1.
| 24) Transfer the material in T2 into R1.
| 25) Charge 475.0 g (9.5 X) (9.0~10.0 X) 5% NaCl solution into R1 at 25° C. (20~30° C.).
| 26) Stir R1 for 25 min (15~35 min) at 25° C. (20~30° C.).
| 27) Stay R1 for 25 min (15~35 min) at 25° C. (20~30° C.).
| 28) Split the material in R1. Transfer the bottom layer into T1.
| 29) Add 225.0 g (4.5 X, 2.5 eq.) (4.2~4.7 X) 9% oxalic acid solution into R1 slowly at 25° C. (20~30° C.).
| 30) Stir R1 for 1.0 h (0.5~1.5 h) at 25° C. (20~30° C.).
| 31) Filter the material in R1. Transfer the mother liquid into T3.
| 32) Rinse R1 with 175.0 g (3.5 X, 3.9 vol.) (3.0~4.0 X) EA and then transfer to funnel to slurry the solid. Transfer the mother liquid into T3. Residual K1 in EA solution.
| 33) Charge the filter cake into R1.
| 34) Charge 4000.0 g (80.0 X) (78.0~82.0 X) MeOH/DCM (m:m = 1:4) into R1.
| 35) Heat R1 to 38° C. (35~40° C.).
| 36) Stir R1 for 45 min (30~60 min) to clear at 38° C. (35~40° C.).
| 37) Filter the material in R1 through diatomite pad and active carbon (0.15 X) (0.13~0.17 X). The filtrate is transferred to R1.
| 38) Rinse filter cake with 500.0 g (10.0 X) (9.0~11.0 X) MeOH/DCM (m:m= 1:4) and then transfer to filter. Transfer the mother liquid into R1.
| 39) Concentrate to 275.0 mL (5.5 vol.) (5.0~6.0 vol.) Under vacuum below 45° C..
| 40) Charge 475.0 g (9.5 X, 12.0 vol.) (9.0~10.0 X) acetone into R1.
| 41) Concentrate to 225.0 mL (4.5 vol.) (4.0~5.0 vol.) Under vacuum below 45° C..
| 42) Charge 475.0 g (9.5 X, 12.0 vol.) (9.0~10.0 X) acetone into R1.
| 43) Concentrate to 275.0 mL (5.5 vol.) (5.0~6.0 vol.) Under vacuum below 45° C..
| 44) Charge 125.0 g (2.5 X, 3.2 vol.) (2.0~3.0 X) acetone into R1. Residual MeOH report.
| 45) Cool R1 to 25° C. (20~30° C.).
| 46) Filter the material in R1. Transfer the mother liquid into T3.
| 47) Rinse R1 with 125.0 g (2.5 X, 3.2 vol.) (2.0~3.0 X) acetone and then transfer to centrifuge to slurry the solid. Transfer the mother liquid into T3. Report: residual K1 in acetone solution; Check purity of K1 wet ≥ 98.5%, if pass proceed to following steps, otherwise repeat step 35-47, Residual Pd ≤ 20 ppm.
| 48) Charge the cake of STEP 47 into R1.
| 49) Charge 525.0 g (10.5 X, 12.2 vol.) (10.0~11.0 X) 2-Me-THF into R1.
| 50) Stir for 25 min (15~35 min) at 25° C. (20~30° C.).
| 51) Charge 310.0 g (6.2 X, 2.5 eq.) (6.0 -6.4 X) 10% K$_2$CO$_3$ aqueous into R1 at 25° C. (20~30° C.).
| 52) Stir R1 at 25° C. (20~30° C.) for 45 min (30~60 min).
| 53) Transfer the bottom layer into T4.

| Process |
| --- |
| 54) Charge 350.0 g (7.0 X, 1.38 eq.) (6.5~7.5 X) 5% Na$_2$SO$_4$ solution into R1 at 25° C. (20~30° C.).
| 55) Stir R1 for 25 min (15~35 min) at 25° C. (20~30° C.).
| 56) Transfer the bottom layer into T4.
| 57) Charge 350.0 g (7.0 X, 1.38 eq.) (6.5~7.5 X) 5% Na$_2$SO$_4$ solution into R1 at 25° C. (20~30° C.).
| 58) Stir R1 for 25 min (15~35 min) at 25° C. (20~30° C.).
| 59) Transfer the bottom layer into T4.
| 60) Charge 475.0 g (9.5 X, 12.5 vol.) (9.0~10.0 X) MTBE into R1.
| 61) Transfer the material in R1 into drum.
| 62) Charge 850.0 g (17.0 X, 25.0 vol.) (16.5~17.5 X) n-heptane into R1.
| 63) Add the material in drum of step 61) into R1 slowly by dropwise at 20° C. (15~25° C.).
| 64) Concentrate to 275 mL (5.5 vol.) (5.0~6.0 vol.) Under vacuum below 45° C..
| 65) Cool R1 to 25° C. (20~30° C.).
| 66) Filter the material in R1. Transfer the mother liquid into T5.
| 67) Rinse R1 with 200.0 g (4.0 X, 5.9 vol.) (3.5~4.5 X) n-heptane and then transfer to funnel to slurry the solid. Transfer the mother liquid into T5. Residual (12) in n-heptane solution.
| 68) Dry the product (12) at 45° C. (40~50° C.) for 18 h (16~20 h).

Deprotection of the trityl group. The deprotection of the trityl group to yield a compound of Formula (1) was accomplished as described in the procedure below.

(12) →TFA→ (1)

| Process |  |
|---|---|
| 1) | Charge TFA into R1. |
| 2) | Charge (12) in portions into R1 maintaining temperature at 15-25° C. |
| 3) | Stir the solution at 15-25° C. for 2 h. |
| 4) | Charge purified water dropwise by maintaining the temperature of solution 0-10° C. |
| 5) | Charge crystal seed of TFA salt of (1) into the reactor. |
| 6) | Charge 2nd lot of purified water dropwise by maintaining the temperature of solution 0-10° C. |
| 7) | Stir the materials in R1 at 5-15° C. for 2 h. |
| 8) | Filtered the solids and washed with aqueous TFA solution. |
| 9) | Transfer the wet cake of step 8 to R1. |
| 10) | Reslurry the solid in 90% EtOH/water at 20-30° C. for 4 h. |
| 11) | Filter the solids. |
| 12) | Suspend the solids in purified water. |
| 13) | Basify the mixture to pH 9-10 by adding 5% Na$_2$CO$_3$ solution. |
| 14) | Stir the mixture at 20-30° C. for 5 h. |
| 15) | Filter the solids and rinse with water. |
| 16) | Transfer the solids into clean R1 again. |
| 17) | Reslurry the solids in purified water at 20-30° C. for 6 h. |
| 18) | Filter the solids. |
| 19) | Transfer the solids into R1 again. |
| 20) | Reslurry the solids in purified water at 20-30° C. for 20 h. |
| 21) | Filter the solids and rinse with water. |
| 22) | Transfer the solids into R1 again. |
| 23) | Reslurry the solids in 90% isopropanol/water at 20-30° C. for 2 h. |
| 24) | Filter the solids and rinse with 90% isopropanol/water. |
| 25) | Transfer the solids into R1 again. |
| 26) | Charge 90% methanol/water into R1. |
| 27) | Charge crystal seed of (1) into R1. |
| 28) | Reslurry the solids in 90% methanol/water at 30-35° C. for 48 h. |
| 29) | Filter the solids and rinse with 90% methanol/water. |
| 30) | Dry the product under vacuum at 40-50° C. |

Example 3: Synthesis of polymorph Form 1 of N-(5-(3-(7-(3-fluorophenyl)-3H-imidazo[4,5-c]pyridin-2-yl)-1H-indazol-5-yl)pyridin-3-yl)-3-methylbutanamide (1)

The synthesis of polymorph Form 1 of compound (1) from compound (12) involved the deprotection of the trityl group followed by crystallization as described below.

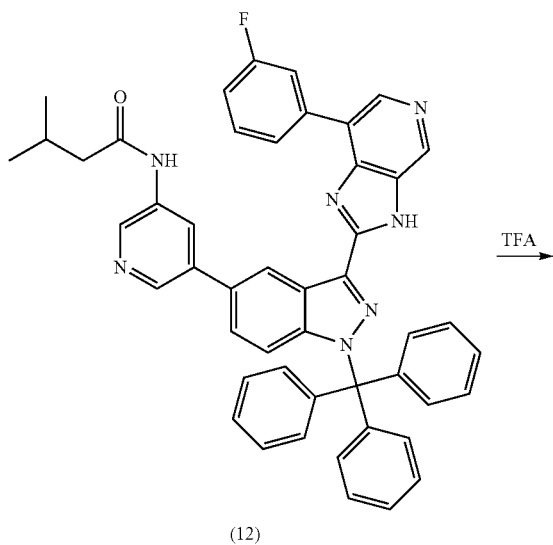

(12)

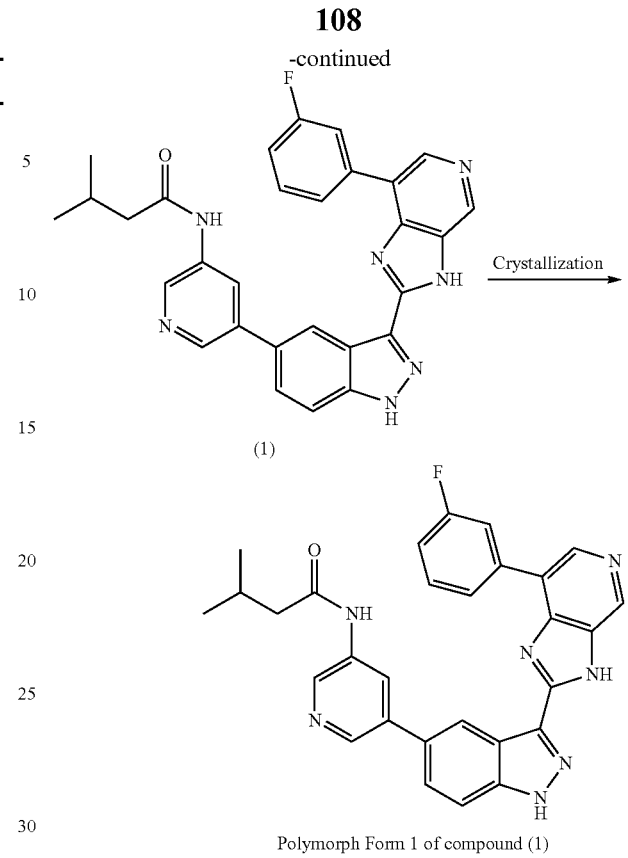

(1)

Polymorph Form 1 of compound (1)

A. Synthesis of Compound (1)

A 3-L 3-neck round bottomed flask was charged with trifluoroacetic acid (TFA, 800 g). Compound (12) (100 g) was slowly added to the flask while maintaining the temperature of the reaction mixture at 20° C. The reaction was stirred until at least 99% conversion to compound (1) was observed (typically 3 to 5 h). The reaction mixture was cooled to 5° C. Water (250 g) was slowly added to the flask while maintaining the temperature of the reaction mixture at 5° C., and stirred for 45 minutes at 5° C. The resulting mixture was filtered. The reaction flask was rinsed with 8:2.5 m:m TFA:water (150 g) and the resulting solution was passed through the filter cake.

A round-bottomed flask was charged with the combined mother liquors of the previous two filtrations, and cooled to 5° C. Water (350 g) was added to the reaction mixture at 5° C., stirred for 1.5 h at 10° C., and the resulting mixture was filtered. The reaction flask was rinsed with 4:3 m/m TFA:water (200 g), the resulting mixture was slurried with the filter cake, and the slurry was filtered. Residual compound (1) was tested for in the mother liquors of the previous two filtrations, as well as the purity of compound (1) in the filter cake.

The filter cake was added to a round-bottomed flask, followed by 90% ethanol (950 g), and was stirred at 30° C. for 3 h. The resulting mixture was stirred at 30° C. for 2-4 hours, filtered, and the filter cake was rinsed with 90% ethanol (200 g). The mother liquors of the previous two filtrations were tested for residual compound (1), and the purity of compound (1) in the filter cake was tested.

The filter cake was added to a round-bottomed flask, followed by water (700 g), and was stirred at 25° C. for 1 h. Aqueous 5% Na$_2$CO$_3$ (740 g) was then added and the solution was stirred at 25° C. for 6 h. The resulting mixture was filtered, and the filter cake was rinsed with water (200 g).

The filter cake was added to a round-bottomed flask, followed by water (950 g), and was stirred at 25° C. for 6.5 h. The resulting mixture was filtered, and the filter cake was rinsed with water (200 g). The filter cake was added to a round-bottomed flask, followed by water (950 g), and was stirred at 25° C. for 3.5 h. The resulting mixture was filtered, and the filter cake was rinsed with water (200 g). The purity of compound (1) was tested, as well as the quantity of residual Pd in the filter cake. The residual TFA and residue on ignition of filter cake was also tested. If the residual TFA was not 0.07% or lower, and/or residue on ignition (after drying) was not 0.4% or lower, the filter cake was added to a round bottomed flask, followed by water (950 g). The resulting mixture was stirred at 25° C. for 3.5 h, filtered, and rinsed with water (200 g). The residual TFA of the filter cake was again tested. If the residual TFA concentration was 0.07% or lower and the residual on ignition (after drying) was 0.4% or lower, the filter cake was added to a round bottomed flask, followed by 90% isopropyl alcohol (950 g). The resulting mixture was stirred at 25° C. for 2 h. The resulting mixture was filtered and the filter cake was rinsed with 90% isopropyl alcohol (200 g).

B. Preparation of Polymorph Form 1 of Compound (1)

The filter cake was added to a round-bottomed flask, followed by 90% methanol (600 g), and the resulting mixture was heated to 25° C. 4.5 g of polymorph Form 1 of compound (1) was added to the mixture, the mixture was heated to 33° C., and the solution was reslurried at 33° C. for 13 h. Formation of polymorph Form 1 of compound (1) was monitored by taking an X-ray powder diffractogram (XRPD) of a small sample, then reslurrying continued at 33° C. for another 13 h. Another sample was obtained. XRPD analysis was performed to test whether complete conversion of compound (1) to the polymorph Form 1 of compound (1) had occurred. Particle size distribution (PSD) was measured to test whether the crystals had a distribution of 2.0 μm≤D50≤5.0 μm, D90≤15.0 μm. If complete conversion to polymorph Form 1 had not occurred or the PSD was outside of the range, reslurrying continued at 33° C. XPRD and particle size distribution analysis occurred every 13-15 hours until both tests yielded a positive result.

The mixture was then filtered, and the filter cake was rinsed with 90% methanol (200 g). Tests were performed to determine whether (1) the purity of compound (1) was at least 98% (positive result), (2) residual palladium had a concentration of, at most, 10 ppm (positive result), (3) the XRPD indicated complete conversion to polymorph Form 1 (positive result), and (4) the particle size distribution was 2.0 μm≤D50≤5.0 μm, D90≤15.0 μm (positive result). When each of the four aforementioned tests yielded a positive result, polymorph Form 1 of compound (1) was dried at 55° C. for 27 h. If any of the four aforementioned tests yielded a negative result, the filter cake was added to a round-bottomed flask, followed by 90% methanol (600 g), and was reslurried at 33° C. for 4 h. The mixture was filtered, and the filter cake was rinsed with 90% methanol (200 g). The filter cake was added to a round-bottomed flask, followed by 90% methanol (600 g), and reslurrying at 33° C. for 18 h. The mixture was filtered, and the filter cake was rinsed with 90% methanol (200 g) to obtain polymorph Form 1 of compound (1). Polymorph Form 1 of compound (1) was dried at 55° C. for 27 h.

Example 4: Polymorph Screen

A polymorph screen was performed on the compound of Formula (1) to determine solubility, polymorphism, and thermodynamic stability.

A. Analysis of the Starting Solid

X-ray powder diffraction (XRD), differential scanning calorimetry (DSC), and thermal gravimetric analysis (TGA) scans of the starting solid compound of Formula (1) obtained from Example 3A, above, indicated that the starting solid was a crystalline material and was a mixture of Form 1 and a non-stoichiometric hydrate of Form 1 having between 1% and about 20% by weight water. According to the DSC scan (FIG. 12B), the solid showed an endotherm between 50° C.-100° C.; it also showed an exotherm at 284° C.; and the solid eventually melted at 364° C. According to the TGA scan (FIG. 12C), a 1.4% weight loss was observed before 100° C.

The solubility of the starting solid was measured by the gravimetric method and indicated that the compound had low solubility at RT and at 50° C. in all solvents tested except DMF and DMSO. Results from the solubility data test at RT and at 50° C. are shown in Table 1.

TABLE 1

Solubility data of the starting solid obtained from Example 3A

| Solvents | Solubility at RT (mg/mL) | Solubility at 50° C. (mg/mL) |
| --- | --- | --- |
| Acetone | 1 | 1 |
| Acetontrile | ~0 | 0 |
| MeOH | 1 | 1 |
| Toluene | 1 | 1 |
| EtOH | 2 | 2 |
| IPAc | ~0 | ~0 |
| EA | 1 | 1 |
| MtBE | ~0 | ~0 |
| IPA | 2 | 5 |
| MEK | 1 | 1 |
| MA | ~0 | ~0 |
| n-Propanol | 1 | 2 |
| MIBK | 1 | 1 |
| n-Butyl acetate | ~0 | ~0 |
| water | 1 | 1 |
| Heptane | ~0 | ~0 |
| n-Butanol | 1 | 2 |
| DMSO | n/a | n/a |
| DMF | 12 | 16 |
| DCM | 2 | 2 |
| Acetic acid | ~0 | 3 |

Reslurry experiments in various solvents were performed. Approximately 30-80 mg of the starting solid (a non-stoichiometric hydrate of Form 1 having between 1% and about 20% by weight water) was slurried in 39 different solvents (pure and binary solvents; the ratio of organic solvent/water (V/V) was 95%/5%) at RT and 50° C. for 5 days. Three solvates, one non-stoichiometric hydrate, and eleven non-solvated forms were identified. A "*" after a particular Form, e.g., Form 2*, indicates that the forms had similar XRD scans with minor differences and were considered to belong to the same class. Generally, the identified forms showed multiple endotherms/exotherms on differential scanning calorimetry (DSC) scans; Form 9 showed a single endotherm. XRD of both wet and dry samples were scanned (FIG. 12A (dry sample)). The data is shown in Tables 2 and 3 below.

TABLE 2

Results of reslurry experiments at RT

| Solvent | Crystalline Form (wet/dry) | Solvent | Crystalline Form (wet/dry) |
|---|---|---|---|
| Acetone | Solvate 1 Form 2 | Acetone/water | Solvate 2 Form 4** |
| Acetontrile | Form 2 Form 1 | Acetontrile/water | Form 12 Form 1 |
| MeOH | Form 13 Form 1 | MeOH/water | Form 12 Form 1 |
| Toluene | Form 1 Form 2* | Toluene/water | Form 13 Form 1 |
| EtOH | Form 2* Form 3 | EtOH/water | Solvate 3 Form 2 |
| IPAc | Form 3 Form 4 | IPAc/water | Form 12 Form 1 |
| EA | Form 4* Form 5 | EA/water | Form 12 Form 1 |
| MtBE | Form 5* Form 6 | MtBE/water | Form 12 Form 1 |
| IPA | Form 6 Form 7 | IPA/water | Form 6 Form 6 |
| MEK | Form 7 Form 4 | MEK/water | Form 7 Form 7 |
| MA | Form 4 Form 4* | MA/water | Form 13 Form 1 |
| n-Propanol | Form 4* Form 8 | n-Propanol/water | Form 2** Form 2** |
| MIBK | Form 8 Form 3 | MIBK/water | Form 12 Form 1 |
| n-Butyl acetate | Form 3* Form 1 | n-Butyl acetate/water | Form 13 Form 12 |
| Water | Form 13 Form 1 | Heptane/water | Form 13 Form 12 |
| Heptane | Form 1 Form 9 | n-Butanol/water | Form 13 Form 13 |
| n-Butanol | Form 9 Form 10 | DMSO/water | amorphous Form 10 |
| DMSO | amorphous Form 11 | DMF/water | Form 11 Form 11 |
| DMF | Form 11 Form 1 | DCM/water | Form 13 Form 1 |
| DCM | Form 1 Form 2 | | |

TABLE 3

Results of reslurry experiments at 50° C.

| Solvent | Crystalline Form (wet/dry) | Solvent | Crystalline Form (wet/dry) |
|---|---|---|---|
| Acetone | Solvate 2 Form 4** | Acetone/water | Form 4** Form 4** |
| Acetontrile | Form 2* Form 2 | Acetontrile/water | Form 13 Form 13 |
| MeOH | Form 1 Form 1 | MeOH/water | Form 13 Form 13 |
| Toluene | Form 1 Form 1 | Toluene/water | Form 13 Form 13 |
| EtOH | Form 2* Form 2* | EtOH/water | Form 9 Form 9 |
| IPAc | Form 9 Form 9 | IPAc/water | Form 13 Form 13 |
| EA | Form 4* Form 4 | EA/water | Form 4* Form 4* |
| MtBE | Form 5* Form 4 | MtBE/water | Form 13 Form 13 |
| IPA | Form 6 Form 6 | IPA/water | Form 6 Form 6 |
| MEK | Form 7 Form 7 | MEK/water | Form 7 Form 7 |
| MA | Form 4 Form 4 | MA/water | Form 12 Form 4 |
| n-Propanol | Form 4 Form 4** | n-Propanol/water | Form 9 Form 9 |
| MIBK | Form 8 Form 8 | MIBK/water | Form 13 Form 1 |
| n-Butyl acetate | Form 9 Form 9 | n-Butyl acetate/water | Form 13 Form 1 |
| water | Form 13 Form 13 | Heptane/water | Form 13 Form 1 |
| Heptane | Form 13 Form 13 | n-Butanol/water | Form 13 Form 1 |
| n-Butanol | Form 9 Form 9 | DMSO/water | Amorphous Form 10 |
| DMSO | Amorphous Form 10* | DMF/water | Form 11 Form 11 |
| DMF | Form 11 Form 11* | DCM/water | Form 13 Form 1 |
| DCM | Form 13 Form 13 | | |

The slurry experiments identified 3 solvated forms from wet samples (Solvates 1, 2, and 3); 2 non-stoichiometric hydrates of Form 1 (Forms 12 and 13); and 11 non-solvated forms (Forms 1-11). In some instances, similar XRD scans with minor differences were obtained. These were considered to be part of the same class (e.g., the same form). For example, XRD scans of Form 2 and Form 2* were similar and were considered to belong to the same class. The solvated forms were obtained from wet sample analysis; after drying, the sample indicated a different XRD.

Solvate 1 was obtained from acetone at RT, and after drying, a low crystallinity solid was generated. Solvate 2 was obtained from acetone (at RT) and acetone/water (at RT), and after drying, Form 4** was generated. Solvate 3 was obtained from EtOH/water at RT, and after drying, Form 2 was generated.

B. Form 1

The experiments that generated Form 1 are shown in Table 4, below. Form 1 was generally obtained from drying Form 13 or Form 12. Form 1 can be considered a dehydrated hydrate. Reslurry in many binary solvents (with 5% water) generated Form 1. Purity of the residual solid was 98.9%. KF of Form 1 (one sample) solid was 5.8%; residual MeOH of Form 1 solid was 0.01%. A TGA scan of fully dried Form 1 solid was performed (FIG. 1C). A 0.33% weight loss was observed before 100° C.

Figure 1B:
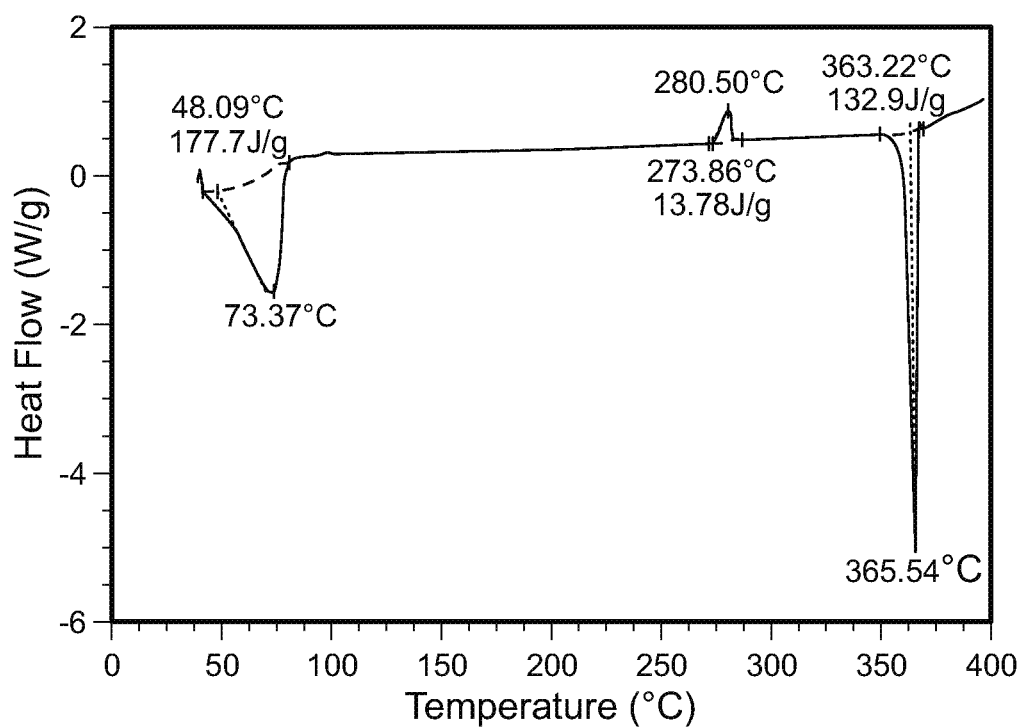
Figure 1C:
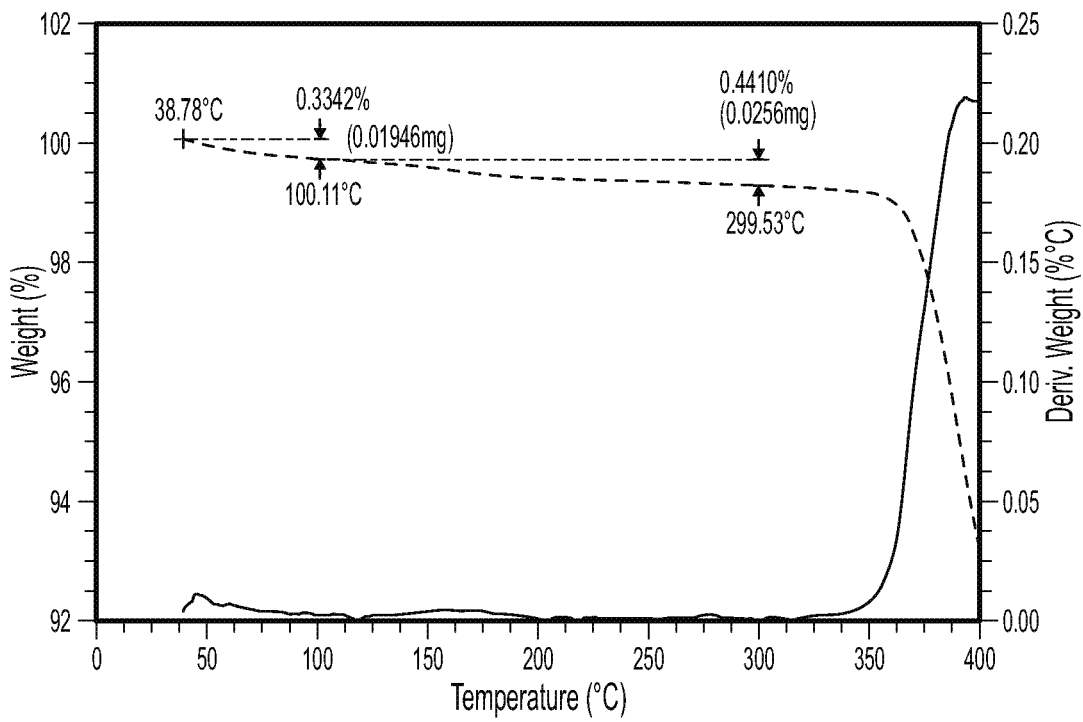

Form 1 showed sharp crystalline peaks on the XRD scan (FIG. 1A). The XRD peaks of Form 1 are shown in Table 5, below. According to the DSC scan (FIG. 1B), the solid showed an endotherm between 50-100° C.; it showed an exotherm at 281° C.; and the melting point was 363° C.

The Form 1 solid was dried at 75° C. under vacuum overnight, and XRD, DSC, and TGA scans were performed. Comparison of the first and the second XRD scans (after drying at 75° C. under vacuum overnight), showed no change. However, the DSC scans indicated the absence of endotherm. The loss of the early peak on the DSC scan had no effect on the XRD trace, showing that the endotherm between 50-100° C. on DSC scan was due to the free solvent.

The Form 1 solid was heated in a DSC chamber to 305° C. (past the endotherm/exotherm around 280° C.), and then scanned by XRD. Comparison of the first and the third XRD and DSC scans showed that after heating to 305° C., Form 1 converted to Form 9. Thus, the endotherm/exotherm around 280° C. might be due to melting/crystallization events.

Form 1 tended to convert to a non-stoichiometric hydrate of Form 1 having between 1% and about 20% by weight water (e.g., Form 13) at a relative humidity (RH) above 4050%. The hydrate lost its water below 30% RH. Form 1 converted to a non-stoichiometric hydrate of Form 1 when exposed to air.

Figure 1D:
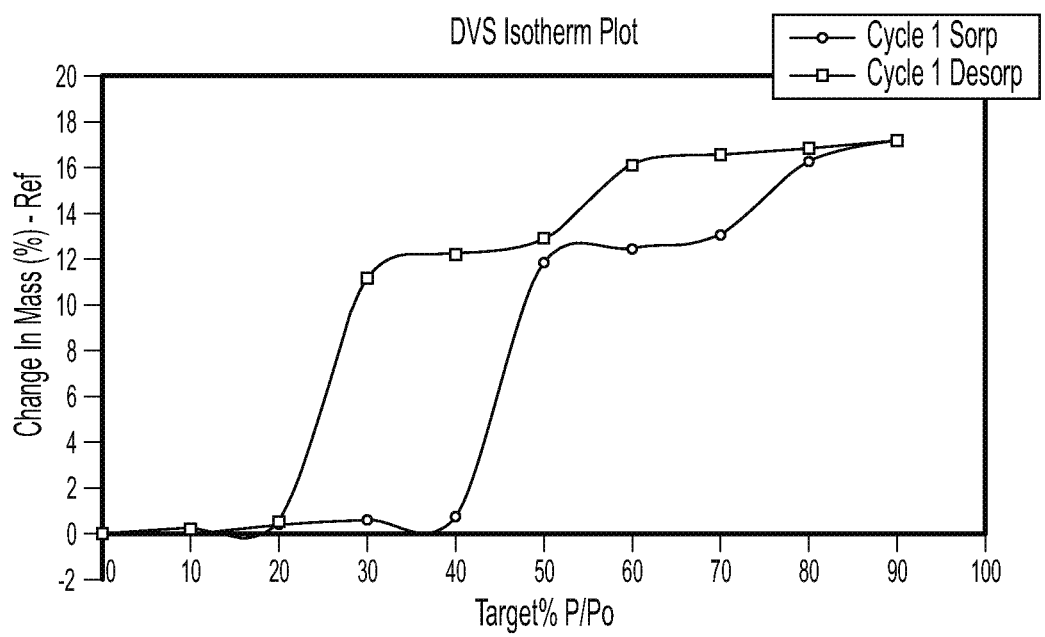

The dynamic vapor sorption (DVS) scan of Form 1 solid showed a 17% water absorption at 90% RH (FIG. 1D). The XRD data indicated that the solid used in the DVS test converted to the hydrate form before the start of the DVS test. However, at 0% RH, water was lost, perhaps indicating that the solid was Form 1.

TABLE 4

Summary of experiments that generated Form 1

| Form | Solvent | Temperature | Wet | Dry |
|---|---|---|---|---|
| Form 1 | MeOH | RT | Form 13 | Form 1 |
| | MeOH | 50° C. | Form 1 | Form 1 |
| | Toluene | RT | Form 1 | Form 1 |
| | Toluene | 50° C. | Form 1 | Form 1 |
| | water | RT | Form 13 | Form 1 |
| | Heptane | RT | Form 1 | Form 1 |
| | DCM | RT | Form 1 | Form 1 |
| | Acetontrile/water | RT | Form 12 | Form 1 |
| | MeOH/water | RT | Form 12 | Form 1 |
| | Toluene/water | RT | Form 13 | Form 1 |
| | IPAc/water | RT | Form 13 | Form 1 |

TABLE 4-continued

Summary of experiments that generated Form 1

| Form | Solvent | Temperature | Wet | Dry |
|---|---|---|---|---|
| | EA/water | RT | Form 12 | Form 1 |
| | MtBE/water | RT | Form 12 | Form 1 |
| | MA/water | RT | Form 13 | Form 1 |
| | MIBK/water | RT | Form 12 | Form 1 |
| | MIBK/water | 50° C. | Form 13 | Form 1 |
| | DCM/water | RT | Form 13 | Form 1 |
| | DCM/water | 50° C. | Form 13 | Form 1 |
| | n-Butyl acetate/water | 50° C. | Form 13 | Form 1 |
| | Heptane/water | 50° C. | Form 13 | Form 1 |
| | n-Butanol/water | 50° C. | Form 13 | Form 1 |

*Amount of water in binary solvents is 5%

TABLE 5

XRD peaks of Form 1

| 2-Theta | d(A) | BG | Height | I % | Area | I % | FWHM |
|---|---|---|---|---|---|---|---|
| 5.778 | 15.2835 | 57 | 97 | 28.3 | 1765 | 18.5 | 0.309 |
| 6.801 | 12.9871 | 19 | 343 | 100 | 8306 | 87.1 | 0.412 |
| 9.26 | 9.5427 | 20 | 178 | 51.9 | 3884 | 40.7 | 0.371 |
| 12.421 | 7.1203 | 30 | 231 | 67.3 | 4862 | 51 | 0.358 |
| 13.919 | 6.357 | 35 | 147 | 42.9 | 3668 | 38.5 | 0.424 |
| 14.501 | 6.1033 | 40 | 133 | 38.8 | 3439 | 36.1 | 0.44 |
| 16.5 | 5.3681 | 47 | 196 | 57.1 | 4286 | 44.9 | 0.372 |
| 17.26 | 5.1333 | 53 | 46 | 13.4 | 560 | 5.9 | 0.207 |
| 18.52 | 4.7868 | 68 | 342 | 99.7 | 9539 | 100 | 0.474 |
| 19.161 | 4.6282 | 54 | 215 | 62.7 | 4130 | 43.3 | 0.327 |
| 20.302 | 4.3706 | 49 | 133 | 38.8 | 2823 | 29.6 | 0.361 |
| 20.619 | 4.304 | 43 | 80 | 23.3 | 2047 | 21.5 | 0.435 |
| 23.056 | 3.8543 | 41 | 38 | 11.1 | 765 | 8 | 0.342 |
| 24.642 | 3.6098 | 33 | 175 | 51 | 7235 | 75.8 | 0.703 |
| 25.302 | 3.5171 | 86 | 80 | 23.3 | 2345 | 24.6 | 0.498 |
| 26.1 | 3.4113 | 83 | 69 | 20.1 | 1545 | 16.2 | 0.381 |
| 27.46 | 3.2453 | 52 | 46 | 13.4 | 872 | 9.1 | 0.322 |
| 28.739 | 3.1038 | 39 | 84 | 24.5 | 2146 | 22.5 | 0.434 |
| 30.444 | 2.9337 | 34 | 32 | 9.3 | 1080 | 11.3 | 0.54 |
| 33.302 | 2.6882 | 30 | 27 | 7.9 | 683 | 7.2 | 0.405 |

C. Forms 2, 2*, and 2***

Figure 2A:
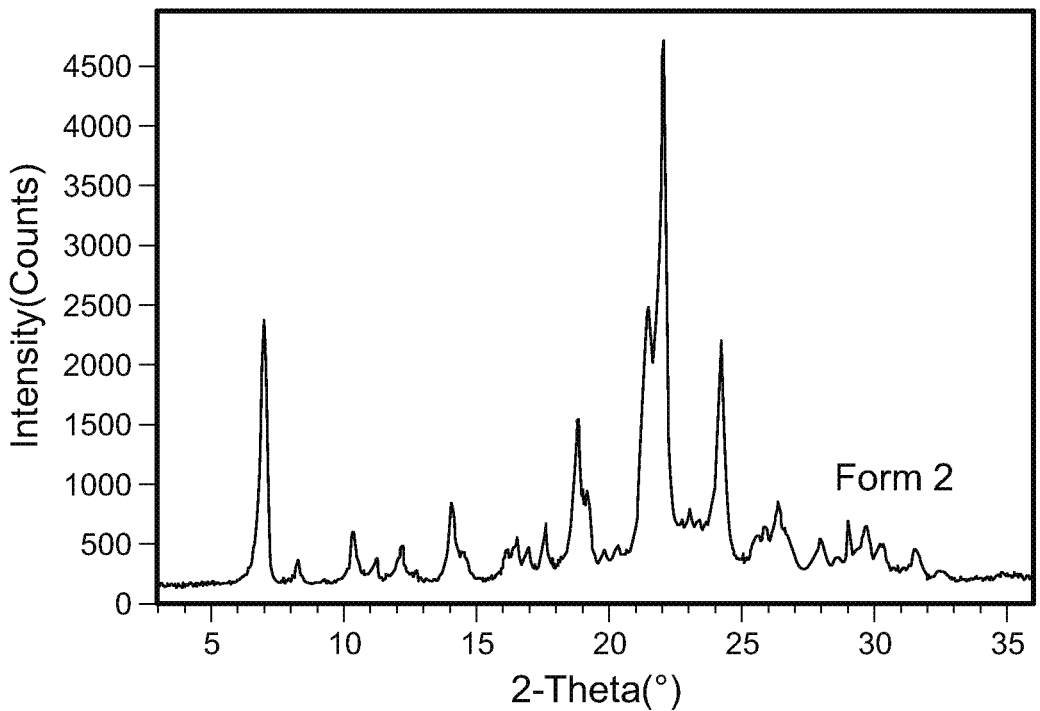
FIGS. 2A-2H are scans of polymorph Forms 2, 2*, and 2** of the compound of Formula (I).
Figure 2B:
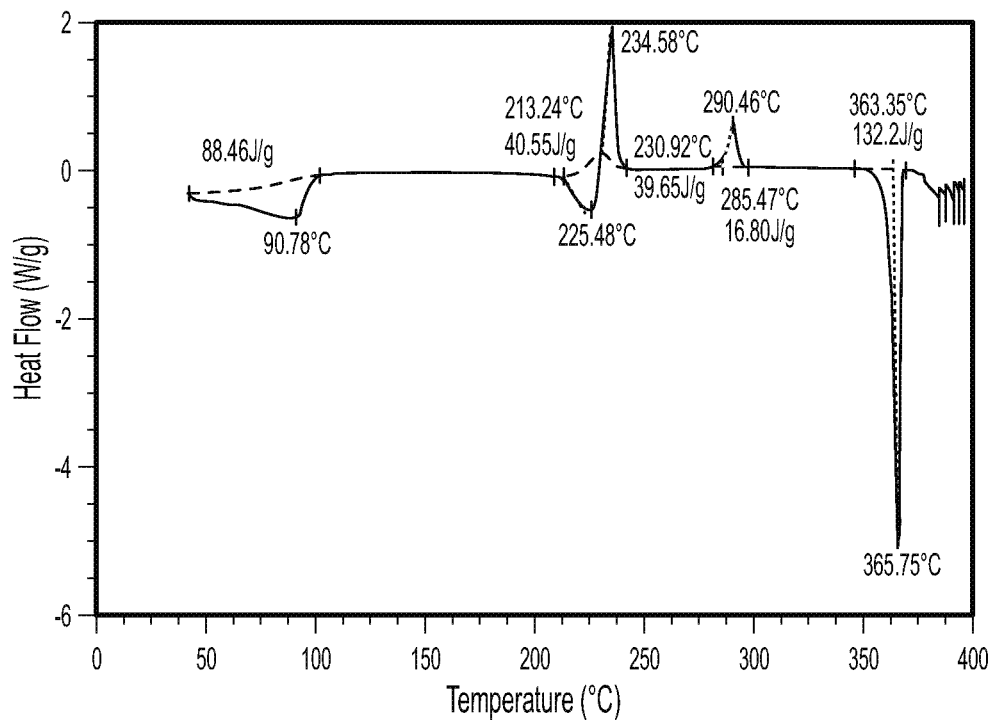
Figure 2C:
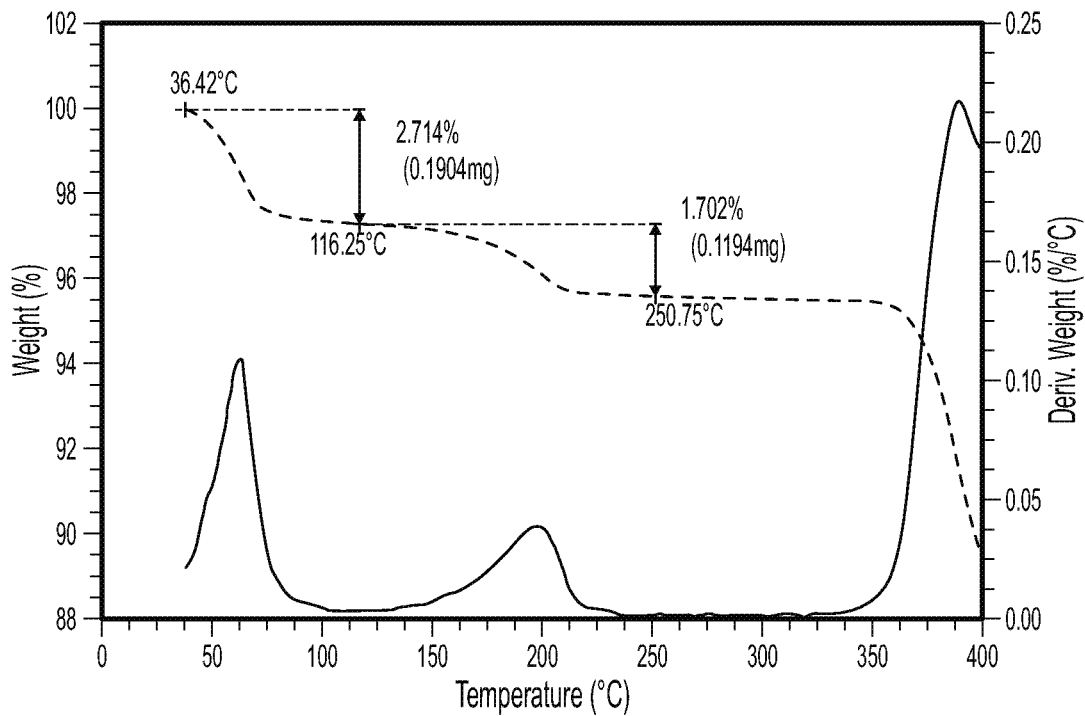
Figure 2D:
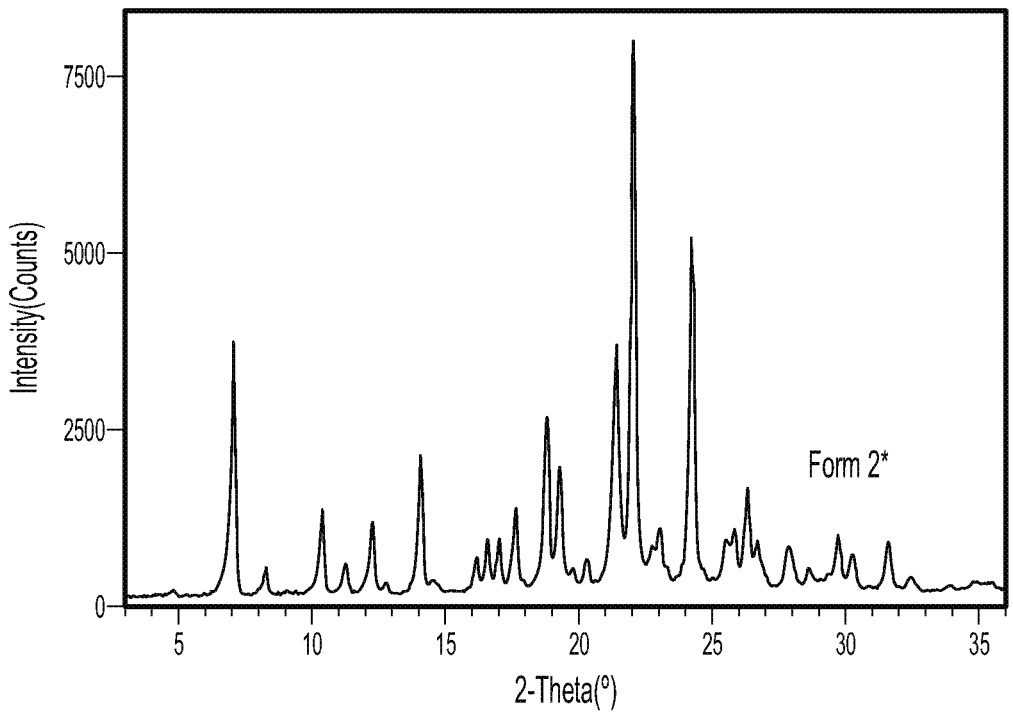
Figure 2E:
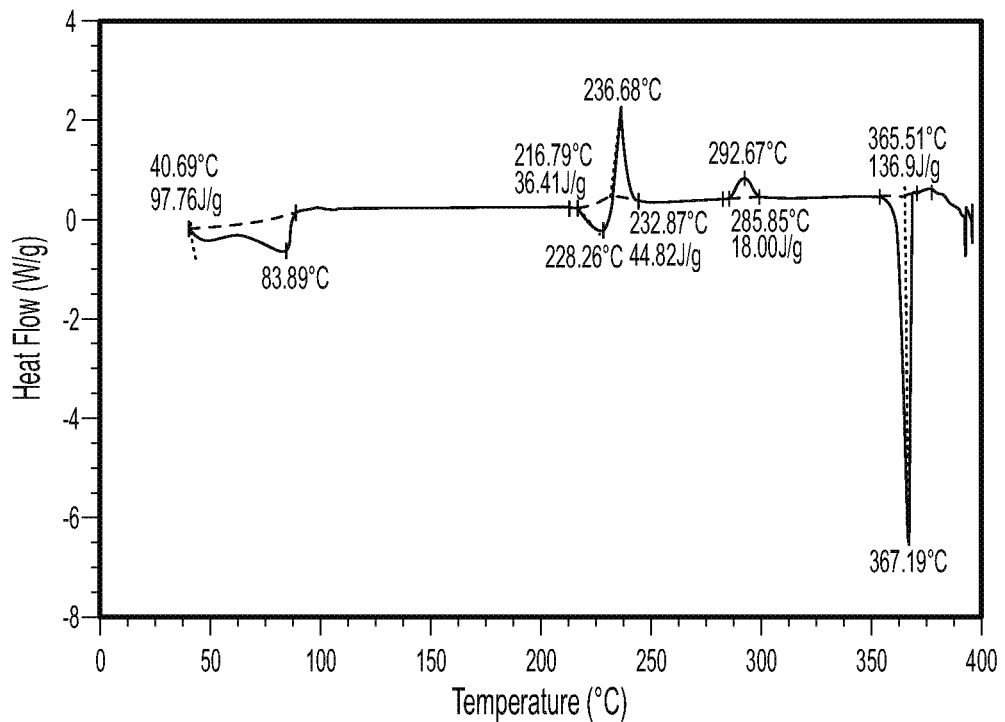
Figure 2F:
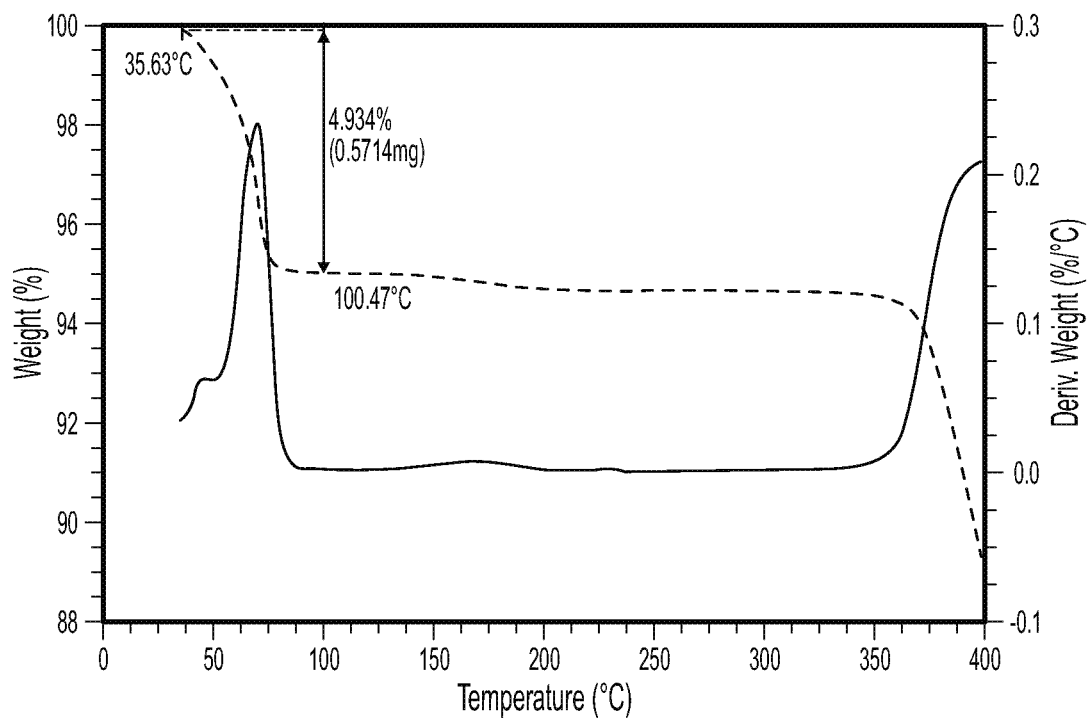
Figure 2G:
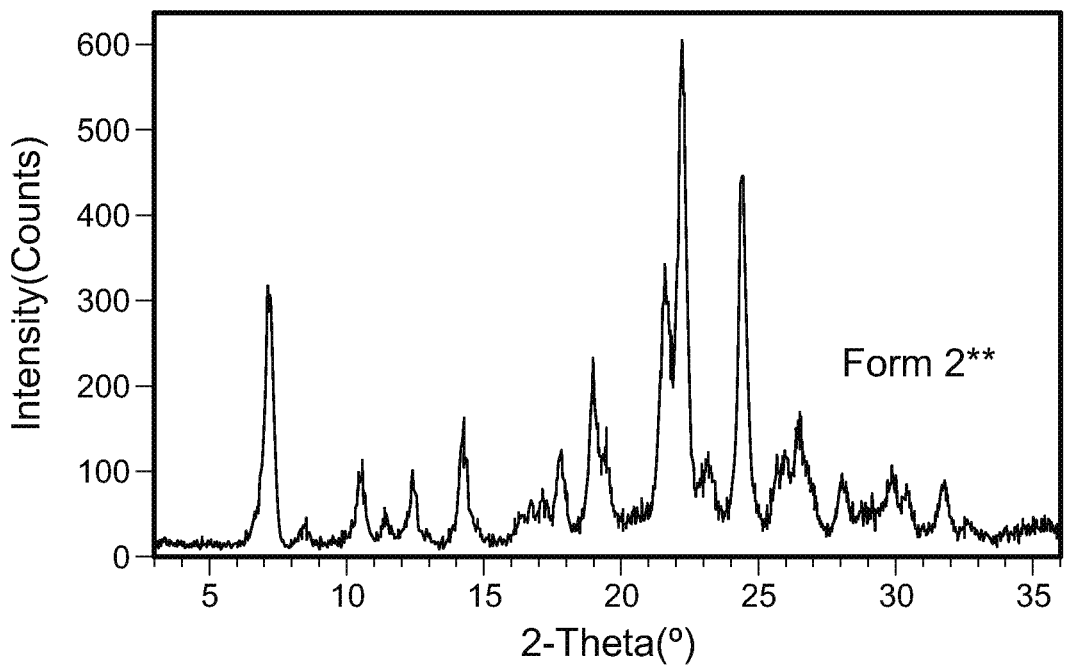
Figure 2H:
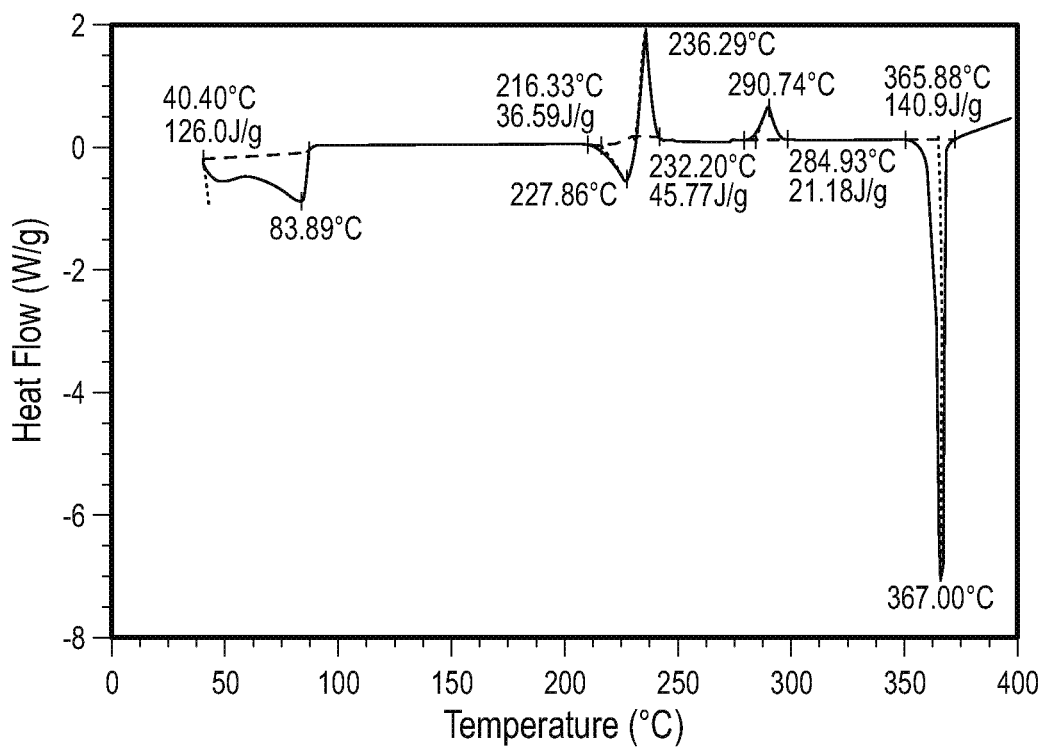

The experiments that generated Forms 2, 2*, and 2** are shown in Table 6, below. XRD scans of Forms 2, 2* and 2** were performed (FIGS. 2A, 2D, and 2G show the XRD scans of Forms 2, 2*, and 2**, respectively). The XRD peaks of Forms 2 and 2* are shown in Tables 7 and 8, below, respectively. DSC scans were also performed (FIGS. 2B, 2E, and 2H show the DSC scans of Forms 2, 2*, and 2**, respectively). According to the DSC scans, Forms 2, 2* and 2** each showed an endotherm between 50° C.-100° C., and multiple endotherms and exotherms before melting at 363° C. The endotherm before 100° C. may be due to the containment of water/solvent in the solid. Form 2 was obtained from acetonitrile; Form 2* from ethanol; Form 2** from n-propanol/5% water.

A TGA scan of Form 2 (FIG. 2C) showed a 2.7% weight loss before 116° C. FIG. 2F shows the TGA scan of Form 2*

A PLM photo of Form 2 was taken (not shown), indicating that the particle size of this solid was around 50 um.

The Form 2 solid was heated in a DSC machine to 90° C. (past the endotherm between 50-100° C.); to 270° C. (past the endotherm/exotherm around 240° C.); and finally to 330° C. (past the exotherm around 330° C.). The residual solid was analyzed by XRD. According to the first and second XRD and DSC scans, the form did not change before and after heating to 90° C. The endotherm between 50-100° C. might be free solvent or hydrate. According to the first and third XRD and DSC scans, after heating a Form 2 sample to 270° C., the solid converted to low crystalline solids. According to the first and fourth XRD and DSC scans, after heating the sample to 330° C., the solid converted to Form 9. Thus, the exotherm around 290° C. was a re-crystallization event. According to an XRD and DSC overlay, the behavior of Form 2* was similar to Form 2.

Residual acetonitrile and EtOH in Form 2 and 2* was not detected.

TABLE 6

Summary of experiments that generated Forms 2, 2*, and 2**

| Form | Solvent | Temperature | Wet | Dry |
|---|---|---|---|---|
| Form 2 | Acetontrile | RT | Form 2 | Form 2 |
| | Acetontrile | 50° C. | Form 2* | Form 2 |
| | EtOH/water | RT | Solvate 3 | Form 2 |
| Form 2* | EtOH | RT | Form 2* | Form 2* |
| | EtOH | 50° C. | Form 2* | Form 2* |
| | Acetontrile | 50° C. | Form 2* | Form 2 |
| Form 2** | n-Propanol/water | RT | Form 2** | Form 2** |

*Amount of water in binary solvents is 5%

TABLE 7

XRD peaks of Form 2

| 2-Theta | d(A) | BG | Height | I % | Area | I % | FWHM |
|---|---|---|---|---|---|---|---|
| 7.021 | 12.5802 | 164 | 2202 | 54.1 | 36151 | 38.2 | 0.279 |
| 8.298 | 10.6462 | 156 | 194 | 4.8 | 2332 | 2.5 | 0.204 |
| 10.399 | 8.5 | 193 | 397 | 9.8 | 6246 | 6.6 | 0.267 |
| 11.258 | 7.8531 | 206 | 151 | 3.7 | 1407 | 1.5 | 0.158 |
| 12.239 | 7.2259 | 181 | 287 | 7 | 5980 | 6.3 | 0.354 |
| 14.1 | 6.2759 | 186 | 648 | 15.9 | 14147 | 15 | 0.371 |
| 14.597 | 6.0632 | 195 | 182 | 4.5 | 7983 | 8.4 | 0.746 |
| 16.18 | 5.4734 | 235 | 201 | 4.9 | 4033 | 4.3 | 0.341 |
| 16.561 | 5.3484 | 251 | 280 | 6.9 | 8382 | 8.9 | 0.509 |
| 17.033 | 5.2013 | 288 | 160 | 3.9 | 1810 | 1.9 | 0.192 |
| 17.639 | 5.0238 | 295 | 366 | 9 | 3542 | 3.7 | 0.165 |
| 18.878 | 4.6968 | 316 | 1210 | 29.7 | 29303 | 31 | 0.412 |
| 19.22 | 4.614 | 333 | 585 | 14.4 | 21169 | 22.4 | 0.615 |
| 19.863 | 4.4662 | 340 | 95 | 2.3 | 437 | 0.5 | 0.078 |
| 20.411 | 4.3474 | 385 | 86 | 2.1 | 671 | 0.7 | 0.133 |
| 21.48 | 4.1335 | 532 | 1944 | 47.8 | 61345 | 64.8 | 0.536 |
| 22.04 | 4.0297 | 647 | 4071 | 100 | 94605 | 100 | 0.395 |
| 23.036 | 3.8576 | 634 | 142 | 3.5 | 1478 | 1.6 | 0.177 |
| 24.24 | 3.6686 | 497 | 1688 | 41.5 | 28976 | 30.6 | 0.292 |
| 25.561 | 3.482 | 422 | 120 | 2.9 | 2545 | 2.7 | 0.361 |
| 25.918 | 3.4349 | 365 | 271 | 6.7 | 11426 | 12.1 | 0.717 |
| 26.379 | 3.3759 | 349 | 497 | 12.2 | 15133 | 16 | 0.518 |
| 26.739 | 3.3313 | 387 | 181 | 4.4 | 2845 | 3 | 0.267 |
| 27.979 | 3.1863 | 297 | 235 | 5.8 | 4050 | 4.3 | 0.293 |
| 29.043 | 3.072 | 338 | 347 | 8.5 | 4584 | 4.8 | 0.225 |
| 29.661 | 3.0094 | 321 | 310 | 7.6 | 7879 | 8.3 | 0.432 |
| 30.204 | 2.9565 | 355 | 135 | 3.3 | 1501 | 1.6 | 0.189 |
| 31.58 | 2.8308 | 232 | 206 | 5.1 | 3991 | 4.2 | 0.329 |
| 32.602 | 2.7443 | 193 | 63 | 1.5 | 1129 | 1.2 | 0.305 |

TABLE 8

XRD peaks of Form 2*

| 2-Theta | d(A) | BG | Height | I % | Area | I % | FWHM |
|---|---|---|---|---|---|---|---|
| 4.859 | 18.1701 | 127 | 87 | 1.2 | 1714 | 1.9 | 0.335 |
| 7.119 | 12.4067 | 148 | 3587 | 48.4 | 44853 | 50.4 | 0.213 |
| 8.321 | 10.6166 | 149 | 407 | 5.5 | 4871 | 5.5 | 0.203 |
| 10.439 | 8.4669 | 186 | 1184 | 16 | 13629 | 15.3 | 0.196 |
| 11.319 | 7.8109 | 190 | 413 | 5.6 | 4673 | 5.3 | 0.192 |
| 12.3 | 7.1899 | 179 | 1010 | 13.6 | 13220 | 14.9 | 0.223 |
| 12.803 | 6.9089 | 182 | 140 | 1.9 | 1587 | 1.8 | 0.193 |

TABLE 8-continued

XRD peaks of Form 2*

| 2-Theta | d(A) | BG | Height | I % | Area | I % | FWHM |
|---|---|---|---|---|---|---|---|
| 14.121 | 6.2667 | 179 | 1966 | 26.5 | 27290 | 30.7 | 0.236 |
| 14.559 | 6.0791 | 199 | 169 | 2.3 | 4381 | 4.9 | 0.441 |
| 16.236 | 5.4546 | 244 | 436 | 5.9 | 5696 | 6.4 | 0.222 |
| 16.62 | 5.3297 | 271 | 674 | 9.1 | 7919 | 8.9 | 0.2 |
| 17.059 | 5.1935 | 313 | 629 | 8.5 | 6279 | 7.1 | 0.17 |
| 17.699 | 5.0071 | 303 | 1094 | 14.7 | 12619 | 14.2 | 0.196 |
| 18.858 | 4.7018 | 359 | 2334 | 31.5 | 31734 | 35.7 | 0.231 |
| 19.321 | 4.5903 | 325 | 1650 | 22.2 | 28313 | 31.8 | 0.292 |
| 19.823 | 4.4751 | 412 | 127 | 1.7 | 582 | 0.7 | 0.078 |
| 20.321 | 4.3665 | 327 | 333 | 4.5 | 3361 | 3.8 | 0.172 |
| 21.479 | 4.1336 | 451 | 3245 | 43.8 | 56365 | 63.3 | 0.295 |
| 22.119 | 4.0154 | 612 | 7417 | 100 | 89000 | 100 | 0.204 |
| 22.782 | 3.9 | 536 | 327 | 4.4 | 11890 | 13.4 | 0.618 |
| 23.098 | 3.8475 | 466 | 638 | 8.6 | 11127 | 12.5 | 0.296 |
| 24.3 | 3.6597 | 361 | 4873 | 65.7 | 61170 | 68.7 | 0.213 |
| 25.599 | 3.4769 | 487 | 475 | 6.4 | 7278 | 8.2 | 0.26 |
| 25.88 | 3.4399 | 541 | 562 | 7.6 | 10968 | 12.3 | 0.332 |
| 26.361 | 3.3782 | 372 | 1289 | 17.4 | 20859 | 23.4 | 0.275 |
| 26.739 | 3.3312 | 266 | 660 | 8.9 | 13196 | 14.8 | 0.34 |
| 27.938 | 3.1909 | 284 | 560 | 7.6 | 9888 | 11.1 | 0.3 |
| 28.641 | 3.1142 | 319 | 210 | 2.8 | 2324 | 2.6 | 0.188 |
| 29.398 | 3.0357 | 357 | 100 | 1.3 | 2376 | 2.7 | 0.404 |
| 29.779 | 2.9977 | 295 | 708 | 9.5 | 13168 | 14.8 | 0.316 |
| 30.3 | 2.9473 | 283 | 451 | 6.1 | 6600 | 7.4 | 0.249 |
| 31.658 | 2.8239 | 239 | 667 | 9 | 9228 | 10.4 | 0.235 |
| 32.519 | 2.7511 | 221 | 191 | 2.6 | 2896 | 3.3 | 0.258 |
| 33.903 | 2.6419 | 213 | 72 | 1 | 876 | 1 | 0.207 |
| 34.82 | 2.5744 | 229 | 110 | 1.5 | 3822 | 4.3 | 0.591 |
| 35.504 | 2.5264 | 230 | 97 | 1.3 | 3876 | 4.4 | 0.679 |

D. Form 3

Figure 3A:
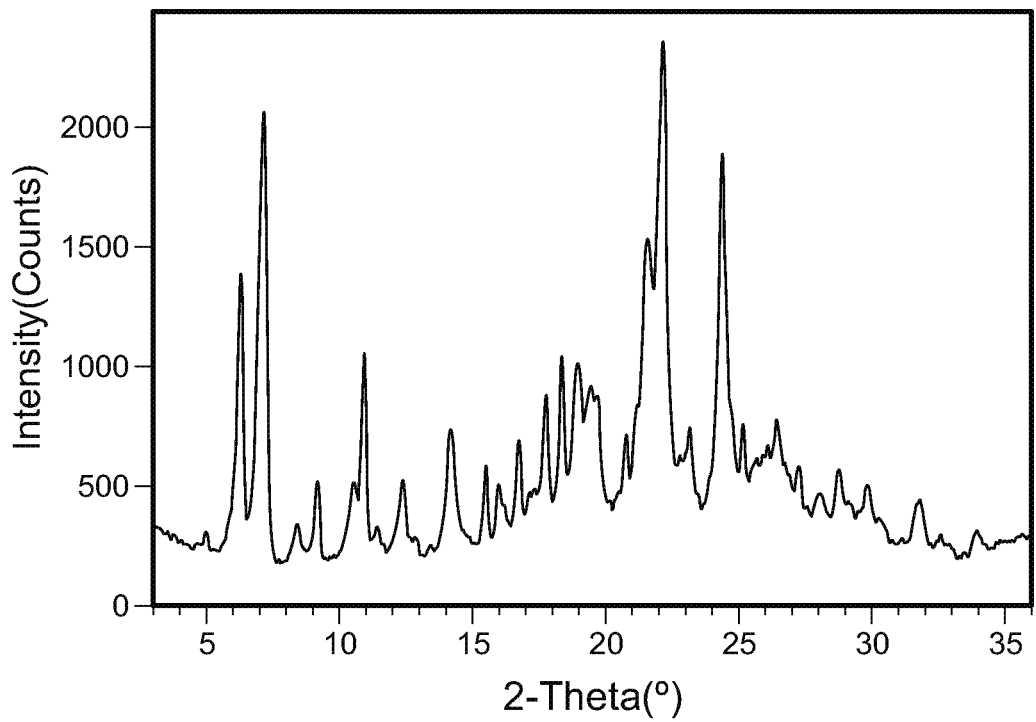
FIGS. 3A-3C are scans of polymorph Form 3 of the compound of Formula (I).
Figure 3B:
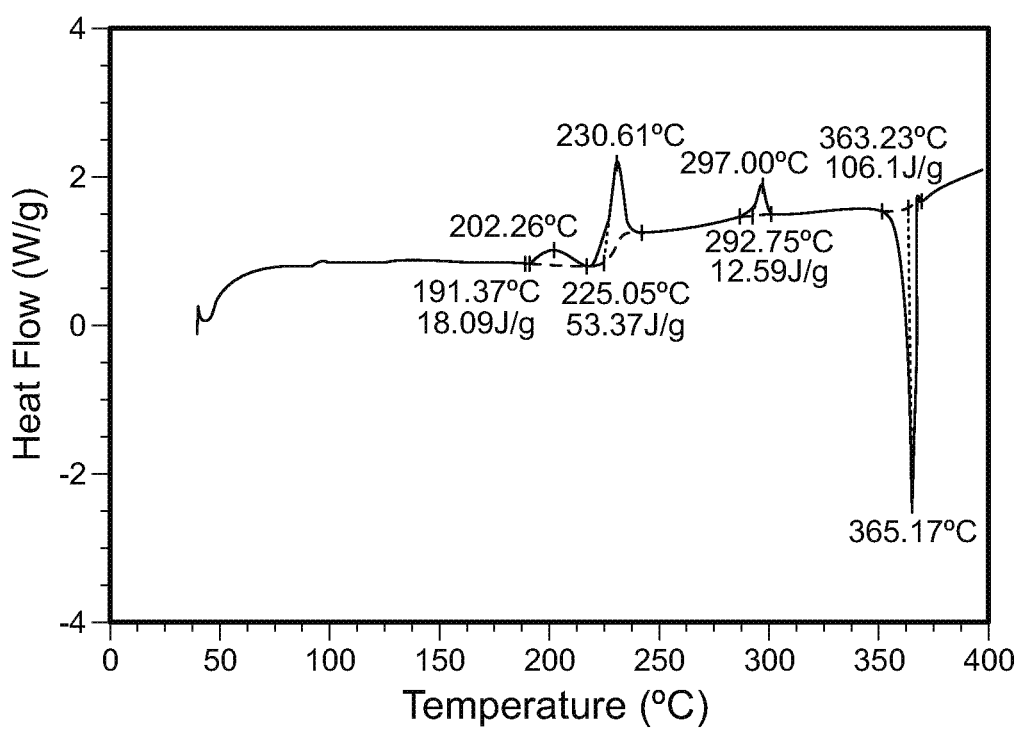

The experiments that generated Form 3 are shown in Table 9, below. XRD and DSC scans of Form 3 were taken (FIGS. 3A and 3B, respectively). Table 10, below, shows the XRD peaks of Form 3. Multiple exotherms and endotherms were observed from the DSC scan of Form 3.

Figure 3C:
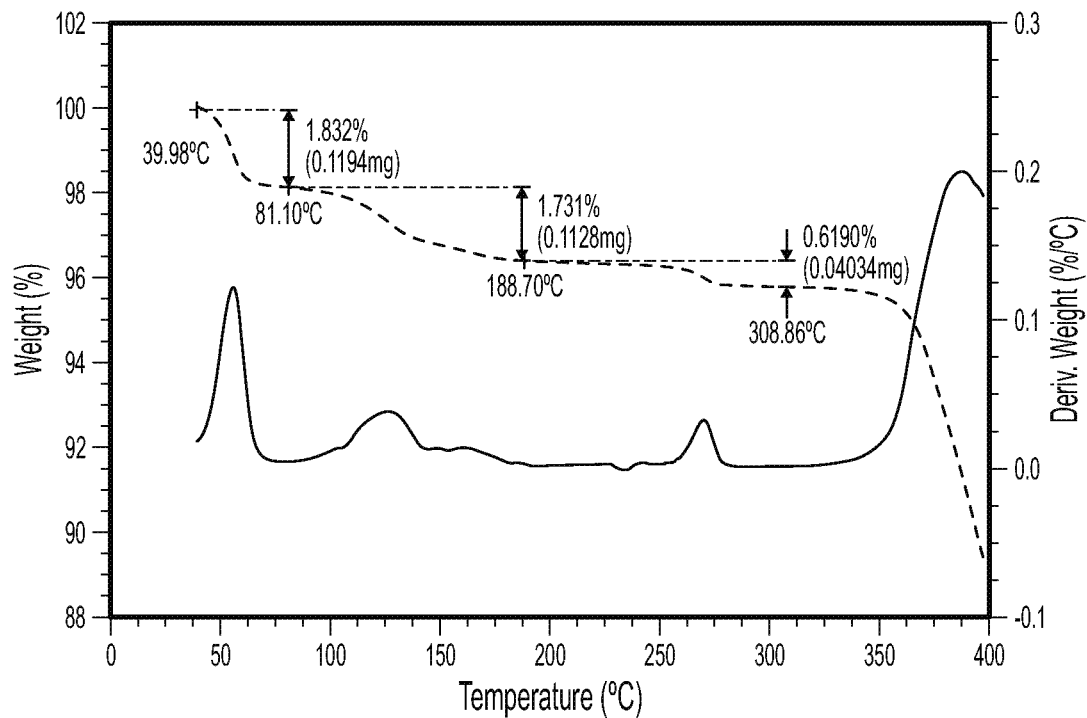

A TGA scan of Form 3 was taken (FIG. 3C) and showed a 1.6% weight loss of the solid before 81° C., followed by a 1.7% weight loss between 81° C. and 169° C.

Form 3 was obtained from IPAc at RT, while Form 3* was obtained from reslurry in n-butyl acetate.

TABLE 9

Summary of experiments that generated Form 3 and Form 3*

| Form | Solvent | Temperature | Wet | Dry |
|---|---|---|---|---|
| Form 3 | IPAc | RT | Form 3 | Form 3 |
|  | n-Butyl acetate | RT | Form 3* | Form 3 |
| Form 3* | n-Butyl acetate | RT | Form 3* | Form 3 |

TABLE 10

XRD peaks of Form 3

| 2-Theta | d(A) | BG | Height | I % | Area | I % | FWHM |
|---|---|---|---|---|---|---|---|
| 5.024 | 17.5739 | 231 | 87 | 4.4 | 845 | 1.9 | 0.165 |
| 6.34 | 13.9294 | 368 | 1030 | 52.5 | 12361 | 27.5 | 0.204 |
| 7.219 | 12.2357 | 182 | 1962 | 100 | 36491 | 81.1 | 0.316 |
| 8.441 | 10.4665 | 188 | 159 | 8.1 | 3261 | 7.2 | 0.349 |
| 9.237 | 9.5659 | 207 | 320 | 16.3 | 3365 | 7.5 | 0.179 |
| 10.561 | 8.37 | 240 | 278 | 14.2 | 6270 | 13.9 | 0.383 |
| 10.998 | 8.0381 | 217 | 849 | 43.3 | 17119 | 38.1 | 0.343 |
| 11.46 | 7.715 | 256 | 87 | 4.4 | 662 | 1.5 | 0.129 |
| 12.439 | 7.11 | 215 | 311 | 15.9 | 6502 | 14.5 | 0.355 |
| 12.865 | 6.8756 | 209 | 92 | 4.7 | 1599 | 3.6 | 0.295 |
| 14.22 | 6.2233 | 231 | 522 | 26.6 | 12265 | 27.3 | 0.399 |
| 15.524 | 5.7034 | 273 | 311 | 15.9 | 2957 | 6.6 | 0.162 |

TABLE 10-continued

XRD peaks of Form 3

| 2-Theta | d(A) | BG | Height | I % | Area | I % | FWHM |
|---|---|---|---|---|---|---|---|
| 16.021 | 5.5276 | 309 | 218 | 11.1 | 2669 | 5.9 | 0.208 |
| 16.78 | 5.2792 | 368 | 330 | 16.8 | 3780 | 8.4 | 0.195 |
| 17.181 | 5.1567 | 384 | 99 | 5 | 2614 | 5.8 | 0.449 |
| 17.782 | 4.9837 | 428 | 496 | 25.3 | 6264 | 13.9 | 0.215 |
| 18.381 | 4.8227 | 509 | 551 | 28.1 | 5102 | 11.3 | 0.157 |
| 19.02 | 4.6622 | 447 | 589 | 30 | 20513 | 45.6 | 0.592 |
| 19.758 | 4.4896 | 487 | 423 | 21.6 | 14362 | 31.9 | 0.577 |
| 20.8 | 4.267 | 520 | 214 | 10.9 | 1518 | 3.4 | 0.121 |
| 21.19 | 4.1893 | 408 | 418 | 21.3 | 4581 | 10.2 | 0.186 |
| 21.6 | 4.1107 | 553 | 1017 | 51.8 | 41986 | 93.3 | 0.702 |
| 22.181 | 4.0044 | 662 | 1736 | 88.5 | 44981 | 100 | 0.44 |
| 23.185 | 3.8333 | 508 | 259 | 13.2 | 3327 | 7.4 | 0.218 |
| 24.44 | 3.6392 | 467 | 1441 | 73.4 | 29510 | 65.6 | 0.348 |
| 25.198 | 3.5313 | 551 | 232 | 11.8 | 1362 | 3 | 0.1 |
| 25.618 | 3.4745 | 557 | 79 | 4 | 365 | 0.8 | 0.079 |
| 26.103 | 3.4109 | 512 | 180 | 9.2 | 7374 | 16.4 | 0.696 |
| 26.479 | 3.3634 | 475 | 306 | 15.6 | 11652 | 25.9 | 0.647 |
| 27.3 | 3.264 | 455 | 133 | 6.8 | 1016 | 2.3 | 0.13 |
| 28.04 | 3.1796 | 378 | 93 | 4.7 | 1485 | 3.3 | 0.271 |
| 28.82 | 3.0953 | 372 | 201 | 10.2 | 3455 | 7.7 | 0.292 |
| 29.258 | 3.0499 | 362 | 76 | 3.9 | 2580 | 5.7 | 0.577 |
| 29.88 | 2.9878 | 334 | 191 | 9.7 | 4011 | 8.9 | 0.357 |
| 31.802 | 2.8115 | 251 | 205 | 10.4 | 4094 | 9.1 | 0.34 |
| 32.62 | 2.7429 | 231 | 87 | 4.4 | 1109 | 2.5 | 0.217 |
| 32.943 | 2.7167 | 215 | 52 | 2.7 | 1107 | 2.5 | 0.362 |
| 33.961 | 2.6375 | 217 | 101 | 5.1 | 1686 | 3.7 | 0.284 |

E. Form 4

Figure 4A:
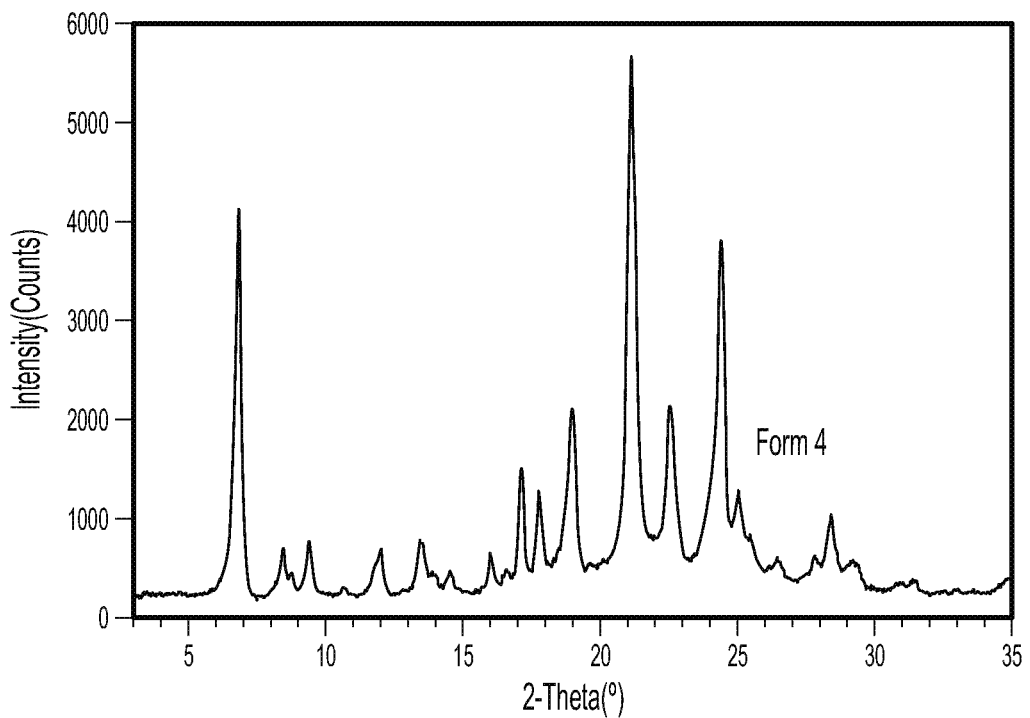
FIGS. 4A-4I are scans of polymorph Forms 4, 4*, and 4** of the compound of Formula (I).
Figure 4B:
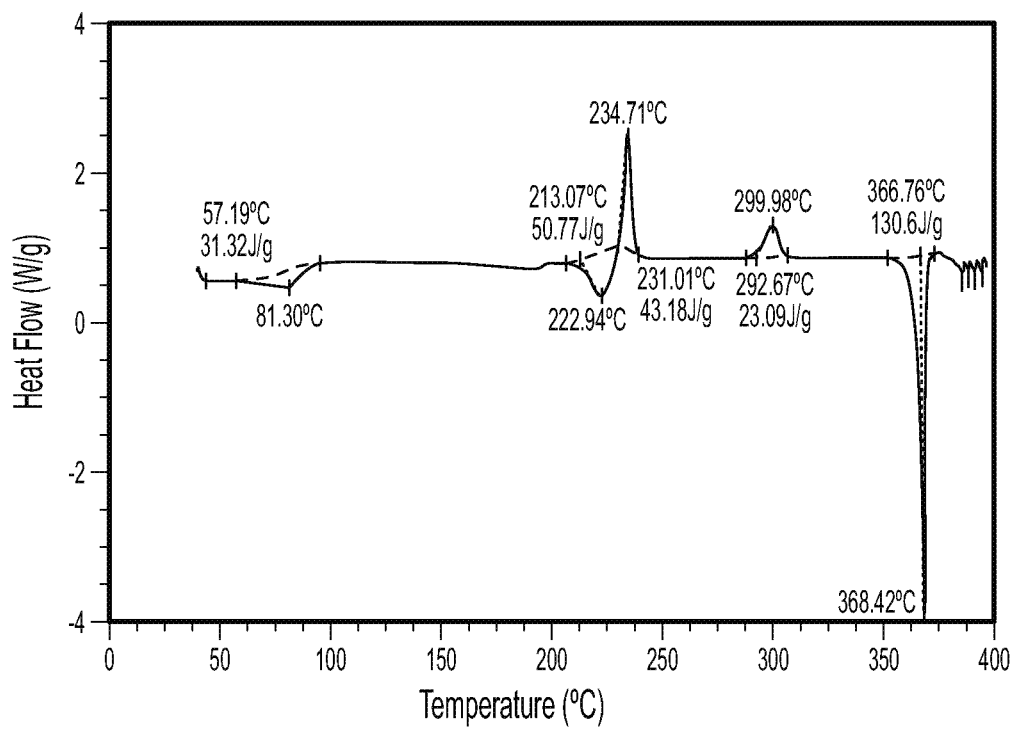

The experiments that generated Forms 4, 4*, and 4** are shown in Table 11, below. XRD of Forms 4, 4*, and 4** were taken (FIGS. 4A, 4D, and 4G, respectively). Tables 12 and 13, below, show the XRD peaks of Form 4 and Form 4*, respectively. DSC scans of Forms 4, 4*, and 4** were also performed (FIGS. 4B, 4E, and 4H, respectively). According to the DSC scans, Form 4 showed an endotherm between 50° C.-100° C., followed by multiple endotherms/exotherms, and then melted at around 367° C. Forms 4* and 4** showed similar DSC patterns as Form 4.

Figure 4C:
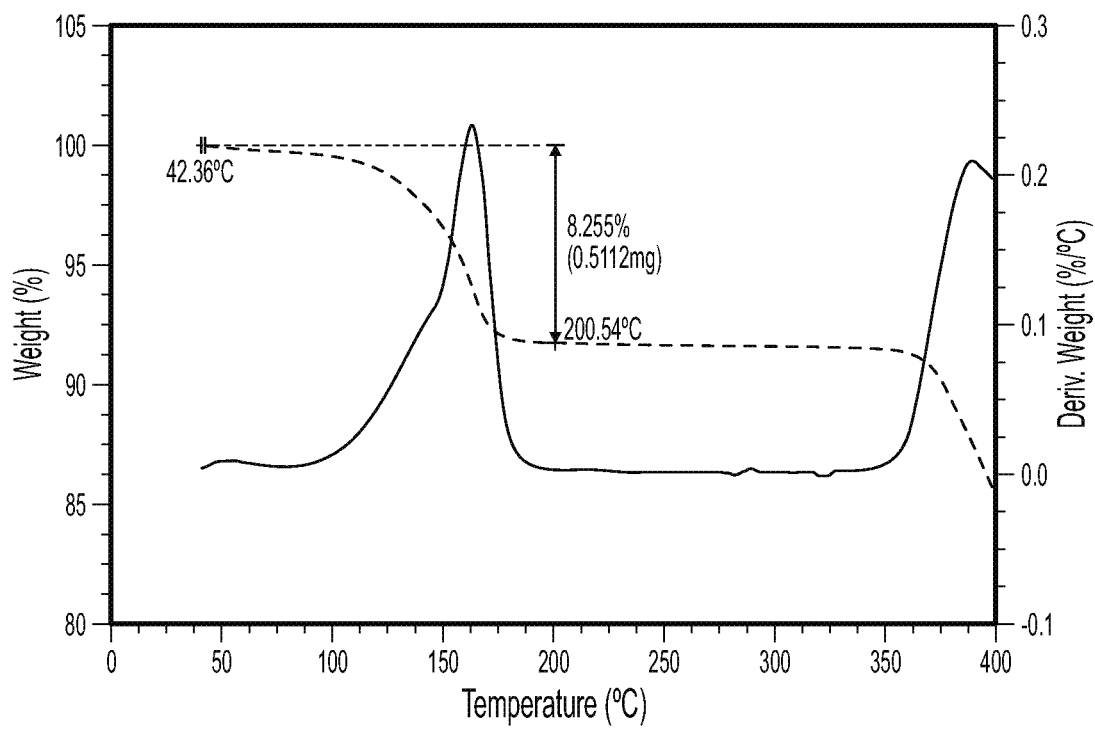
Figure 4D:
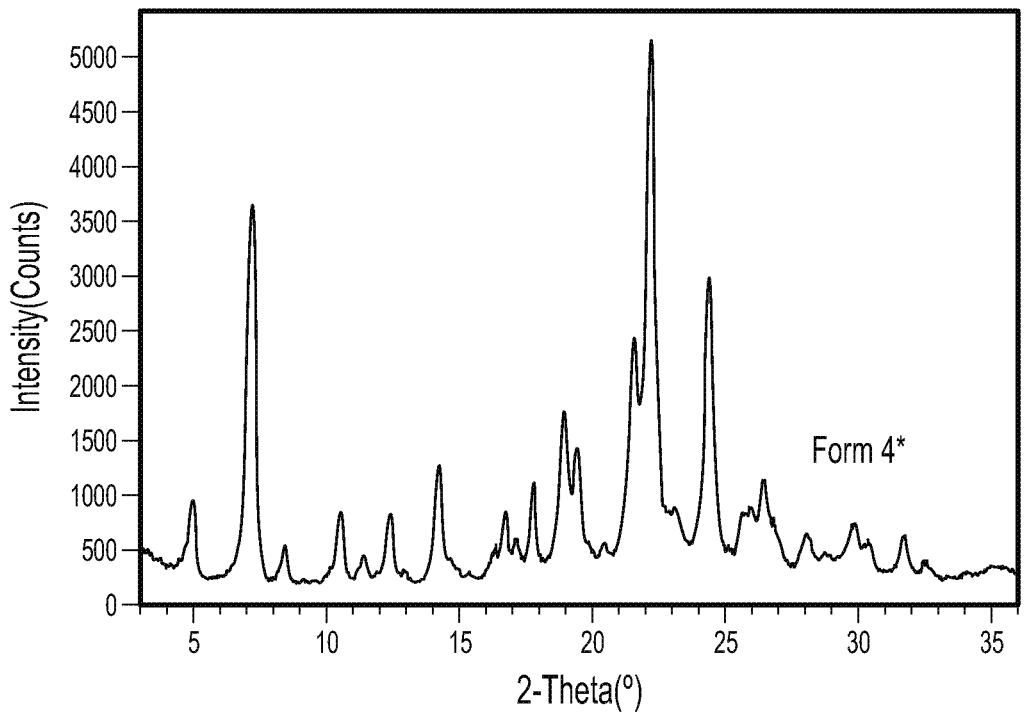
Figure 4E:
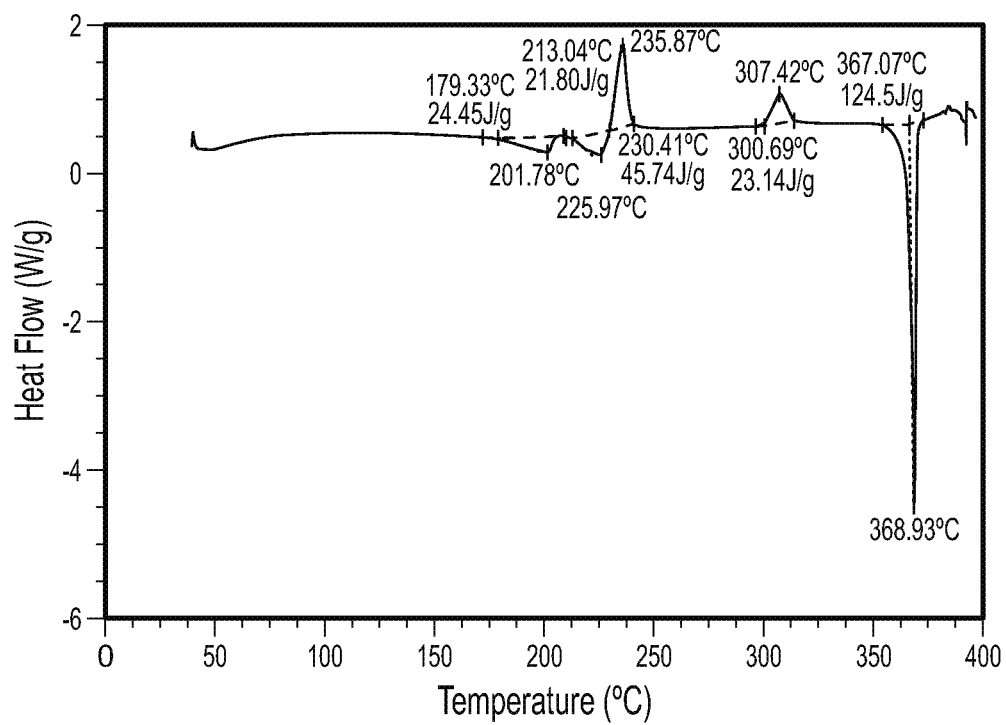
Figure 4F:
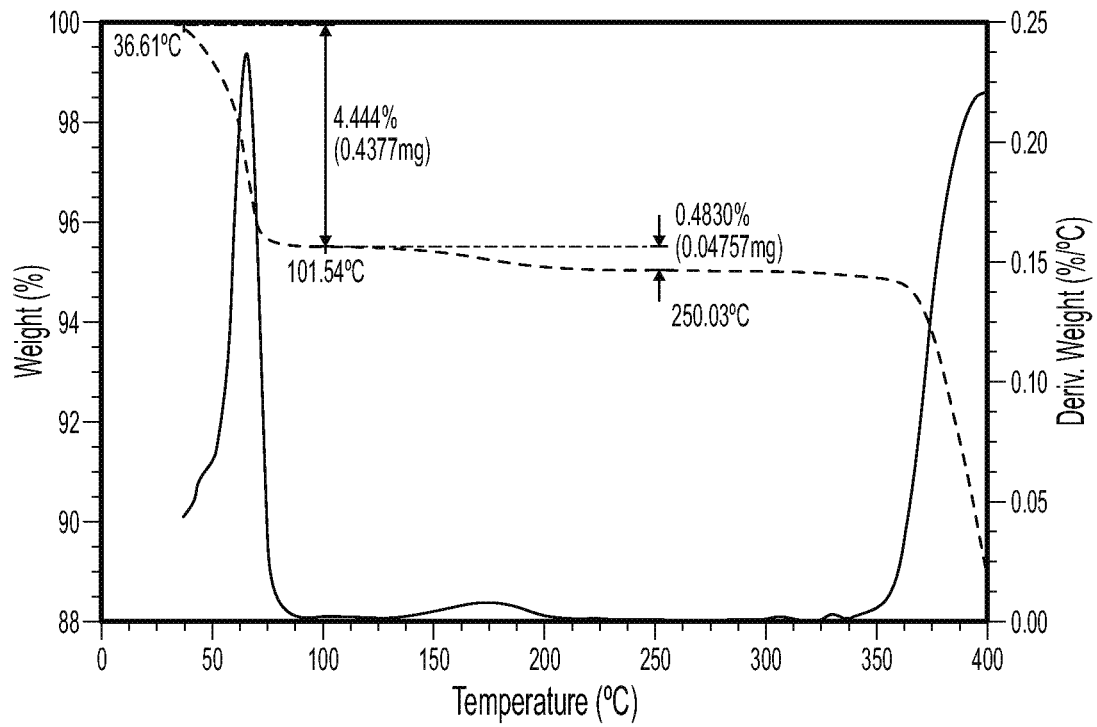
Figure 4G:
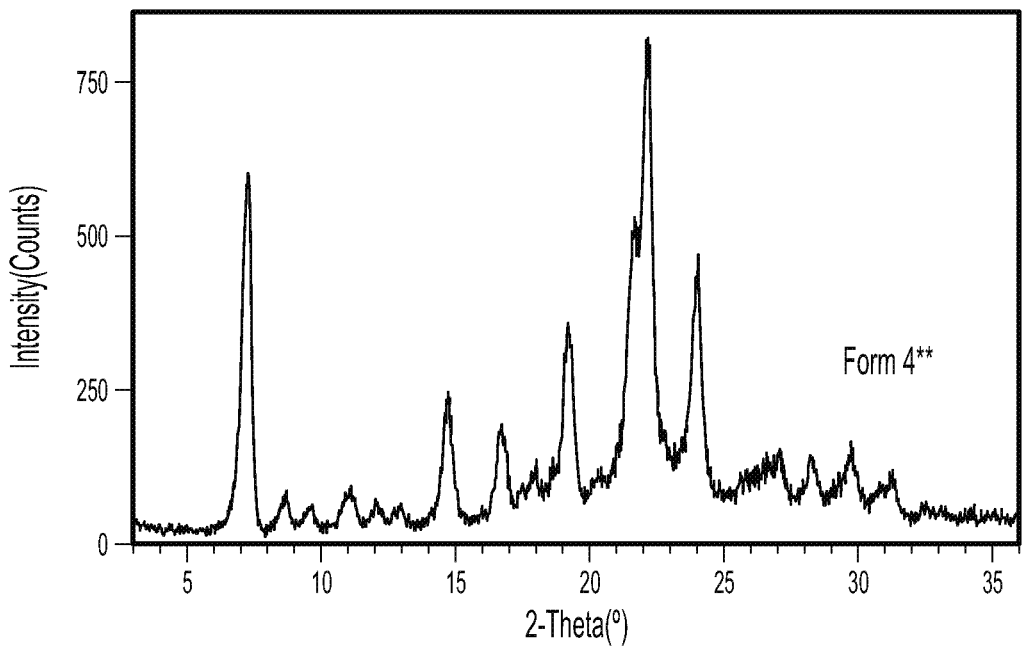
Figure 4H:
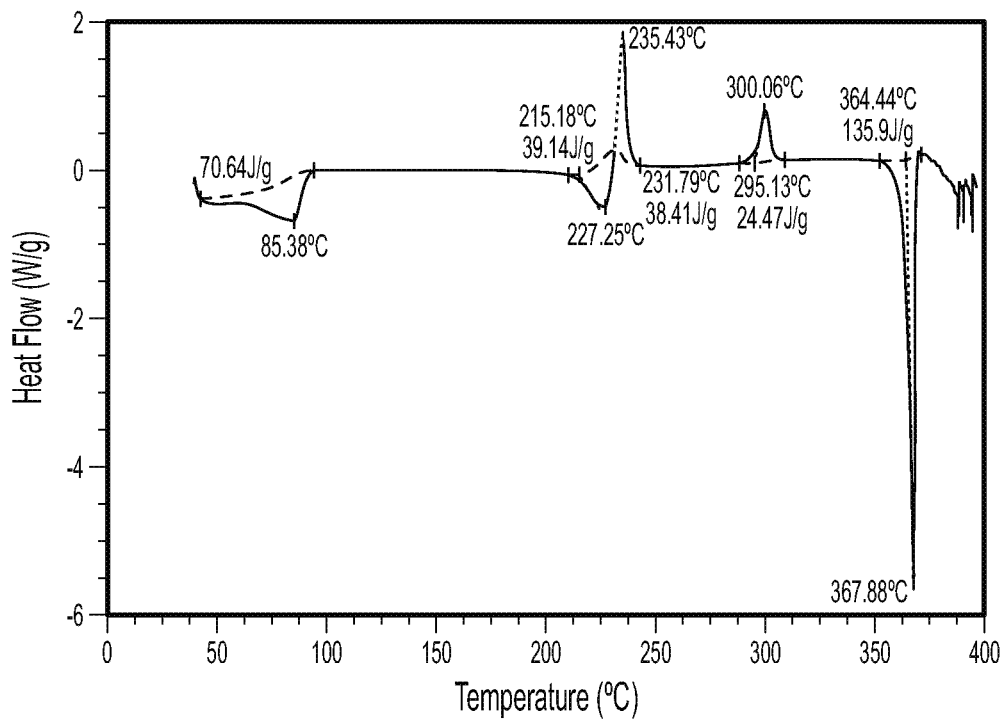
Figure 4I:
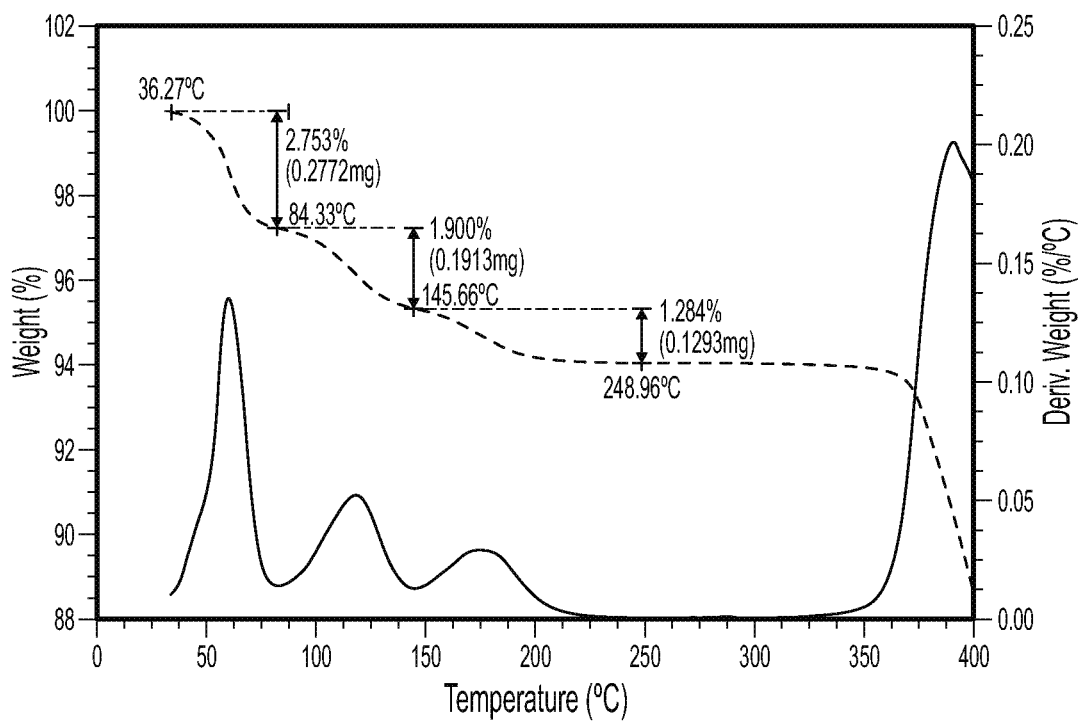

TGA scans of Form 4, Form 4*, and Form 4** were taken (FIGS. 4C, 4F, and 4I, respectively). For Form 4, there was an 8.3% weight loss before 200° C.; for Form 4*, there was a 4.4% weight loss before 102° C., followed by a 0.5% weight loss between 102° C. and 250° C.; and for Form 4**, there were three stages of weight loss, which were 2.8%, 1.9%, and 1.3%, respectively.

These solid forms were obtained from methyl acetate, n-propanol, MIBK, MtBE, ethyl acetate, acetone/water, and ethyl acetate/water.

TABLE 11

Summary of experiments that generated Forms 4, 4*, and 4**

| Form | Solvent | Temperature | Wet | Dry |
|---|---|---|---|---|
| Form 4 | EA | RT | Form 4* | Form 4 |
|  | EA | 50° C. | Form 4* | Form 4 |
|  | MA | RT | Form 4 | Form 4 |
|  | MA | 50° C. | Form 4 | Form 4 |
|  | MA/water | 50° C. | Form 12 | Form 4 |
|  | MtBE | 50° C. | Form 5* | Form 4 |
|  | n-Propanol | RT | Form 4 | Form 4* |
| Form 4* | EA | RT | Form 4* | Form 4* |
|  | EA | 50° C. | Form 4* | Form 4 |
|  | EA/water | 50° C. | Form 4* | Form 4* |
|  | n-Propanol | RT | Form 4 | Form 4* |

TABLE 11-continued

Summary of experiments that generated Forms 4, 4*, and 4**

| Form | Solvent | Temperature | Wet | Dry |
|---|---|---|---|---|
| Form 4** | Acetone/water | RT | Solvate 2 | Form 4** |
| | Acetone | 50° C. | Solvate 2 | Form 4** |
| | n-Propanol | 50° C. | Form 4 | Form 4** |
| | Acetone/water | 50° C. | Form 4** | Form 4** |

*Amount of water in binary solvents is 5%

TABLE 12

XRD peaks of Form 4

| 2-Theta | d(A) | BG | Height | I % | Area | I % | FWHM |
|---|---|---|---|---|---|---|---|
| 3.433 | 25.7129 | 197 | 48 | 1 | 697 | 0.7 | 0.247 |
| 7.019 | 12.5829 | 222 | 3897 | 77.3 | 66968 | 69.4 | 0.292 |
| 8.659 | 10.203 | 242 | 448 | 8.9 | 8198 | 8.5 | 0.311 |
| 8.98 | 9.8395 | 223 | 219 | 4.3 | 7649 | 7.9 | 0.594 |
| 9.64 | 9.1672 | 251 | 516 | 10.2 | 6969 | 7.2 | 0.23 |
| 10.917 | 8.0978 | 210 | 77 | 1.5 | 1041 | 1.1 | 0.23 |
| 12.339 | 7.1673 | 220 | 465 | 9.2 | 9572 | 9.9 | 0.35 |
| 13.82 | 6.4023 | 268 | 501 | 9.9 | 11493 | 11.9 | 0.39 |
| 14.278 | 6.1981 | 271 | 192 | 3.8 | 7288 | 7.6 | 0.645 |
| 14.923 | 5.9314 | 288 | 172 | 3.4 | 1636 | 1.7 | 0.162 |
| 16.462 | 5.3804 | 310 | 329 | 6.5 | 3066 | 3.2 | 0.158 |
| 17.041 | 5.199 | 375 | 105 | 2.1 | 942 | 1 | 0.153 |
| 17.638 | 5.0241 | 435 | 1073 | 21.3 | 13511 | 14 | 0.214 |
| 18.281 | 4.8488 | 487 | 772 | 15.3 | 9782 | 10.1 | 0.215 |
| 19.52 | 4.5437 | 504 | 1590 | 31.5 | 31949 | 33.1 | 0.342 |
| 21.759 | 4.081 | 677 | 5040 | 100 | 96504 | 100 | 0.326 |
| 23.22 | 3.8275 | 693 | 1457 | 28.9 | 28109 | 29.1 | 0.328 |
| 25.12 | 3.5421 | 710 | 3091 | 61.3 | 69330 | 71.8 | 0.381 |
| 25.76 | 3.4556 | 455 | 827 | 16.4 | 22029 | 22.8 | 0.453 |
| 27.221 | 3.2733 | 419 | 180 | 3.6 | 2915 | 3 | 0.275 |
| 28.638 | 3.1145 | 409 | 210 | 4.2 | 4338 | 4.5 | 0.351 |
| 29.259 | 3.0498 | 461 | 568 | 11.3 | 11998 | 12.4 | 0.359 |
| 30.137 | 2.9629 | 409 | 149 | 3 | 1946 | 2 | 0.222 |
| 31.817 | 2.8102 | 253 | 110 | 2.2 | 4034 | 4.2 | 0.623 |
| 32.319 | 2.7677 | 245 | 137 | 2.7 | 3829 | 4 | 0.475 |

TABLE 13

XRD peaks of Form 4*

| 2-Theta | d(A) | BG | Height | I % | Area | I % | FWHM |
|---|---|---|---|---|---|---|---|
| 4.981 | 17.7282 | 270 | 684 | 15.8 | 12231 | 12.6 | 0.304 |
| 7.22 | 12.2329 | 244 | 3416 | 79 | 65744 | 67.8 | 0.327 |
| 8.459 | 10.4447 | 202 | 335 | 7.7 | 4814 | 5 | 0.244 |
| 10.56 | 8.3707 | 219 | 629 | 14.5 | 10739 | 11.1 | 0.29 |
| 11.42 | 7.7419 | 240 | 203 | 4.7 | 2908 | 3 | 0.244 |
| 12.42 | 7.1209 | 221 | 614 | 14.2 | 11445 | 11.8 | 0.317 |
| 13.019 | 6.7947 | 238 | 59 | 1.4 | 423 | 0.4 | 0.122 |
| 14.26 | 6.2057 | 227 | 1052 | 24.3 | 20787 | 21.4 | 0.336 |
| 16.318 | 5.4274 | 409 | 85 | 2 | 665 | 0.7 | 0.133 |
| 16.722 | 5.2973 | 332 | 496 | 11.5 | 8980 | 9.3 | 0.308 |
| 17.199 | 5.1515 | 393 | 226 | 5.2 | 3448 | 3.6 | 0.259 |
| 17.82 | 4.9733 | 402 | 725 | 16.8 | 8502 | 8.8 | 0.199 |
| 18.98 | 4.672 | 432 | 1352 | 31.3 | 36895 | 38.1 | 0.464 |
| 19.44 | 4.5623 | 439 | 990 | 22.9 | 28546 | 29.4 | 0.49 |
| 20.46 | 4.3371 | 444 | 119 | 2.8 | 1163 | 1.2 | 0.166 |
| 21.58 | 4.1144 | 458 | 1982 | 45.8 | 71568 | 73.8 | 0.614 |
| 22.22 | 3.9974 | 837 | 4325 | 100 | 96937 | 100 | 0.381 |
| 23.16 | 3.8373 | 758 | 114 | 2.6 | 1085 | 1.1 | 0.162 |
| 24.42 | 3.6421 | 522 | 2466 | 57 | 48977 | 50.5 | 0.338 |
| 25.679 | 3.4663 | 590 | 252 | 5.8 | 5211 | 5.4 | 0.352 |
| 26.5 | 3.3607 | 470 | 671 | 15.5 | 23177 | 23.9 | 0.587 |
| 26.95 | 3.3056 | 356 | 313 | 7.2 | 3645 | 3.8 | 0.198 |
| 28.118 | 3.1709 | 385 | 255 | 5.9 | 5045 | 5.2 | 0.336 |
| 29.9 | 2.9858 | 360 | 383 | 8.9 | 13112 | 13.5 | 0.582 |
| 30.421 | 2.9359 | 346 | 239 | 5.5 | 5602 | 5.8 | 0.398 |

TABLE 13-continued

XRD peaks of Form 4*

| 2-Theta | d(A) | BG | Height | I % | Area | I % | FWHM |
|---|---|---|---|---|---|---|---|
| 31.779 | 2.8134 | 293 | 336 | 7.8 | 5905 | 6.1 | 0.299 |
| 32.618 | 2.743 | 267 | 124 | 2.9 | 1934 | 2 | 0.265 |

F. Forms 5 and 5*

Figure 5A:
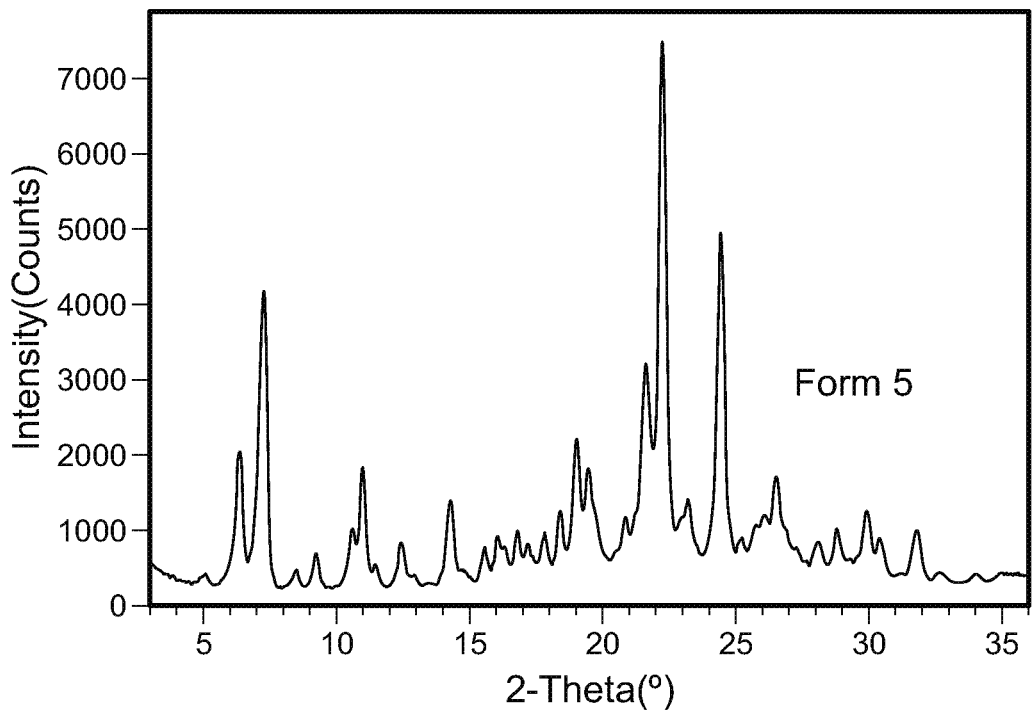
FIGS. 5A-5D are scans of polymorph Forms 5 and 5* of the compound of Formula (I).
Figure 5B:
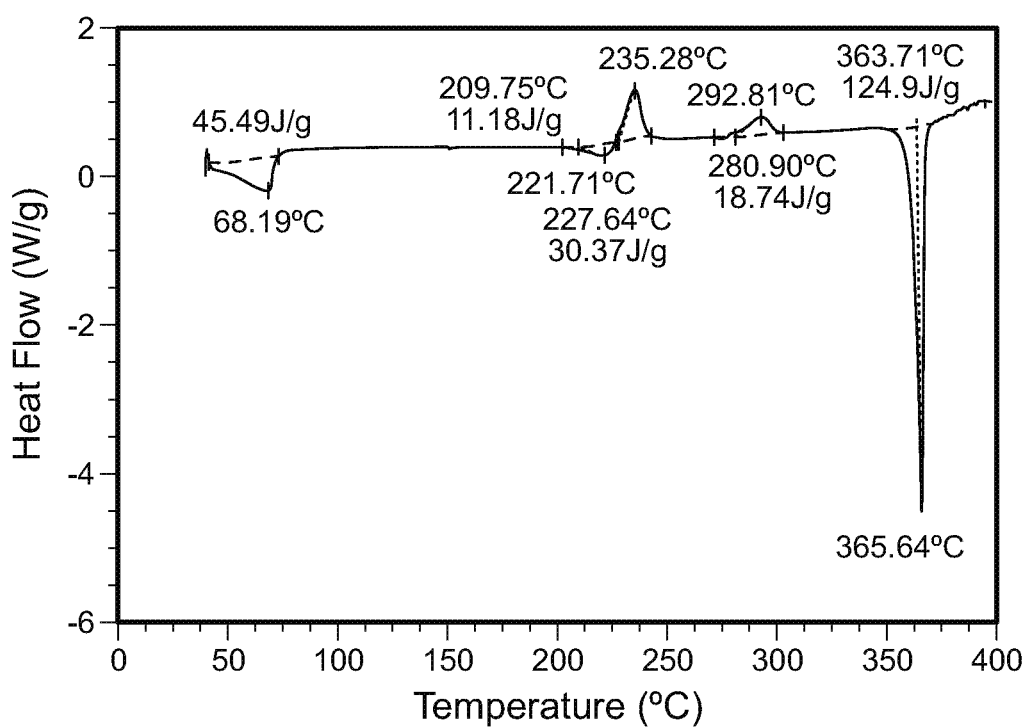
Figure 5C:
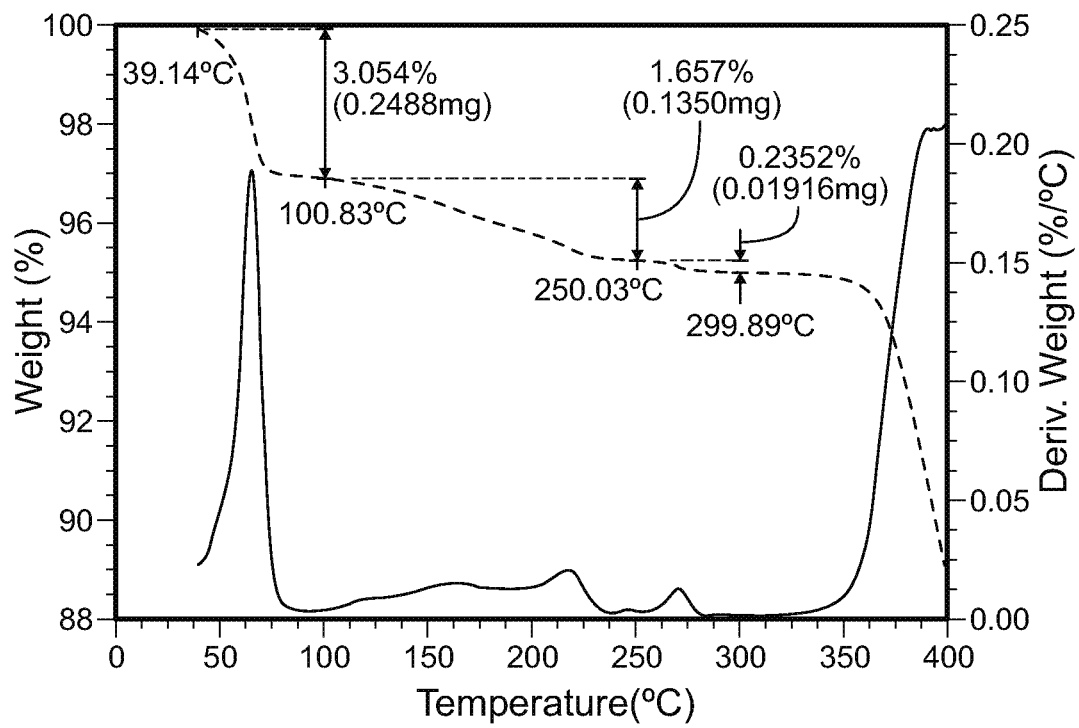
Figure 5D:
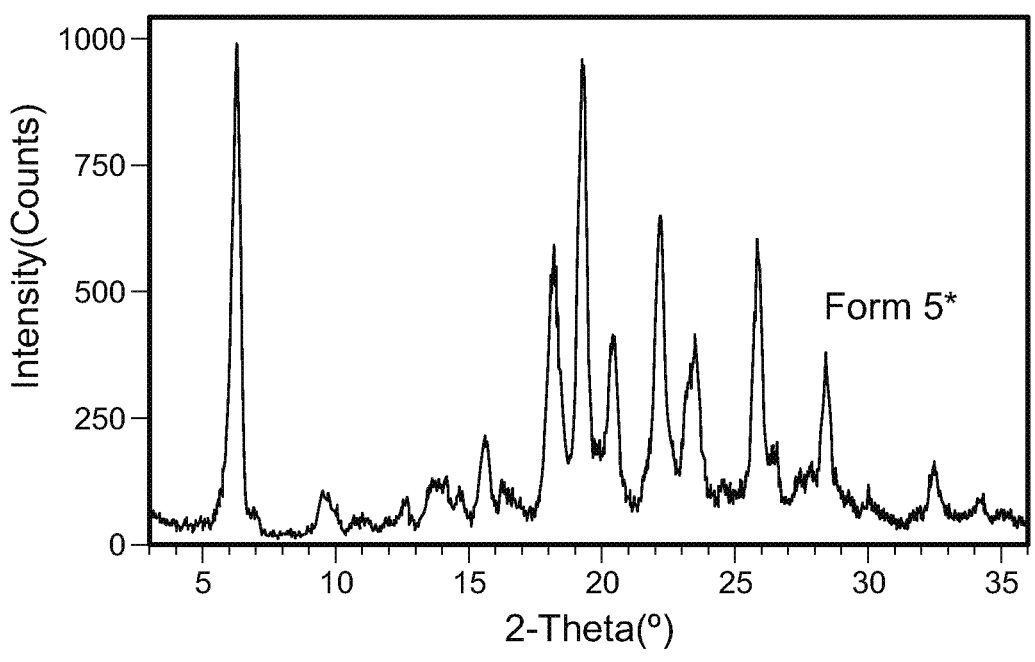

The experiments that generated Forms 5 and 5* are shown in Table 14, below. XRD scans of Forms 5 and 5* were taken (FIGS. 5A and 5D, respectively). The XRD peaks of Form 5 are shown in Table 15, below. A DSC scan of Form 5 was also performed and showed an endotherm between 50° C.-100° C., and multiple endotherms and exotherms before melting at 363° C. (FIG. 5B).

A TGA scan of Form 5 solid showed a 3.1% weight loss before 100° C., followed by a 1.7% weight loss between 100° C. and 250° C. (FIG. 5C).

Forms 5 and 5* were obtained from reslurrying Form 12 in MtBE at RT and 50° C. Wet solid showed Form 5*, while dry solid indicated Form 5.

TABLE 14

Summary of experiments that generated Forms 5 and 5*

| Form | Solvent | Temperature | Wet | Dry |
|---|---|---|---|---|
| Form 5 | MtBE | RT | Form 5* | Form 5 |
| Form 5* | MtBE | RT | Form 5* | Form 5 |
| | MtBE | 50° C. | Form 5* | Form 4 |

TABLE 15

XRD peaks of Form 5

| 2-Theta | d(A) | BG | Height | I % | Area | I % | FWHM |
|---|---|---|---|---|---|---|---|
| 5.098 | 17.3185 | 260 | 155 | 2.4 | 2464 | 2.1 | 0.27 |
| 6.38 | 13.8428 | 256 | 1778 | 27.7 | 34733 | 29.6 | 0.332 |
| 7.28 | 12.1332 | 214 | 3964 | 61.6 | 78158 | 66.5 | 0.335 |
| 8.518 | 10.3715 | 234 | 241 | 3.7 | 3170 | 2.7 | 0.224 |
| 9.24 | 9.5627 | 227 | 472 | 7.3 | 6614 | 5.6 | 0.238 |
| 10.639 | 8.3083 | 266 | 765 | 11.9 | 20508 | 17.5 | 0.456 |
| 11.019 | 8.0226 | 242 | 1596 | 24.8 | 37620 | 32 | 0.401 |
| 11.483 | 7.6998 | 398 | 133 | 2.1 | 949 | 0.8 | 0.121 |
| 12.44 | 7.1091 | 246 | 584 | 9.1 | 11910 | 10.1 | 0.347 |
| 12.94 | 6.8358 | 249 | 152 | 2.4 | 4189 | 3.6 | 0.469 |
| 14.301 | 6.1883 | 279 | 1114 | 17.3 | 22226 | 18.9 | 0.339 |
| 14.839 | 5.9648 | 300 | 167 | 2.6 | 5989 | 5.1 | 0.61 |
| 15.581 | 5.6827 | 404 | 376 | 5.8 | 4045 | 3.4 | 0.183 |
| 16.08 | 5.5073 | 452 | 459 | 7.1 | 9013 | 7.7 | 0.334 |
| 16.357 | 5.4146 | 509 | 260 | 4 | 11967 | 10.2 | 0.782 |
| 16.839 | 5.2606 | 521 | 473 | 7.4 | 7195 | 6.1 | 0.259 |
| 17.254 | 5.1351 | 550 | 258 | 4 | 4373 | 3.7 | 0.288 |
| 17.839 | 4.968 | 562 | 414 | 6.4 | 4207 | 3.6 | 0.173 |
| 18.439 | 4.8078 | 667 | 590 | 9.2 | 5946 | 5.1 | 0.171 |
| 19.059 | 4.6527 | 616 | 1603 | 24.9 | 35964 | 30.6 | 0.381 |
| 19.5 | 4.5486 | 671 | 1163 | 18.1 | 30384 | 25.9 | 0.444 |
| 20.882 | 4.2506 | 850 | 305 | 4.7 | 2860 | 2.4 | 0.159 |
| 21.679 | 4.0959 | 935 | 2272 | 35.3 | 66194 | 56.4 | 0.495 |
| 22.28 | 3.9867 | 1083 | 6430 | 100 | 117449 | 100 | 0.311 |
| 23.221 | 3.8273 | 856 | 564 | 8.8 | 9429 | 8 | 0.284 |
| 24.461 | 3.6361 | 697 | 4250 | 66.1 | 74709 | 63.6 | 0.299 |
| 25.276 | 3.5206 | 726 | 170 | 2.6 | 1349 | 1.1 | 0.135 |
| 26.081 | 3.4137 | 756 | 442 | 6.9 | 17518 | 14.9 | 0.674 |
| 26.52 | 3.3582 | 689 | 1014 | 15.8 | 34615 | 29.5 | 0.58 |
| 28.139 | 3.1686 | 528 | 306 | 4.8 | 4846 | 4.1 | 0.269 |
| 28.821 | 3.0952 | 533 | 463 | 7.2 | 7067 | 6 | 0.259 |
| 29.94 | 2.9819 | 499 | 755 | 11.7 | 15565 | 13.3 | 0.35 |
| 30.458 | 2.9324 | 435 | 467 | 7.3 | 9861 | 8.4 | 0.359 |

TABLE 15-continued

XRD peaks of Form 5

| 2-Theta | d(A) | BG | Height | I % | Area | I % | FWHM |
|---|---|---|---|---|---|---|---|
| 31.86 | 2.8065 | 343 | 648 | 10.1 | 13697 | 11.7 | 0.359 |
| 32.642 | 2.741 | 314 | 125 | 1.9 | 2403 | 2 | 0.327 |
| 34.002 | 2.6344 | 298 | 123 | 1.9 | 1956 | 1.7 | 0.27 |

G. Form 6

Figure 6A:
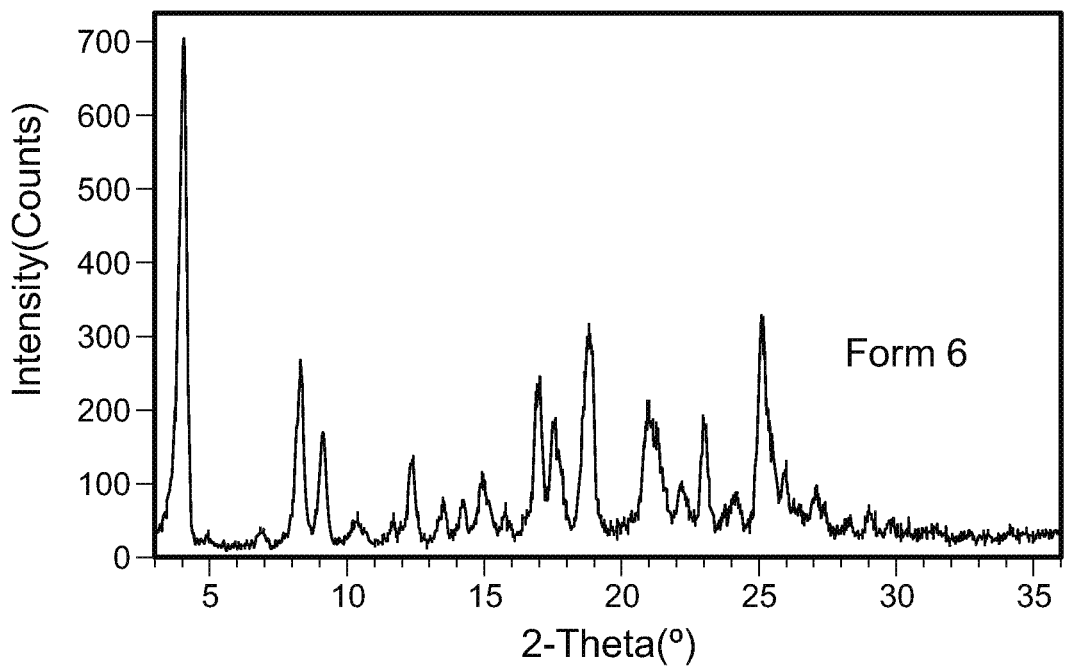
FIGS. 6A and 6B are scans of polymorph Form 6 of the compound of Formula (I).
Figure 6B:
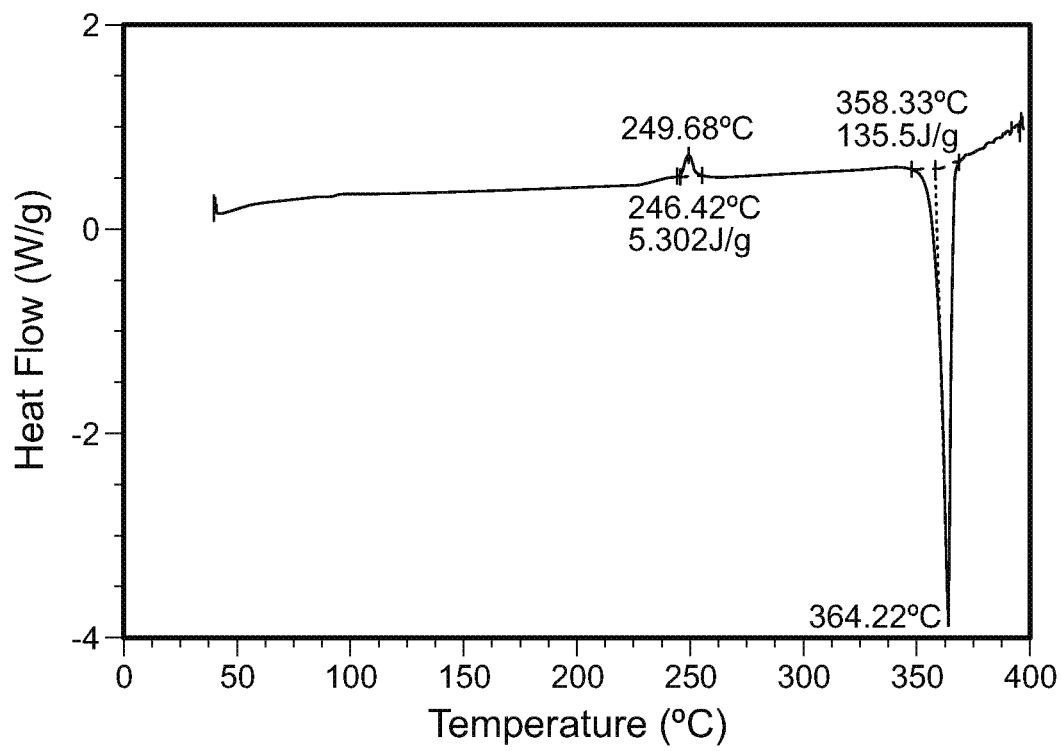

The experiments that generated Form 6 are shown in Table 16, below. XRD and DSC scans of Form 6 were taken (FIGS. 6A and 6B, respectively). According to the DSC scan, the solid showed a small exotherm at 250° C. and a melting endotherm at 358° C.

Form 6 was obtained by reslurrying starting material in IPA and IPA/5% water at RT and 50° C.

TABLE 16

Summary of experiments that generated Form 6

| Form | Solvent | Temperature | Wet | Dry |
|---|---|---|---|---|
| Form 6 | IPA | RT | Form 6 | Form 6 |
|  | IPA | 50° C. | Form 6 | Form 6 |
|  | IPA/water | RT | Form 6 | Form 6 |
|  | IPA/water | 50° C. | Form 6 | Form 6 |

*Amount of water in binary solvents is 5%

H. Form 7

Figure 7A:
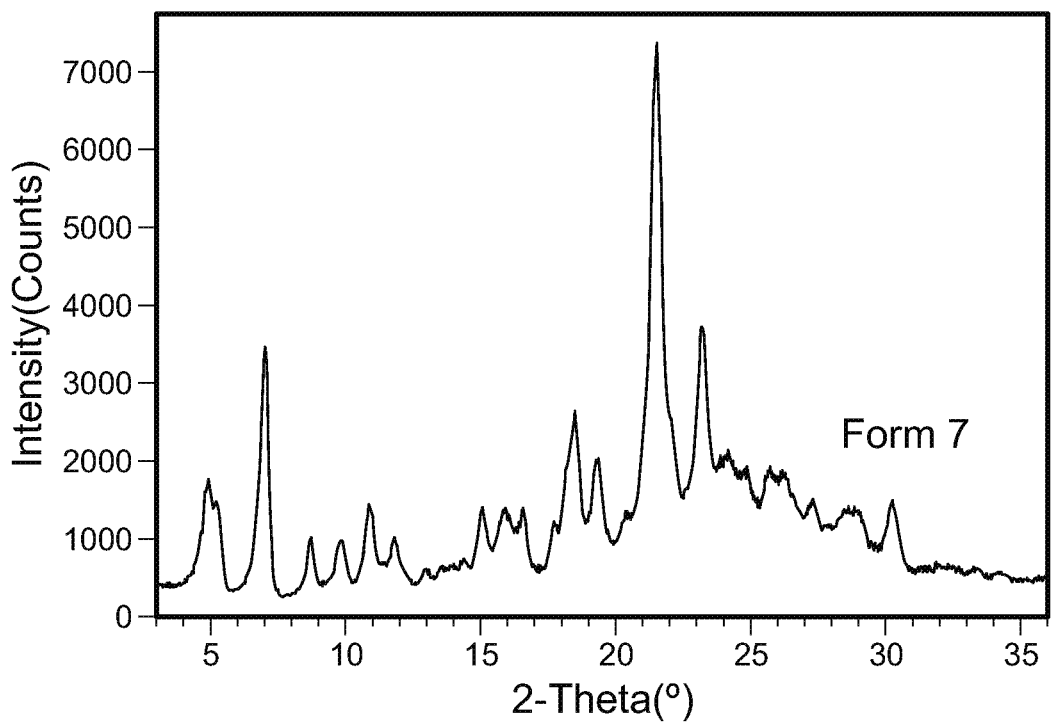
FIGS. 7A-7C are scans of polymorph Form 7 of the compound of Formula (I).
Figure 7B:
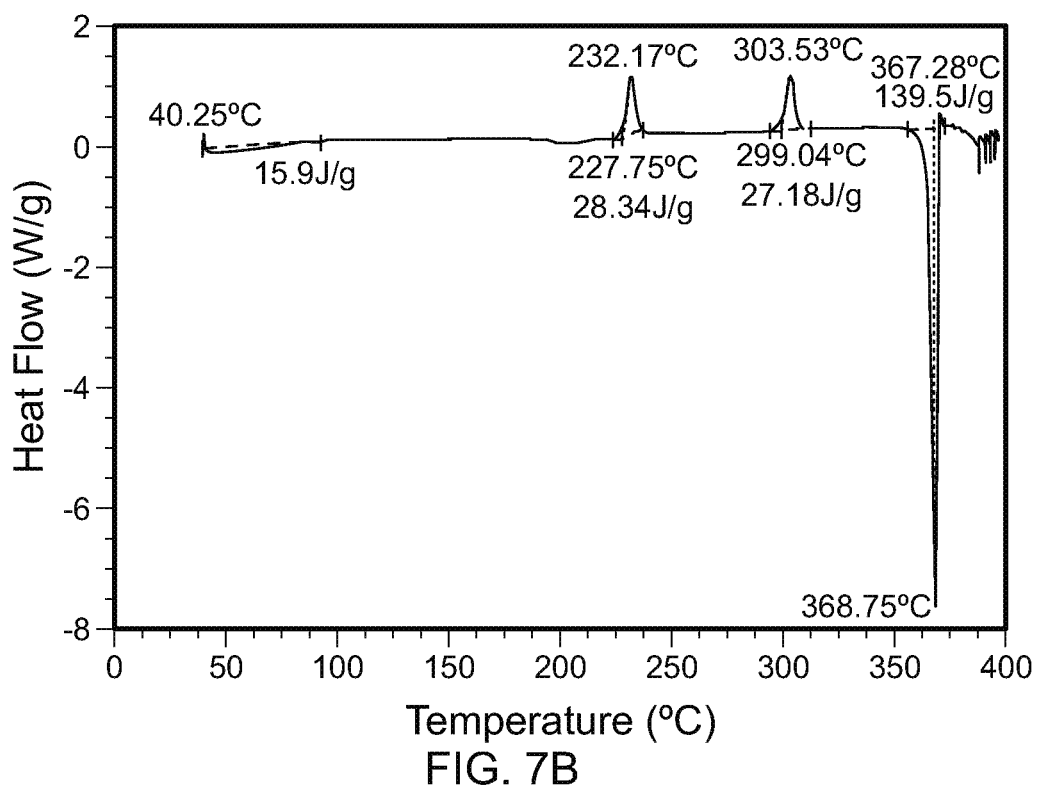

The experiments that generated Form 7 are shown in Table 17, below. XRD and DSC scans of Form 7 were taken (FIGS. 7A and 7B, respectively). The XRD peaks of Form 7 are shown in Table 18, below. According to the DSC scan, the solid showed two exotherms at 227° C. and 299° C., followed by a melting endotherm at 365° C. Form 7 showed a low degree of crystallinity on XRD. The double exotherm on the DSC scans may be associated with the low crystallinity observed on the XRD scan.

Figure 7C:
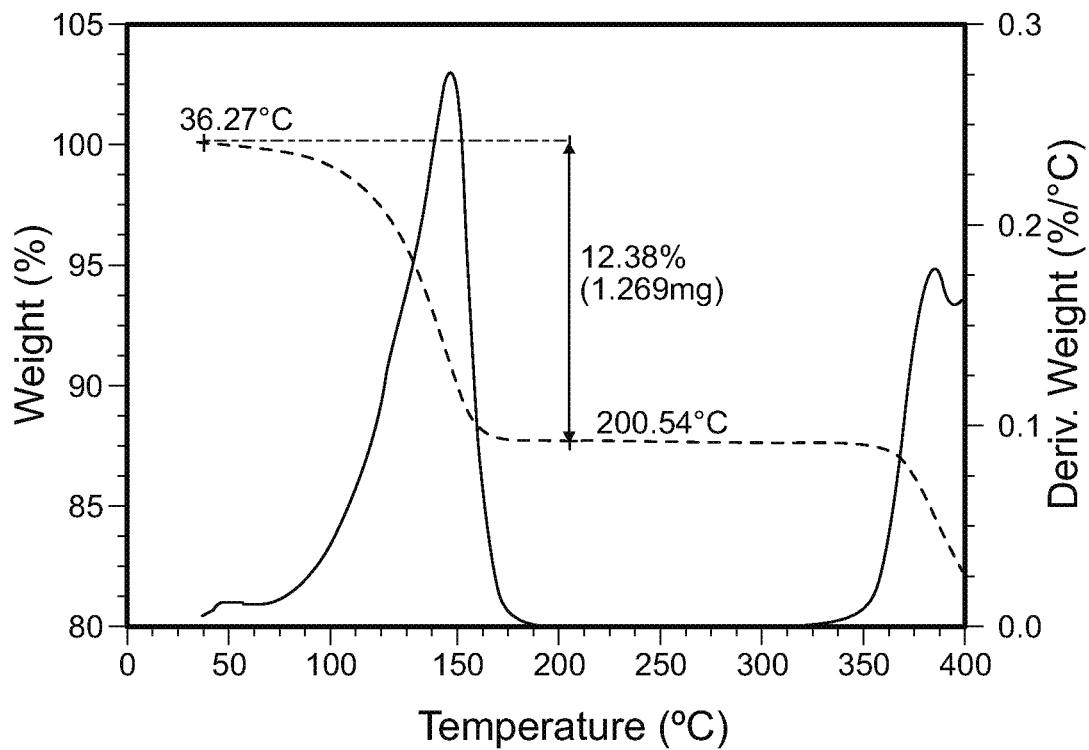

A TGA scan of Form 7 solid showed a 12% weight loss before 200° C. (FIG. 7C).

Form 7 was obtained from MEK and MEK/5% water at RT and 50° C.

TABLE 17

Summary of experiments that generated Form 7

| Form | Solvent | Temperature | Wet | Dry |
|---|---|---|---|---|
| Form 7 | MEK | RT | Form 7 | Form 7 |
|  | MEK | 50° C. | Form 7 | Form 7 |
|  | MEK/water | RT | Form 7 | Form 7 |
|  | MEK/water | 50° C. | Form 7 | Form 7 |

*Amount of water in binary solvents is 5%

TABLE 18

XRD peaks of Form 7

| 2-Theta | d(A) | BG | Height | I % | Area | I % | FWHM |
|---|---|---|---|---|---|---|---|
| 4.94 | 17.8745 | 362 | 1384 | 23.3 | 50829 | 29.2 | 0.624 |
| 7.06 | 12.5111 | 286 | 3171 | 53.3 | 69159 | 39.8 | 0.371 |
| 8.759 | 10.0876 | 370 | 628 | 10.6 | 9606 | 5.5 | 0.26 |
| 9.9 | 8.9272 | 429 | 537 | 9 | 11110 | 6.4 | 0.352 |
| 10.881 | 8.1241 | 546 | 879 | 14.8 | 16425 | 9.4 | 0.318 |
| 11.84 | 7.4681 | 588 | 413 | 6.9 | 7187 | 4.1 | 0.296 |
| 12.997 | 6.8061 | 463 | 135 | 2.3 | 1351 | 0.8 | 0.17 |

TABLE 18-continued

XRD peaks of Form 7

| 2-Theta | d(A) | BG | Height | I % | Area | I % | FWHM |
|---|---|---|---|---|---|---|---|
| 14.404 | 6.1442 | 604 | 126 | 2.1 | 3331 | 1.9 | 0.449 |
| 15.1 | 5.8626 | 791 | 596 | 10 | 8819 | 5.1 | 0.252 |
| 15.92 | 5.5622 | 792 | 593 | 10 | 24460 | 14.1 | 0.701 |
| 16.581 | 5.3421 | 739 | 641 | 10.8 | 14919 | 8.6 | 0.396 |
| 18.5 | 4.7919 | 1066 | 1555 | 26.1 | 43174 | 24.8 | 0.472 |
| 19.4 | 4.5717 | 1087 | 930 | 15.6 | 17521 | 10.1 | 0.32 |
| 20.382 | 4.3535 | 1178 | 154 | 2.6 | 867 | 0.5 | 0.096 |
| 21.56 | 4.1183 | 1424 | 5949 | 100 | 173972 | 100 | 0.497 |
| 22.098 | 4.0192 | 1830 | 692 | 11.6 | 17678 | 10.2 | 0.434 |
| 23.22 | 3.8275 | 1749 | 1971 | 33.1 | 42151 | 24.2 | 0.364 |
| 24.203 | 3.6743 | 1776 | 351 | 5.9 | 11935 | 6.9 | 0.578 |
| 24.884 | 3.5751 | 1658 | 271 | 4.6 | 2378 | 1.4 | 0.149 |
| 25.759 | 3.4556 | 1416 | 492 | 8.3 | 19894 | 11.4 | 0.687 |
| 26.3 | 3.3858 | 1335 | 499 | 8.4 | 23631 | 13.6 | 0.805 |
| 27.34 | 3.2594 | 1192 | 307 | 5.2 | 4494 | 2.6 | 0.249 |
| 28.641 | 3.1142 | 1004 | 382 | 6.4 | 18030 | 10.4 | 0.802 |
| 29.078 | 3.0684 | 979 | 324 | 5.4 | 14234 | 8.2 | 0.747 |
| 30.28 | 2.9492 | 759 | 711 | 12 | 16004 | 9.2 | 0.383 |
| 31.985 | 2.7959 | 551 | 111 | 1.9 | 4816 | 2.8 | 0.738 |
| 33.402 | 2.6804 | 509 | 102 | 1.7 | 2060 | 1.2 | 0.343 |
| 34.24 | 2.6167 | 474 | 92 | 1.5 | 1901 | 1.1 | 0.351 |

I. Form 8

Figure 8A:
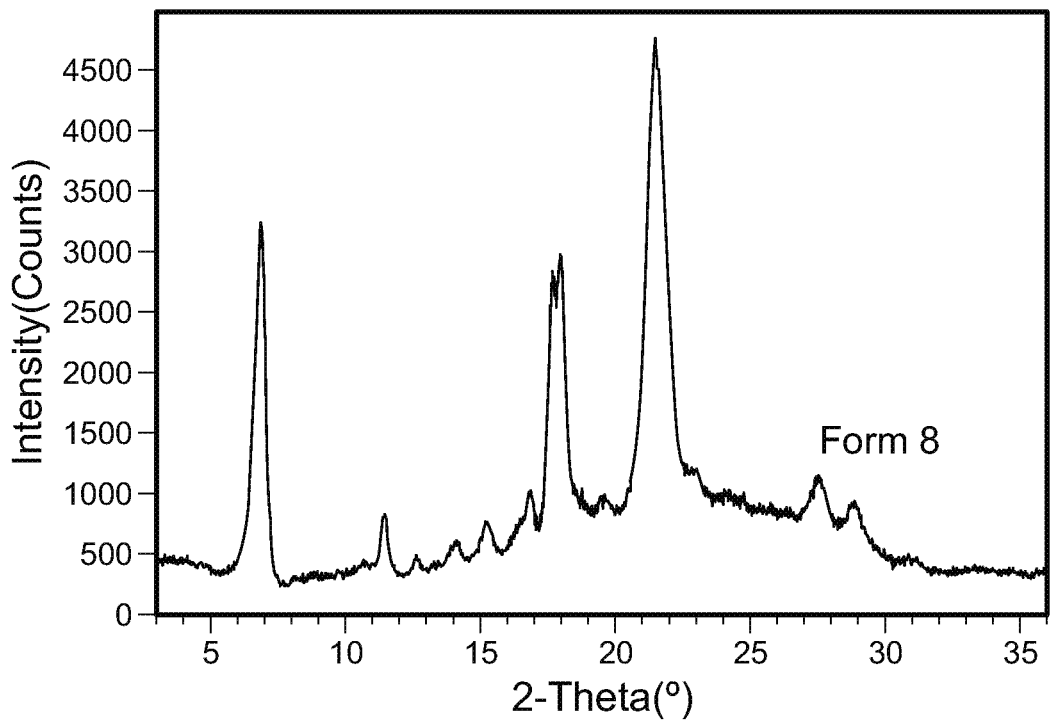
FIGS. 8A-8C are scans of polymorph Form 8 of the compound of Formula (I).
Figure 8B:
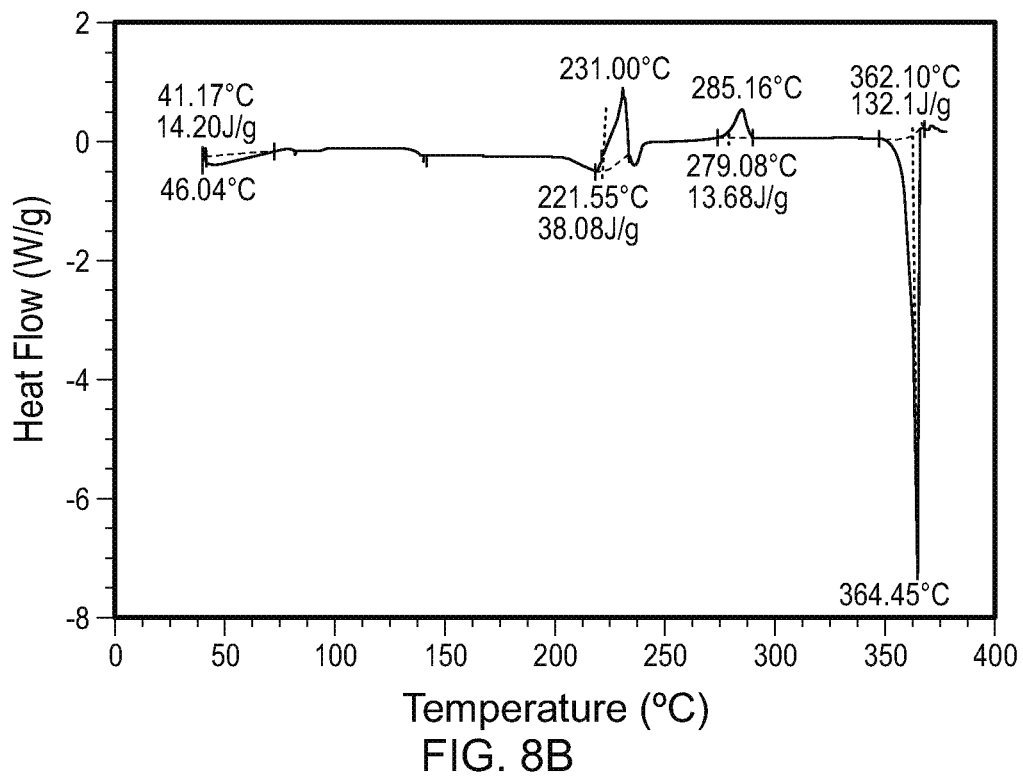

The experiments that generated Form 8 are shown in Table 19, below. XRD and DSC scans of Form 8 were taken (FIGS. 8A and 8B, respectively). The XRD peaks of Form 8 are shown in Table 20, below. According to the DSC scan, the solid showed two endotherms at 205° C. and 231° C., followed by an exotherm at 279° C., followed by a melting endotherm at 362° C. Form 8 showed a low degree of crystallinity on the XRD scan. The double exotherm on the DSC scan may confirm the low crystallinity seen on XRD (low crystalline material convert to higher crystallinity solid).

Figure 8C:
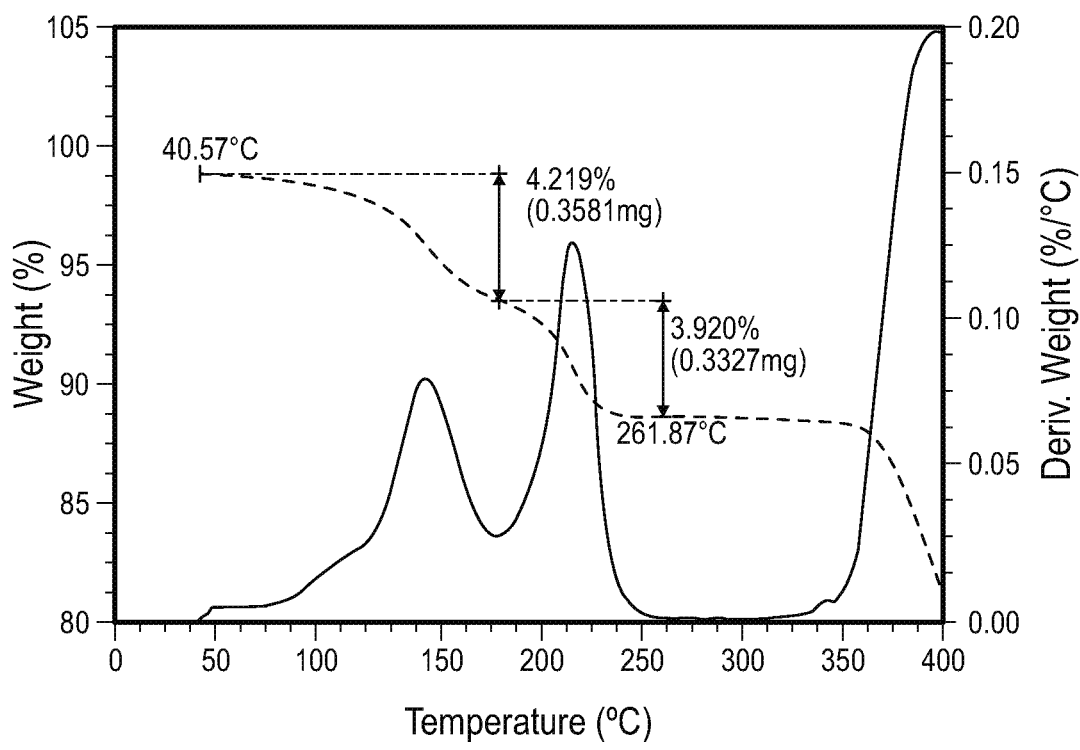

A TGA scan of Form 8 showed a 4.2% weight loss before 190° C., followed by a 3.9% weight loss between 190° C. and 261° C. (FIG. 8C).

Form 8 was obtained from MIBK at RT and 50° C. An MIBK/5% water reslurry does not produce the same form.

TABLE 19

Summary of experiments that generated Form 8

| Form | Solvent | Temperature | Wet | Dry |
|---|---|---|---|---|
| Form 8 | MIBK | RT | Form 8 | Form 8 |
|  | MIBK | 50° C. | Form 8 | Form 8 |

TABLE 20

XRD peaks of Form 8

| 2-Theta | d(A) | BG | Height | I % | Area | I % | FWHM |
|---|---|---|---|---|---|---|---|
| 6.88 | 12.8368 | 318 | 2815 | 80.8 | 71578 | 51.7 | 0.432 |
| 10.699 | 8.2619 | 380 | 70 | 2 | 722 | 0.5 | 0.175 |
| 11.48 | 7.7016 | 344 | 466 | 13.4 | 9513 | 6.9 | 0.347 |
| 12.66 | 6.9866 | 348 | 136 | 3.9 | 1759 | 1.3 | 0.22 |
| 14.16 | 6.2496 | 435 | 166 | 4.8 | 3298 | 2.4 | 0.338 |
| 15.259 | 5.8017 | 483 | 269 | 7.7 | 6267 | 4.5 | 0.396 |
| 16.879 | 5.2484 | 669 | 333 | 9.6 | 7638 | 5.5 | 0.39 |
| 17.681 | 5.0121 | 780 | 1959 | 56.2 | 76035 | 54.9 | 0.66 |
| 19.618 | 4.5213 | 833 | 134 | 3.8 | 2110 | 1.5 | 0.268 |
| 21.5 | 4.1296 | 1116 | 3484 | 100 | 138450 | 100 | 0.676 |
| 24.244 | 3.6682 | 899 | 99 | 2.8 | 2643 | 1.9 | 0.454 |
| 27.559 | 3.234 | 753 | 366 | 10.5 | 11182 | 8.1 | 0.519 |
| 28.881 | 3.0889 | 636 | 279 | 8 | 8137 | 5.9 | 0.496 |

TABLE 20-continued

XRD peaks of Form 8

| 2-Theta | d(A) | BG | Height | I % | Area | I % | FWHM |
|---|---|---|---|---|---|---|---|
| 30.878 | 2.8935 | 403 | 87 | 2.5 | 1890 | 1.4 | 0.369 |
| 31.221 | 2.8624 | 386 | 69 | 2 | 1898 | 1.4 | 0.468 |

J. Form 9

Figure 9A:
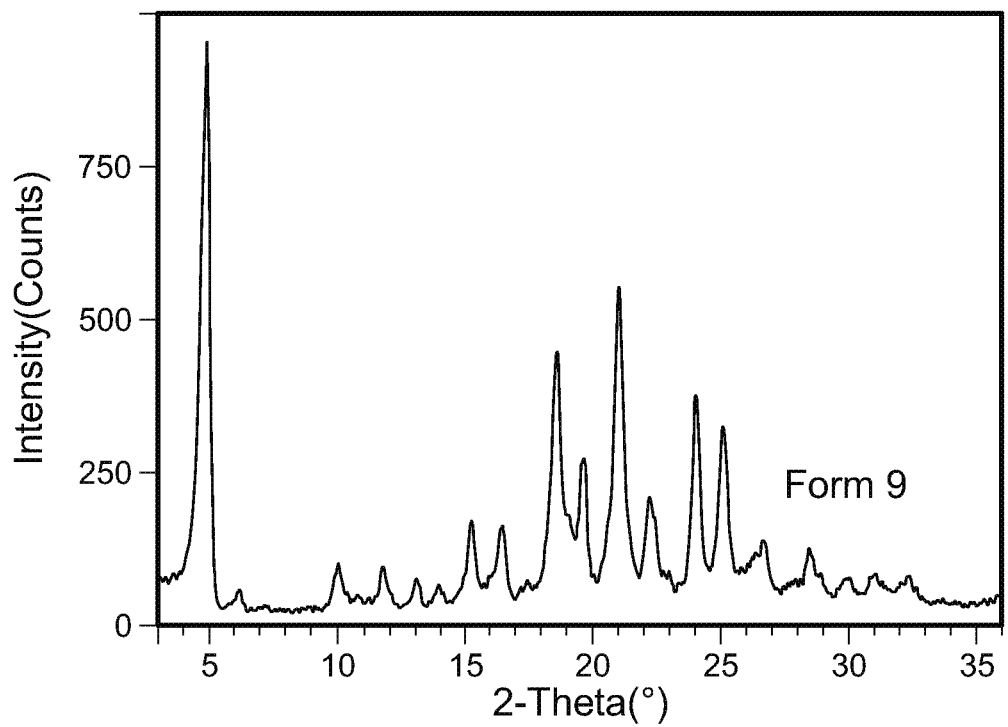
FIGS. 9A-9D are scans of polymorph Form 9 of the compound of Formula (I).
Figure 9B:
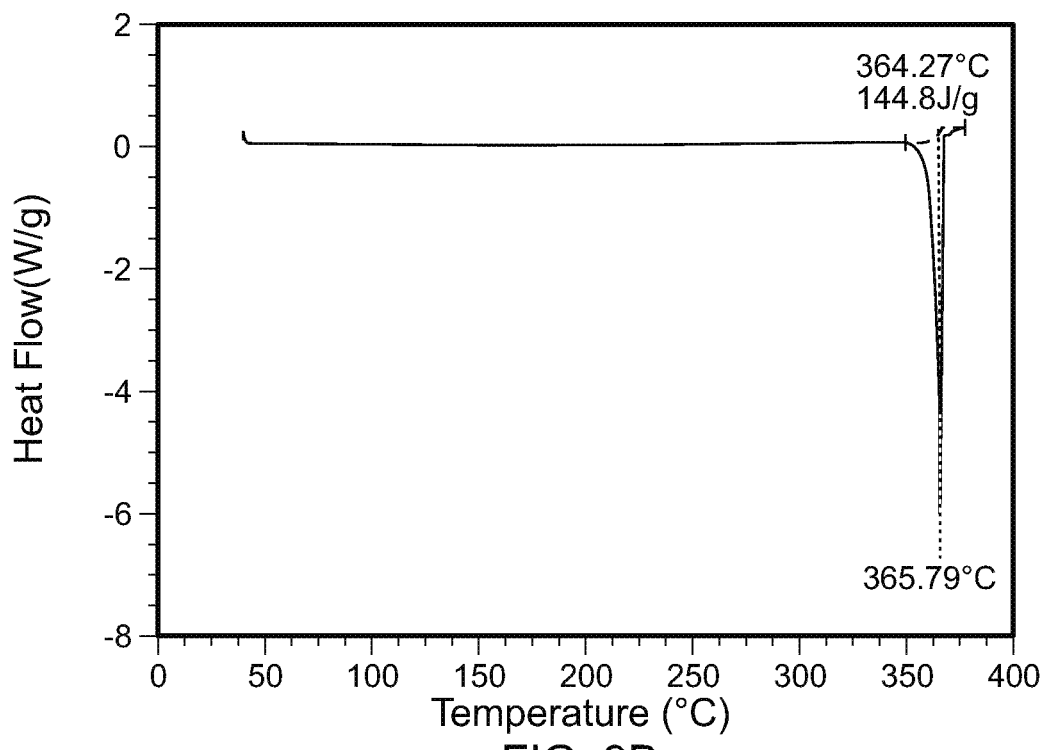

The experiments that generated Form 9 are shown in Table 21, below. XRD and DSC scans of Form 9 were taken (FIGS. 9A and 9B, respectively). The XRD peaks of Form 9 are shown in Table 22, below. According to the DSC scan, the solid showed a single melting endotherm at 364° C.

Figure 9C:
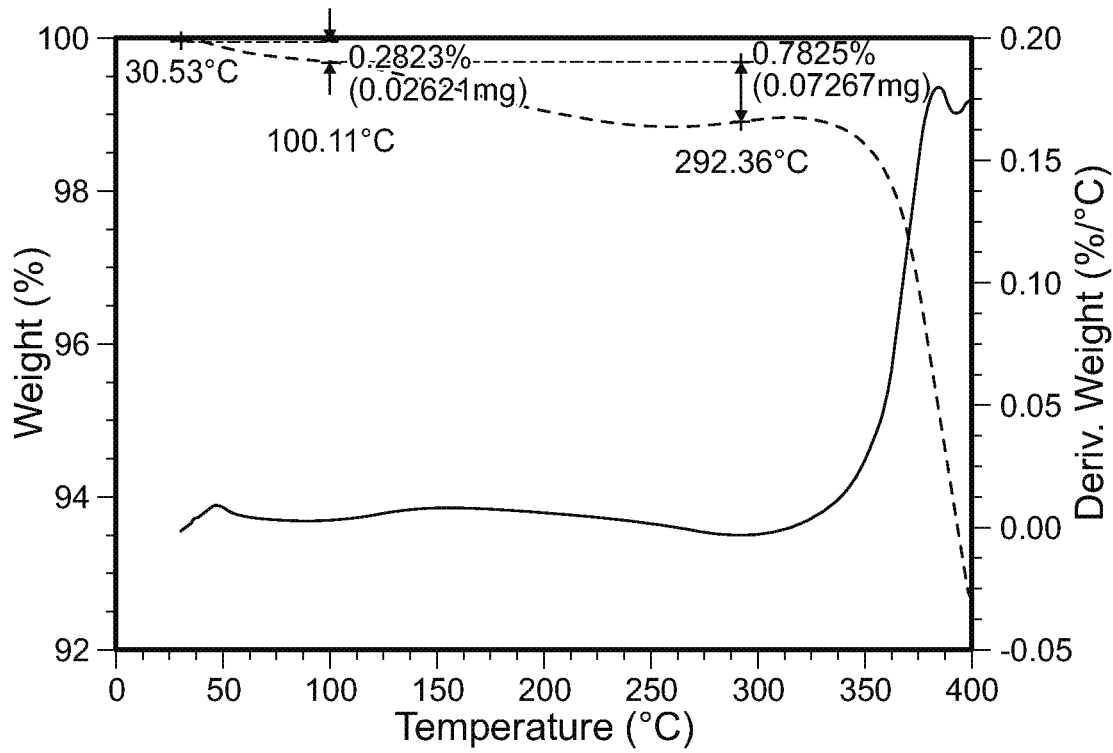

A TGA scan of Form 9 showed a 0.28% weight loss before 100° C. (FIG. 9C).

Other forms, when heated to just before melting at 364° C., seemed to convert to Form 9. This has been confirmed for Forms 1 and 2.

Figure 9D:
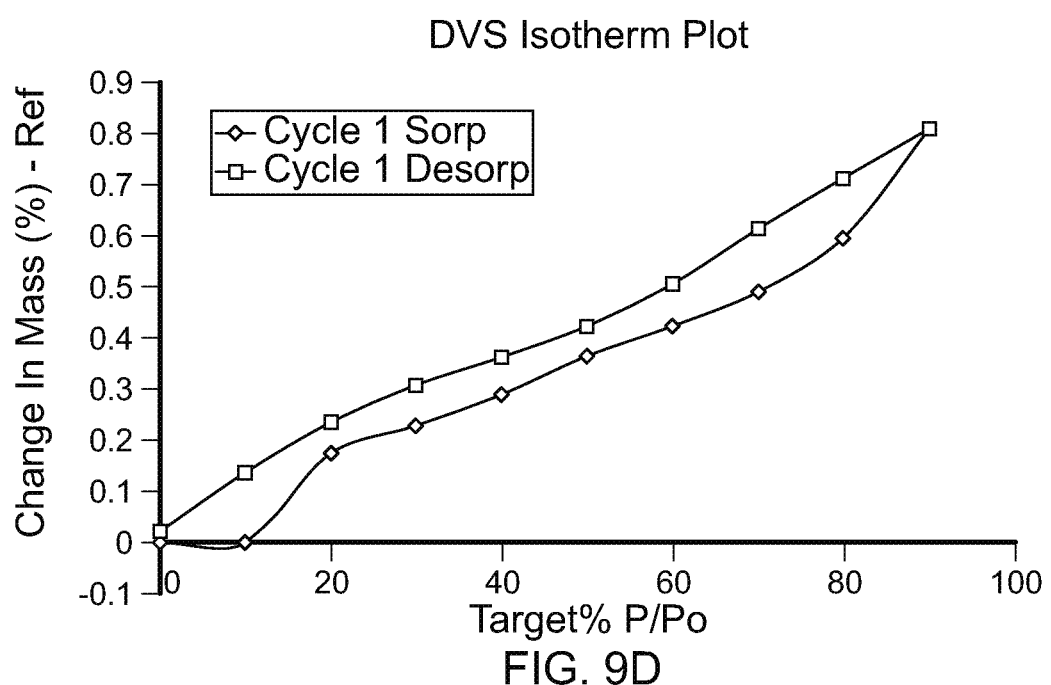

A DVS scan of Form 9 showed a 0.8% water absorption at 90% RH. Form 9 did not change its form before and after the DVS scan (FIG. 9D).

TABLE 21

Summary of experiments that generated Form 9

| Form | Solvent | Temperature | Wet | Dry |
|---|---|---|---|---|
| Form 9 | n-Butanol | RT | Form 9 | Form 9 |
| | IPAc | 50° C. | Form 9 | Form 9 |
| | n-Butyl acetate | 50° C. | Form 9 | Form 9 |
| | n-Butanol | 50° C. | Form 9 | Form 9 |
| | EtOH/water | 50° C. | Form 9 | Form 9 |
| | n-Propanol/water | 50° C. | Form 9 | Form 9 |

*Amount of water in binary solvents is 5%

TABLE 22

XRD peaks of Form 9

| 2-Theta | d(A) | BG | Height | I % | Area | I % | FWHM |
|---|---|---|---|---|---|---|---|
| 4.94 | 17.8746 | 21 | 895 | 100 | 23398 | 100 | 0.444 |
| 6.26 | 14.1076 | 21 | 34 | 3.8 | 513 | 2.2 | 0.257 |
| 10.099 | 8.7516 | 28 | 66 | 7.4 | 1172 | 5 | 0.302 |
| 11.883 | 7.4413 | 30 | 46 | 5.1 | 828 | 3.5 | 0.306 |
| 13.16 | 6.7221 | 27 | 37 | 4.1 | 400 | 1.7 | 0.184 |
| 15.341 | 5.771 | 39 | 71 | 7.9 | 1541 | 6.6 | 0.369 |
| 16.518 | 5.3622 | 40 | 93 | 10.4 | 1728 | 7.4 | 0.316 |
| 18.622 | 4.7608 | 46 | 260 | 29.1 | 7069 | 30.2 | 0.462 |
| 19.74 | 4.4938 | 80 | 138 | 15.4 | 1937 | 8.3 | 0.239 |
| 21.101 | 4.2068 | 64 | 342 | 38.2 | 8314 | 35.5 | 0.413 |
| 22.42 | 3.9622 | 56 | 77 | 8.6 | 1721 | 7.4 | 0.38 |
| 24.1 | 3.6897 | 58 | 198 | 22.1 | 3904 | 16.7 | 0.335 |
| 25.2 | 3.5311 | 63 | 157 | 17.5 | 3615 | 15.5 | 0.391 |
| 26.897 | 3.312 | 46 | 44 | 4.9 | 1307 | 5.6 | 0.505 |
| 28.577 | 3.121 | 35 | 54 | 6 | 1754 | 7.5 | 0.552 |
| 29.884 | 2.9874 | 32 | 30 | 3.4 | 477 | 2 | 0.254 |
| 30.926 | 2.8891 | 35 | 32 | 3.6 | 682 | 2.9 | 0.341 |

K. Forms 10 and 10*

Figure 10A:
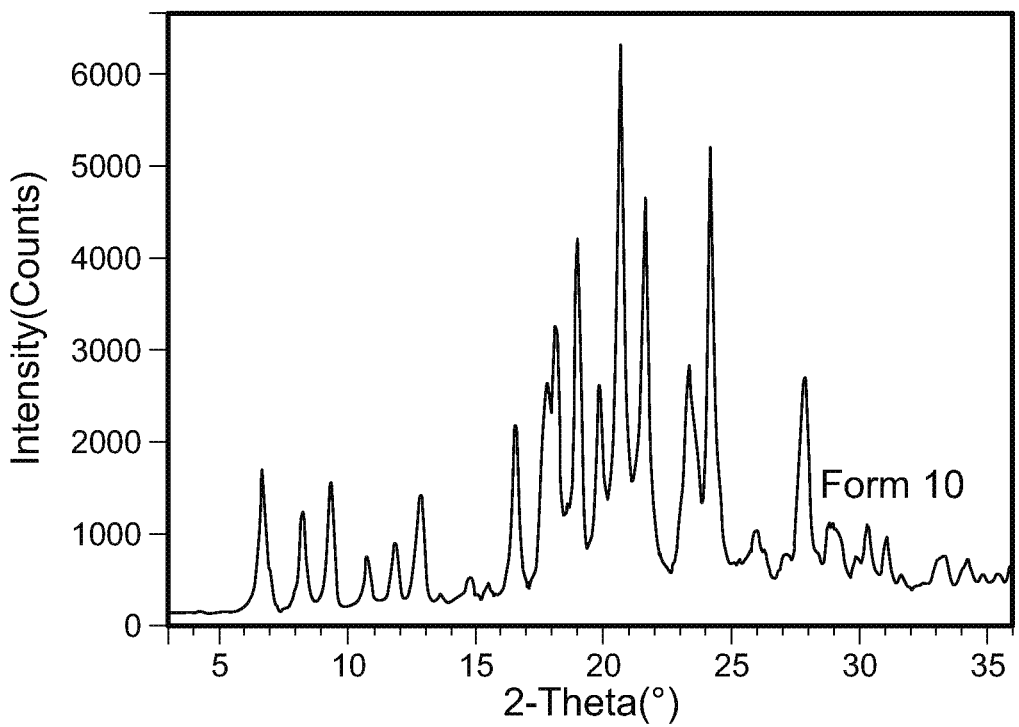
FIGS. 10A-10E are scans of polymorph Forms 10 and 10* of the compound of Formula (I).
Figure 10B:
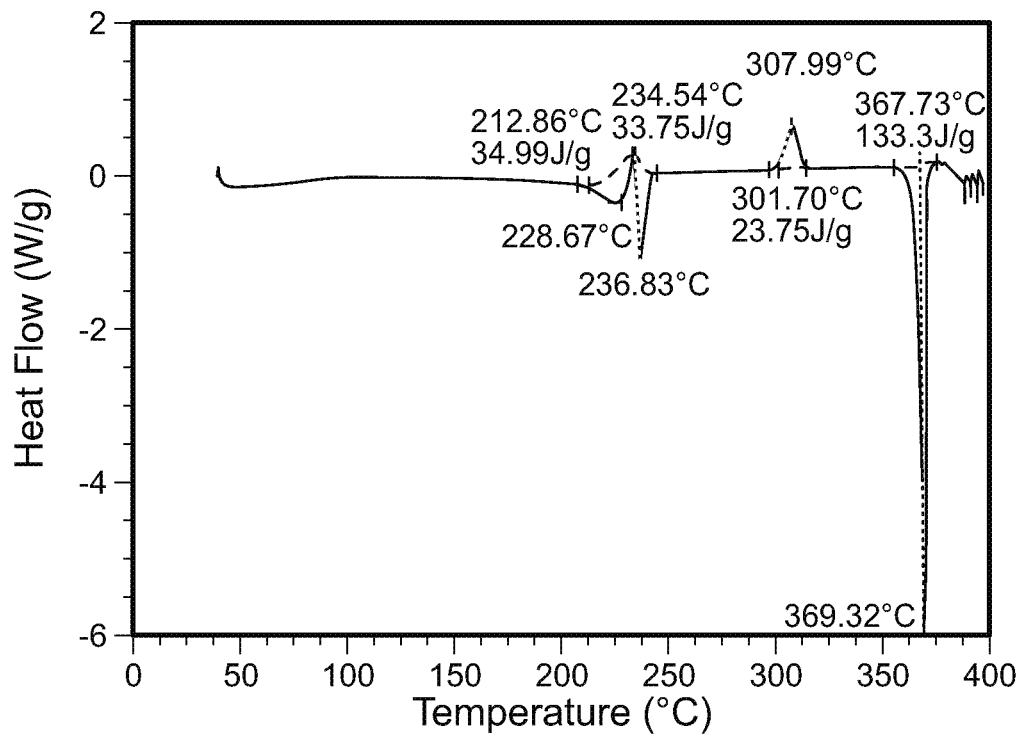
Figure 10C:
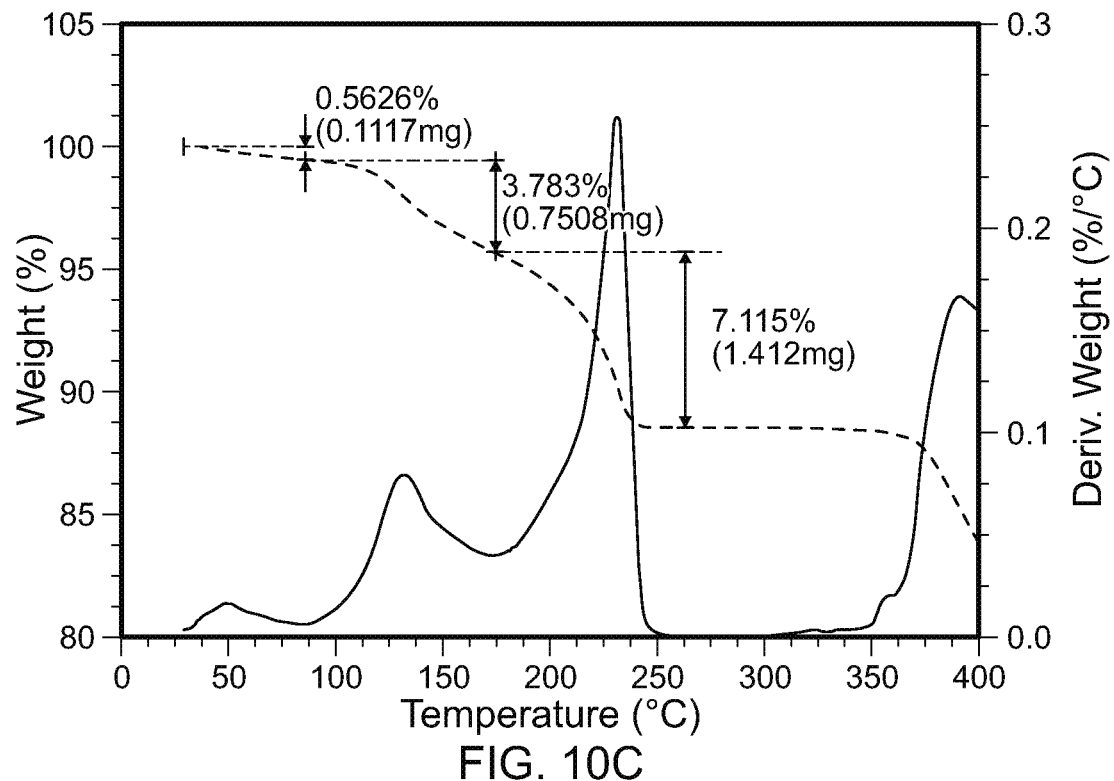
Figure 10D:
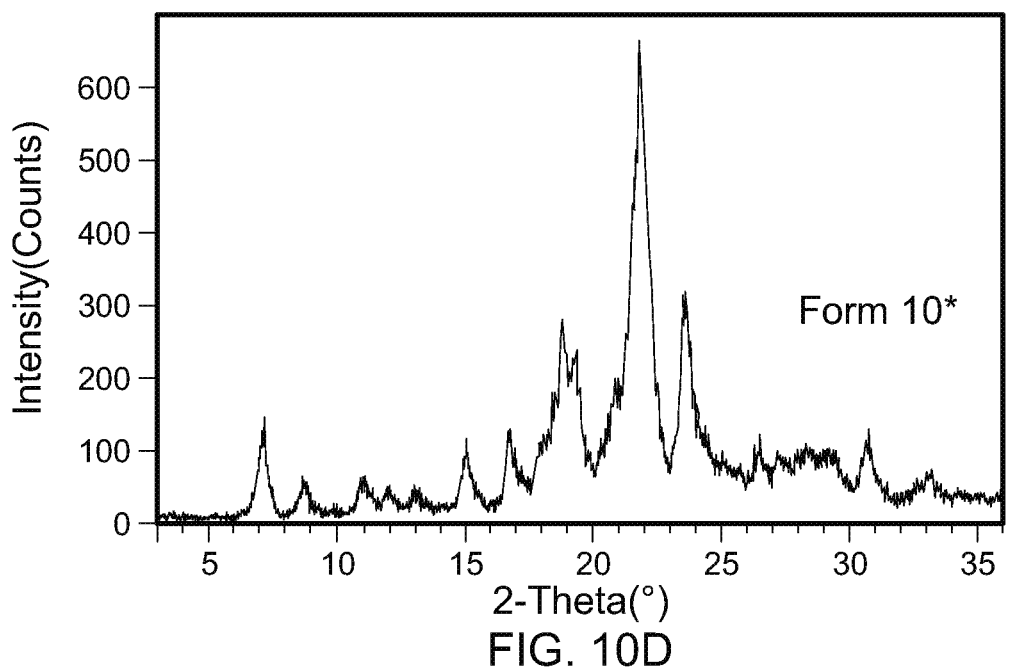
Figure 10E:
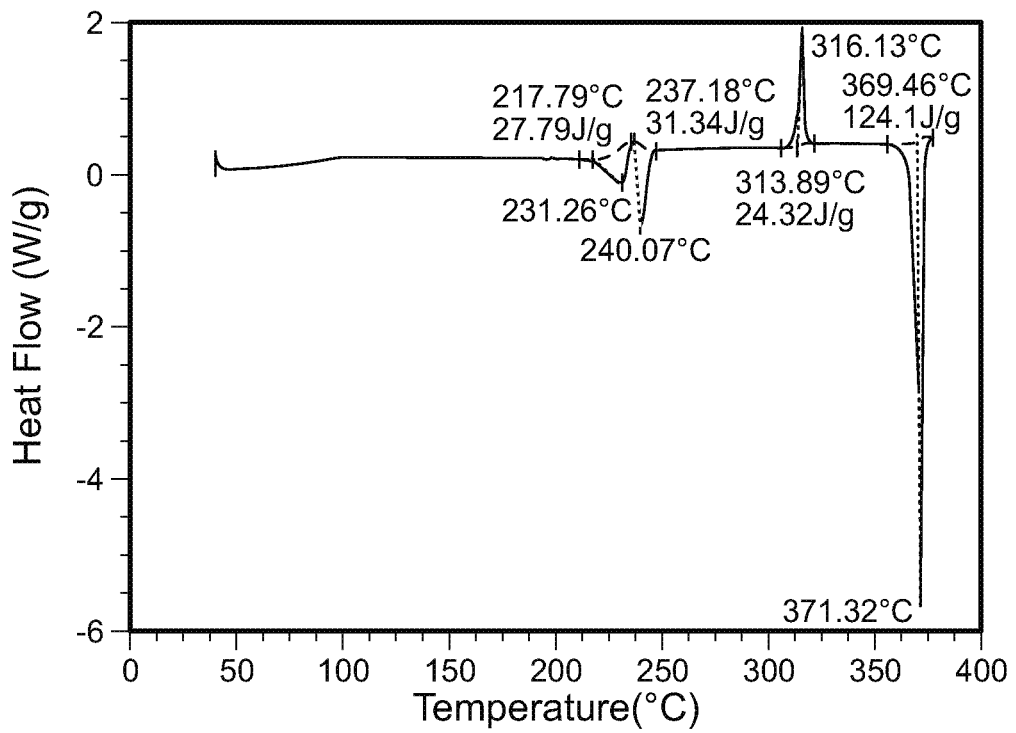

The experiments that generated Forms 10 and 10* are shown in Table 23, below. XRD scans of Forms 10 and 10* were taken (FIGS. 10A and 10D, respectively). The XRD peaks of Form 10 are shown in Table 24, below. DSC scans of Forms 10 and 10* were also taken and indicated multiple endotherms/exotherms, followed by melting at 367° C. (FIGS. 10B and 10E, respectively).

Forms 10 and 10* were produced by drying of amorphous solids (obtained from DMSO and DMSO/water reslurry at RT and 50° C.). Both Form 10 and 10* are associated with DMSO.

A TGA scan of Form 10 solid showed a 0.6% weight loss before 100° C., followed by a 3.8% weight loss between 100° C. and 170° C., followed by a 7.1% weight loss between 170° C. and 260° C. (FIG. 10C).

TABLE 23

Summary of experiments that generated Forms 10 and 10*

| Form | Solvent | Temperature | Wet | Dry |
|---|---|---|---|---|
| Form 10 | DMSO | RT | amorphous | Form 10 |
| | DMSO/water | RT | amorphous | Form 10 |
| | DMSO/water | 50° C. | amorphous | Form 10 |
| Form 10* | DMSO | 50° C. | amorphous | Form 10* |

*Amount of water in binary solvents is 5%

TABLE 24

XRD peaks of Form 10

| 2-Theta | d(A) | BG | Height | I % | Area | I % | FWHM |
|---|---|---|---|---|---|---|---|
| 6.701 | 13.1792 | 148 | 1553 | 32.1 | 31364 | 34.4 | 0.343 |
| 8.3 | 10.6444 | 207 | 1026 | 21.2 | 17914 | 19.6 | 0.297 |
| 9.38 | 9.4203 | 212 | 1352 | 27.9 | 21528 | 23.6 | 0.271 |
| 10.819 | 8.1705 | 223 | 514 | 10.6 | 8714 | 9.6 | 0.288 |
| 11.919 | 7.4192 | 271 | 635 | 13.1 | 9435 | 10.3 | 0.253 |
| 12.919 | 6.8469 | 266 | 1160 | 24 | 22094 | 24.2 | 0.324 |
| 13.718 | 6.45 | 242 | 81 | 1.7 | 856 | 0.9 | 0.18 |
| 14.84 | 5.9646 | 271 | 244 | 5 | 4716 | 5.2 | 0.329 |
| 15.536 | 5.6988 | 312 | 147 | 3 | 1304 | 1.4 | 0.151 |
| 16.58 | 5.3424 | 392 | 1813 | 37.5 | 30451 | 33.4 | 0.286 |
| 17.821 | 4.9731 | 434 | 2208 | 45.6 | 58342 | 64 | 0.449 |
| 18.16 | 4.881 | 434 | 2862 | 59.2 | 89029 | 97.6 | 0.529 |
| 19.001 | 4.6667 | 1021 | 3215 | 66.5 | 45840 | 50.2 | 0.242 |
| 19.88 | 4.4623 | 1163 | 1454 | 30.1 | 19014 | 20.8 | 0.222 |
| 20.701 | 4.2873 | 1514 | 4838 | 100 | 78140 | 85.7 | 0.275 |
| 21.66 | 4.0994 | 596 | 4067 | 84.1 | 91229 | 100 | 0.381 |
| 23.38 | 3.8017 | 596 | 2251 | 46.5 | 64928 | 71.2 | 0.49 |
| 24.22 | 3.6717 | 663 | 4578 | 94.6 | 84228 | 92.3 | 0.313 |
| 26 | 3.4242 | 595 | 430 | 8.9 | 11172 | 12.2 | 0.442 |
| 27.12 | 3.2853 | 639 | 146 | 3 | 1986 | 2.2 | 0.231 |
| 27.88 | 3.1974 | 642 | 2073 | 42.8 | 48132 | 52.8 | 0.395 |
| 28.88 | 3.089 | 638 | 477 | 9.9 | 14155 | 15.5 | 0.504 |
| 29.867 | 2.9891 | 544 | 205 | 4.2 | 4572 | 5 | 0.379 |
| 30.32 | 2.9454 | 528 | 568 | 11.7 | 11936 | 13.1 | 0.357 |
| 31.098 | 2.8735 | 517 | 443 | 9.2 | 5841 | 6.4 | 0.224 |
| 31.661 | 2.8236 | 433 | 118 | 2.4 | 953 | 1 | 0.137 |
| 33.379 | 2.6822 | 433 | 311 | 6.4 | 9235 | 10.1 | 0.505 |
| 34.22 | 2.6181 | 444 | 281 | 5.8 | 6059 | 6.6 | 0.367 |
| 34.822 | 2.5743 | 460 | 84 | 1.7 | 2707 | 3 | 0.548 |
| 35.438 | 2.5309 | 465 | 89 | 1.8 | 858 | 0.9 | 0.164 |

L. Forms 11 and 11*

Figure 11A:
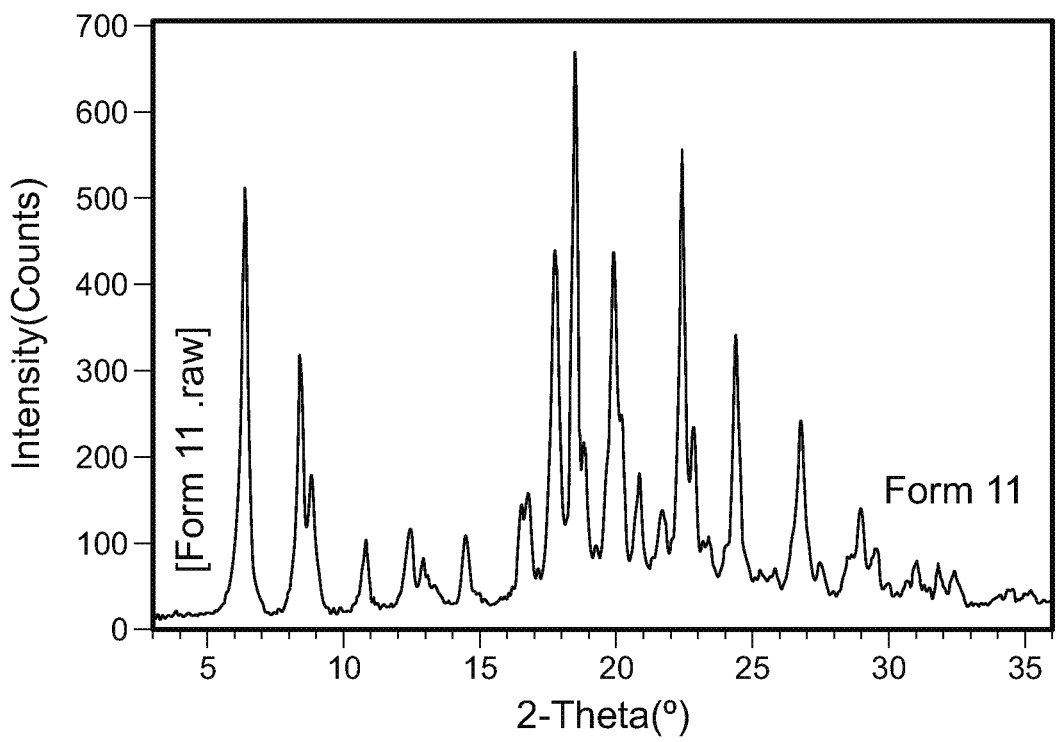
FIGS. 11A-11F are scans of polymorph Forms 11 and 11* of the compound of Formula (I).
Figure 11B:
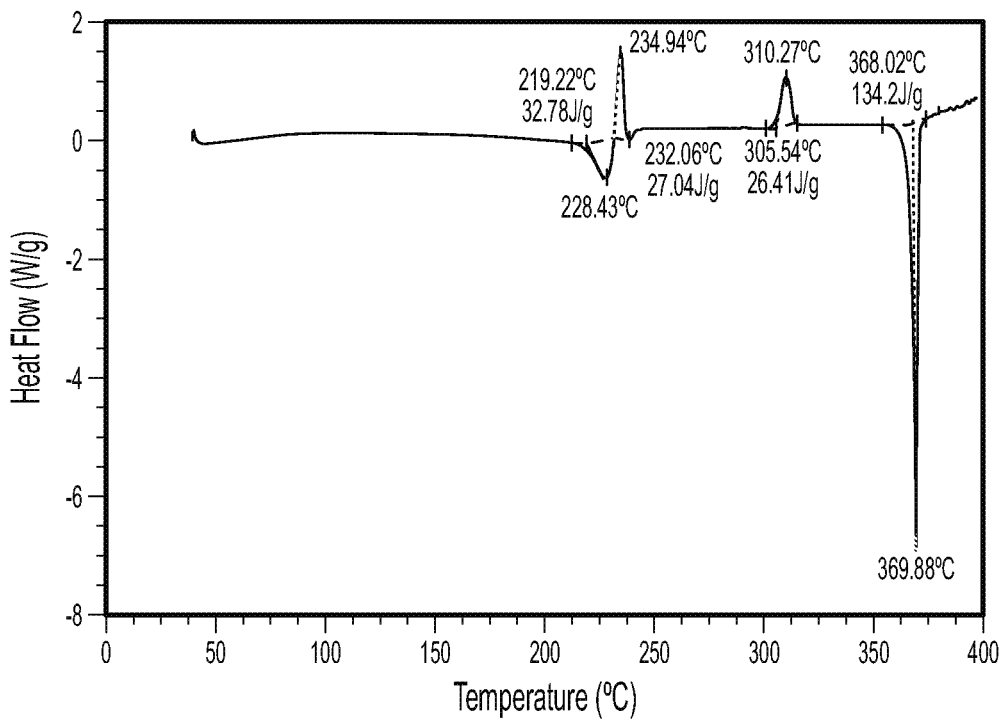

The experiments that generated Forms 11 and 11* are shown in Table 25, below. XRD scans of Forms 11 and 11* were taken (FIGS. 11A and 11D, respectively). The XRD peaks of Form 11 and Form 11* are shown in Tables 26 and 27, below, respectively. DSC scans of Forms 11 and 11* were also taken (FIGS. 11B and 11E, respectively). According to the DSC scans, the solid showed multiple endotherms/exotherms and eventually melted at 368° C. Amorphous halo was observed in the XRD of both Forms. The double exotherm on the DSC of both forms may also be associated with the amorphous halo observed on XRD scans.

Figure 11C:
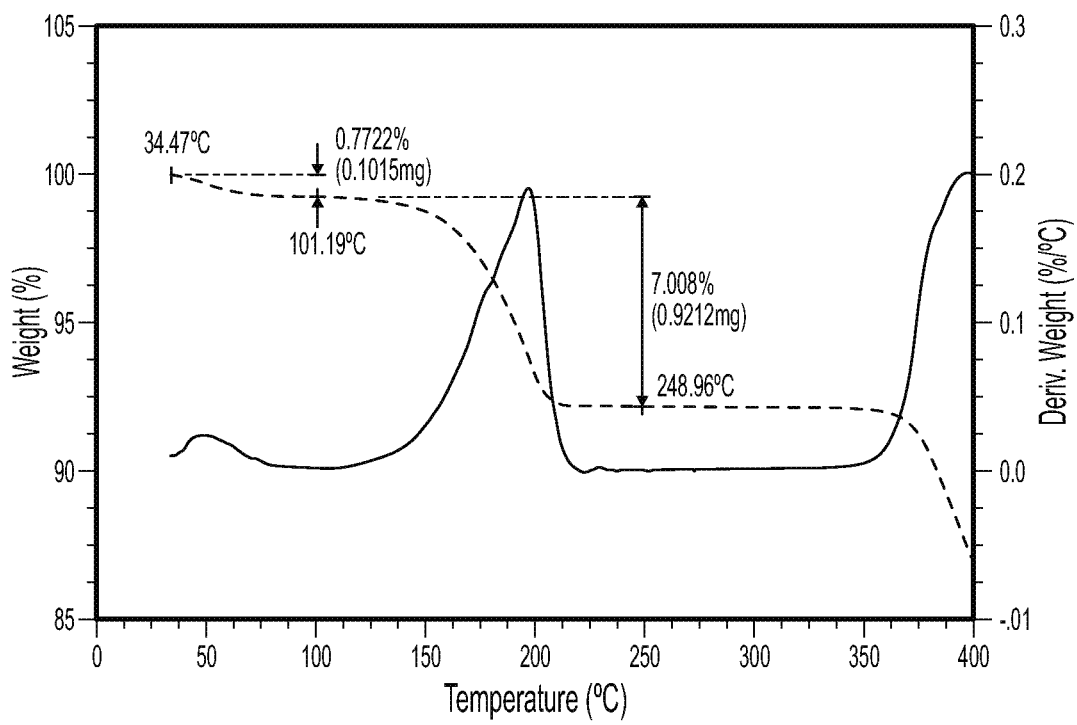
Figure 11D:
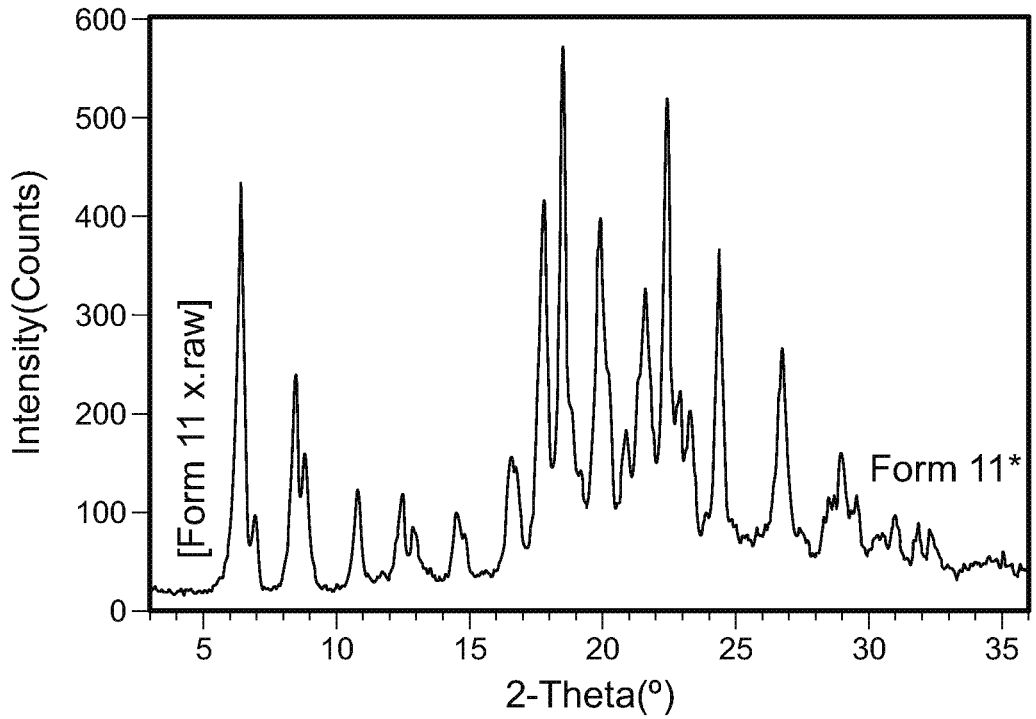
Figure 11E:
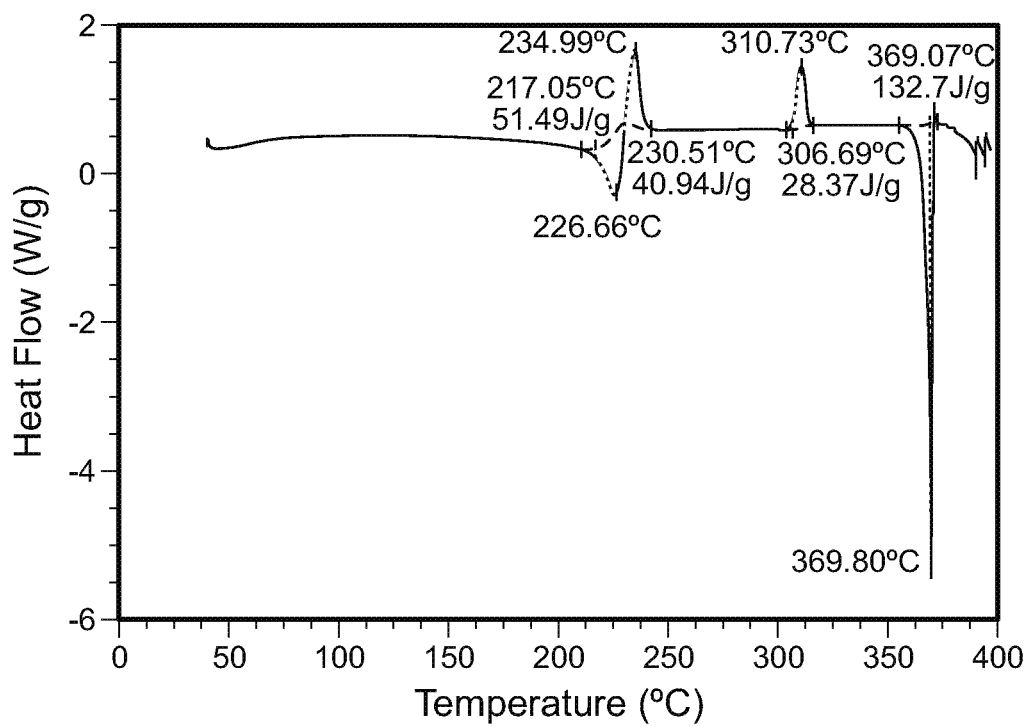
Figure 11F:
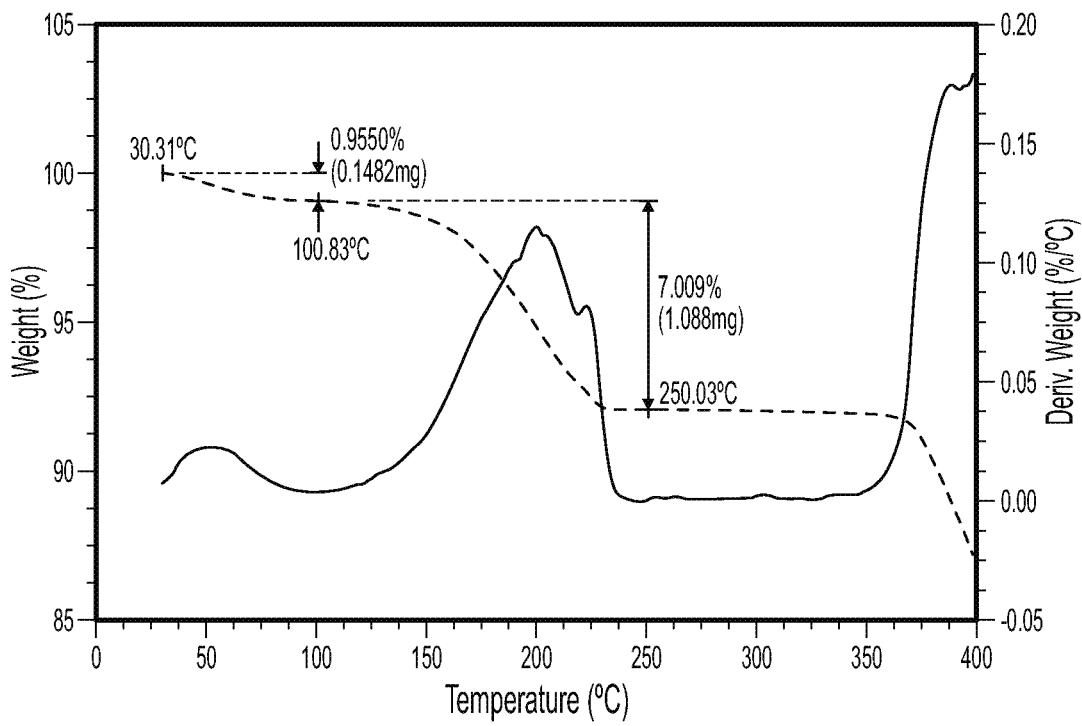

TGA scans of Form 11 and 11* were taken (FIGS. 11C and 11F, respectively). Form 11 solids showed a 0.8% weight loss before 100° C., followed by a 7.0% weight loss between 100° C. and 249° C. Form 11* solids showed a 1.0% weight loss before 100° C., followed by a 7.0% weight loss before 250° C.

Forms 11 and 11* were obtained from DMF and DMF/5% water at RT and 50° C.

TABLE 25

Summary of experiments that generated Forms 11 and 11*

| Form | Solvent | Temperature | Wet | Dry |
|---|---|---|---|---|
| Form 11 | DMF | RT | Form 11 | Form 11 |
|  | DMF | 50° C. | Form 11 | Form 11* |
|  | DMF/water | RT | Form 11 | Form 11 |
|  | DMF/water | 50° C. | Form 11 | Form 11 |
| Form 11* | DMF | 50° C. | Form 11 | Form 11* |

*Amount of water in binary solvents is 5%

TABLE 26

XRD peaks of Form 11

| 2-Theta | d(A) | BG | Height | I % | Area | I % | FWHM |
|---|---|---|---|---|---|---|---|
| 6.42 | 13.7554 | 19 | 496 | 81.7 | 9502 | 100 | 0.326 |
| 8.421 | 10.4908 | 20 | 335 | 55.2 | 5775 | 60.8 | 0.293 |
| 8.86 | 9.9726 | 24 | 166 | 27.3 | 4268 | 44.9 | 0.437 |
| 10.859 | 8.1404 | 21 | 91 | 15 | 1292 | 13.6 | 0.241 |
| 12.479 | 7.0871 | 44 | 83 | 13.7 | 1004 | 10.6 | 0.206 |
| 12.977 | 6.8165 | 29 | 51 | 8.4 | 1542 | 16.2 | 0.514 |
| 14.519 | 6.0957 | 28 | 91 | 15 | 1421 | 15 | 0.265 |
| 16.801 | 5.2727 | 57 | 104 | 17.1 | 2226 | 23.4 | 0.364 |
| 17.801 | 4.9787 | 103 | 358 | 59 | 5109 | 53.8 | 0.243 |
| 18.519 | 4.7871 | 101 | 607 | 100 | 8460 | 89 | 0.237 |
| 18.861 | 4.7011 | 102 | 125 | 20.6 | 1763 | 18.6 | 0.24 |
| 19.922 | 4.453 | 85 | 383 | 63.1 | 7376 | 77.6 | 0.327 |
| 20.258 | 4.38 | 79 | 180 | 29.7 | 5778 | 60.8 | 0.546 |
| 20.899 | 4.247 | 76 | 105 | 17.3 | 1291 | 13.6 | 0.209 |
| 21.738 | 4.085 | 86 | 55 | 9.1 | 757 | 8 | 0.234 |
| 22.441 | 3.9585 | 94 | 471 | 77.6 | 7125 | 75 | 0.257 |
| 22.859 | 3.8871 | 78 | 167 | 27.5 | 3724 | 39.2 | 0.379 |
| 24.458 | 3.6365 | 60 | 298 | 49.1 | 4544 | 47.8 | 0.259 |
| 26.82 | 3.3213 | 45 | 195 | 32.1 | 4777 | 50.3 | 0.416 |
| 29 | 3.0764 | 43 | 99 | 16.3 | 3112 | 32.8 | 0.534 |
| 29.524 | 3.023 | 63 | 37 | 6.1 | 190 | 2 | 0.087 |
| 31.04 | 2.8788 | 38 | 46 | 7.6 | 826 | 8.7 | 0.305 |
| 31.825 | 2.8095 | 36 | 56 | 9.2 | 737 | 7.8 | 0.224 |
| 32.456 | 2.7563 | 31 | 40 | 6.6 | 857 | 9 | 0.364 |

TABLE 27

XRD peaks of Form 11*

| 2-Theta | d(A) | BG | Height | I % | Area | I % | FWHM |
|---|---|---|---|---|---|---|---|
| 6.441 | 13.7116 | 24 | 424 | 93.4 | 8643 | 100 | 0.347 |
| 6.944 | 12.7196 | 20 | 84 | 18.5 | 2078 | 24 | 0.421 |
| 8.518 | 10.3718 | 22 | 227 | 50 | 4871 | 56.4 | 0.365 |
| 8.86 | 9.9721 | 23 | 147 | 32.4 | 3581 | 41.4 | 0.414 |
| 10.859 | 8.141 | 26 | 107 | 23.6 | 1695 | 19.6 | 0.269 |
| 12.519 | 7.0648 | 34 | 90 | 19.8 | 2165 | 25 | 0.409 |
| 13.021 | 6.7935 | 31 | 54 | 11.9 | 1517 | 17.6 | 0.478 |
| 14.618 | 6.0547 | 32 | 76 | 16.7 | 1605 | 18.6 | 0.359 |
| 16.638 | 5.3238 | 55 | 115 | 25.3 | 2410 | 27.9 | 0.356 |
| 17.838 | 4.9684 | 71 | 368 | 81.1 | 6709 | 77.6 | 0.31 |
| 18.522 | 4.7864 | 130 | 454 | 100 | 7473 | 86.5 | 0.28 |
| 19.96 | 4.4447 | 109 | 315 | 69.4 | 6433 | 74.4 | 0.347 |
| 20.26 | 4.3795 | 109 | 146 | 32.2 | 5359 | 62 | 0.624 |
| 20.904 | 4.2461 | 127 | 58 | 12.8 | 559 | 6.5 | 0.164 |
| 21.639 | 4.1034 | 142 | 194 | 42.7 | 4690 | 54.3 | 0.411 |
| 22.441 | 3.9586 | 161 | 368 | 81.1 | 5409 | 62.6 | 0.25 |
| 22.94 | 3.8735 | 78 | 150 | 33 | 6057 | 70.1 | 0.686 |
| 23.398 | 3.7988 | 78 | 116 | 25.6 | 2330 | 27 | 0.341 |
| 24.44 | 3.6391 | 75 | 305 | 67.2 | 5097 | 59 | 0.284 |
| 26.819 | 3.3215 | 68 | 206 | 45.4 | 4795 | 55.5 | 0.396 |

TABLE 27-continued

XRD peaks of Form 11*

| 2-Theta | d(A) | BG | Height | I % | Area | I % | FWHM |
|---|---|---|---|---|---|---|---|
| 29.018 | 3.0745 | 56 | 109 | 24 | 4093 | 47.4 | 0.638 |
| 29.566 | 3.0188 | 82 | 43 | 9.5 | 341 | 3.9 | 0.135 |
| 31.022 | 2.8804 | 58 | 55 | 12.1 | 509 | 5.9 | 0.157 |
| 31.881 | 2.8047 | 49 | 48 | 10.6 | 482 | 5.6 | 0.171 |
| 32.338 | 2.7661 | 42 | 50 | 11 | 1360 | 15.7 | 0.462 |

M. Form 13 and Form 12

Figure 12A:
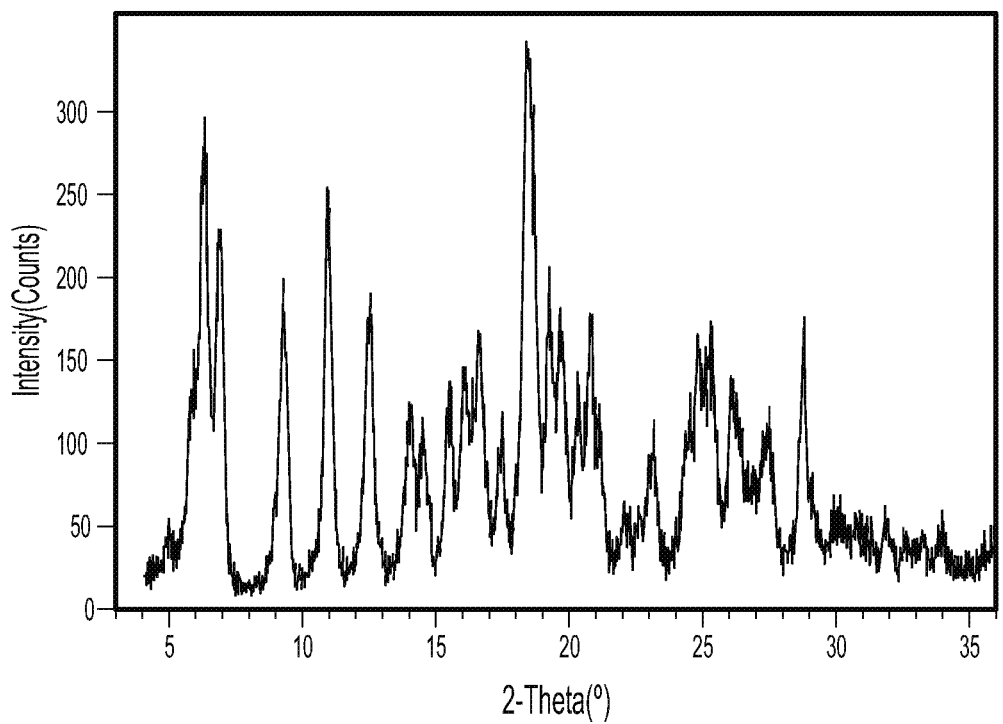
FIGS. 12A-12C are scans of Form 12, an example of a non-stoichiometric hydrate of polymorph Form 1 of the compound of Formula (I).
Figure 12B:
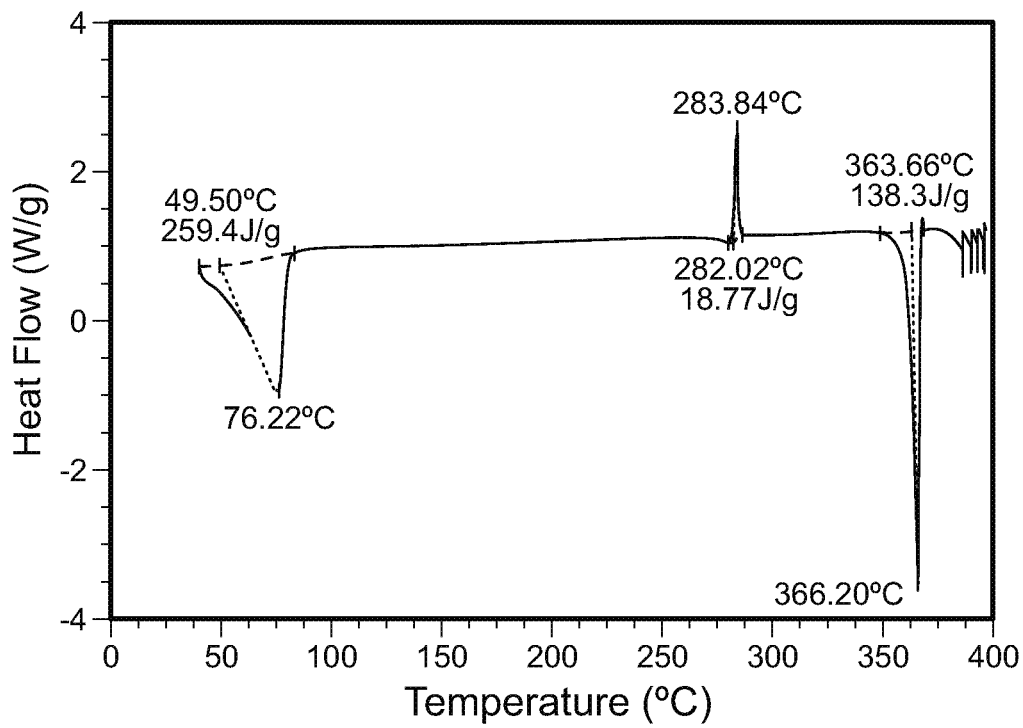
Figure 12C:
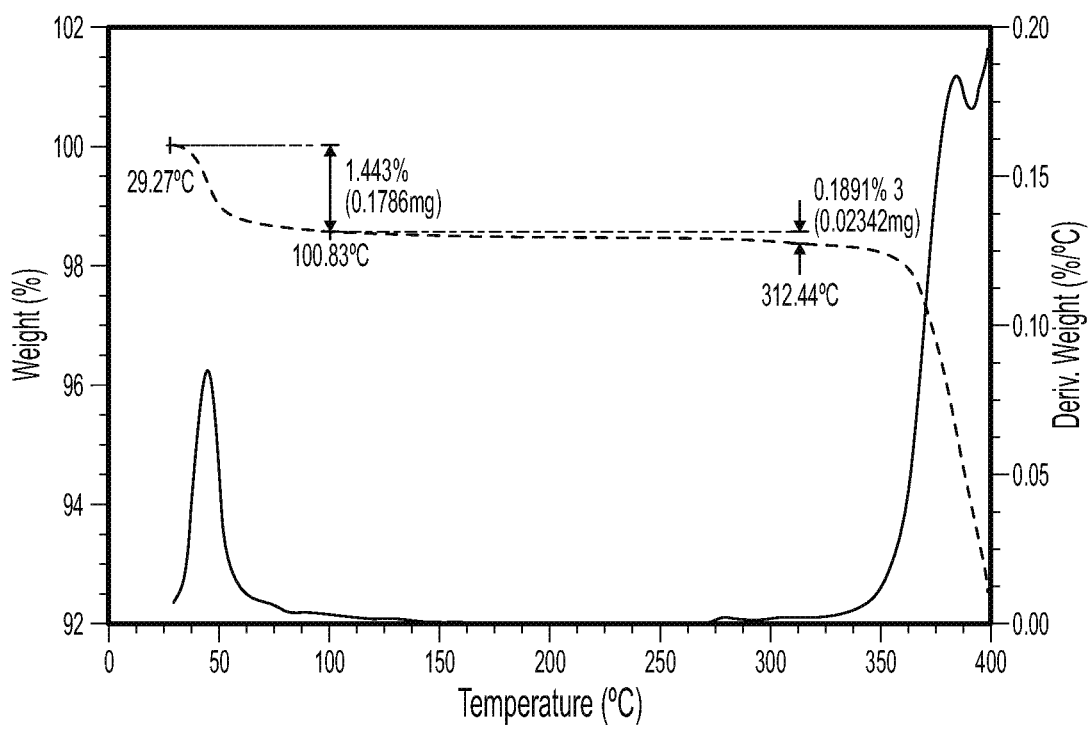
Figure 13A:
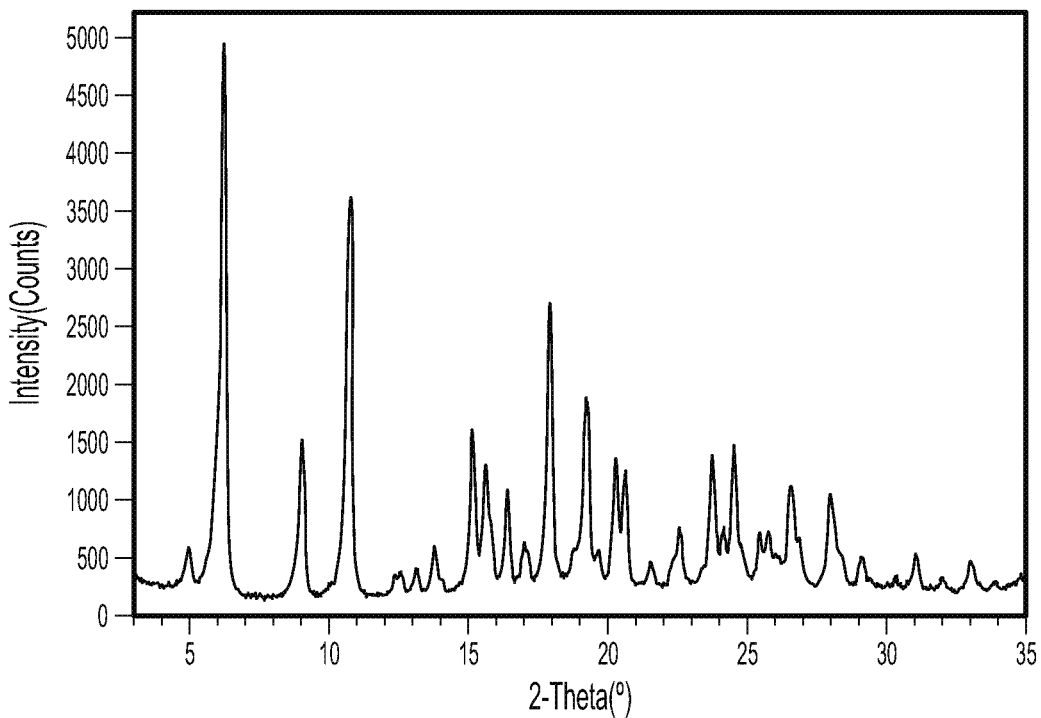
FIGS. 13A-13D are scans of Form 13, an example of a non-stoichiometric hydrate of polymorph Form 1 of the compound of Formula (I).
Figure 13B:
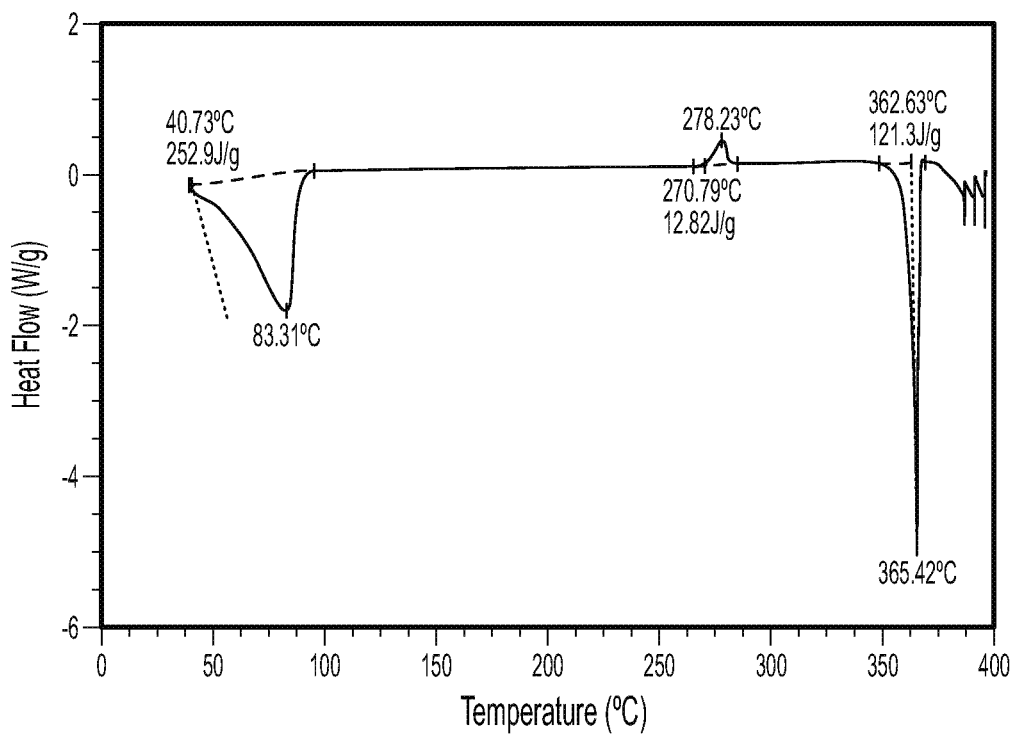

The experiments that generated Form 13 and Form 12 are shown in Tables 28 and 30, below, respectively. Forms 12 and 13 are examples of non-stoichiometric hydrate forms of Form 1 that have between 1% and about 20% by weight water. XRD scans of Form 13 and Form 12 were taken (FIGS. 13A and 12A, respectively). The XRD peaks of Form 13 are shown in Table 29, below. DSC scans of Form 13 and Form 12 were also taken (FIGS. 13B and 12B, respectively). According to the DSC scan, Form 13 solids showed an endotherm between 50° C.-100° C., followed by a small exotherm at 278° C.; and a melting endotherm at 363° C. According to the DSC scan, Form 12 solids showed an endotherm between 50° C.-100° C., followed by an exotherm at 283° C.; and a melting endotherm at 364° C.

Figure 13C:
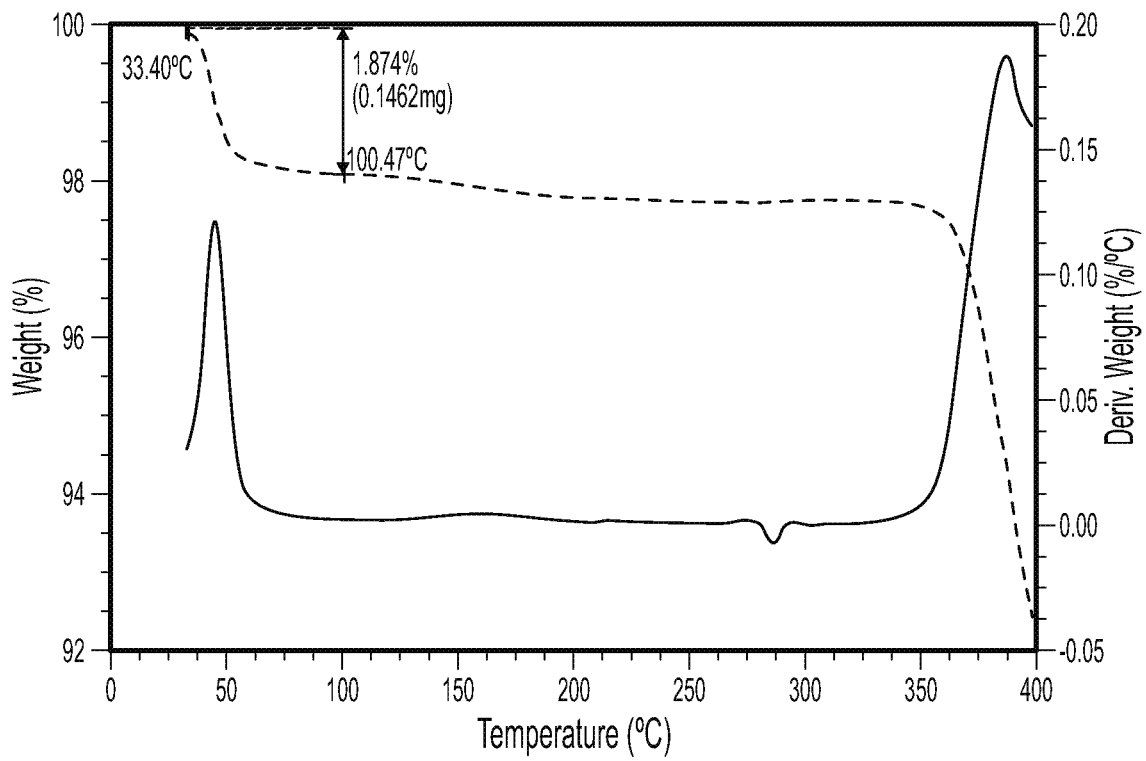
Figure 13D:
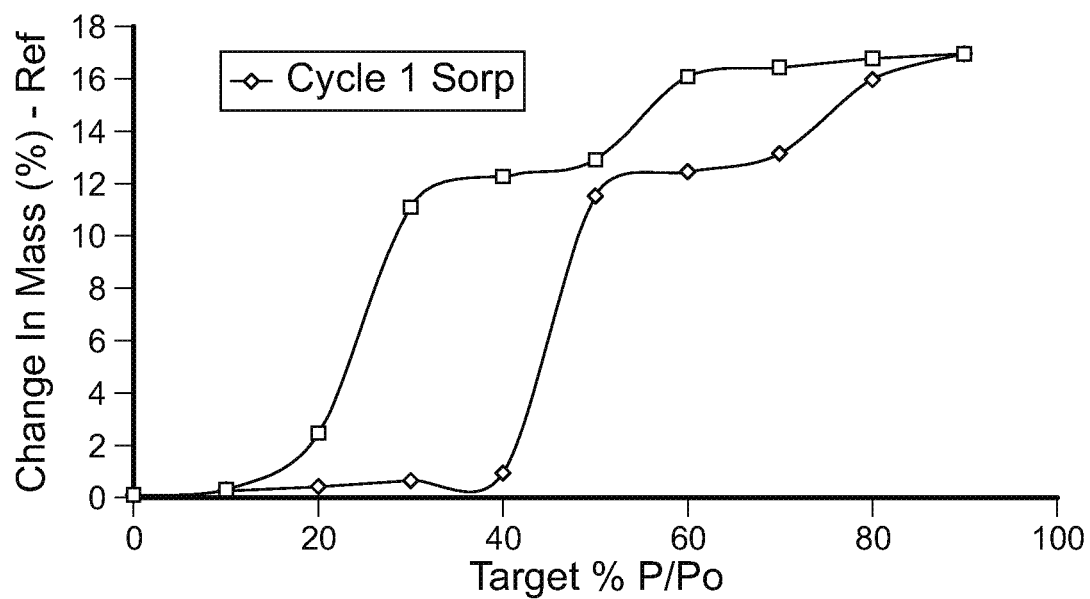

The purity of the Form 13 sample was 98.8%; the KF of an undried Form 13 sample was 35.7%. A DVS scan of Form 13 solid showed a 17% water sorption at 90% RH (FIG. 13D). Form 13 converted to Form 1 upon drying.

A TGA scan of Form 13 solid showed a 1.9% weight loss before 100° C. (FIG. 13C).

Form 13 solid was heated in a DSC chamber to 170° C. (past the endotherm between 50-100° C.), and then scanned by XRD. A comparison of the first and the second XRD and DSC scans, after heating to 170° C., showed that Form 13 converted to Form 1. It can be concluded that the endotherm between 50-100° C. is due to bonded water.

Form 13 solid was heated in a DSC chamber to 330° C. (past the endotherm/exotherm around 300° C.), and then scanned by XRD. A comparison of the first and the third XRD and DSC scans, after heating to 170° C., showed that Form 13 converted to Form 9. It can be concluded that the endotherm/exotherm is due to melting/crystallization events.

TABLE 28

Summary of experiments that generated Form 13

| Form | Solvent | Temperature | Wet | Dry |
|---|---|---|---|---|
| Form 13 | MeOH | RT | Form 13 | Form 1 |
|  | MeOH/water | 50° C. | Form 13 | Form 13 |
|  | water | RT | Form 13 | Form 1 |
|  | water | 50° C. | Form 13 | Form 13 |
|  | Toluene/water | RT | Form 13 | Form 1 |
|  | Toluene/water | 50° C. | Form 13 | Form 13 |
|  | MA/water | RT | Form 13 | Form 1 |
|  | n-Butyl acetate/water | RT | Form 13 | Form 12 |
|  | n-Butyl acetate/water | 50° C. | Form 13 | Form 1 |
|  | Heptane | 50° C. | Form 13 | Form 13 |
|  | Heptane/water | RT | Form 13 | Form 12 |
|  | Heptane/water | 50° C. | Form 13 | Form 1 |
|  | n-Butanol/water | RT | Form 13 | Form 1 |
|  | n-Butanol/water | 50° C. | Form 13 | Form 1 |
|  | DCM | 50° C. | Form 13 | Form 13 |
|  | DCM/water | RT | Form 13 | Form 1 |
|  | DCM/water | 50° C. | Form 13 | Form 1 |

TABLE 28-continued

Summary of experiments that generated Form 13

| Form | Solvent | Temperature | Wet | Dry |
|------|---------|-------------|-----|-----|
|  | Acetontrile/water | 50° C. | Form 13 | Form 13 |
|  | IPAc/water | 50° C. | Form 13 | Form 13 |
|  | MtBE/water | 50° C. | Form 13 | Form 13 |
|  | MIBK/water | 50° C. | Form 13 | Form 1 |

*Amount of water in binary solvents is 5%

TABLE 29

XRD peaks of Form 13

| 2-Theta | d(A) | BG | Height | I % | Area | I % | FWHM |
|---------|------|-----|--------|-----|------|-----|------|
| 5.06 | 17.45 | 278 | 309 | 6.5 | 3685 | 4.8 | 0.203 |
| 6.379 | 13.8451 | 223 | 4743 | 100 | 76110 | 100 | 0.273 |
| 9.24 | 9.5632 | 164 | 1370 | 28.9 | 20018 | 26.3 | 0.248 |
| 11 | 8.0364 | 173 | 3445 | 72.6 | 51777 | 68 | 0.256 |
| 12.899 | 6.8574 | 195 | 173 | 3.6 | 3114 | 4.1 | 0.306 |
| 13.462 | 6.572 | 199 | 204 | 4.3 | 2376 | 3.1 | 0.198 |
| 14.159 | 6.2498 | 202 | 390 | 8.2 | 5424 | 7.1 | 0.236 |
| 15.56 | 5.6901 | 262 | 1335 | 28.1 | 19295 | 25.4 | 0.246 |
| 16.059 | 5.5145 | 302 | 1002 | 21.1 | 17561 | 23.1 | 0.298 |
| 16.841 | 5.26 | 313 | 774 | 16.3 | 7797 | 10.2 | 0.171 |
| 17.46 | 5.075 | 322 | 314 | 6.6 | 3863 | 5.1 | 0.209 |
| 18.419 | 4.8128 | 339 | 2354 | 49.6 | 29374 | 38.6 | 0.212 |
| 19.3 | 4.5951 | 357 | 210 | 4.4 | 8112 | 10.7 | 0.657 |
| 19.741 | 4.4935 | 329 | 1566 | 33 | 30236 | 39.7 | 0.328 |
| 20.202 | 4.3919 | 342 | 210 | 4.4 | 2880 | 3.8 | 0.233 |
| 20.84 | 4.2589 | 300 | 1054 | 22.2 | 18033 | 23.7 | 0.291 |
| 21.201 | 4.1873 | 284 | 964 | 20.3 | 15700 | 20.6 | 0.277 |
| 22.121 | 4.015 | 259 | 197 | 4.2 | 2208 | 2.9 | 0.191 |
| 23.2 | 3.8307 | 268 | 482 | 10.2 | 7844 | 10.3 | 0.277 |
| 24.42 | 3.642 | 280 | 1101 | 23.2 | 16244 | 21.3 | 0.251 |
| 24.839 | 3.5816 | 303 | 468 | 9.9 | 9306 | 12.2 | 0.338 |
| 25.219 | 3.5284 | 385 | 1093 | 23 | 16646 | 21.9 | 0.259 |
| 26.164 | 3.4032 | 359 | 357 | 7.5 | 5064 | 6.7 | 0.241 |
| 26.499 | 3.3609 | 402 | 317 | 6.7 | 7316 | 9.6 | 0.392 |
| 26.798 | 3.324 | 346 | 179 | 3.8 | 8025 | 10.5 | 0.762 |
| 27.339 | 3.2594 | 394 | 720 | 15.2 | 13063 | 17.2 | 0.308 |
| 27.639 | 3.2247 | 341 | 318 | 6.7 | 5673 | 7.5 | 0.303 |
| 28.799 | 3.0974 | 256 | 805 | 17 | 16756 | 22 | 0.354 |
| 29.902 | 2.9857 | 262 | 234 | 4.9 | 3508 | 4.6 | 0.255 |
| 31.234 | 2.8613 | 230 | 106 | 2.2 | 1473 | 1.9 | 0.236 |
| 31.96 | 2.798 | 226 | 308 | 6.5 | 3908 | 5.1 | 0.216 |
| 32.939 | 2.717 | 208 | 117 | 2.5 | 1444 | 1.9 | 0.21 |
| 33.962 | 2.6375 | 199 | 266 | 5.6 | 4617 | 6.1 | 0.295 |
| 34.917 | 2.5675 | 217 | 73 | 1.5 | 736 | 1 | 0.171 |

TABLE 30

Summary of experiments that generated Form 12

| Form | Solvent | Temperature | Wet | Dry |
|------|---------|-------------|-----|-----|
| Form 12 | Acetonitrile/water | RT | Form 12 | Form 1 |
|  | MeOH/water | RT | Form 12 | Form 1 |
|  | IPAc/water | RT | Form 12 | Form 1 |
|  | EA/water | RT | Form 12 | Form 1 |
|  | MtBE/water | RT | Form 12 | Form 1 |
|  | MIBK/water | RT | Form 12 | Form 1 |
|  | n-Butyl acetate/water | RT | Form 13 | Form 12 |
|  | Heptane/water | RT | Form 13 | Form 12 |
|  | MA/water | 50° C. | Form 12 | Form 4 |

*Amount of water in binary solvents is 5%

N. Solvates 1-3

The experiments that generated Solvates 1, 2, and 3 are shown in Table 31, below. Solvates 1 and 2 solids were exposed to air overnight, and then analyzed by XRD. After the analysis, the solids were dried at 50° C. under vacuum, and then analyzed by XRD again.

After exposure to air overnight, Solvate 1 converted to low crystallinity; after drying at 50° C., the sample was still a low crystallinity solid. After exposure to air overnight, the XRD pattern of Solvate 2 changed a little; after drying at 50° C., the form remained the same as the solid exposed to air overnight.

TABLE 31

Summary of experiments that generated solvates 1-3

| Form | Solvent | Temperature | Wet | Dry |
|------|---------|-------------|-----|-----|
| Solvate 1 | Acetone | RT | Solvate 1 | Low crystallinity |
| Solvate 2 | Acetone/water | RT | Solvate 2 | Form 4** |
|  | Acetone | 50° C. | Solvate 2 | Form 4** |
| Solvate 3 | EtOH/water | RT | Solvate 3 | Form 2 |

*Amount of water in binary solvent is 5%

Example 5: Competitive Reslurry Experiments Between Polymorph Forms

In order to find out the thermodynamic stability between the different forms, several competitive reslurry experiments were carried out. Form 1, Form 2, Form 2*, Form 3, Form 4, Form 4*, Form 4**, Form 5, Form 7, Form 8, Form 9, Form 10, Form 11, Form 11*, and Form 13 (10 mg for each) were mixed and slurried in 2 mL of solvent at both RT and 50° C. The solids were slurried for 3-5 days and then analyzed by XRD. According to the analytical data, Form 2* was the most stable form in a MeOH, EtOH, and acetone system at both RT and 50° C. Form 4 or 4* was most stable in EA at RT and 50° C. Form 13 was most stable in water at RT and 50° C. Table 32 shows the XRD scan results from the competitive reslurry experiments.

TABLE 32

XRD scan results of competitive reslurry experiments

| Temperature | Solvent | Form after 3 days; wet/dry | Form after 5 days; wet/dry |
|-------------|---------|----------------------------|----------------------------|
| RT | MeOH | Form 2*/Form 2* | Form 2*/Form 2* |
|  | EtOH | Form 2*/Form 2* | Form 2*/Form 2* |
|  | Acetone | Form 2*/Form 2* | Form 2*/Form 2* |
|  | EA | Form 4/Form 4 | Form 4/Form 4 |
|  | water | Form 13/Form 13 | Form 13/Form 1&Form 13 |
| 50° C. | MeOH | Form 2*/Form 2* | Form 2*/Form 2* |
|  | EtOH | Form 2*/Form 2* | Form 2*/Form 2* |
|  | Acetone | Form 2*/Form 2* | Form 2*/Form 2* |
|  | EA | Form 4/Form 4 | Form 4*/Form 4* |
|  | water | Form 13/Form 13 | Form 13/Form 13 |

In order to find out the thermodynamic stability between Form 13 and Form 9, several competitive reslurry experiments were carried out. 15 mg of Form 1, Form 9 and Form 13 solids were mixed in 1 mL of toluene, IPAc, and n-butyl acetate, and slurried for 3 days at RT and 50° C.

The residual solid was analyzed by XRD. After a three-day reslurry, it was difficult to tell which one was more stable between Form 13 and Form 9. The XRD scan results of the experiment are shown in Table 33, below.

TABLE 33

XRD scan results competitive reslurry experiments

| Temperature | Solvent | Form after 3 days; wet/dry |
| --- | --- | --- |
| RT | Toluene | Form 13/Form 1 |
| | IPAc | Form 9 + Form 13/Form 9 + Form 1 |
| | n-Butyl acetate | Form 9 + Form 13/Form 9 + Form 1 |
| 50° C. | Toluene | Form 9 + Form 13/Form 9 + Form 1 |
| | IPAc | Form 9/Form 9 |
| | n-Butyl acetate | Form 9 + Form 13/Form 9 + Form 1 |

What is claimed is:

1. A process for preparing a polymorph form of a compound of Formula (1)

(1)

the process comprising:
(a) reacting a compound of Formula (8)

(8)

or a salt thereof, with bis(pinacolato)diboron and Pd(dppf)Cl$_2$ to produce a compound of Formula (9)

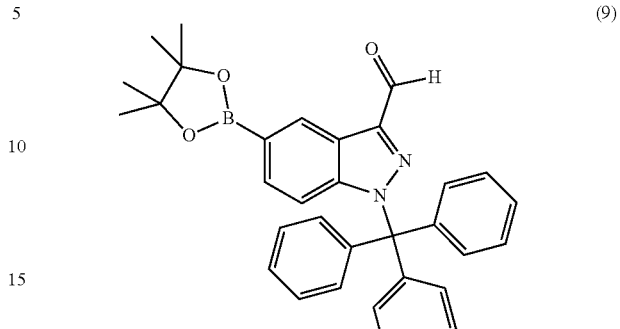

(9)

or a salt thereof;
(b) reacting the compound of Formula (9), or the salt thereof, with a compound of Formula (10)

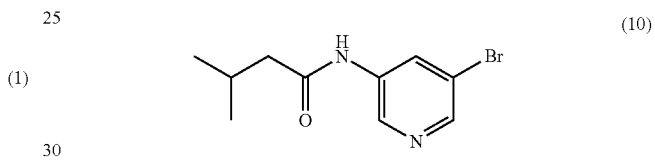

(10)

or a salt thereof, Pd(PPh$_3$)$_4$ and K$_3$PO$_4$ to prepare a compound of Formula (11)

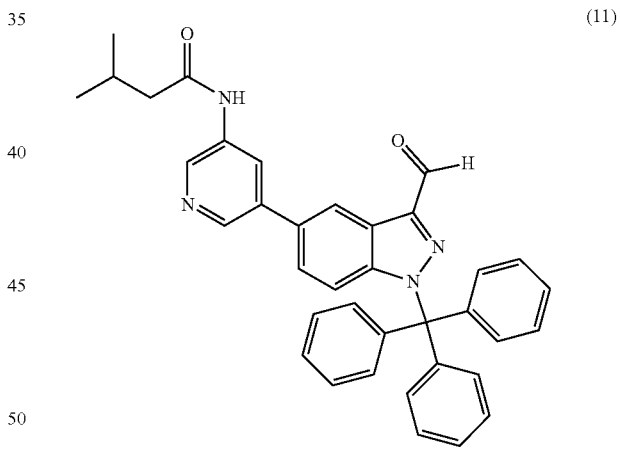

(11)

or a salt thereof,
(c) reacting the compound of Formula (11), or the salt thereof, with a compound of Formula (6)

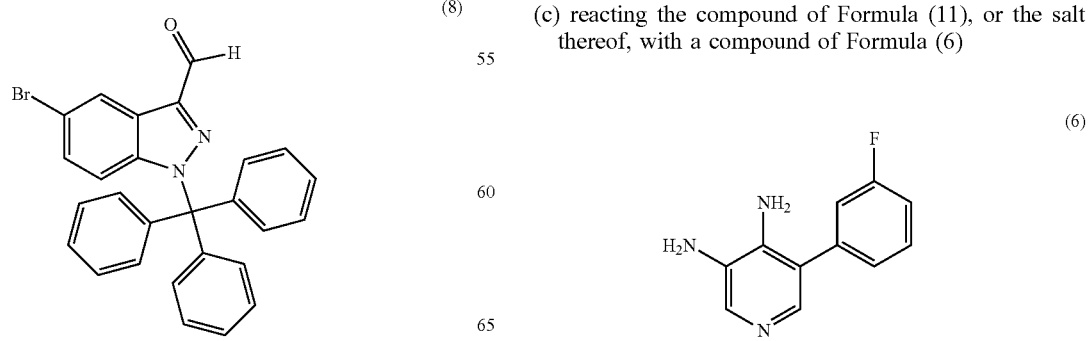

(6)

or a salt thereof, to prepare a compound of Formula (12)

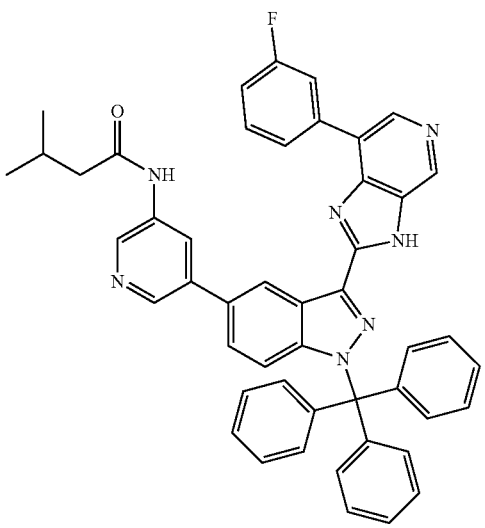

(12)

or a salt thereof;
- (d) deprotecting the compound of Formula (12), or the salt thereof, to prepare the compound of Formula (1), or a salt thereof, wherein deprotecting the compound of Formula (12) to prepare the compound of Formula (1) comprises reacting the compound of Formula (12) with trifluoroacetic acid;
- (e) reslurrying the compound of Formula (1) in a solvent, wherein the solvent is selected from acetonitrile, n-butyl acetate, n-butanol, dichloromethane (DCM), heptane, isopropyl alcohol, methanol, methyl acetate (MA), methyl tert-butyl ether (MtBE), methyl isobutyl ketone (MIRK), toluene, water, and a mixture thereof; wherein reslurrying is performed at a temperature of about room temperature to about 50° C.; wherein reslurrying is performed for a time of about 10 hours to about 80 hours;
- (f) filtering to provide the compound of Formula (1) as a residual solid;
- (g) drying the residual solid;
- (h) reslurrying the residual solid in a solvent to generate the polymorph Form 2, wherein the reslurrying is performed at room temperature, wherein the solvent is ethanol/water, and wherein the water is present in an amount of about 5% by weight; and
- (i) filtering to provide the polymorph as a residual solid; wherein the polymorph Form 2 has an XRPD pattern with at least peaks at °2θ positions of 7.0±0.2, 21.5±0.2, and 22.0±0.2.

2. The process of claim 1, wherein the trifluoroacetic acid in step (d) is neat trifluoroacetic acid.

3. The process of claim 1, wherein the reslurrying in step (e) is performed at room temperature.

4. The process of claim 1, wherein the reslurrying in step (e) is performed at a temperature of about 50° C.

5. The process of claim 1, wherein the reslurrying in step (e) is performed at a temperature of about 30° C. to about 35° C.

6. The process of claim 1, wherein the reslurrying in step (e) is performed for a time of about 58 hours to about 80 hours.

7. The process of claim 6, wherein the solvent in step (e) is selected from methanol, water, and a mixture thereof.

8. The process of claim 7, wherein the solvent in step (e) is 90% methanol/water.

9. The process of claim 7, wherein the solvent in step (e) is methanol; and wherein the reslurrying is performed at a temperature of about 50° C.

10. The process of claim 1, wherein the drying in step (g) is performed under vacuum.

11. The process of claim 10, wherein the drying in step (g) is at a temperature of between about 60° C. and 90° C.

12. The process of claim 11, wherein the drying in step (g) is at a temperature of about 75° C.

13. The process of claim 1, wherein the polymorph Form 2 in step (i) has an XRPD pattern with at least peaks at °2θ positions 7.0±0.2, 18.9±0.2, 21.5±0.2, 22.0±0.2, and 24.2±0.2.

14. The process of claim 13, wherein the polymorph Form 2 in step (i) has an XRPD pattern with at least peaks at °2θ positions 7.0±0.2, 10.4±0.2, 14.1±0.2, 17.6±0.2, 18.9±0.2, 19.2±0.2, 21.5±0.2, 22.0±0.2, 24.2±0.2, and 26.4±0.2.

15. The process of claim 1, wherein the polymorph Form 2 exhibits an endotherm between about 220-230° C. as measured by DSC.

16. The process of claim 1, wherein the polymorph Form 2 exhibits an exotherm between about 233-238° C. as measured by DSC.

17. The process of claim 1, wherein the polymorph Form 2 exhibits an exotherm between about 290-295° C. as measured by DSC.

18. The process of claim 1, wherein the polymorph Form 2 undergoes a weight loss of about 2.7% between about 36° C. to about 116° C., as measured by TGA.

* * * * *

UNITED STATES PATENT AND TRADEMARK OFFICE
CERTIFICATE OF CORRECTION

| | |
|---|---|
| PATENT NO. | : 12,012,401 B2 |
| APPLICATION NO. | : 17/205558 |
| DATED | : June 18, 2024 |
| INVENTOR(S) | : Sunil Kumar KC |

It is certified that error appears in the above-identified patent and that said Letters Patent is hereby corrected as shown below:

In the Claims

Column 129, Approximately Line 38, in Claim 1, delete "(MIRK)," and insert -- (MIBK), --.

Column 129, Approximately Line 47, in Claim 1, before "polymorph" delete "the".

Signed and Sealed this
Sixth Day of August, 2024

Katherine Kelly Vidal
*Director of the United States Patent and Trademark Office*